(12) United States Patent
Gu et al.

(10) Patent No.: US 11,028,164 B2
(45) Date of Patent: Jun. 8, 2021

(54) ANTI-CXCL13 ANTIBODIES

(71) Applicant: I-Mab Biopharma US Limited, Gaithersburg, MD (US)

(72) Inventors: Haijuan Gu, Shanghai (CN); Qiumei Yang, Shanghai (CN)

(73) Assignee: I-Mab Biopharma US Limited, Gaithersburg, MD (US)

( * ) Notice: Subject to any disclaimer, the term of this patent is extended or adjusted under 35 U.S.C. 154(b) by 0 days.

(21) Appl. No.: 16/963,130

(22) PCT Filed: Sep. 18, 2019

(86) PCT No.: PCT/CN2019/106409
§ 371 (c)(1),
(2) Date: Jul. 17, 2020

(87) PCT Pub. No.: WO2020/057540
PCT Pub. Date: Mar. 26, 2020

(65) Prior Publication Data
US 2020/0399360 A1 Dec. 24, 2020

(30) Foreign Application Priority Data

Sep. 18, 2018 (WO) ............... PCT/CN2018/106158

(51) Int. Cl.
| | | |
|---|---|---|
| C07K 16/24 | (2006.01) | |
| A61P 37/02 | (2006.01) | |
| C07K 16/28 | (2006.01) | |
| A61K 39/00 | (2006.01) | |
| A61P 35/00 | (2006.01) | |
| G01N 33/68 | (2006.01) | |

(52) U.S. Cl.
CPC .............. *C07K 16/24* (2013.01); *A61P 35/00* (2018.01); *A61P 37/02* (2018.01); *C07K 16/2875* (2013.01); *G01N 33/6863* (2013.01); *A61K 2039/505* (2013.01); *C07K 2317/24* (2013.01); *C07K 2317/31* (2013.01); *C07K 2317/56* (2013.01); *C07K 2317/565* (2013.01); *C07K 2317/76* (2013.01); *C07K 2317/92* (2013.01); *G01N 2333/521* (2013.01)

(58) Field of Classification Search
None
See application file for complete search history.

(56) References Cited

FOREIGN PATENT DOCUMENTS

| WO | WO 2008/102123 | 8/2008 |
| WO | WO 2014/137355 | 9/2014 |

OTHER PUBLICATIONS

International Search Report and Written Opinion for PCT/CN2019/106409 dated Dec. 20, 2019, 10 pages.

*Primary Examiner* — Elly-Gerald Stoica
(74) *Attorney, Agent, or Firm* — Sheppard Mullin Richter & Hampton LLP

(57) ABSTRACT

Provided are antibodies or fragments thereof having binding specificity to the human chemokine (C-X-C motif) ligand 13 (CXCL 13) protein. In various examples, the antibodies or fragments thereof include a VH and VL CDRs as disclosed herein, or variants thereof. Methods of using the antibodies or fragments thereof for treating autoimmune diseases and disorders are also provided.

14 Claims, 11 Drawing Sheets
Specification includes a Sequence Listing.

SEQUENCE LISTING

<160> NUMBER OF SEQ ID NOS: 373

<210> SEQ ID NO 1
<211> LENGTH: 138
<212> TYPE: PRT
<213> ORGANISM: Artificial Sequence
<220> FEATURE:
<223> OTHER INFORMATION: Synthetic

<400> SEQUENCE: 1

Met Asp Phe Gly Leu Ile Phe Phe Ile Val Ala Leu Leu Lys Gly Val
1               5                   10                  15

Gln Cys Glu Val Lys Leu Leu Gln Ser Gly Gly Gly Leu Val Gln Pro
            20                  25                  30

Gly Gly Ser Leu Lys Leu Ser Cys Ala Ala Ser Gly Ile Asp Phe Ser
        35                  40                  45

Arg Tyr Trp Met Ser Trp Val Arg Arg Ala Pro Gly Lys Gly Leu Glu
50                  55                  60

Trp Ile Gly Glu Ile Asn Pro Asp Ser Ser Thr Ile Asn Tyr Ala Pro
65                  70                  75                  80

Ser Leu Lys Asp Lys Phe Ile Ile Ser Arg Asp Asn Ala Lys Asn Thr
                85                  90                  95

Leu Tyr Leu Gln Met Ser Lys Val Arg Ser Glu Asp Thr Ala Leu Tyr
            100                 105                 110

Tyr Cys Ala Arg Gln Asp Asp Tyr Asp Tyr Tyr Ala Met Asp Tyr Trp
        115                 120                 125

Gly Gln Gly Thr Ser Val Thr Val Ser Ser
    130                 135

<210> SEQ ID NO 2
<211> LENGTH: 131
<212> TYPE: PRT
<213> ORGANISM: Artificial Sequence
<220> FEATURE:
<223> OTHER INFORMATION: Synthetic

<400> SEQUENCE: 2

Met Gly Ile Lys Met Glu Ser Gln Ile Gln Val Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ser Thr Gly Val Ala Trp Tyr Gln Gln Lys Pro
50                  55                  60

Gly Gln Ser Pro Lys Leu Leu Ile Tyr Ser Ala Ser Tyr Arg Tyr Thr
65                  70                  75                  80

Gly Val Pro Asp Arg Phe Thr Gly Ser Gly Ser Arg Thr Asp Phe Thr
                85                  90                  95

Phe Thr Ile Ser Ser Val Gln Thr Glu Asp Pro Ala Val Tyr Tyr Cys
            100                 105                 110

His Gln Tyr Tyr Thr Ile Pro Leu Thr Phe Gly Ala Gly Thr Glu Leu
        115                 120                 125

Glu Leu Lys
    130

<210> SEQ ID NO 3
<211> LENGTH: 133

<212> TYPE: PRT
<213> ORGANISM: Artificial Sequence
<220> FEATURE:
<223> OTHER INFORMATION: Synthetic

<400> SEQUENCE: 3

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
        35                  40                  45

Thr Glu Tyr Ile Met His Trp Val Lys Gln Ser His Gly Arg Ser Leu
    50                  55                  60

Glu Trp Ile Gly Gly Ile Asn Pro Asp Asn Gly Asp Thr Thr Tyr Asn
65                  70                  75                  80

Gln Lys Phe Lys Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Gly Gly Val Leu Asp Tyr Trp Gly Gln Gly Thr Ser
        115                 120                 125

Val Thr Val Ser Ser
    130

<210> SEQ ID NO 4
<211> LENGTH: 132
<212> TYPE: PRT
<213> ORGANISM: Artificial Sequence
<220> FEATURE:
<223> OTHER INFORMATION: Synthetic

<400> SEQUENCE: 4

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Phe Tyr
            100                 105                 110

Cys Trp Gln Gly Thr His Phe Pro Phe Thr Phe Gly Ser Gly Thr Lys
        115                 120                 125

Leu Glu Ile Lys
    130

<210> SEQ ID NO 5
<211> LENGTH: 133
<212> TYPE: PRT
<213> ORGANISM: Artificial Sequence
<220> FEATURE:
<223> OTHER INFORMATION: Synthetic

<400> SEQUENCE: 5

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Thr Ser Gly Tyr Thr Phe
        35                  40                  45

Thr Glu Tyr Ile Met His Trp Val Lys Gln Ser His Glu Arg Ser Leu
    50                  55                  60

Glu Trp Ile Gly Gly Ile His Pro Asp Asn Gly Asp Thr Thr Tyr Asn
65                  70                  75                  80

Gln Lys Phe Thr Gly Lys Ala Thr Leu Thr Val Asp Lys Ser Ser Thr
                85                  90                  95

Thr Ala Tyr Met Glu Leu Arg Ser Leu Thr Ser Glu Asp Ser Ala Val
            100                 105                 110

Tyr Tyr Cys Ala Gly Gly Val Leu Asp Tyr Trp Gly Gln Gly Thr Ser
        115                 120                 125

Val Thr Val Ser Ser
    130

<210> SEQ ID NO 6
<211> LENGTH: 132
<212> TYPE: PRT
<213> ORGANISM: Artificial Sequence
<220> FEATURE:
<223> OTHER INFORMATION: Synthetic

<400> SEQUENCE: 6

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Val Thr Phe Gly Gln Pro Ala Ser Ile Ser Cys Lys Ser Ser Gln Ser
        35                  40                  45

Leu Leu Asp Ser Asp Gly Arg Thr Tyr Leu Asn Trp Leu Leu Gln Arg
    50                  55                  60

Pro Gly Gln Ser Pro Gln Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Phe Tyr
            100                 105                 110

Cys Trp Gln Gly Thr His Phe Pro Phe Thr Phe Gly Ser Gly Thr Lys
        115                 120                 125

Leu Glu Ile Lys
    130

<210> SEQ ID NO 7
<211> LENGTH: 139
<212> TYPE: PRT
<213> ORGANISM: Artificial Sequence
<220> FEATURE:
<223> OTHER INFORMATION: Synthetic

<400> SEQUENCE: 7

Met Asp Ile Arg Leu Ser Leu Val Phe Leu Val Leu Phe Ile Lys Gly
1               5                   10                  15

Val Gln Cys Glu Val Gln Leu Ala Glu Ser Gly Gly Gly Leu Val Gln
            20                  25                  30

Pro Gly Arg Ser Leu Lys Leu Ser Cys Ser Ala Ser Gly Phe Thr Phe
        35                  40                  45

Ser Asp Tyr Tyr Met Ala Trp Phe Arg Gln Ala Pro Pro Lys Gly Leu
50                      55                  60

Glu Trp Val Ala Ser Ile Ser Tyr Asp Gly Asp Ser Phe Tyr Arg
65                  70                  75                  80

Asp Ser Val Lys Gly Arg Phe Thr Ile Ser Arg Asp Asn Ala Lys Ser
                85                  90                  95

Ser Leu Tyr Leu Gln Met Asp Ser Leu Arg Ser Glu Asp Thr Ala Thr
            100                 105                 110

Tyr Tyr Cys Thr Thr Glu Glu Asp Tyr Ser Gly Ser Phe Pro Asp Tyr
        115                 120                 125

Trp Gly Gln Gly Val Met Val Thr Val Ser Ser
        130                 135

<210> SEQ ID NO 8
<211> LENGTH: 126
<212> TYPE: PRT
<213> ORGANISM: Artificial Sequence
<220> FEATURE:
<223> OTHER INFORMATION: Synthetic

<400> SEQUENCE: 8

Met Met Ala Pro Val Gln Leu Leu Gly Leu Leu Ile Trp Leu Pro
1               5                   10                  15

Ala Met Arg Cys Asp Ile Gln Met Thr Gln Ser Pro Ser Phe Leu Ser
            20                  25                  30

Ala Ser Val Gly Asp Arg Val Thr Ile Asn Cys Lys Ala Ser Gln Asn
        35                  40                  45

Ile Asn Lys Tyr Leu Asn Trp Tyr Gln Gln Lys Leu Gly Glu Ala Pro
50                  55                  60

Lys Arg Leu Ile Tyr Asp Thr Asn Asn Leu Gln Ala Gly Ile Pro Ser
65                  70                  75                  80

Arg Phe Ser Gly Ser Gly Ser Gly Thr Asp Tyr Thr Leu Thr Ile Asn
                85                  90                  95

Ser Leu Gln Pro Glu Asp Phe Ala Thr Tyr Phe Cys Leu Gln His Asn
            100                 105                 110

Ser Leu Tyr Thr Phe Gly Gly Gly Thr Lys Leu Glu Leu Lys
        115                 120                 125

<210> SEQ ID NO 9
<211> LENGTH: 132
<212> TYPE: PRT
<213> ORGANISM: Artificial Sequence
<220> FEATURE:
<223> OTHER INFORMATION: Synthetic

<400> SEQUENCE: 9

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Asn Arg Gln Phe Pro Gly Asn Lys Leu
50                  55                  60

```
Glu Trp Met Gly Tyr Ile Ser Tyr Ser Gly Asp Thr Ser Tyr Asn Pro
 65                  70                  75                  80

Ser Leu Arg Ser Arg Ile Ser Ile Thr Arg Asp Thr Ser Lys Asn Gln
                 85                  90                  95

Phe Phe Leu Gln Leu Asn Ser Val Thr Ala Glu Asp Thr Ala Lys Tyr
            100                 105                 110

Tyr Cys Val Ala Gly His Phe Asp Tyr Trp Gly Gln Gly Thr Thr Leu
        115                 120                 125

Thr Val Ser Ser
    130

<210> SEQ ID NO 10
<211> LENGTH: 132
<212> TYPE: PRT
<213> ORGANISM: Artificial Sequence
<220> FEATURE:
<223> OTHER INFORMATION: Synthetic

<400> SEQUENCE: 10

Met Met Ser Pro Ala Gln Phe Leu Phe Leu Leu Val Leu Trp Ile Arg
 1               5                  10                  15

Glu Thr Asn Gly Asp Val Val Met Thr Gln Thr Pro Leu Thr Leu Ser
                 20                  25                  30

Ile Thr Leu Gly Gln Pro Ala Ser Ile Ser Cys Lys Ser Ser Gln Ser
            35                  40                  45

Leu Leu Asp Ser Asp Gly Glu Thr Tyr Leu Asn Trp Leu Leu Gln Arg
 50                  55                  60

Pro Gly Gln Ser Pro Lys Arg Leu Ile Tyr Leu Val Ser Lys Leu Asp
 65                  70                  75                  80

Ser Gly Val Pro Asp Arg Phe Thr Gly Ser Gly Ser Gly Thr Asp Phe
                 85                  90                  95

Thr Leu Lys Ile Ser Arg Val Glu Ala Glu Asp Leu Gly Val Tyr Tyr
            100                 105                 110

Cys Trp Gln Gly Thr His Phe Pro Tyr Thr Phe Gly Gly Gly Thr Lys
        115                 120                 125

Leu Glu Ile Lys
    130

<210> SEQ ID NO 11
<211> LENGTH: 133
<212> TYPE: PRT
<213> ORGANISM: Artificial Sequence
<220> FEATURE:
<223> OTHER INFORMATION: Synthetic

<400> SEQUENCE: 11

Met Gly Trp Ser Trp Ile Phe Leu Phe Leu Leu Ser Gly Thr Ala Gly
 1               5                  10                  15

Val Leu Ser Glu Val Gln Leu Gln Gln Ser Gly Pro Glu Leu Val Lys
                 20                  25                  30

Pro Gly Ala Ser Val Lys Ile Ser Cys Lys Thr Ser Gly Tyr Thr Phe
            35                  40                  45

Thr Glu Tyr Ile Met His Trp Val Lys Gln Ser His Gly Arg Ser Leu
 50                  55                  60

Glu Trp Ile Gly Gly Ile Asn Pro Asn Asn Gly Gly Thr Thr Tyr Asn
 65                  70                  75                  80

Gln Lys Phe Lys Gly Lys Ala Thr Leu Thr Val Asp Lys Ser Ser Ser
```

```
                    85                  90                  95

Thr Ala Tyr Met Glu Leu Arg Ser Leu Thr Ser Glu Asp Ser Ala Val
                100                 105                 110

Tyr Tyr Cys Ala Gly Gly Val Met Asp Tyr Trp Gly Gln Gly Thr Ser
            115                 120                 125

Val Thr Val Ser Ser
        130

<210> SEQ ID NO 12
<211> LENGTH: 132
<212> TYPE: PRT
<213> ORGANISM: Artificial Sequence
<220> FEATURE:
<223> OTHER INFORMATION: Synthetic

<400> SEQUENCE: 12

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
                20                  25                  30

Val Thr Ile Gly Gln Pro Ala Ser Ile Ser Cys Lys Ser Ser Gln Ser
            35                  40                  45

Leu Leu Asp Ser Asp Gly Lys Thr Tyr Leu Asn Trp Leu Leu Gln Arg
        50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Phe Tyr
                100                 105                 110

Cys Trp Gln Gly Thr His Phe Pro Phe Thr Phe Gly Ser Gly Thr Lys
            115                 120                 125

Leu Glu Ile Lys
        130

<210> SEQ ID NO 13
<211> LENGTH: 132
<212> TYPE: PRT
<213> ORGANISM: Artificial Sequence
<220> FEATURE:
<223> OTHER INFORMATION: Synthetic

<400> SEQUENCE: 13

Met Arg Val Leu Ile Leu Leu Trp Leu Thr Ala Leu Pro Gly Ile
1               5                   10                  15

Leu Ser Asp Val Gln Leu Gln Glu Ser Gly Pro Gly Leu Val Lys Pro
                20                  25                  30

Ser Gln Ser Leu Ser Leu Thr Cys Thr Val Thr Gly Tyr Ser Ile Thr
            35                  40                  45

Ser Asp Tyr Ala Trp Asn Trp Ile Arg His Phe Pro Gly Asn Lys Leu
        50                  55                  60

Glu Trp Met Gly Tyr Ile Ser Tyr Thr Gly Ser Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Ser Glu Asp Thr Ala Thr Tyr
                100                 105                 110
```

Tyr Cys Val Ala Gly His Phe Asp Tyr Trp Gly Pro Gly Thr Thr Leu
            115                 120                 125

Thr Val Ser Ser
    130

<210> SEQ ID NO 14
<211> LENGTH: 132
<212> TYPE: PRT
<213> ORGANISM: Artificial Sequence
<220> FEATURE:
<223> OTHER INFORMATION: Synthetic

<400> SEQUENCE: 14

Met Met Ser Pro Ala Gln Phe Leu Phe Leu Leu Val Leu Trp Ile Arg
1               5                   10                  15

Glu Ala Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Gln Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Tyr Thr Phe Gly Gly Gly Thr Lys
        115                 120                 125

Leu Glu Ile Lys
    130

<210> SEQ ID NO 15
<211> LENGTH: 135
<212> TYPE: PRT
<213> ORGANISM: Artificial Sequence
<220> FEATURE:
<223> OTHER INFORMATION: Synthetic

<400> SEQUENCE: 15

Met Gly Trp Ser Trp Ile Phe Leu Phe Leu Leu Ser Gly Thr Ala Gly
1               5                   10                  15

Val His Ser Glu Val Gln Leu Gln Gln Ser Gly Pro Val Leu Val Arg
            20                  25                  30

Pro Gly Ala Ser Val Lys Met Ser Cys Lys Ala Ser Gly Tyr Thr Phe
        35                  40                  45

Thr Asp Tyr Tyr Met Asn Trp Val Lys Gln Ser His Gly Lys Ser Leu
    50                  55                  60

Glu Trp Ile Gly Val Ile Asn Pro Asn Asn Gly Gly Thr Thr Tyr Lys
65                  70                  75                  80

Glu Lys Phe Lys Gly Lys Ala Thr Leu Thr Val Asp Lys Ser Ser Gly
                85                  90                  95

Thr Ala Tyr Met Glu Leu Asn Ser Leu Thr Ser Glu Asp Ser Ala Val
            100                 105                 110

Tyr Tyr Cys Ala Arg Asp Asp Tyr Asp Ala Gly Tyr Trp Gly Gln Gly
        115                 120                 125

Thr Thr Leu Thr Val Ser Ser
    130                 135

<210> SEQ ID NO 16
<211> LENGTH: 131
<212> TYPE: PRT
<213> ORGANISM: Artificial Sequence
<220> FEATURE:
<223> OTHER INFORMATION: Synthetic

<400> SEQUENCE: 16

```
Met Gly Phe Lys Met Glu Phe His Thr Gln Val Phe Val Phe
1               5                   10                  15

Leu Trp Leu Ser Gly Val Asp Gly Asp Ile Val Met Thr Gln Phe Gln
                20                  25                  30

Lys Phe Met Ser Thr Thr Val Gly Asp Arg Val Ser Ile Thr Cys Lys
                35                  40                  45

Ala Ser Gln Asn Val Asp Thr Ala Val Ala Trp Tyr Gln His Lys Pro
            50                  55                  60

Gly Gln Ser Pro Lys Leu Leu Ile Tyr Ser Ala Ser His Arg Tyr Thr
65                  70                  75                  80

Gly Val Pro Asp Arg Phe Thr Gly Ser Gly Ser Gly Thr Asp Phe Thr
                    85                  90                  95

Leu Thr Ile Ser Asn Val Gln Ser Glu Asp Leu Ala Asp Tyr Phe Cys
                100                 105                 110

Gln Gln Tyr Thr Asp Phe Pro Leu Thr Phe Gly Ala Gly Thr Lys Leu
            115                 120                 125

Glu Leu Lys
    130
```

<210> SEQ ID NO 17
<211> LENGTH: 141
<212> TYPE: PRT
<213> ORGANISM: Artificial Sequence
<220> FEATURE:
<223> OTHER INFORMATION: Synthetic

<400> SEQUENCE: 17

```
Met Asp Arg Leu Thr Ser Ser Ile Leu Leu Leu Leu Val Pro Ala Tyr
1               5                   10                  15

Val Leu Ser His Val Thr Leu Arg Glu Ser Gly Pro Gly Val Leu Gln
                20                  25                  30

Pro Ser Lys Thr Leu Ser Leu Thr Cys Ser Phe Ser Gly Phe Ser Leu
            35                  40                  45

Ser Thr Ser Ala Met Val Val Ser Trp Ile Arg Gln Ser Ser Gly Met
        50                  55                  60

Ser Leu Glu Trp Leu Ala Ala Ile Asp Trp Glu Gly Asp Lys Tyr Tyr
65                  70                  75                  80

Asn Pro Ser Leu Glu Ser Arg Leu Thr Val Ser Arg Asp Ile Ser Asp
                85                  90                  95

Thr Gln Val Phe Leu Arg Ile Thr Ser Val Asp Val Ala Asp Thr Ala
            100                 105                 110

Thr Tyr Tyr Cys Ala Val Met Ser Ser Ala Asp Ser His Ser Val Leu
        115                 120                 125

Asp Ala Trp Gly Gln Gly Val Ser Val Thr Val Ser Ser
    130                 135                 140
```

<210> SEQ ID NO 18
<211> LENGTH: 126
<212> TYPE: PRT

<213> ORGANISM: Artificial Sequence
<220> FEATURE:
<223> OTHER INFORMATION: Synthetic

<400> SEQUENCE: 18

Met Met Ala Ala Leu Gln Leu Leu Gly Val Leu Leu Leu Trp Leu Pro
1               5                   10                  15

Ala Met Arg Cys Asp Ile Lys Met Thr Gln Ser Pro Ser Phe Leu Ser
            20                  25                  30

Ala Ser Val Gly Asp Arg Val Thr Ile Asn Cys Lys Ala Ser Gln Asn
        35                  40                  45

Ile His Asn Tyr Leu Asn Trp Tyr Gln Gln Lys Phe Gly Glu Ala Pro
    50                  55                  60

Arg Leu Leu Ile Tyr Asn Thr Asn Leu Gln Thr Gly Ile Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Val Ala Thr Tyr Phe Cys Leu Gln His Ser
            100                 105                 110

Ser Ser Leu Thr Phe Gly Ser Gly Thr Lys Leu Glu Ile Asn
        115                 120                 125

<210> SEQ ID NO 19
<211> LENGTH: 145
<212> TYPE: PRT
<213> ORGANISM: Artificial Sequence
<220> FEATURE:
<223> OTHER INFORMATION: Synthetic

<400> SEQUENCE: 19

Met Lys Leu Trp Leu Asn Trp Ile Phe Leu Leu Thr Leu Leu Asn Gly
1               5                   10                  15

Ile Gln Cys Glu Val Lys Leu Leu Glu Ser Gly Gly Gly Leu Val Gln
            20                  25                  30

Ala Gly Gly Ser Met Arg Leu Ser Cys Gly Ala Phe Gly Phe Thr Val
        35                  40                  45

Thr Asp Phe Tyr Ile Asn Trp Ile Arg Gln Pro Ala Gly Lys Ala Pro
    50                  55                  60

Glu Trp Leu Gly Phe Met Arg Asn Lys Ala Asn Gly Tyr Thr Thr Glu
65                  70                  75                  80

Tyr Asn Pro Ser Val Lys Gly Arg Phe Thr Ile Ser Arg Asn Asn Thr
                85                  90                  95

Gln Asn Met Pro Tyr Leu Gln Met Asn Thr Leu Arg Thr Glu Asp Thr
            100                 105                 110

Ala Ile Tyr Tyr Cys Ala Arg Ser Arg Tyr Asn Ala Asp Asp Tyr Tyr
        115                 120                 125

Val Gly Val Met Asp Val Trp Gly Gln Gly Ala Ser Val Thr Val Ser
    130                 135                 140

Ser
145

<210> SEQ ID NO 20
<211> LENGTH: 127
<212> TYPE: PRT
<213> ORGANISM: Artificial Sequence
<220> FEATURE:
<223> OTHER INFORMATION: Synthetic

<400> SEQUENCE: 20

```
Met Gly Val Pro Thr Gln Leu Leu Val Leu Leu Leu Trp Ile Thr
1               5                   10                  15

Asp Ala Ile Cys Asp Ile Gln Met Thr Gln Phe Pro Ala Ser Leu Ser
            20                  25                  30

Ala Ser Leu Gly Glu Thr Val Ser Ile Glu Cys Leu Ala Ser Glu Asp
        35                  40                  45

Ile Tyr Asn Asn Leu Ala Trp Tyr Gln Gln Lys Pro Gly Lys Ser Pro
    50                  55                  60

Gln Leu Leu Ile Tyr Tyr Thr Asn Ser Leu Gln Asp Gly Val Pro Ser
65              70                  75                  80

Arg Phe Ser Gly Thr Gly Ser Gly Thr Gln Tyr Ser Leu Lys Ile Asn
            85                  90                  95

Ser Leu Glu Ser Glu Asp Ala Ala Thr Tyr Phe Cys Leu Gln Asp Ser
        100                 105                 110

Glu Tyr Pro Trp Thr Phe Gly Gly Gly Thr Lys Leu Lys Leu Lys
    115                 120                 125
```

<210> SEQ ID NO 21
<211> LENGTH: 132
<212> TYPE: PRT
<213> ORGANISM: Artificial Sequence
<220> FEATURE:
<223> OTHER INFORMATION: Synthetic

<400> SEQUENCE: 21

```
Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Asn Trp Ile Arg Gln Phe Pro Gly Asn Lys Leu
    50                  55                  60

Glu Trp Met Gly Tyr Ile Ser Tyr Ser Gly Asp Thr Ser Tyr Asn Pro
65              70                  75                  80

Ser Leu Lys Ser Arg Ile Ser Ile Thr Arg Asp Thr Ser Lys Asn Gln
            85                  90                  95

Phe Phe Leu Gln Leu Asn Ser Val Thr Thr Glu Asp Thr Ala Thr Tyr
        100                 105                 110

Tyr Cys Val Ala Gly His Phe Asp Tyr Trp Gly Gln Gly Thr Thr Leu
    115                 120                 125

Thr Val Ser Ser
    130
```

<210> SEQ ID NO 22
<211> LENGTH: 132
<212> TYPE: PRT
<213> ORGANISM: Artificial Sequence
<220> FEATURE:
<223> OTHER INFORMATION: Synthetic

<400> SEQUENCE: 22

```
Met Met Ser Pro Ala Gln Phe Leu Phe Leu Leu Val Leu Trp Ile Arg
1               5                   10                  15

Glu Thr Asn Gly Asp Val Val Met Ala Gln Thr Pro Leu Thr Leu Ser
            20                  25                  30

Val Thr Ile Gly Gln Pro Ala Ser Ile Ser Cys Lys Ser Ser Gln Ser
```

```
                35                  40                  45
Leu Leu Asp Ser Asp Gly Lys Thr Tyr Leu Asn Trp Leu Leu Gln Arg
 50                  55                  60

Pro Gly Gln Ser Pro Lys Arg Leu Ile Tyr Leu Val Ser Asn Leu Asp
 65                  70                  75                  80

Ser Gly Val Pro Asp Arg Phe Thr Gly Ser Gly Ser Gly Thr Asp Phe
                 85                  90                  95

Thr Leu Lys Ile Ile Arg Val Glu Ala Glu Asp Leu Gly Leu Tyr Tyr
                100                 105                 110

Cys Trp Gln Gly Thr His Phe Pro Tyr Thr Phe Gly Gly Gly Thr Lys
                115                 120                 125

Leu Glu Ile Lys
    130

<210> SEQ ID NO 23
<211> LENGTH: 132
<212> TYPE: PRT
<213> ORGANISM: Artificial Sequence
<220> FEATURE:
<223> OTHER INFORMATION: Synthetic

<400> SEQUENCE: 23

Met Arg Val Leu Ile Leu Leu Trp Leu Phe Thr Ala Phe Pro Gly Ile
  1               5                  10                  15

Leu Ser Asp Val Gln Leu Gln Glu Ser Gly Pro Gly Leu Val Lys Pro
                 20                  25                  30

Ser Gln Ser Leu Ser Leu Thr Cys Thr Val Thr Gly Tyr Ser Ile Thr
                 35                  40                  45

Ser Asp Tyr Ala Trp Asn Trp Ile Arg Gln Phe Pro Gly Asn Lys Leu
 50                  55                  60

Glu Trp Met Gly Tyr Ile Ser Tyr Ser Gly Ser Thr Ser Tyr Asn Pro
 65                  70                  75                  80

Ser Leu Lys Ser Arg Ile Ser Ile Thr Arg Asp Thr Ser Lys Asn Gln
                 85                  90                  95

Phe Phe Leu Gln Leu Asn Ser Val Thr Thr Glu Asp Thr Ala Thr Tyr
                100                 105                 110

Tyr Cys Val Ala Gly His Phe Asp Tyr Trp Gly Gln Gly Thr Thr Leu
                115                 120                 125

Thr Val Ser Ser
    130

<210> SEQ ID NO 24
<211> LENGTH: 132
<212> TYPE: PRT
<213> ORGANISM: Artificial Sequence
<220> FEATURE:
<223> OTHER INFORMATION: Synthetic

<400> SEQUENCE: 24

Met Met Ser Pro Ala Gln Phe Leu Phe Leu Leu Val Leu Trp Ile Arg
  1               5                  10                  15

Glu Thr Asn Gly Asp Val Val Met Thr Gln Thr Pro Leu Thr Leu Ser
                 20                  25                  30

Ile Thr Ile Gly Gln Pro Ala Ser Ile Ser Cys Lys Ser Ser Gln Ser
                 35                  40                  45

Leu Leu Asp Ser Asp Gly Lys Thr Tyr Leu Asn Trp Leu Leu Gln Arg
 50                  55                  60
```

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Tyr Thr Phe Gly Gly Gly Thr Lys
            115                 120                 125

Leu Glu Ile Lys
        130

<210> SEQ ID NO 25
<211> LENGTH: 142
<212> TYPE: PRT
<213> ORGANISM: Artificial Sequence
<220> FEATURE:
<223> OTHER INFORMATION: Synthetic

<400> SEQUENCE: 25

Met Asn Phe Gly Leu Ser Leu Ile Phe Leu Val Leu Val Leu Lys Gly
1               5                   10                  15

Val Gln Cys Glu Val Gln Leu Val Glu Ser Gly Gly Gly Leu Val Lys
            20                  25                  30

Pro Gly Gly Ser Leu Lys Leu Ser Cys Ala Ala Ser Gly Phe Thr Phe
        35                  40                  45

Ser Ser Tyr Ala Met Ser Trp Val Arg Gln Thr Pro Glu Lys Arg Leu
    50                  55                  60

Glu Trp Val Ala Thr Ile Ser Asp Gly Gly Ser Asp Thr Tyr Tyr Pro
65                  70                  75                  80

Asp Asn Val Lys Gly Arg Phe Thr Ile Ser Arg Asp Asn Ala Lys Asn
                85                  90                  95

Asn Leu Tyr Leu Gln Met Ser His Leu Lys Ser Glu Asp Thr Ala Met
            100                 105                 110

Tyr Tyr Cys Ala Arg Asp Tyr Tyr Gly Ser Ser Tyr Glu Asp Tyr Ala
            115                 120                 125

Met Asp Tyr Trp Gly Gln Gly Thr Ser Val Thr Val Ser Ser
        130                 135                 140

<210> SEQ ID NO 26
<211> LENGTH: 126
<212> TYPE: PRT
<213> ORGANISM: Artificial Sequence
<220> FEATURE:
<223> OTHER INFORMATION: Synthetic

<400> SEQUENCE: 26

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Lys Tyr Ile Thr Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Asn Leu Tyr Thr Phe Gly Gly Thr Lys Leu Glu Ile Lys
            115                 120                 125

<210> SEQ ID NO 27
<211> LENGTH: 132
<212> TYPE: PRT
<213> ORGANISM: Artificial Sequence
<220> FEATURE:
<223> OTHER INFORMATION: Synthetic

<400> SEQUENCE: 27

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Ser Trp Ile Arg Gln Phe Pro Gly Asn Lys Leu
    50                  55                  60

Glu Trp Met Gly Tyr Ile Ser Tyr Ser Asp Thr Ser Tyr Asn Pro
65                  70                  75                  80

Ser Leu Lys Ser Arg Ile Ser Ile Thr Arg Asp Thr Ser Lys Asn Gln
            85                  90                  95

Phe Phe Leu Gln Leu Asn Ser Val Thr Ala Glu Asp Thr Ala Thr Tyr
            100                 105                 110

Tyr Cys Ala Ala Gly His Phe Asp Tyr Trp Gly Gln Gly Thr Ile Leu
        115                 120                 125

Thr Val Ser Ser
    130

<210> SEQ ID NO 28
<211> LENGTH: 132
<212> TYPE: PRT
<213> ORGANISM: Artificial Sequence
<220> FEATURE:
<223> OTHER INFORMATION: Synthetic

<400> SEQUENCE: 28

Met Met Ser Pro Ala Gln Phe Leu Phe Leu Leu Val Leu Trp Ile Arg
1               5                   10                  15

Glu Ile Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
            85                  90                  95

Thr Leu Lys Ile Ser Arg Val Glu Ala Glu Asp Leu Gly Val Tyr Tyr
            100                 105                 110

Cys Trp Gln Gly Thr His Phe Pro Tyr Thr Phe Gly Gly Gly Thr Lys
        115                 120                 125

Leu Glu Ile Lys

<210> SEQ ID NO 29
<211> LENGTH: 132
<212> TYPE: PRT
<213> ORGANISM: Artificial Sequence
<220> FEATURE:
<223> OTHER INFORMATION: Synthetic

<400> SEQUENCE: 29

Met Arg Val Leu Ile Leu Leu Trp Leu Phe Thr Ala Phe Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Thr Val Thr Gly Tyr Ser Ile Thr
        35                  40                  45

Ser Asp Tyr Ala Trp Ser Trp Ile Arg Gln Phe Pro Gly Asn Lys Leu
    50                  55                  60

Glu Trp Met Gly Tyr Ile Thr Tyr Ser Asp Ser Thr Ser Tyr Asn Pro
65                  70                  75                  80

Ser Leu Lys Ser Arg Ile Ser Ile Thr Arg Asp Thr Ser Lys Asn Gln
                85                  90                  95

Phe Phe Leu Gln Leu Asn Ser Val Thr Ala Glu Asp Thr Ala Thr Tyr
            100                 105                 110

Tyr Cys Ala Ala Gly His Phe Asp Tyr Trp Gly Gln Gly Thr Ile Leu
        115                 120                 125

Thr Val Ser Ser
    130

<210> SEQ ID NO 30
<211> LENGTH: 132
<212> TYPE: PRT
<213> ORGANISM: Artificial Sequence
<220> FEATURE:
<223> OTHER INFORMATION: Synthetic

<400> SEQUENCE: 30

Met Met Ser Pro Ala Gln Phe Leu Phe Leu Leu Val Leu Trp Ile Arg
1               5                   10                  15

Glu Ile Asn Gly Asp Val Val Met Thr Gln Thr Pro Leu Thr Leu Ser
            20                  25                  30

Val Thr Ile Gly Gln Pro Ala Ser Ile Ser Cys Lys Ser Ser Gln Ser
        35                  40                  45

Leu Leu Asp Ser Asp Gly Lys Thr Tyr Leu Asn Trp Leu Leu Gln Arg
    50                  55                  60

Pro Gly Gln Ser Pro Lys Arg Leu Ile Tyr Leu Val Ser Lys Leu Asp
65                  70                  75                  80

Ser Gly Val Pro Asp Arg Phe Thr Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Trp Gln Gly Thr His Phe Pro Tyr Thr Phe Gly Gly Gly Thr Lys
        115                 120                 125

Leu Glu Ile Lys
    130

<210> SEQ ID NO 31
<211> LENGTH: 138

```
<212> TYPE: PRT
<213> ORGANISM: Artificial Sequence
<220> FEATURE:
<223> OTHER INFORMATION: Synthetic

<400> SEQUENCE: 31

Met Gly Trp Ser Trp Ile Phe Leu Phe Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Gln Ala Ser Gly Tyr Ala Phe
        35                  40                  45

Ser Asp Tyr Tyr Met Asn Trp Val Lys Gln Ser His Gly Lys Arg Leu
    50                  55                  60

Glu Trp Ile Gly Asp Ile Asn Pro Asn Asn Asp Gly Thr Thr Tyr Asn
65                  70                  75                  80

Gln Lys Phe Lys Asp Lys Ala Thr Leu Thr Val Asp Lys Ser Ser Ser
                85                  90                  95

Thr Ala Tyr Met Asp Leu Arg Ser Leu Thr Ser Glu Asp Ser Ala Val
            100                 105                 110

Tyr Tyr Cys Ala Arg Leu Ser Trp Ser Phe Phe Ala Met Asp Tyr Trp
        115                 120                 125

Gly Gln Gly Thr Ser Val Thr Val Ser Ser
    130                 135

<210> SEQ ID NO 32
<211> LENGTH: 131
<212> TYPE: PRT
<213> ORGANISM: Artificial Sequence
<220> FEATURE:
<223> OTHER INFORMATION: Synthetic

<400> SEQUENCE: 32

Met Gly Ile Lys Met Glu Ser Gln Ile Gln Val Phe Val Phe Val Phe
1               5                   10                  15

Leu Trp Val Ser Gly Val Asp Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ser Ser Gly Val Ala Trp Tyr Gln Gln Lys Pro
    50                  55                  60

Gly Gln Ser Pro Lys Val Leu Ile Tyr Ser Ala Ser His Arg His Thr
65                  70                  75                  80

Gly Val Pro Asp Arg Phe Thr Ala Ser Gly Ser Gly Thr Asp Phe Thr
                85                  90                  95

Phe Thr Ile Ser Ser Val Gln Ala Glu Asp Leu Ala Val Tyr Tyr Cys
            100                 105                 110

Gln Gln Tyr Tyr Asn Thr Pro Trp Thr Phe Gly Gly Gly Thr Lys Leu
        115                 120                 125

Glu Ile Lys
    130

<210> SEQ ID NO 33
<211> LENGTH: 140
<212> TYPE: PRT
<213> ORGANISM: Artificial Sequence
<220> FEATURE:
<223> OTHER INFORMATION: Synthetic
```

```
<400> SEQUENCE: 33

Met Asp Ile Arg Leu Ser Leu Gly Phe Leu Val Leu Phe Ile Lys Gly
1               5                   10                  15

Val Gln Cys Glu Val Gln Leu Val Glu Ser Gly Gly Gly Leu Val Gln
            20                  25                  30

Pro Gly Gly Ser Leu Lys Leu Ser Cys Val Val Ser Gly Phe Thr Phe
            35                  40                  45

Ser Asp Tyr Tyr Met Ala Trp Val Arg Gln Thr Pro Thr Lys Gly Leu
    50                  55                  60

Glu Trp Val Ala Ser Ile Asn Tyr Asp Gly Gly Asp Thr Tyr Tyr Arg
65                  70                  75                  80

Asp Ser Val Lys Gly Arg Phe Thr Val Ser Arg Asn Asn Ala Lys Ser
                85                  90                  95

Ser Leu Phe Leu Gln Met Asp Ser Leu Arg Ser Glu Thr Ala Thr
            100                 105                 110

Tyr Tyr Cys Lys Thr Glu Glu Asp Tyr Asp Gly Ser Tyr Val Met Asp
            115                 120                 125

Ala Trp Gly Gln Gly Ala Ser Val Ile Val Ser Ser
            130                 135                 140

<210> SEQ ID NO 34
<211> LENGTH: 126
<212> TYPE: PRT
<213> ORGANISM: Artificial Sequence
<220> FEATURE:
<223> OTHER INFORMATION: Synthetic

<400> SEQUENCE: 34

Met Met Ala Pro Val Gln Leu Leu Gly Leu Leu Leu Ile Trp Leu Pro
1               5                   10                  15

Ala Met Arg Cys Asp Ile Gln Met Thr Gln Ser Pro Ser Phe Leu Ser
            20                  25                  30

Ala Ser Val Gly Asp Arg Val Thr Ile Ser Cys Lys Ala Ser Gln Asn
            35                  40                  45

Ile Asn Lys Glu Leu Thr Trp Tyr Gln Gln Lys Leu Gly Lys Ala Pro
    50                  55                  60

Lys Arg Leu Ile Tyr Asn Thr Asn Ile Leu Gln Thr Gly Ile Pro Ser
65                  70                  75                  80

Arg Phe Ser Gly Ser Gly Ser Asn Thr Asp Tyr Thr Leu Thr Ile Ser
                85                  90                  95

Ser Leu Gln Pro Glu Asp Phe Ala Thr Tyr Phe Cys Leu Gln Gln Ser
            100                 105                 110

Ser Leu Tyr Thr Phe Gly Ala Gly Thr Lys Leu Glu Leu Lys
            115                 120                 125

<210> SEQ ID NO 35
<211> LENGTH: 142
<212> TYPE: PRT
<213> ORGANISM: Artificial Sequence
<220> FEATURE:
<223> OTHER INFORMATION: Synthetic

<400> SEQUENCE: 35

Met Asn Phe Gly Leu Ser Leu Ile Phe Leu Val Leu Val Leu Lys Gly
1               5                   10                  15

Ile Gln Cys Glu Val Gln Leu Val Glu Ser Gly Gly Gly Leu Val Lys
            20                  25                  30
```

```
Pro Gly Gly Ser Leu Lys Leu Ser Cys Ala Ala Ser Gly Phe Thr Phe
            35                  40                  45

Ser Ser Tyr Ala Met Ser Trp Val Arg Gln Thr Pro Glu Lys Arg Leu
 50                  55                  60

Glu Trp Val Ala Thr Ile Ser Asp Gly Gly Ser Asp Ala Tyr Tyr Pro
 65                  70                  75                  80

Asp Asn Val Lys Gly Arg Phe Thr Ile Ser Arg Asp Asn Ala Lys Asn
                 85                  90                  95

Asn Leu Tyr Leu Gln Met Ser His Leu Lys Ser Glu Asp Thr Ala Met
            100                 105                 110

Tyr Tyr Cys Ala Arg Asp Tyr Tyr Gly Ser Gly Tyr Glu Asp Ser Pro
            115                 120                 125

Met Asp Tyr Trp Gly Gln Gly Thr Ser Val Thr Val Ser Ser
    130                 135                 140
```

<210> SEQ ID NO 36
<211> LENGTH: 126
<212> TYPE: PRT
<213> ORGANISM: Artificial Sequence
<220> FEATURE:
<223> OTHER INFORMATION: Synthetic

<400> SEQUENCE: 36

```
Met Arg Pro Ser Ile Gln Phe Leu Gly Leu Leu Leu Phe Trp Leu His
 1               5                  10                  15

Gly Ala Gln Cys Asp Ile Gln Met Thr Gln Ser Pro Ser Ser Leu Ser
             20                  25                  30

Ala Ser Leu Gly Gly Lys Val Thr Ile Thr Cys Lys Ala Ser Gln Asp
         35                  40                  45

Ile Asn Lys Tyr Ile Ala Trp Tyr Gln His Lys Pro Gly Lys Gly Pro
     50                  55                  60

Arg Leu Leu Ile His Tyr Thr Ser Thr Leu Gln Pro Gly Ile Pro Ser
 65                  70                  75                  80

Arg Phe Ser Gly Ser Gly Ser Gly Arg Asp Tyr Ser Phe Ser Ile Ser
                 85                  90                  95

Asn Leu Glu Pro Glu Asp Phe Ala Thr Tyr Tyr Cys Leu Gln Tyr Asp
            100                 105                 110

Asn Leu Tyr Thr Phe Gly Gly Gly Thr Lys Leu Glu Ile Lys
        115                 120                 125
```

<210> SEQ ID NO 37
<211> LENGTH: 132
<212> TYPE: PRT
<213> ORGANISM: Artificial Sequence
<220> FEATURE:
<223> OTHER INFORMATION: Synthetic

<400> SEQUENCE: 37

```
Met Arg Val Leu Ile Leu Leu Trp Leu Phe Thr Ala Phe Pro Gly Ile
 1               5                  10                  15

Leu Ser Asp Val Gln Leu Gln Glu Ser Gly Pro Gly Leu Val Lys Pro
             20                  25                  30

Ser Gln Ser Leu Ser Leu Thr Cys Thr Val Thr Gly Tyr Ser Ile Thr
         35                  40                  45

Ser Asp Tyr Ala Trp Asn Trp Ile Arg Gln Phe Pro Gly Asn Lys Leu
     50                  55                  60

Glu Trp Met Gly Tyr Ile Ser Tyr Ser Gly Ser Thr Ser Tyr Asn Pro
 65                  70                  75                  80
```

-continued

Ser Leu Lys Ser Arg Ile Ser Ile Asn Arg Asp Thr Ser Lys Asn Gln
            85                  90                  95

Phe Phe Leu Gln Leu Asn Ser Val Thr Thr Glu Asp Thr Ala Thr Tyr
            100                 105                 110

Tyr Cys Val Ala Gly His Phe Asp Tyr Trp Gly Gln Gly Thr Thr Leu
            115                 120                 125

Thr Val Ser Ser
    130

<210> SEQ ID NO 38
<211> LENGTH: 132
<212> TYPE: PRT
<213> ORGANISM: Artificial Sequence
<220> FEATURE:
<223> OTHER INFORMATION: Synthetic

<400> SEQUENCE: 38

Met Met Ser Pro Ala Gln Phe Leu Phe Leu Leu Val Leu Trp Ile Arg
1               5                   10                  15

Glu Thr Asn Gly Asp Val Val Met Thr Gln Thr Pro Leu Thr Leu Ser
            20                  25                  30

Ile Thr Ile Gly Gln Ser Ala Ser Ile Ser Cys Lys Ser Ser Gln Ser
            35                  40                  45

Leu Leu Asp Ser Asp Gly Lys Thr Tyr Leu Asn Trp Leu Leu Gln Arg
50                  55                  60

Pro Gly Gln Ser Pro Lys Arg Leu Ile Ser Leu Val Ser Lys Leu Asp
65                  70                  75                  80

Ser Gly Val Pro Asp Arg Phe Thr Gly Ser Gly Ser Gly Thr Asp Phe
            85                  90                  95

Thr Leu Lys Ile Ser Arg Val Glu Ala Glu Asp Leu Gly Val Tyr Tyr
            100                 105                 110

Cys Trp Gln Gly Thr His Phe Pro Tyr Thr Phe Gly Gly Gly Thr Lys
            115                 120                 125

Leu Glu Ile Lys
    130

<210> SEQ ID NO 39
<211> LENGTH: 138
<212> TYPE: PRT
<213> ORGANISM: Artificial Sequence
<220> FEATURE:
<223> OTHER INFORMATION: Synthetic

<400> SEQUENCE: 39

Met Asp Phe Gly Leu Ile Phe Phe Ile Val Ala Leu Leu Lys Gly Val
1               5                   10                  15

Gln Cys Glu Val Lys Leu Leu Gln Ser Gly Gly Gly Leu Val Gln Pro
            20                  25                  30

Gly Gly Ser Leu Lys Leu Ser Cys Ala Ala Ser Gly Ile Asp Phe Ser
            35                  40                  45

Arg Tyr Trp Met Ser Trp Val Arg Arg Ala Pro Gly Lys Gly Leu Glu
50                  55                  60

Trp Ile Gly Glu Ile Asn Pro Asp Ser Ser Thr Ile Asn Tyr Ala Pro
65                  70                  75                  80

Ser Leu Lys Asp Lys Phe Ile Ile Ser Arg Asp Asn Ala Lys Asn Thr
            85                  90                  95

Leu Tyr Leu Gln Met Ser Lys Val Arg Ser Glu Asp Thr Ala Leu Tyr

```
                100                 105                 110
Tyr Cys Ala Arg Gln Asp Asp Tyr Glu Tyr Tyr Ala Met Asp Tyr Trp
            115                 120                 125

Gly Gln Gly Thr Ser Val Thr Val Ser Ser
        130                 135

<210> SEQ ID NO 40
<211> LENGTH: 131
<212> TYPE: PRT
<213> ORGANISM: Artificial Sequence
<220> FEATURE:
<223> OTHER INFORMATION: Synthetic

<400> SEQUENCE: 40

Met Gly Ile Lys Met Glu Ser Gln Ile Gln Val Ser Val Phe Val Ile
1               5                   10                  15

Leu Trp Leu Ser Gly Val Asp Gly Asp Ile Val Met Thr Gln Ser His
            20                  25                  30

Lys Ser Met Ser Thr Ser Val Gly Asp Arg Val Ser Ile Thr Cys Lys
        35                  40                  45

Ala Ser Gln Asp Val Asn Thr Gly Val Ala Trp Tyr Arg Gln Lys Pro
    50                  55                  60

Gly Gln Ser Pro Lys Leu Leu Ile Tyr Ser Ala Ser Tyr Arg Tyr Thr
65                  70                  75                  80

Gly Val Pro Asp Arg Phe Thr Gly Ser Gly Ser Gly Thr Asp Phe Thr
                85                  90                  95

Phe Thr Ile Ser Ser Val Gln Ala Glu Asp Leu Ala Val Tyr Tyr Cys
            100                 105                 110

Gln Gln Tyr Tyr Ser Thr Pro Leu Thr Phe Gly Ala Gly Thr Lys Leu
        115                 120                 125

Glu Leu Lys
    130

<210> SEQ ID NO 41
<211> LENGTH: 137
<212> TYPE: PRT
<213> ORGANISM: Artificial Sequence
<220> FEATURE:
<223> OTHER INFORMATION: Synthetic

<400> SEQUENCE: 41

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Thr Gly Tyr Thr Phe
        35                  40                  45

Asn Thr Tyr Trp Ile Glu Trp Val Lys Gln Arg Pro Gly His Gly Leu
    50                  55                  60

Glu Trp Ile Gly Glu Ile Leu Pro Gly Ser Glu Ser Thr Asp Tyr Asn
65                  70                  75                  80

Glu Lys Phe Lys Asp Lys Ala Thr Phe Thr Ala Asp Ile Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Asp Tyr Tyr Gly Tyr Tyr Phe Asp Tyr Trp Gly
        115                 120                 125
```

-continued

Gln Gly Thr Thr Leu Thr Val Ser Ser
        130                 135

<210> SEQ ID NO 42
<211> LENGTH: 131
<212> TYPE: PRT
<213> ORGANISM: Artificial Sequence
<220> FEATURE:
<223> OTHER INFORMATION: Synthetic

<400> SEQUENCE: 42

Met Gly Ile Lys Met Glu Ser Gln Ile Gln Val Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ser Thr Ala Val Val Trp Tyr Gln Gln Lys Pro
    50                  55                  60

Gly Gln Ser Pro Lys Leu Leu Ile Tyr Ser Ala Ser Tyr Arg Tyr Thr
65                  70                  75                  80

Gly Val Pro Asp Arg Phe Ser Gly Ser Gly Ser Gly Thr Asp Phe Thr
                85                  90                  95

Phe Thr Ile Ser Ser Val Gln Ala Glu Asp Leu Ala Val Tyr Tyr Cys
            100                 105                 110

Gln Gln His Tyr Ser Ser Pro Arg Thr Phe Gly Gly Gly Thr Lys Leu
        115                 120                 125

Glu Ile Lys
    130

<210> SEQ ID NO 43
<211> LENGTH: 137
<212> TYPE: PRT
<213> ORGANISM: Artificial Sequence
<220> FEATURE:
<223> OTHER INFORMATION: Synthetic

<400> SEQUENCE: 43

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ser Thr Gly Tyr Thr Phe
        35                  40                  45

Ser Thr Tyr Trp Ile Glu Trp Val Lys Gln Arg Pro Gly His Gly Leu
    50                  55                  60

Glu Trp Ile Gly Glu Ile Leu Pro Gly Ser Asp Ser Thr Asn Ser Asn
65                  70                  75                  80

Glu Lys Phe Glu Gly Lys Ala Thr Phe Thr Ala Asp Thr Ser Ser Asn
                85                  90                  95

Thr Ala Tyr Met Gln Leu Ser Ser Leu Thr Ser Glu Asp Ser Ala Val
            100                 105                 110

Tyr Tyr Cys Ala Arg Asp Tyr Tyr Gly Phe Tyr Phe Asp Tyr Trp Gly
        115                 120                 125

Gln Gly Thr Thr Leu Thr Val Ser Ser
        130                 135

<210> SEQ ID NO 44

-continued

<211> LENGTH: 131
<212> TYPE: PRT
<213> ORGANISM: Artificial Sequence
<220> FEATURE:
<223> OTHER INFORMATION: Synthetic

<400> SEQUENCE: 44

Met Gly Ile Lys Met Glu Ser Gln Ile Gln Val Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Gly Asp Arg Val Asn Ile Thr Cys Lys
        35                  40                  45

Ala Ser Gln Asp Val Ser Thr Ala Val Ala Trp Tyr Gln Gln Lys Pro
    50                  55                  60

Gly Gln Ser Pro Lys Leu Leu Ile Tyr Ser Thr Ser Tyr Arg Tyr Thr
65                  70                  75                  80

Gly Val Pro Asp Arg Phe Thr Gly Ser Gly Ser Gly Thr Asp Phe Thr
                85                  90                  95

Phe Thr Ile Ser Asn Val Gln Ala Glu Asp Leu Ala Val Tyr Tyr Cys
            100                 105                 110

Gln Gln His Tyr Thr Thr Pro Arg Thr Phe Gly Gly Gly Thr Lys Leu
        115                 120                 125

Glu Ile Lys
    130

<210> SEQ ID NO 45
<211> LENGTH: 138
<212> TYPE: PRT
<213> ORGANISM: Artificial Sequence
<220> FEATURE:
<223> OTHER INFORMATION: Synthetic

<400> SEQUENCE: 45

Met Gly Trp Ser Trp Ile Phe Leu Phe Leu Leu Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Tyr Thr Phe
        35                  40                  45

Thr Asp Tyr Tyr Met Asn Trp Val Arg Gln Ser His Gly Lys Ser Leu
    50                  55                  60

Glu Trp Ile Gly Asp Ile Asn Pro Asn Asn Gly Asp Thr Thr Tyr Asn
65                  70                  75                  80

Gln Lys Phe Lys Gly Lys Ala Thr Leu Thr Val Asp Thr Ser Ser Ser
                85                  90                  95

Thr Val Tyr Met Glu Leu Arg Ser Leu Thr Ser Glu Asp Ser Ala Val
            100                 105                 110

Tyr Tyr Cys Ala Gly Tyr Asp Glu Asp His Tyr Ala Met Asp Tyr Trp
        115                 120                 125

Gly Gln Gly Thr Ser Val Thr Val Ser Ser
    130                 135

<210> SEQ ID NO 46
<211> LENGTH: 131
<212> TYPE: PRT
<213> ORGANISM: Artificial Sequence
<220> FEATURE:
<223> OTHER INFORMATION: Synthetic

<400> SEQUENCE: 46

Met Gly Ile Lys Met Glu Ser Gln Met Gln Val Phe Val Phe Val Phe
1               5                   10                  15

Leu Trp Leu Ser Gly Val Asp Gly Asp Tyr Val Met Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ser Thr Gly Val Ala Trp Tyr Gln Gln Asn Pro
    50                  55                  60

Gly Gln Ser Pro Lys Leu Leu Ile Tyr Ser Ala Ser His Arg Tyr Thr
65                  70                  75                  80

Gly Val Pro Asp Arg Phe Thr Gly Ser Gly Ser Gly Thr Asp Phe Thr
                85                  90                  95

Phe Thr Ile Ser Ser Val Gln Ala Glu Asp Leu Ala Val Tyr Tyr Cys
            100                 105                 110

Gln Gln Tyr Tyr Thr Thr Pro Trp Thr Phe Gly Gly Gly Thr Lys Leu
        115                 120                 125

Glu Ile Lys
    130

<210> SEQ ID NO 47
<211> LENGTH: 139
<212> TYPE: PRT
<213> ORGANISM: Artificial Sequence
<220> FEATURE:
<223> OTHER INFORMATION: Synthetic

<400> SEQUENCE: 47

Met Gly Trp Ser Trp Ile Ile Leu Phe Leu Val Ser Gly Thr Ala Gly
1               5                   10                  15

Val Leu Ser Glu Val Gln Leu Gln Gln Ser Gly Pro Glu Leu Val Lys
            20                  25                  30

Pro Gly Ala Ser Val Lys Ile Ser Cys Lys Ala Ser Gly Asn Thr Leu
        35                  40                  45

Thr Asp Tyr Tyr Met Asn Trp Val Lys Gln Ser His Gly Lys Ser Leu
    50                  55                  60

Glu Trp Ile Gly Asp Ile Asn Pro Asn Asn Gly Asp Ile Ile Tyr Asn
65                  70                  75                  80

Gln Lys Phe Lys Gly Lys Ala Thr Leu Thr Val Ala Lys Ser Ser Ser
                85                  90                  95

Thr Ala Tyr Met Glu Leu Arg Ser Leu Thr Ser Glu Asp Ser Ala Val
            100                 105                 110

Tyr Tyr Cys Ala Ile Tyr Tyr Asp Pro Tyr Tyr His Ala Met Asp Tyr
        115                 120                 125

Trp Gly Gln Gly Thr Ser Val Thr Val Ser Ser
    130                 135

<210> SEQ ID NO 48
<211> LENGTH: 131
<212> TYPE: PRT
<213> ORGANISM: Artificial Sequence
<220> FEATURE:
<223> OTHER INFORMATION: Synthetic

<400> SEQUENCE: 48

Met Gly Ile Lys Met Glu Ser Gln Ile Gln Val Phe Val Phe Val Phe
1               5                   10                  15

Leu Trp Leu Ser Gly Val Asp Gly Asp Ile Val Met Thr Gln Ser His
            20                  25                  30

Lys Phe Met Ser Thr Ser Val Arg Asp Arg Val Ser Ile Thr Cys Lys
                35                  40                  45

Ala Ser Gln Asp Val Ser Thr Gly Val Ala Trp Tyr Gln Gln Lys Pro
 50                  55                  60

Gly Gln Ser Pro Lys Leu Leu Ile Tyr Ser Ala Ser Tyr Arg Tyr Thr
 65                  70                  75                  80

Gly Val Pro Asp Arg Phe Thr Gly Ser Gly Ser Gly Thr Asp Phe Thr
                85                  90                  95

Phe Thr Ile Ser Ser Val Gln Ala Glu Asp Leu Ala Val Tyr Tyr Cys
                100                 105                 110

Gln Gln Gln Tyr Ser Val Pro Leu Thr Phe Gly Ala Gly Thr Lys Leu
            115                 120                 125

Glu Leu Lys
    130

<210> SEQ ID NO 49
<211> LENGTH: 143
<212> TYPE: PRT
<213> ORGANISM: Artificial Sequence
<220> FEATURE:
<223> OTHER INFORMATION: Synthetic

<400> SEQUENCE: 49

Met Gly Trp Ser Cys Ile Met Leu Phe Leu Ala Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Gln Ala Ser Gly Tyr Thr Phe
        35                  40                  45

Thr Ser Tyr Trp Met His Trp Val Lys Gln Arg Pro Gly Arg Gly Leu
    50                  55                  60

Glu Trp Ile Gly Gly Ile Asp Pro Asp Ser Gly Ala Thr Lys Asp Asn
65                  70                  75                  80

Glu Lys Phe Lys Thr Lys Ala Thr Leu Thr Val Asp Lys Pro Ser Arg
                85                  90                  95

Thr Ala Tyr Ile Gln Leu Ser Ser Leu Thr Ser Glu Asp Ser Ala Val
            100                 105                 110

Phe Tyr Cys Ala Arg Gly Ser Thr Val Val Ala Pro Gly Asp Tyr Phe
        115                 120                 125

Ala Met Asp Tyr Trp Gly Gln Gly Thr Ser Val Thr Val Ser Ser
    130                 135                 140

<210> SEQ ID NO 50
<211> LENGTH: 131
<212> TYPE: PRT
<213> ORGANISM: Artificial Sequence
<220> FEATURE:
<223> OTHER INFORMATION: Synthetic

<400> SEQUENCE: 50

Met Glu Thr Asp Thr Leu Leu Leu Trp Val Leu Leu Leu Trp Val Pro
1               5                   10                  15

Gly Ser Thr Gly Asp Ile Val Leu Thr Pro Ser Pro Thr Ser Leu Ala
            20                  25                  30

Val Ser Leu Gly Gln Arg Ala Thr Met Ser Cys Arg Ala Ser Glu Ser

```
                    35                  40                  45
Val Asp Asn Tyr Gly Ile Ser Phe Met His Trp Tyr Gln Gln Lys Pro
 50                  55                  60

Gly Gln Pro Pro Lys Leu Leu Ile Tyr Arg Ala Ser Asn Leu Asp Ser
 65                  70                  75                  80

Gly Ile Pro Ala Arg Phe Ser Ala Ser Gly Ser Arg Thr Asp Phe Thr
                 85                  90                  95

Leu Thr Ile Asn Pro Val Glu Thr Asp Asp Val Ala Thr Tyr Tyr Cys
                100                 105                 110

Gln Gln Ser Asn Lys Asp Pro Trp Thr Phe Gly Gly Gly Thr Lys Leu
                115                 120                 125

Glu Ile Lys
    130

<210> SEQ ID NO 51
<211> LENGTH: 138
<212> TYPE: PRT
<213> ORGANISM: Artificial Sequence
<220> FEATURE:
<223> OTHER INFORMATION: Synthetic

<400> SEQUENCE: 51

Met Gly Arg Leu Thr Ser Ser Phe Leu Leu Ile Val Pro Ala Tyr
 1               5                  10                  15

Val Leu Ser Gln Val Thr Leu Lys Glu Ser Gly Pro Gly Ile Leu Gln
                 20                  25                  30

Pro Ser Gln Thr Leu Ser Leu Thr Cys Ser Phe Ser Glu Phe Ser Leu
                 35                  40                  45

Ser Val Phe Gly Met Gly Val Gly Trp Ile Arg Gln Pro Ser Gly Lys
 50                  55                  60

Gly Leu Glu Trp Leu Ala His Ile Trp Trp Asp Asp Glu Lys Tyr Tyr
 65                  70                  75                  80

Asn Pro Ala Leu Lys Ser Arg Leu Thr Ile Ser Lys Asp Thr Ser Lys
                 85                  90                  95

Asn Gln Val Phe Leu Lys Ile Ala Asn Val Asp Thr Ala Asp Thr Ala
                100                 105                 110

Thr Tyr Phe Cys Ala Arg Ile Asp Gly Tyr Tyr Asp Phe Asp Tyr Trp
                115                 120                 125

Gly Gln Gly Thr Thr Leu Thr Val Ser Ser
                130                 135

<210> SEQ ID NO 52
<211> LENGTH: 131
<212> TYPE: PRT
<213> ORGANISM: Artificial Sequence
<220> FEATURE:
<223> OTHER INFORMATION: Synthetic

<400> SEQUENCE: 52

Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
                 20                  25                  30

Ser Leu Gly Thr Gln Ala Ser Ile Phe Cys Arg Ser Ser His Ser Ile
                 35                  40                  45

Val Gln Asp Asn Gly Asn Thr Tyr Leu Gln Trp Tyr Leu Gln Lys Pro
 50                  55                  60
```

```
Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Asp Phe Thr
                 85                  90                  95

Leu Lys Ile Ser Arg Val Glu Ala Glu Asp Leu Gly Val Tyr Tyr Cys
            100                 105                 110

Phe Gln Gly Ser Tyr Val Pro Tyr Thr Phe Gly Gly Gly Thr Lys Leu
        115                 120                 125

Glu Ile Lys
        130

<210> SEQ ID NO 53
<211> LENGTH: 142
<212> TYPE: PRT
<213> ORGANISM: Artificial Sequence
<220> FEATURE:
<223> OTHER INFORMATION: Synthetic

<400> SEQUENCE: 53

Met Asp Arg Leu Thr Ser Ser Phe Leu Leu Leu Ile Val Pro Ala Tyr
 1               5                  10                  15

Val Leu Ser Gln Ile Ala Leu Lys Glu Ser Gly Pro Gly Ile Leu Gln
            20                  25                  30

Ser Ser Gln Thr Leu Ser Leu Thr Cys Ser Phe Ser Gly Phe Ser Leu
        35                  40                  45

Ser Thr Ser Gly Met His Val Gly Trp Phe Arg Gln Pro Ser Gly Lys
    50                  55                  60

Thr Leu Glu Trp Leu Ala His Ile Tyr Trp Asp Asp Lys Arg Tyr
 65                  70                  75                  80

Asn Pro Ser Leu Lys Ser Arg Leu Thr Ile Ser Lys Asp Thr Ser Arg
                 85                  90                  95

Asn Gln Val Phe Leu Asn Leu Thr Asn Val Asp Thr Ala Asp Thr Ala
            100                 105                 110

Thr Tyr Tyr Cys Ala Arg Arg Gly Gly Asp Tyr Asp Tyr Asp Glu Gly
        115                 120                 125

Phe Asp Tyr Trp Gly Gln Gly Thr Thr Leu Thr Val Ser Ser
    130                 135                 140

<210> SEQ ID NO 54
<211> LENGTH: 131
<212> TYPE: PRT
<213> ORGANISM: Artificial Sequence
<220> FEATURE:
<223> OTHER INFORMATION: Synthetic

<400> SEQUENCE: 54

Met Lys Leu Pro Val Arg Leu Leu Val Leu Met Phe Trp Ile Pro Ala
 1               5                  10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Phe Thr Tyr Leu His Trp Tyr Leu Gln Lys Pro
    50                  55                  60

Gly Gln Ser Pro Lys Leu Leu Ile Tyr Lys Val Ser Asn Arg Phe Ser
 65                  70                  75                  80

Gly Val Pro Asp Arg Phe Ser Gly Ser Gly Ser Gly Thr Glu Phe Thr
                 85                  90                  95
```

-continued

Leu Arg Ile Ser Arg Val Glu Ala Glu Asp Leu Gly Val Tyr Phe Cys
            100                 105                 110

Ser Gln Ser Thr His Val Pro Tyr Thr Phe Gly Gly Gly Thr Lys Leu
        115                 120                 125

Glu Ile Lys
        130

<210> SEQ ID NO 55
<211> LENGTH: 139
<212> TYPE: PRT
<213> ORGANISM: Artificial Sequence
<220> FEATURE:
<223> OTHER INFORMATION: Synthetic

<400> SEQUENCE: 55

Met Tyr Phe Arg Leu Ser Ser Val Phe Leu Val Leu Ile Leu Lys Gly
1               5                   10                  15

Val Gln Cys Glu Val Lys Leu Val Glu Ser Glu Gly Gly Leu Val Gln
            20                  25                  30

Pro Gly Ser Ser Met Lys Leu Ser Cys Thr Ala Ser Gly Phe Thr Phe
        35                  40                  45

Thr Asp Tyr Tyr Met Thr Trp Val Arg Gln Val Pro Glu Lys Gly Leu
50                  55                  60

Glu Trp Val Ala Asn Ile Asn Tyr Asp Gly Ser Arg Thr Asn Tyr Leu
65                  70                  75                  80

Asp Ser Leu Lys Ser Arg Phe Ile Ile Ser Arg Asp Asn Ala Lys Asn
                85                  90                  95

Ile Leu Tyr Leu Gln Met Ser Ser Leu Lys Ser Glu Asp Thr Ala Thr
            100                 105                 110

Tyr Tyr Cys Ala Arg Asp Gly Asn Tyr His Phe Tyr Gly Met Asp Tyr
        115                 120                 125

Trp Gly Gln Gly Thr Ser Val Thr Val Ser Ser
        130                 135

<210> SEQ ID NO 56
<211> LENGTH: 131
<212> TYPE: PRT
<213> ORGANISM: Artificial Sequence
<220> FEATURE:
<223> OTHER INFORMATION: Synthetic

<400> SEQUENCE: 56

Met Gly Ile Lys Met Glu Ser Gln Ile Gln Ala Phe Val Phe Val Phe
1               5                   10                  15

Leu Trp Leu Ser Gly Val Asp Gly Asp Phe Val Leu Thr Gln Ser His
            20                  25                  30

Lys Phe Met Ser Thr Ser Val Gly Asp Arg Val Ser Ile Thr Cys Lys
        35                  40                  45

Ala Ser Gln Asp Val Ser Thr Ala Val Ala Trp Tyr Gln Gln Lys Pro
    50                  55                  60

Gly Gln Ser Pro Gln Leu Leu Ile Tyr Trp Ala Ser Thr Arg His Thr
65                  70                  75                  80

Gly Val Pro Asp Arg Phe Thr Gly Ser Gly Ser Gly Thr Asp Tyr Thr
                85                  90                  95

Leu Thr Ile Ser Ser Val Gln Ala Glu Asp Leu Ala Leu Tyr Tyr Cys
            100                 105                 110

Gln Gln His Tyr Ser Thr Pro Trp Thr Phe Gly Gly Gly Thr Lys Leu

-continued

```
            115                 120                 125

Glu Ile Lys
    130

<210> SEQ ID NO 57
<211> LENGTH: 141
<212> TYPE: PRT
<213> ORGANISM: Artificial Sequence
<220> FEATURE:
<223> OTHER INFORMATION: Synthetic

<400> SEQUENCE: 57

Met Glu Trp Ser Arg Val Phe Ile Phe Leu Leu Ser Val Thr Ala Gly
1               5                   10                  15

Ile His Ser Gln Val Gln Leu Gln Gln Ser Gly Ala Glu Leu Val Arg
            20                  25                  30

Pro Gly Thr Ser Val Lys Val Ser Cys Lys Ala Ser Gly Tyr Ala Phe
        35                  40                  45

Thr Asn His Leu Ile Glu Trp Val Lys Gln Arg Pro Gly Gln Gly Leu
    50                  55                  60

Glu Trp Ile Gly Val Ile Asn Pro Gly Ser Gly Gly Thr Lys Tyr Asn
65                  70                  75                  80

Glu Lys Phe Lys Gly Lys Ala Thr Val Thr Ala Asp Lys Ser Ser Ser
                85                  90                  95

Thr Val Tyr Met Gln Leu Asn Ser Leu Thr Ser Glu Asp Ser Ala Val
            100                 105                 110

Tyr Phe Cys Ala Arg Ser Ser Asp Gly Tyr Tyr Glu Glu Asp Tyr Phe
        115                 120                 125

Asp Tyr Trp Gly Gln Gly Thr Thr Leu Thr Val Ser Ser
    130                 135                 140

<210> SEQ ID NO 58
<211> LENGTH: 128
<212> TYPE: PRT
<213> ORGANISM: Artificial Sequence
<220> FEATURE:
<223> OTHER INFORMATION: Synthetic

<400> SEQUENCE: 58

Met Asp Phe Gln Val Gln Ile Phe Ser Phe Leu Leu Ile Ser Ala Ser
1               5                   10                  15

Val Ile Ile Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Val Asn Tyr Met Gln Trp Tyr Gln Gln Lys Ser Gly Thr Ser
    50                  55                  60

Pro Lys Arg Trp Ile Tyr Asp Thr Ser Glu Leu Ala Ser Gly Val Pro
65                  70                  75                  80

Asp Arg Phe Ser Gly Ser Gly Ser Gly Thr Ser Tyr Ser Leu Thr Ile
                85                  90                  95

Ser Ser Met Glu Ala Glu Asp Val Ala Thr Tyr Tyr Cys Gln Gln Trp
            100                 105                 110

Ser Ser Asp Pro Ile Thr Phe Gly Ala Gly Thr Lys Leu Glu Leu Lys
        115                 120                 125

<210> SEQ ID NO 59
<211> LENGTH: 140
```

```
<212> TYPE: PRT
<213> ORGANISM: Artificial Sequence
<220> FEATURE:
<223> OTHER INFORMATION: Synthetic

<400> SEQUENCE: 59

Met Tyr Phe Arg Leu Ser Ser Val Phe Val Leu Ile Leu Lys Gly
1               5                   10                  15

Val Gln Cys Glu Val Lys Leu Val Glu Ser Glu Gly Gly Leu Val Gln
            20                  25                  30

Pro Gly Ser Ser Met Lys Leu Ser Cys Thr Ala Ser Gly Phe Thr Phe
        35                  40                  45

Ser Asp Tyr Tyr Met Ala Trp Val Arg Gln Val Pro Glu Lys Gly Leu
    50                  55                  60

Glu Trp Val Ala Asn Ile Asn Tyr Asp Gly Ser Asp Thr Tyr Tyr Leu
65                  70                  75                  80

Asp Ser Leu Lys Ser Arg Phe Ile Ile Ser Arg Asp Asn Ala Lys Asn
                85                  90                  95

Ile Leu Tyr Leu Gln Met Ser Ser Leu Lys Ser Glu Asp Thr Ala Thr
            100                 105                 110

Tyr Tyr Cys Val Arg Asp Val Ala Tyr Asp Ser Tyr Ala Met Asp
        115                 120                 125

Tyr Trp Gly Gln Gly Thr Ser Val Thr Val Ser Ser
    130                 135                 140

<210> SEQ ID NO 60
<211> LENGTH: 126
<212> TYPE: PRT
<213> ORGANISM: Artificial Sequence
<220> FEATURE:
<223> OTHER INFORMATION: Synthetic

<400> SEQUENCE: 60

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Leu Gly Gly Lys Val Thr Ile Thr Cys Lys Ala Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Ser Leu Tyr Thr Phe Gly Gly Gly Thr Lys Leu Glu Ile Lys
        115                 120                 125

<210> SEQ ID NO 61
<211> LENGTH: 138
<212> TYPE: PRT
<213> ORGANISM: Artificial Sequence
<220> FEATURE:
<223> OTHER INFORMATION: Synthetic

<400> SEQUENCE: 61

Met Gly Arg Leu Thr Ser Ser Phe Leu Leu Leu Ile Val Pro Ala Tyr
```

```
                1               5                  10                  15
            Val Leu Ser Gln Val Thr Leu Lys Glu Ser Gly Pro Gly Ile Leu Gln
                         20                  25                  30

Pro Ser Gln Thr Leu Ser Leu Thr Cys Ser Phe Ser Glu Phe Ser Leu
                         35                  40                  45

Ser Val Phe Gly Met Gly Val Gly Trp Ile Arg Gln Pro Ser Gly Lys
                 50                      55                  60

Gly Leu Glu Trp Leu Ala His Ile Trp Trp Asp Asp Glu Lys Tyr Tyr
             65                      70                  75                  80

Asn Pro Ala Leu Lys Ser Arg Leu Thr Ile Ser Lys Asp Thr Ser Lys
                             85                  90                  95

Asn Gln Val Phe Leu Lys Ile Ala Asn Val Asp Thr Ala Asp Thr Ala
                         100                 105                 110

Thr Tyr Tyr Cys Ala Arg Ile Asp Gly Tyr Tyr Asp Phe Asp Tyr Trp
                         115                 120                 125

Gly Gln Gly Thr Thr Leu Thr Val Ser Ser
                         130                 135
```

<210> SEQ ID NO 62
<211> LENGTH: 131
<212> TYPE: PRT
<213> ORGANISM: Artificial Sequence
<220> FEATURE:
<223> OTHER INFORMATION: Synthetic

<400> SEQUENCE: 62

```
            Met Lys Leu Pro Val Arg Leu Leu Val Leu Met Phe Trp Ile Pro Ala
             1               5                  10                  15

Ser Ser Ser Asp Val Leu Met Thr Gln Thr Pro Leu Ser Leu Pro Val
                         20                  25                  30

Ser Leu Gly Thr Gln Ala Ser Ile Ser Cys Arg Ser Ser His Ser Ile
                         35                  40                  45

Val Gln Asp Asn Gly Asn Thr Tyr Leu Gln Trp Tyr Leu Gln Lys Pro
                 50                      55                  60

Gly Gln Ser Pro Gln Leu Leu Ile Tyr Lys Val Ser Asn Arg Phe Ser
             65                      70                  75                  80

Gly Val Pro Asp Arg Phe Ser Gly Ser Gly Ser Gly Thr Asp Phe Thr
                             85                  90                  95

Leu Lys Ile Ser Arg Val Glu Ala Glu Asp Leu Gly Val Tyr Tyr Cys
                         100                 105                 110

Phe Gln Gly Ser Tyr Val Pro Tyr Thr Phe Gly Gly Gly Thr Lys Leu
                         115                 120                 125

Glu Ile Lys
                 130
```

<210> SEQ ID NO 63
<211> LENGTH: 138
<212> TYPE: PRT
<213> ORGANISM: Artificial Sequence
<220> FEATURE:
<223> OTHER INFORMATION: Synthetic

<400> SEQUENCE: 63

```
            Met Gly Arg Leu Thr Ser Ser Phe Leu Leu Leu Ile Val Pro Ala Tyr
             1               5                  10                  15

Val Leu Ser Gln Val Thr Leu Lys Glu Ser Gly Pro Gly Ile Leu Gln
                         20                  25                  30
```

```
Pro Ser Gln Thr Leu Ser Leu Thr Cys Ser Phe Ser Gly Phe Ser Leu
        35                  40                  45

Ser Thr Ser Asn Met Gly Val Gly Trp Ile Arg Gln Pro Ser Gly Lys
 50                  55                  60

Gly Leu Glu Trp Leu Ala His Ile Trp Trp Asp Asp Val Lys Arg Tyr
 65                  70                  75                  80

Asn Pro Ala Leu Lys Ser Arg Leu Thr Ile Ser Lys Asp Thr Ser Ser
                 85                  90                  95

Ser Gln Val Phe Leu Lys Ile Ala Ser Val Asp Thr Ala Asp Thr Ala
            100                 105                 110

Thr Tyr Tyr Cys Ala Arg Ser Thr Thr Leu Val Ala Phe Asp Tyr Trp
        115                 120                 125

Gly Gln Gly Thr Thr Leu Thr Val Ser Ser
    130                 135

<210> SEQ ID NO 64
<211> LENGTH: 132
<212> TYPE: PRT
<213> ORGANISM: Artificial Sequence
<220> FEATURE:
<223> OTHER INFORMATION: Synthetic

<400> SEQUENCE: 64

Met Glu Ser Gln Thr Gln Val Leu Met Ser Leu Leu Phe Trp Val Ser
 1               5                  10                  15

Gly Thr Cys Gly Asp Ile Val Met Thr Gln Ser Pro Ser Ser Leu Thr
            20                  25                  30

Val Thr Ala Gly Glu Lys Val Thr Met Ser Cys Lys Ser Ser Gln Ser
        35                  40                  45

Leu Leu Asn Ser Gly Asn Gln Lys Asn Tyr Leu Thr Trp Tyr Gln Gln
 50                  55                  60

Lys Pro Gly Gln Pro Pro Lys Leu Leu Ile Tyr Trp Ala Ser Thr Arg
 65                  70                  75                  80

Glu Ser Gly Val Pro Asp Arg Phe Thr Gly Ser Gly Ser Gly Thr Asp
                 85                  90                  95

Phe Thr Leu Thr Ile Ser Ser Val Gln Ala Glu Asp Leu Ala Val Tyr
            100                 105                 110

Tyr Cys Gln Asn Asp Tyr Ser Tyr Pro Thr Phe Gly Gly Gly Thr Lys
        115                 120                 125

Leu Glu Ile Lys
    130

<210> SEQ ID NO 65
<211> LENGTH: 138
<212> TYPE: PRT
<213> ORGANISM: Artificial Sequence
<220> FEATURE:
<223> OTHER INFORMATION: Synthetic

<400> SEQUENCE: 65

Met Gly Arg Leu Thr Ser Ser Phe Leu Leu Leu Ile Val Pro Ala Tyr
 1               5                  10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Ile Gly Trp Ile Arg Gln Pro Ser Gly Lys
 50                  55                  60
```

Gly Leu Glu Trp Leu Ala His Ile Trp Trp Asp Asp Ile Lys Arg Tyr
65                  70                  75                  80

Asn Pro Ala Leu Lys Ser Arg Leu Thr Val Ser Lys Asp Thr Ser Thr
                85                  90                  95

Ser Gln Val Phe Leu Asn Ile Ala Ser Val Asp Thr Ala Asp Ile Ala
            100                 105                 110

Thr Tyr Phe Cys Ala Arg Ser Thr Val Val Ala Phe Asp Tyr Trp
        115                 120                 125

Gly Gln Gly Thr Thr Leu Thr Val Ser Ser
    130                 135

<210> SEQ ID NO 66
<211> LENGTH: 132
<212> TYPE: PRT
<213> ORGANISM: Artificial Sequence
<220> FEATURE:
<223> OTHER INFORMATION: Synthetic

<400> SEQUENCE: 66

Met Glu Ser Gln Thr Gln Val Leu Met Ser Leu Leu Phe Trp Val Ser
1               5                   10                  15

Gly Thr Cys Gly Asp Ile Leu Met Thr Gln Ser Pro Ser Ser Leu Thr
                20                  25                  30

Val Thr Ala Gly Glu Lys Val Thr Met Ser Cys Lys Ser Ser Gln Ser
            35                  40                  45

Leu Leu Asn Ser Gly Asn Gln Lys Asn Tyr Leu Thr Trp Tyr Gln Gln
50                  55                  60

Lys Pro Gly Gln Pro Pro Lys Leu Leu Ile Tyr Trp Ala Ser Thr Arg
65                  70                  75                  80

Glu Ser Gly Val Pro Asp Arg Phe Thr Gly Thr Gly Ser Gly Thr Asp
                85                  90                  95

Phe Thr Leu Thr Ile Ser Ser Val Gln Ala Glu Asp Leu Ala Ile Tyr
            100                 105                 110

Tyr Cys Gln Asn Asp Tyr Asp Tyr Pro Thr Phe Gly Gly Gly Thr Lys
        115                 120                 125

Leu Glu Ile Lys
    130

<210> SEQ ID NO 67
<211> LENGTH: 141
<212> TYPE: PRT
<213> ORGANISM: Artificial Sequence
<220> FEATURE:
<223> OTHER INFORMATION: Synthetic

<400> SEQUENCE: 67

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
                20                  25                  30

Pro Ser Gln Thr Leu Ser Leu Thr Cys Thr Phe Ser Gly Phe Ser Leu
            35                  40                  45

Ser Thr Tyr Gly Met Gly Val Gly Trp Ile Arg Gln Pro Ser Gly Lys
50                  55                  60

Gly Leu Glu Trp Leu Ala Asn Ile Trp Trp Asp Asp Lys Tyr Tyr
65                  70                  75                  80

Asn Pro Ser Leu Gln Asn Arg Leu Thr Ile Ser Lys Asp Thr Ser Asn

```
                    85                  90                  95

Asn Gln Ala Phe Leu Lys Ile Asn Asn Val Asp Thr Ala Asp Thr Ala
            100                 105                 110

Thr Tyr Tyr Cys Ala Arg Ser Glu Leu Ile Met Pro Tyr Val Pro Phe
            115                 120                 125

Asp Tyr Trp Gly Gln Gly Val Arg Val Thr Val Ser Ser
            130                 135                 140

<210> SEQ ID NO 68
<211> LENGTH: 129
<212> TYPE: PRT
<213> ORGANISM: Artificial Sequence
<220> FEATURE:
<223> OTHER INFORMATION: Synthetic

<400> SEQUENCE: 68

Met Asp Met Arg Ala His Thr Gln Phe Leu Gly Phe Leu Leu Leu Trp
1               5                   10                  15

Phe Pro Gly Ala Arg Cys Asp Ile Gln Met Thr Gln Ser Pro Ser Ser
            20                  25                  30

Met Ser Ala Ser Leu Gly Asp Arg Val Thr Ile Thr Cys Gln Ala Ser
        35                  40                  45

Gln Asp Ile Asp Asn His Leu Ile Trp Phe Gln Gln Lys Pro Gly Lys
    50                  55                  60

Ser Pro Arg Pro Met Ile Tyr Tyr Ala Thr Asn Leu Ala Asn Gly Val
65                  70                  75                  80

Pro Ser Arg Phe Ser Gly Ser Arg Ser Gly Ser Asp Tyr Ser Leu Thr
                85                  90                  95

Ile Ser Ser Leu Glu Ser Glu Asp Met Ala Asp Tyr His Cys Leu Gln
            100                 105                 110

Phe Lys Gln Tyr Pro Phe Thr Phe Gly Ser Gly Thr Lys Leu Glu Ile
            115                 120                 125

Lys

<210> SEQ ID NO 69
<211> LENGTH: 120
<212> TYPE: PRT
<213> ORGANISM: Artificial Sequence
<220> FEATURE:
<223> OTHER INFORMATION: Synthetic

<400> SEQUENCE: 69

Glu Val Gln Leu Gln Gln Ser Gly Pro Gly Leu Val Lys Pro Ser Gly
1               5                   10                  15

Thr Leu Ser Leu Thr Cys Ala Val Ser Gly Gly Ser Ile Thr Ser Ser
            20                  25                  30

Tyr Trp Trp Thr Trp Val Arg Gln Pro Pro Gly Lys Gly Leu Glu Trp
        35                  40                  45

Ile Gly Glu Ile Tyr His Ser Gly Arg Pro Asn Tyr Asn Pro Ser Leu
    50                  55                  60

Lys Ser Arg Ala Thr Ile Ser Val Asp Lys Ser Arg Asn Gln Phe Ser
65                  70                  75                  80

Leu Asn Leu Thr Ser Val Thr Ala Ala Asp Thr Ala Val Tyr Tyr Cys
                85                  90                  95

Ala Lys Thr Ala Ala Val Ser Tyr Trp Tyr Phe Asp Leu Trp Gly Arg
            100                 105                 110

Gly Thr Leu Val Thr Val Ser Ser
```

<210> SEQ ID NO 70
<211> LENGTH: 107
<212> TYPE: PRT
<213> ORGANISM: Artificial Sequence
<220> FEATURE:
<223> OTHER INFORMATION: Synthetic

<400> SEQUENCE: 70

Asp Ile Lys Met Asn Gln Ser Pro Ser Ser Met Ser Ala Ser Leu Gly
1               5                   10                  15

Asp Arg Val Thr Ile Thr Cys Gln Ala Ser Gln Asp Ile Gly Asn Asp
            20                  25                  30

Leu Ile Trp Phe Gln Gln Lys Pro Gly Lys Ser Pro Arg Pro Leu Ile
        35                  40                  45

Tyr Tyr Ala Ser Asn Leu Ala Asn Gly Val Pro Ser Arg Phe Ser Gly
    50                  55                  60

Arg Arg Ser Glu Ser Asn Tyr Ser Leu Thr Ile Ser Ser Leu Glu Ser
65                  70                  75                  80

Glu Asp Met Ala Asp Tyr His Cys Leu Gln Phe Lys Gln Tyr Pro Phe
                85                  90                  95

Thr Phe Gly Ala Gly Thr Lys Leu Glu Leu Lys
            100                 105

<210> SEQ ID NO 71
<211> LENGTH: 120
<212> TYPE: PRT
<213> ORGANISM: Artificial Sequence
<220> FEATURE:
<223> OTHER INFORMATION: Synthetic

<400> SEQUENCE: 71

Glu Val Gln Leu Gln Gln Ser Gly Pro Gly Leu Val Arg Pro Ser Gly
1               5                   10                  15

Thr Leu Ser Leu Thr Cys Ala Val Ser Gly Ser Ile Ser Ser Arg
            20                  25                  30

Asn Trp Trp Gly Trp Val Arg Gln Pro Pro Gly Lys Gly Leu Glu Trp
        35                  40                  45

Ile Gly Glu Ile Tyr His Ser Gly Gly Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Glu Phe Gly Asp Ser Val Trp Tyr Phe Asp Leu Trp Gly Arg
            100                 105                 110

Gly Thr Leu Val Thr Val Ser Ser
        115                 120

<210> SEQ ID NO 72
<211> LENGTH: 107
<212> TYPE: PRT
<213> ORGANISM: Artificial Sequence
<220> FEATURE:
<223> OTHER INFORMATION: Synthetic

<400> SEQUENCE: 72

Asp Ile Val Ile Thr Gln Ser Pro Ser Ser Met Ser Ala Ser Leu Gly
1               5                   10                  15

Asp Arg Val Thr Ile Thr Cys Gln Ala Ser Gln Asp Ile Gly Asn Asp
            20                  25                  30

Leu Val Trp Phe Gln Gln Lys Pro Gly Lys Ser Pro Arg Pro Leu Ile
        35                  40                  45

Tyr Tyr Ala Thr Asn Leu Ala Asp Gly Val Pro Ser Arg Phe Ser Gly
    50                  55                  60

Arg Arg Ser Glu Ser Lys Tyr Ser Leu Thr Ile Ser Asn Leu Glu Ser
65                  70                  75                  80

Glu Asp Met Ala Asp Tyr His Cys Leu Gln Phe Lys Gln Tyr Pro Tyr
                85                  90                  95

Thr Phe Gly Ala Gly Thr Lys Leu Glu Leu Lys
            100                 105

<210> SEQ ID NO 73
<211> LENGTH: 120
<212> TYPE: PRT
<213> ORGANISM: Artificial Sequence
<220> FEATURE:
<223> OTHER INFORMATION: Synthetic

<400> SEQUENCE: 73

Glu Val Gln Leu Gln Gln Ser Gly Pro Gly Leu Val Lys Pro Ser Gly
1               5                   10                  15

Thr Leu Ser Leu Thr Cys Ala Val Ser Gly Gly Ser Ile Thr Ser Ser
            20                  25                  30

Tyr Trp Trp Ile Trp Val Arg Gln Pro Pro Gly Lys Gly Leu Glu Trp
        35                  40                  45

Ile Gly Glu Ile Tyr His Ser Gly Arg Pro Asn Tyr Asn Pro Ser Leu
    50                  55                  60

Glu Ser Arg Val Thr Ile Ser Val Asp Lys Ser Lys Asn Gln Phe Ser
65                  70                  75                  80

Leu Thr Leu Ser Ser Val Thr Ala Ala Asp Thr Ala Val Tyr Tyr Cys
                85                  90                  95

Ala Arg Glu Ala Gly Asp Ser Val Trp Tyr Phe Asp Leu Trp Gly Arg
            100                 105                 110

Gly Thr Leu Val Thr Val Ser Ser
        115                 120

<210> SEQ ID NO 74
<211> LENGTH: 107
<212> TYPE: PRT
<213> ORGANISM: Artificial Sequence
<220> FEATURE:
<223> OTHER INFORMATION: Synthetic

<400> SEQUENCE: 74

Asp Ile Leu Leu Thr Gln Ser Pro Ser Ser Ile Ser Ala Ser Leu Gly
1               5                   10                  15

Asp Arg Val Thr Ile Thr Cys Gln Ala Ser Gln Asp Ile Gly Asn Glu
            20                  25                  30

Leu Ile Trp Phe Gln Gln Lys Pro Gly Lys Ser Pro Arg Pro Met Ile
        35                  40                  45

Tyr Tyr Ala Thr Ser Leu Ala Asp Gly Val Pro Ser Arg Phe Ser Gly
    50                  55                  60

Ser Thr Ser Gly Ser Asp Tyr Ser Leu Thr Ile Gly Ser Leu Glu Ser
65                  70                  75                  80

Glu Asp Met Ala Asp Tyr His Arg Leu Gln Phe Lys Gln Tyr Pro Phe

Thr Phe Gly Ser Gly Thr Arg Leu Glu Ile Lys
            100                 105

<210> SEQ ID NO 75
<211> LENGTH: 122
<212> TYPE: PRT
<213> ORGANISM: Artificial Sequence
<220> FEATURE:
<223> OTHER INFORMATION: Synthetic

<400> SEQUENCE: 75

Gln Val Thr Leu Lys Glu Ser Gly Pro Glu Ile Leu Gln Pro Ser Gln
1               5                   10                  15

Thr Leu Ser Leu Thr Cys Thr Phe Ser Gly Phe Ser Leu Ser Pro Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Lys Tyr Tyr Asn Pro Ser
50                  55                  60

Leu Ile Asn Arg Leu Thr Ile Ser Lys Asp Thr Ser Asn Asn Gln Ala
65                  70                  75                  80

Phe Leu Lys Ile Thr Asn Val Asp Thr Thr Asp Ser Ala Thr Tyr Tyr
                85                  90                  95

Cys Val Arg Ser Glu Leu Val Met Pro Tyr Val Pro Phe Asp Tyr Trp
            100                 105                 110

Gly Gln Gly Val Met Val Thr Val Ser Ser
        115                 120

<210> SEQ ID NO 76
<211> LENGTH: 107
<212> TYPE: PRT
<213> ORGANISM: Artificial Sequence
<220> FEATURE:
<223> OTHER INFORMATION: Synthetic

<400> SEQUENCE: 76

Asp Ile Gln Met Thr Gln Ser Pro Ser Ser Met Ser Ala Ser Leu Gly
1               5                   10                  15

Asp Arg Val Thr Ile Thr Cys Gln Ala Ser Gln Asp Ile Glu Asn Asp
            20                  25                  30

Leu Val Trp Phe Gln Gln Lys Pro Gly Arg Ser Pro Arg Pro Leu Ile
        35                  40                  45

Tyr Tyr Ala Thr Asn Leu Ala Asn Gly Val Pro Ser Arg Phe Ser Gly
    50                  55                  60

Arg Arg Ser Glu Ser Asp Tyr Ser Leu Thr Ile Ser Ser Leu Glu Ser
65                  70                  75                  80

Glu Asp Met Ala Asp Tyr His Cys Leu Gln Phe Lys Gln Tyr Pro Tyr
                85                  90                  95

Thr Phe Gly Ala Gly Thr Lys Leu Glu Leu Lys
            100                 105

<210> SEQ ID NO 77
<211> LENGTH: 122
<212> TYPE: PRT
<213> ORGANISM: Artificial Sequence
<220> FEATURE:
<223> OTHER INFORMATION: Synthetic

<400> SEQUENCE: 77

-continued

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Lys Tyr Tyr Asn Pro Ser
50                  55                  60

Leu Ile Asn Arg Leu Thr Ile Ser Lys Asn Thr Ser Asn Asn Gln Ala
65                  70                  75                  80

Phe Leu Lys Ile Thr Asn Val Asp Ala Pro Asp Thr Ala Thr Tyr Tyr
                85                  90                  95

Cys Ala Arg Ser Glu Leu Val Met Pro Tyr Val Pro Phe Asp Phe Trp
            100                 105                 110

Gly Gln Gly Ile Met Val Thr Val Ser Ser
        115                 120

<210> SEQ ID NO 78
<211> LENGTH: 107
<212> TYPE: PRT
<213> ORGANISM: Artificial Sequence
<220> FEATURE:
<223> OTHER INFORMATION: Synthetic

<400> SEQUENCE: 78

Asp Ile Gln Met Thr Gln Ser Pro Ser Ser Leu Ser Ala Ser Leu Gly
1               5                   10                  15

Asp Arg Ile Thr Met Thr Cys Gln Ala Ser Gln Asp Ile Gly Ile Glu
            20                  25                  30

Leu Ile Trp Phe Gln Gln Lys Pro Gly Lys Ser Pro Trp Pro Val Ile
        35                  40                  45

Tyr Tyr Thr Ala Asn Leu Ala Ser Gly Val Pro Ser Arg Phe Ser Gly
    50                  55                  60

Ser Arg Ser Gly Ser His Tyr Ser Leu Thr Ile Ser Ser Leu Glu Ser
65                  70                  75                  80

Glu Asp Met Ala Asp Tyr His Cys Leu Gln Tyr Lys Gln Tyr Pro Phe
                85                  90                  95

Thr Phe Gly Ser Gly Thr Lys Leu Glu Ile Lys
            100                 105

<210> SEQ ID NO 79
<211> LENGTH: 122
<212> TYPE: PRT
<213> ORGANISM: Artificial Sequence
<220> FEATURE:
<223> OTHER INFORMATION: Synthetic

<400> SEQUENCE: 79

Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Lys Tyr Tyr Asn Pro Ser
50                  55                  60

Leu Gln Asn Arg Leu Thr Ile Ser Lys Asp Thr Ser Asn Asn Gln Ala

```
                65                  70                  75                  80
Phe Leu Lys Ile Thr Asn Val Asp Thr Ala Asp Thr Ala Thr Tyr Tyr
                    85                  90                  95

Cys Ala Arg Ser Glu Leu Ile Met Pro Tyr Val Pro Phe Asp Tyr Trp
                100                 105                 110

Gly Gln Gly Val Arg Val Thr Val Ser Ser
                115                 120

<210> SEQ ID NO 80
<211> LENGTH: 107
<212> TYPE: PRT
<213> ORGANISM: Artificial Sequence
<220> FEATURE:
<223> OTHER INFORMATION: Synthetic

<400> SEQUENCE: 80

Asp Ile Gln Met Thr Gln Ser Pro Ser Ser Met Ser Ala Ser Leu Gly
1               5                   10                  15

Asp Arg Val Thr Ile Thr Cys Gln Ala Ser Gln Asp Ile Asp Asn His
                20                  25                  30

Leu Ile Trp Phe Gln Gln Lys Pro Gly Lys Ser Pro Arg Pro Met Ile
            35                  40                  45

Tyr Tyr Ala Thr Asn Leu Ala Asn Gly Val Pro Ser Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Met Ala Asp Tyr His Cys Leu Gln Phe Lys Gln Tyr Pro Phe
                85                  90                  95

Thr Phe Gly Ser Gly Thr Lys Leu Glu Ile Lys
                100                 105

<210> SEQ ID NO 81
<211> LENGTH: 141
<212> TYPE: PRT
<213> ORGANISM: Artificial Sequence
<220> FEATURE:
<223> OTHER INFORMATION: Synthetic

<400> SEQUENCE: 81

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Glu Ile Leu Gln
                20                  25                  30

Pro Ser Gln Thr Leu Thr Leu Thr Cys Thr Phe Ser Gly Phe Ser Leu
            35                  40                  45

Ser Pro Tyr Gly Met Gly Val Gly Trp Ile Arg Gln Pro Ser Gly Lys
    50                  55                  60

Gly Leu Glu Trp Leu Ala Asn Ile Trp Trp Asp Asp Lys Tyr Tyr
65                  70                  75                  80

Asn Pro Ser Leu Ile Asn Arg Leu Thr Ile Ser Lys Asp Thr Ser Asn
                85                  90                  95

Asn Gln Ala Phe Leu Lys Ile Thr Asn Val Asp Thr Thr Asp Ser Ala
                100                 105                 110

Thr Tyr Tyr Cys Val Arg Ser Glu Leu Val Met Pro Tyr Val Pro Phe
            115                 120                 125

Asp Tyr Trp Gly Gln Gly Val Met Val Thr Val Ser Ser
    130                 135                 140
```

<210> SEQ ID NO 82
<211> LENGTH: 129
<212> TYPE: PRT
<213> ORGANISM: Artificial Sequence
<220> FEATURE:
<223> OTHER INFORMATION: Synthetic

<400> SEQUENCE: 82

```
Met Asp Met Arg Ala His Thr Gln Phe Leu Gly Phe Leu Leu Leu Trp
1               5                   10                  15

Phe Pro Gly Ala Arg Cys Asp Ile Gln Met Thr Gln Ser Pro Ser Ser
            20                  25                  30

Met Ser Ala Ser Leu Gly Asp Arg Val Thr Ile Thr Cys Gln Ala Ser
        35                  40                  45

Gln Asp Ile Glu Asn Asp Leu Ile Trp Phe Gln Gln Lys Pro Gly Lys
    50                  55                  60

Ser Pro Arg Pro Leu Ile Tyr Tyr Ala Thr Asn Leu Ala Asn Gly Val
65                  70                  75                  80

Pro Ser Arg Phe Ser Gly Arg Arg Ser Glu Ser Asn Tyr Ala Leu Thr
                85                  90                  95

Ile Ser Ser Leu Glu Ser Glu Asp Met Ala Asp Tyr His Cys Leu Gln
            100                 105                 110

Phe Lys Gln Tyr Pro Tyr Thr Phe Gly Ala Gly Thr Lys Leu Glu Leu
        115                 120                 125

Lys
```

<210> SEQ ID NO 83
<211> LENGTH: 122
<212> TYPE: PRT
<213> ORGANISM: Artificial Sequence
<220> FEATURE:
<223> OTHER INFORMATION: Synthetic

<400> SEQUENCE: 83

```
Gln Val Thr Leu Lys Glu Ser Gly Pro Gly Ile Leu Gln Pro Ser Gln
1               5                   10                  15

Thr Leu Ser Leu Thr Cys Thr Phe Ser Gly Phe Ser Leu Thr Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Lys Tyr Ser Asn Pro Ser
    50                  55                  60

Leu Gln Ser Arg Leu Thr Ile Ser Lys Asp Thr Ser Asn Asn Gln Ala
65                  70                  75                  80

Phe Leu Thr Ile Thr Asn Val Asp Thr Ala Asp Thr Ala Thr Tyr Tyr
                85                  90                  95

Cys Ala Arg Ser Glu Leu Val Met Pro Tyr Val Pro Phe Asp Tyr Trp
            100                 105                 110

Gly Gln Gly Val Arg Val Thr Val Ser Ser
        115                 120
```

<210> SEQ ID NO 84
<211> LENGTH: 107
<212> TYPE: PRT
<213> ORGANISM: Artificial Sequence
<220> FEATURE:
<223> OTHER INFORMATION: Synthetic

<400> SEQUENCE: 84

```
Asp Ile Gln Met Thr Gln Ser Pro Ser Ser Met Ser Ala Ser Leu Gly
1               5                   10                  15

Asp Arg Val Thr Ile Thr Cys Gln Ala Ser Gln Asp Ile Asp Asn His
            20                  25                  30

Leu Ile Trp Phe Gln Lys Pro Gly Arg Ser Pro Arg Pro Met Ile
        35                  40                  45

Tyr Tyr Ala Thr Asn Leu Ala Asn Gly Val Pro Ser Arg Phe Ser Gly
50                  55                  60

Ser Arg Ser Gly Ser Asp Tyr Ser Leu Thr Ile Ser Ser Leu Glu Ser
65              70                  75                  80

Glu Asp Met Ala Asp Tyr His Cys Leu Gln Phe Lys Gln Tyr Pro Phe
            85                  90                  95

Thr Phe Gly Ser Gly Thr Lys Leu Glu Ile Lys
            100                 105
```

<210> SEQ ID NO 85
<211> LENGTH: 141
<212> TYPE: PRT
<213> ORGANISM: Artificial Sequence
<220> FEATURE:
<223> OTHER INFORMATION: Synthetic

<400> SEQUENCE: 85

```
Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Glu Ile Leu Gln
            20                  25                  30

Pro Ser Gln Thr Leu Ser Leu Thr Cys Thr Phe Ser Gly Phe Ser Leu
        35                  40                  45

Ser Pro Tyr Gly Met Gly Val Gly Trp Ile Arg Gln Pro Ser Gly Lys
50                  55                  60

Gly Leu Glu Trp Leu Ala Asn Ile Trp Trp Asp Asp Asp Lys Tyr Tyr
65              70                  75                  80

Asn Pro Ser Leu Ile Asn Arg Leu Thr Ile Ser Lys Asp Thr Ser Asn
            85                  90                  95

Asn Gln Ala Phe Leu Lys Ile Thr Asn Val Asp Thr Asp Ser Ala
            100                 105                 110

Thr Tyr Tyr Cys Val Arg Ser Glu Leu Val Met Pro Tyr Val Pro Phe
        115                 120                 125

Asp Tyr Trp Gly Gln Gly Val Met Val Thr Val Ser Ser
        130                 135                 140
```

<210> SEQ ID NO 86
<211> LENGTH: 129
<212> TYPE: PRT
<213> ORGANISM: Artificial Sequence
<220> FEATURE:
<223> OTHER INFORMATION: Synthetic

<400> SEQUENCE: 86

```
Met Asp Met Arg Ala His Thr Gln Phe Leu Gly Phe Leu Leu Leu Trp
1               5                   10                  15

Phe Pro Gly Ala Arg Cys Asp Ile Gln Met Thr Gln Ser Pro Ser Ser
            20                  25                  30

Met Ser Ala Ser Leu Gly Asp Arg Val Thr Ile Thr Cys Gln Ala Ser
        35                  40                  45

Gln Asp Ile Glu Asn Asp Leu Ile Trp Phe Gln Gln Lys Pro Gly Lys
```

```
                50                  55                  60
Ser Pro Arg Pro Leu Ile Tyr Tyr Ala Thr Asn Leu Ala Asn Gly Val
 65                  70                  75                  80

Pro Ser Arg Phe Ser Gly Arg Ser Glu Ser Asn Tyr Ser Leu Thr
                 85                  90                  95

Ile Ser Ser Leu Glu Ser Glu Asp Met Ala Asp Tyr His Cys Leu Gln
                100                 105                 110

Phe Lys Gln Tyr Pro Tyr Thr Phe Gly Ala Gly Thr Lys Leu Glu Leu
            115                 120                 125

Lys

<210> SEQ ID NO 87
<211> LENGTH: 122
<212> TYPE: PRT
<213> ORGANISM: Artificial Sequence
<220> FEATURE:
<223> OTHER INFORMATION: Synthetic

<400> SEQUENCE: 87

Gln Val Thr Leu Lys Glu Ser Gly Pro Gly Ile Leu Gln Pro Ser Gln
 1               5                  10                  15

Thr Leu Ser Leu Thr Cys Thr Phe Ser Gly Phe Ser Leu Ser Thr Tyr
                 20                  25                  30

Gly Met Gly Val Gly Trp Ile Arg Gln Pro Ser Gly Lys Gly Leu Glu
             35                  40                  45

Trp Leu Ala Asn Ile Trp Trp Asp Asp Lys Tyr Tyr Asn Pro Ser
 50                  55                  60

Leu Lys Asn Arg Leu Thr Ile Ser Lys Asp Thr Ser Asn Asn Gln Ala
 65                  70                  75                  80

Phe Leu Lys Ile Thr Asn Val Asp Thr Ala Asp Thr Ala Thr Tyr Tyr
                 85                  90                  95

Cys Ala Arg Ser Glu Ile Val Met Pro Tyr Val Pro Phe Asp Tyr Trp
                100                 105                 110

Gly Gln Gly Val Met Val Thr Val Ser Ser
            115                 120

<210> SEQ ID NO 88
<211> LENGTH: 107
<212> TYPE: PRT
<213> ORGANISM: Artificial Sequence
<220> FEATURE:
<223> OTHER INFORMATION: Synthetic

<400> SEQUENCE: 88

Asp Ile Gln Met Thr Gln Ser Pro Ser Ser Met Ser Ala Ser Leu Gly
 1               5                  10                  15

Asp Arg Val Thr Ile Thr Cys Gln Ala Ser Gln Asp Ile Gly Asn Asp
                 20                  25                  30

Leu Ile Trp Phe Gln Gln Lys Pro Gly Lys Ser Pro Arg Pro Met Ile
             35                  40                  45

Tyr Tyr Ala Thr Asn Leu Ala Asn Gly Val Pro Ser Arg Phe Ser Gly
             50                  55                  60

Ser Gly Ser Gly Ser Val Tyr Ser Leu Thr Ile Ser Ser Leu Glu Ser
 65                  70                  75                  80

Glu Asp Met Ala Asp Tyr His Cys Leu Gln Phe Lys Gln Tyr Pro Phe
                 85                  90                  95

Thr Phe Gly Ser Gly Thr Lys Leu Glu Ile Lys
```

<210> SEQ ID NO 89
<211> LENGTH: 122
<212> TYPE: PRT
<213> ORGANISM: Artificial Sequence
<220> FEATURE:
<223> OTHER INFORMATION: Synthetic

<400> SEQUENCE: 89

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asp Asp Lys Tyr Tyr Asn Pro Ser
    50                  55                  60

Leu Ile Asn Arg Leu Thr Ile Ser Lys Asn Thr Ser Asn Asn Gln Ala
65                  70                  75                  80

Phe Leu Lys Ile Thr Asn Val Asp Ala Pro Asp Thr Ala Thr Tyr Tyr
                85                  90                  95

Cys Ala Arg Ser Glu Leu Val Met Pro Tyr Val Pro Phe Asp Phe Trp
            100                 105                 110

Gly Gln Gly Ile Met Val Thr Val Ser Ser
        115                 120

<210> SEQ ID NO 90
<211> LENGTH: 107
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Leu Gly
1               5                   10                  15

Asp Arg Ile Thr Ile Thr Cys Gln Ala Ser Gln Asp Ile Gly Ile Asp
            20                  25                  30

Leu Ile Trp Phe Gln Gln Lys Pro Gly Lys Ser Pro Trp Pro Val Ile
        35                  40                  45

Tyr Tyr Thr Ala Asn Leu Ala Ser Gly Val Pro Ser Arg Phe Ser Gly
    50                  55                  60

Ser Arg Ser Gly Ser His Tyr Ser Leu Thr Ile Ser Ser Leu Glu Ser
65                  70                  75                  80

Glu Asp Met Ala Asp Tyr His Cys Leu Gln Tyr Lys Gln Tyr Pro Phe
                85                  90                  95

Thr Phe Gly Ser Gly Thr Lys Leu Glu Ile Lys
            100                 105

<210> SEQ ID NO 91
<211> LENGTH: 122
<212> TYPE: PRT
<213> ORGANISM: Artificial Sequence
<220> FEATURE:
<223> OTHER INFORMATION: Synthetic

<400> SEQUENCE: 91

Gln Val Thr Leu Lys Glu Ser Gly Pro Glu Ile Leu Gln Pro Ser Gln
1               5                   10                  15

```
Thr Leu Ser Leu Thr Cys Thr Phe Ser Gly Phe Ser Leu Ser Pro Tyr
            20                  25                  30

Gly Met Gly Val Gly Trp Ile Arg Gln Pro Ser Gly Lys Gly Leu Glu
            35                  40                  45

Trp Leu Ala Asn Ile Trp Trp Asp Asp Lys Tyr Tyr Asn Pro Ser
 50                  55                  60

Leu Ile Asn Arg Leu Thr Ile Ser Lys Asp Thr Ser Asn Asn Gln Ala
 65                  70                  75                  80

Phe Leu Lys Ile Thr Asn Val Asp Thr Thr Asp Ser Ala Thr Tyr Tyr
                85                  90                  95

Cys Val Arg Ser Glu Leu Val Met Pro Tyr Val Pro Phe Asp Tyr Trp
            100                 105                 110

Gly Gln Gly Val Met Val Thr Val Ser Ser
            115                 120

<210> SEQ ID NO 92
<211> LENGTH: 107
<212> TYPE: PRT
<213> ORGANISM: Artificial Sequence
<220> FEATURE:
<223> OTHER INFORMATION: Synthetic

<400> SEQUENCE: 92

Asp Ile Gln Met Thr Gln Ser Pro Ser Ser Met Ser Ala Ser Leu Gly
 1               5                  10                  15

Asp Arg Val Thr Ile Thr Cys Gln Ala Ser Gln Asp Ile Gly Asn Asp
            20                  25                  30

Leu Ile Trp Phe Gln Gln Lys Pro Gly Lys Ser Pro Arg Pro Leu Ile
            35                  40                  45

Tyr Tyr Ala Thr Asn Leu Ala Asn Gly Val Pro Ser Arg Phe Ser Gly
 50                  55                  60

Arg Arg Ser Glu Ser Asn Tyr Ser Leu Thr Ile Ser Ser Leu Glu Ser
 65                  70                  75                  80

Glu Asp Met Ala Asp Tyr His Cys Leu Gln Phe Lys Gln Tyr Pro Tyr
                85                  90                  95

Thr Phe Gly Ala Gly Thr Lys Leu Glu Leu Lys
            100                 105

<210> SEQ ID NO 93
<211> LENGTH: 146
<212> TYPE: PRT
<213> ORGANISM: Artificial Sequence
<220> FEATURE:
<223> OTHER INFORMATION: Synthetic

<400> SEQUENCE: 93

Met Asp Ile Arg Leu Ser Leu Val Phe Leu Val Leu Phe Ile Lys Gly
 1               5                  10                  15

Val Gln Cys Glu Val Gln Leu Val Glu Ser Gly Gly Gly Leu Val Leu
            20                  25                  30

Pro Gly Arg Ser Leu Lys Leu Ser Cys Ala Ala Ser Gly Phe Thr Phe
            35                  40                  45

Ser Asp Tyr Ala Met Ala Trp Val Arg Gln Ala Pro Lys Lys Gly Leu
 50                  55                  60

Glu Trp Val Ala Thr Val Phe Tyr Asp Gly Ser Asp Thr Phe Tyr Arg
 65                  70                  75                  80

Asp Ser Val Lys Gly Arg Phe Thr Ile Ser Arg Asp Asn Ala Lys Ser
```

```
                    85                  90                  95

Thr Leu Tyr Leu Gln Met Asp Ser Leu Arg Ser Glu Asp Thr Ala Thr
                100                 105                 110

Tyr Tyr Cys Ala Arg Glu Gly Asp Tyr Tyr Ser Arg His Val Tyr Val
            115                 120                 125

Gly Tyr Asn Trp Phe Pro His Trp Gly Gln Gly Thr Leu Val Thr Val
        130                 135                 140

Ser Ser
145

<210> SEQ ID NO 94
<211> LENGTH: 127
<212> TYPE: PRT
<213> ORGANISM: Artificial Sequence
<220> FEATURE:
<223> OTHER INFORMATION: Synthetic

<400> SEQUENCE: 94

Met Gly Val Pro Thr His Leu Leu Gly Leu Leu Leu Leu Trp Ile Thr
1               5                  10                  15

His Ala Met Cys Asp Ile Arg Met Thr Gln Ser Pro Ala Ser Leu Ser
                20                  25                  30

Ala Ser Leu Gly Glu Thr Val Asn Ile Glu Cys Leu Thr Ser Glu Asp
            35                  40                  45

Ile Asn Ser Glu Leu Ala Trp Tyr Gln Gln Lys Pro Gly Lys Phe Pro
        50                  55                  60

Gln Phe Leu Ile Tyr Asn Ala Asn Ser Leu Gln Asp Gly Val Pro Ser
65                  70                  75                  80

Arg Phe Ser Gly Ser Gly Ser Gly Thr Gln Tyr Ser Leu Lys Ile Asn
                85                  90                  95

Ser Leu Gln Ser Glu Asp Val Ala Thr Tyr Phe Cys Gln Gln Tyr Asn
                100                 105                 110

Ser Tyr Pro Leu Thr Phe Gly Ser Gly Thr Glu Leu Glu Ile Lys
            115                 120                 125

<210> SEQ ID NO 95
<211> LENGTH: 116
<212> TYPE: PRT
<213> ORGANISM: Artificial Sequence
<220> FEATURE:
<223> OTHER INFORMATION: Synthetic

<400> SEQUENCE: 95

Glu Val Gln Leu Gln Gln Ser Gly Pro Val Leu Val Arg Pro Gly Ala
1               5                   10                  15

Ser Val Lys Met Ser Cys Lys Ala Ser Gly Tyr Thr Phe Thr Asp Tyr
                20                  25                  30

Tyr Met Asn Trp Val Lys Gln Ser His Gly Lys Ser Leu Glu Trp Ile
            35                  40                  45

Gly Val Ile Asn Pro Asn Asn Gly Gly Thr Thr Tyr Lys Glu Lys Phe
        50                  55                  60

Lys Gly Lys Ala Thr Leu Thr Val Asp Lys Ser Ser Gly Thr Ala Tyr
65                  70                  75                  80

Met Glu Leu Asn Ser Leu Thr Ser Glu Asp Ser Ala Val Tyr Tyr Cys
                85                  90                  95

Ala Arg Asp Asp Tyr Asp Ala Gly Tyr Trp Gly Gln Gly Thr Thr Leu
            100                 105                 110
```

Thr Val Ser Ser
        115

<210> SEQ ID NO 96
<211> LENGTH: 107
<212> TYPE: PRT
<213> ORGANISM: Artificial Sequence
<220> FEATURE:
<223> OTHER INFORMATION: Synthetic

<400> SEQUENCE: 96

Asp Ile Val Met Thr Gln Phe Gln Lys Phe Met Ser Thr Thr Val Gly
1               5                   10                  15

Asp Arg Val Ser Ile Thr Cys Lys Ala Ser Gln Asn Val Asp Thr Ala
            20                  25                  30

Val Ala Trp Tyr Gln His Lys Pro Gly Gln Ser Pro Lys Leu Leu Ile
        35                  40                  45

Tyr Ser Ala Ser His Arg Tyr Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Thr Asp Phe Pro Leu
                85                  90                  95

Thr Phe Gly Ala Gly Thr Lys Leu Glu Leu Lys
            100                 105

<210> SEQ ID NO 97
<211> LENGTH: 5
<212> TYPE: PRT
<213> ORGANISM: Artificial Sequence
<220> FEATURE:
<223> OTHER INFORMATION: Synthetic

<400> SEQUENCE: 97

Asp Tyr Tyr Met Asn
1               5

<210> SEQ ID NO 98
<211> LENGTH: 17
<212> TYPE: PRT
<213> ORGANISM: Artificial Sequence
<220> FEATURE:
<223> OTHER INFORMATION: Synthetic

<400> SEQUENCE: 98

Val Ile Asn Pro Asn Asn Gly Gly Thr Thr Tyr Lys Glu Lys Phe Lys
1               5                   10                  15

Gly

<210> SEQ ID NO 99
<211> LENGTH: 7
<212> TYPE: PRT
<213> ORGANISM: Artificial Sequence
<220> FEATURE:
<223> OTHER INFORMATION: Synthetic

<400> SEQUENCE: 99

Asp Asp Tyr Asp Ala Gly Tyr
1               5

<210> SEQ ID NO 100
<211> LENGTH: 11
<212> TYPE: PRT

-continued

<213> ORGANISM: Artificial Sequence
<220> FEATURE:
<223> OTHER INFORMATION: Synthetic

<400> SEQUENCE: 100

Lys Ala Ser Gln Asn Val Asp Thr Ala Val Ala
1               5                   10

<210> SEQ ID NO 101
<211> LENGTH: 7
<212> TYPE: PRT
<213> ORGANISM: Artificial Sequence
<220> FEATURE:
<223> OTHER INFORMATION: Synthetic

<400> SEQUENCE: 101

Ser Ala Ser His Arg Tyr Thr
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic

<400> SEQUENCE: 102

Gln Gln Tyr Thr Asp Phe Pro Leu Thr
1               5

<210> SEQ ID NO 103
<211> LENGTH: 116
<212> TYPE: PRT
<213> ORGANISM: Artificial Sequence
<220> FEATURE:
<223> OTHER INFORMATION: Synthetic

<400> SEQUENCE: 103

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Val Ile Asn Pro Asn Asn Gly Gly Thr Thr Tyr Lys Glu Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Ala Arg Asp Asp Tyr Asp Ala Gly Tyr Trp Gly Gln Gly Thr Leu Val
                100                 105                 110

Thr Val Ser Ser
        115

<210> SEQ ID NO 104
<211> LENGTH: 116
<212> TYPE: PRT
<213> ORGANISM: Artificial Sequence
<220> FEATURE:
<223> OTHER INFORMATION: Synthetic

<400> SEQUENCE: 104

```
Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Met
        35                  40                  45

Gly Val Ile Asn Pro Asn Asn Gly Gly Thr Thr Tyr Lys Glu Lys Phe
    50                  55                  60

Lys Gly Arg Val Thr Met Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Tyr Asp Ala Gly Tyr Trp Gly Gln Gly Thr Leu Val
            100                 105                 110

Thr Val Ser Ser
        115

<210> SEQ ID NO 105
<211> LENGTH: 116
<212> TYPE: PRT
<213> ORGANISM: Artificial Sequence
<220> FEATURE:
<223> OTHER INFORMATION: Synthetic

<400> SEQUENCE: 105

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Val Ile Asn Pro Asn Asn Gly Gly Thr Thr Tyr Lys Glu Lys Phe
    50                  55                  60

Lys Gly Arg Ala Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Asp Tyr Asp Ala Gly Tyr Trp Gly Gln Gly Thr Leu Val
            100                 105                 110

Thr Val Ser Ser
        115

<210> SEQ ID NO 106
<211> LENGTH: 116
<212> TYPE: PRT
<213> ORGANISM: Artificial Sequence
<220> FEATURE:
<223> OTHER INFORMATION: Synthetic

<400> SEQUENCE: 106

Gln Val Gln Leu Val Gln Ser Gly Ala Glu Val Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Arg Gln Ala Pro Gly Gln Gly Leu Glu Trp Ile
        35                  40                  45

Gly Val Ile Asn Pro Asn Asn Gly Gly Thr Thr Tyr Lys Glu Lys Phe
    50                  55                  60
```

```
Lys Gly Arg Ala Thr Leu Thr Val Asp Thr Ser Ile Gly Thr Ala Tyr
 65                  70                  75                  80

Met Glu Leu Ser Arg Leu Arg Ser Asp Asp Thr Ala Val Tyr Tyr Cys
                 85                  90                  95

Ala Arg Asp Asp Tyr Asp Ala Gly Tyr Trp Gly Gln Gly Thr Leu Leu
            100                 105                 110

Thr Val Ser Ser
        115

<210> SEQ ID NO 107
<211> LENGTH: 107
<212> TYPE: PRT
<213> ORGANISM: Artificial Sequence
<220> FEATURE:
<223> OTHER INFORMATION: Synthetic

<400> SEQUENCE: 107

Asp Ile Gln Met Thr Gln Ser Pro Ser Ser Val Ser Ala Ser Val Gly
 1               5                  10                  15

Asp Arg Val Thr Ile Thr Cys Lys Ala Ser Gln Asn Val Asp Thr Ala
             20                  25                  30

Val Ala Trp Tyr Gln Gln Lys Pro Gly Lys Ala Pro Lys Leu Leu Ile
         35                  40                  45

Tyr Ser Ala Ser His Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Thr Asp Phe Pro Leu
                 85                  90                  95

Thr Phe Gly Gln Gly Thr Arg Leu Glu Ile Lys
            100                 105

<210> SEQ ID NO 108
<211> LENGTH: 107
<212> TYPE: PRT
<213> ORGANISM: Artificial Sequence
<220> FEATURE:
<223> OTHER INFORMATION: Synthetic

<400> SEQUENCE: 108

Asp Ile Gln Met Thr Gln Ser Pro Ser Ser Val Ser Thr Ser Val Gly
 1               5                  10                  15

Asp Arg Val Thr Ile Thr Cys Lys Ala Ser Gln Asn Val Asp Thr Ala
             20                  25                  30

Val Ala Trp Tyr Gln Gln Lys Pro Gly Lys Ala Pro Lys Leu Leu Ile
         35                  40                  45

Tyr Ser Ala Ser His Arg Tyr Thr Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Thr Asp Phe Pro Leu
                 85                  90                  95

Thr Phe Gly Gln Gly Thr Arg Leu Glu Ile Lys
            100                 105

<210> SEQ ID NO 109
<211> LENGTH: 107
<212> TYPE: PRT
```

```
<213> ORGANISM: Artificial Sequence
<220> FEATURE:
<223> OTHER INFORMATION: Synthetic

<400> SEQUENCE: 109

Asp Ile Gln Met Thr Gln Ser Pro Ser Ser Val Ser Val Gly
1               5                   10                  15

Asp Arg Val Thr Ile Thr Cys Lys Ala Ser Gln Asn Val Asp Thr Ala
            20                  25                  30

Val Ala Trp Tyr Gln Gln Lys Pro Gly Lys Ala Pro Lys Leu Leu Ile
        35                  40                  45

Tyr Ser Ala Ser His Arg Tyr Thr Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Thr Tyr Tyr Cys Gln Gln Tyr Thr Asp Phe Pro Leu
                85                  90                  95

Thr Phe Gly Gln Gly Thr Arg Leu Glu Ile Lys
            100                 105

<210> SEQ ID NO 110
<211> LENGTH: 123
<212> TYPE: PRT
<213> ORGANISM: Artificial Sequence
<220> FEATURE:
<223> OTHER INFORMATION: Synthetic

<400> SEQUENCE: 110

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

Ala Thr Ile Ser Asp Gly Gly Ser Asp Ala Tyr Tyr Pro Asp Asn Val
    50                  55                  60

Lys Gly Arg Phe Thr Ile Ser Arg Asp Asn Ala Lys Asn Asn Leu Tyr
65                  70                  75                  80

Leu Gln Met Ser His Leu Lys Ser Glu Asp Thr Ala Met Tyr Tyr Cys
                85                  90                  95

Ala Arg Asp Tyr Tyr Gly Ser Gly Tyr Glu Asp Ser Pro Met Asp Tyr
            100                 105                 110

Trp Gly Gln Gly Thr Ser Val Thr Val Ser Ser
        115                 120

<210> SEQ ID NO 111
<211> LENGTH: 106
<212> TYPE: PRT
<213> ORGANISM: Artificial Sequence
<220> FEATURE:
<223> OTHER INFORMATION: Synthetic

<400> SEQUENCE: 111

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45
```

His Tyr Thr Ser Thr Leu Gln Pro Gly Ile Pro Ser Arg Phe Ser Gly
            50                  55                  60

Ser Gly Ser Gly Arg Asp Tyr Ser Phe Ser Ile Ser Asn Leu Glu Pro
65                  70                  75                  80

Glu Asp Phe Ala Thr Tyr Tyr Cys Leu Gln Tyr Asp Asn Leu Tyr Thr
                85                  90                  95

Phe Gly Gly Gly Thr Lys Leu Glu Ile Lys
            100                 105

<210> SEQ ID NO 112
<211> LENGTH: 5
<212> TYPE: PRT
<213> ORGANISM: Artificial Sequence
<220> FEATURE:
<223> OTHER INFORMATION: Synthetic

<400> SEQUENCE: 112

Ser Tyr Ala Met Ser
1               5

<210> SEQ ID NO 113
<211> LENGTH: 17
<212> TYPE: PRT
<213> ORGANISM: Artificial Sequence
<220> FEATURE:
<223> OTHER INFORMATION: Synthetic

<400> SEQUENCE: 113

Thr Ile Ser Asp Gly Gly Ser Asp Ala Tyr Tyr Pro Asp Asn Val Lys
1               5                   10                  15

Gly

<210> SEQ ID NO 114
<211> LENGTH: 17
<212> TYPE: PRT
<213> ORGANISM: Artificial Sequence
<220> FEATURE:
<223> OTHER INFORMATION: Synthetic

<400> SEQUENCE: 114

Thr Ile Ser Glu Gly Gly Ser Asp Ala Tyr Tyr Pro Asp Asn Val Lys
1               5                   10                  15

Gly

<210> SEQ ID NO 115
<211> LENGTH: 14
<212> TYPE: PRT
<213> ORGANISM: Artificial Sequence
<220> FEATURE:
<223> OTHER INFORMATION: Synthetic

<400> SEQUENCE: 115

Asp Tyr Tyr Gly Ser Gly Tyr Glu Asp Ser Pro Met Asp Tyr
1               5                   10

<210> SEQ ID NO 116
<211> LENGTH: 14
<212> TYPE: PRT
<213> ORGANISM: Artificial Sequence
<220> FEATURE:
<223> OTHER INFORMATION: Synthetic

<400> SEQUENCE: 116

```
Asp Tyr Tyr Gly Ser Gly Tyr Glu Glu Ser Pro Met Asp Tyr
1               5                   10
```

<210> SEQ ID NO 117
<211> LENGTH: 11
<212> TYPE: PRT
<213> ORGANISM: Artificial Sequence
<220> FEATURE:
<223> OTHER INFORMATION: Synthetic

<400> SEQUENCE: 117

```
Lys Ala Ser Gln Asp Ile Asn Lys Tyr Ile Ala
1               5                   10
```

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

```
Tyr Thr Ser Thr Leu Gln Pro
1               5
```

<210> SEQ ID NO 119
<211> LENGTH: 8
<212> TYPE: PRT
<213> ORGANISM: Artificial Sequence
<220> FEATURE:
<223> OTHER INFORMATION: Synthetic

<400> SEQUENCE: 119

```
Leu Gln Tyr Asp Asn Leu Tyr Thr
1               5
```

<210> SEQ ID NO 120
<211> LENGTH: 123
<212> TYPE: PRT
<213> ORGANISM: Artificial Sequence
<220> FEATURE:
<223> OTHER INFORMATION: Synthetic

<400> SEQUENCE: 120

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
            35                  40                  45

Ala Thr Ile Ser Asp Gly Gly Ser Asp Ala Tyr Tyr Pro Asp Asn Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Tyr Gly Ser Gly Tyr Glu Asp Ser Pro Met Asp Tyr
            100                 105                 110

Trp Gly Gln Gly Thr Leu Val Thr Val Ser Ser
            115                 120
```

<210> SEQ ID NO 121
<211> LENGTH: 106

```
<212> TYPE: PRT
<213> ORGANISM: Artificial Sequence
<220> FEATURE:
<223> OTHER INFORMATION: Synthetic

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

Tyr Tyr Thr Ser Thr Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Leu Gln Tyr Asp Asn Leu Tyr Thr
                85                  90                  95

Phe Gly Gly Gly Thr Lys Leu Glu Ile Lys
            100                 105

<210> SEQ ID NO 122
<211> LENGTH: 106
<212> TYPE: PRT
<213> ORGANISM: Artificial Sequence
<220> FEATURE:
<223> OTHER INFORMATION: Synthetic

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Tyr Asp Asn Leu Tyr Thr
                85                  90                  95

Phe Gly Gly Gly Thr Lys Leu Glu Ile Lys
            100                 105

<210> SEQ ID NO 123
<211> LENGTH: 106
<212> TYPE: PRT
<213> ORGANISM: Artificial Sequence
<220> FEATURE:
<223> OTHER INFORMATION: Synthetic

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Pro Gly Ile Pro Ser Arg Phe Ser Gly
```

```
                    50                  55                  60
Ser Gly Ser Gly Thr Asp Phe Thr Phe Thr Ile Ser Ser Leu Gln Pro
 65                  70                  75                  80

Glu Asp Phe Ala Thr Tyr Tyr Cys Leu Gln Tyr Asp Asn Leu Tyr Thr
                 85                  90                  95

Phe Gly Gly Gly Thr Lys Leu Glu Ile Lys
                100                 105

<210> SEQ ID NO 124
<211> LENGTH: 106
<212> TYPE: PRT
<213> ORGANISM: Artificial Sequence
<220> FEATURE:
<223> OTHER INFORMATION: Synthetic

<400> SEQUENCE: 124

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Ile Asn Lys Tyr
                20                  25                  30

Ile Ala Trp Tyr Gln Gln Lys Pro Gly Lys Ala Pro Lys Leu Leu Ile
             35                  40                  45

His Tyr Thr Ser Thr Leu Gln Pro Gly Ile Pro Ser Arg Phe Ser Gly
         50                  55                  60

Ser Gly Ser Gly Thr Asp Tyr Thr Phe Thr Ile Ser Ser Leu Gln Pro
 65                  70                  75                  80

Glu Asp Phe Ala Thr Tyr Tyr Cys Leu Gln Tyr Asp Asn Leu Tyr Thr
                 85                  90                  95

Phe Gly Gly Gly Thr Lys Leu Glu Ile Lys
                100                 105

<210> SEQ ID NO 125
<211> LENGTH: 120
<212> TYPE: PRT
<213> ORGANISM: Artificial Sequence
<220> FEATURE:
<223> OTHER INFORMATION: Synthetic

<400> SEQUENCE: 125

Glu Val Lys Leu Leu Gln Ser Gly Gly Gly Leu Val Gln Pro Gly Gly
 1               5                  10                  15

Ser Leu Lys Leu Ser Cys Ala Ala Ser Gly Ile Asp Phe Ser Arg Tyr
                20                  25                  30

Trp Met Ser Trp Val Arg Arg Ala Pro Gly Lys Gly Leu Glu Trp Ile
             35                  40                  45

Gly Glu Ile Asn Pro Asp Ser Ser Thr Ile Asn Tyr Ala Pro Ser Leu
         50                  55                  60

Lys Asp Lys Phe Ile Ile Ser Arg Asp Asn Ala Lys Asn Thr Leu Tyr
 65                  70                  75                  80

Leu Gln Met Ser Lys Val Arg Ser Glu Asp Thr Ala Leu Tyr Tyr Cys
                 85                  90                  95

Ala Arg Gln Asp Asp Tyr Glu Tyr Tyr Ala Met Asp Tyr Trp Gly Gln
                100                 105                 110

Gly Thr Ser Val Thr Val Ser Ser
            115                 120

<210> SEQ ID NO 126
<211> LENGTH: 107
```

```
<212> TYPE: PRT
<213> ORGANISM: Artificial Sequence
<220> FEATURE:
<223> OTHER INFORMATION: Synthetic

<400> SEQUENCE: 126

Asp Ile Val Met Thr Gln Ser His Lys Ser Met Ser Thr Ser Val Gly
1               5                   10                  15

Asp Arg Val Ser Ile Thr Cys Lys Ala Ser Gln Asp Val Asn Thr Gly
                20                  25                  30

Val Ala Trp Tyr Arg Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ser Thr Pro Leu
                85                  90                  95

Thr Phe Gly Ala Gly Thr Lys Leu Glu Leu Lys
            100                 105

<210> SEQ ID NO 127
<211> LENGTH: 5
<212> TYPE: PRT
<213> ORGANISM: Artificial Sequence
<220> FEATURE:
<223> OTHER INFORMATION: Synthetic

<400> SEQUENCE: 127

Arg Tyr Trp Met Ser
1               5

<210> SEQ ID NO 128
<211> LENGTH: 17
<212> TYPE: PRT
<213> ORGANISM: Artificial Sequence
<220> FEATURE:
<223> OTHER INFORMATION: Synthetic

<400> SEQUENCE: 128

Glu Ile Asn Pro Asp Ser Ser Thr Ile Asn Tyr Ala Pro Ser Leu Lys
1               5                   10                  15

Asp

<210> SEQ ID NO 129
<211> LENGTH: 17
<212> TYPE: PRT
<213> ORGANISM: Artificial Sequence
<220> FEATURE:
<223> OTHER INFORMATION: Synthetic

<400> SEQUENCE: 129

Glu Ile Asn Pro Glu Ser Ser Thr Ile Asn Tyr Ala Pro Ser Leu Lys
1               5                   10                  15

Asp

<210> SEQ ID NO 130
<211> LENGTH: 11
<212> TYPE: PRT
<213> ORGANISM: Artificial Sequence
<220> FEATURE:
<223> OTHER INFORMATION: Synthetic
```

```
<400> SEQUENCE: 130

Gln Asp Asp Tyr Glu Tyr Tyr Ala Met Asp Tyr
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic

<400> SEQUENCE: 131

Lys Ala Ser Gln Asp Val Asn Thr Gly Val Ala
1               5                   10

<210> SEQ ID NO 132
<211> LENGTH: 7
<212> TYPE: PRT
<213> ORGANISM: Artificial Sequence
<220> FEATURE:
<223> OTHER INFORMATION: Synthetic

<400> SEQUENCE: 132

Ser Ala Ser Tyr Arg Tyr Thr
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic

<400> SEQUENCE: 133

Gln Gln Tyr Tyr Ser Thr Pro Leu Thr
1               5

<210> SEQ ID NO 134
<211> LENGTH: 120
<212> TYPE: PRT
<213> ORGANISM: Artificial Sequence
<220> FEATURE:
<223> OTHER INFORMATION: Synthetic

<400> SEQUENCE: 134

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Asp Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Glu Tyr Tyr Ala Met Asp Tyr Trp Gly Gln
                100                 105                 110

Gly Thr Thr Val Thr Val Ser Ser
            115                 120
```

```
<210> SEQ ID NO 135
<211> LENGTH: 120
<212> TYPE: PRT
<213> ORGANISM: Artificial Sequence
<220> FEATURE:
<223> OTHER INFORMATION: Synthetic

<400> SEQUENCE: 135

Glu Val Gln Leu Val Gln Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Asp Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Glu Tyr Tyr Ala Met Asp Tyr Trp Gly Gln
            100                 105                 110

Gly Thr Thr Val Thr Val Ser Ser
        115                 120

<210> SEQ ID NO 136
<211> LENGTH: 120
<212> TYPE: PRT
<213> ORGANISM: Artificial Sequence
<220> FEATURE:
<223> OTHER INFORMATION: Synthetic

<400> SEQUENCE: 136

Glu Val Gln Leu Val Gln Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Gly Glu Ile Asn Pro Asp Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Val Arg Ala Glu Asp Thr Ala Val Tyr Tyr Cys
                85                  90                  95

Ala Arg Gln Asp Asp Tyr Glu Tyr Tyr Ala Met Asp Tyr Trp Gly Gln
            100                 105                 110

Gly Thr Thr Val Thr Val Ser Ser
        115                 120

<210> SEQ ID NO 137
<211> LENGTH: 120
<212> TYPE: PRT
<213> ORGANISM: Artificial Sequence
<220> FEATURE:
<223> OTHER INFORMATION: Synthetic

<400> SEQUENCE: 137

Glu Val Gln Leu Val Gln Ser Gly Gly Gly Leu Val Gln Pro Gly Gly
1               5                   10                  15
```

```
Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Ala Pro Ser Leu
 50                  55                  60

Lys Asp Arg Phe Thr Ile Ser Arg Asp Asn Ala Lys Asn Ser Leu Tyr
 65                  70                  75                  80

Leu Gln Met Asn Ser Val Arg Ala Glu Asp Thr Ala Val Tyr Tyr Cys
                85                  90                  95

Ala Arg Gln Asp Asp Tyr Glu Tyr Tyr Ala Met Asp Tyr Trp Gly Gln
               100                 105                 110

Gly Thr Thr Val Thr Val Ser Ser
           115                 120

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Asn Thr Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Tyr Ser Thr Pro Leu
                85                  90                  95

Thr Phe Gly Gly Gly Thr Lys Leu Glu Ile Lys
               100                 105

<210> SEQ ID NO 139
<211> LENGTH: 107
<212> TYPE: PRT
<213> ORGANISM: Artificial Sequence
<220> FEATURE:
<223> OTHER INFORMATION: Synthetic

<400> SEQUENCE: 139

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Asn Thr Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Phe Thr Ile Ser Ser Val Gln Pro
 65                  70                  75                  80

Glu Asp Ile Ala Thr Tyr Tyr Cys Gln Gln Tyr Tyr Ser Thr Pro Leu
```

```
                    85                  90                  95

Thr Phe Gly Gly Gly Thr Lys Leu Glu Ile Lys
                   100                 105

<210> SEQ ID NO 140
<211> LENGTH: 121
<212> TYPE: PRT
<213> ORGANISM: Artificial Sequence
<220> FEATURE:
<223> OTHER INFORMATION: Synthetic

<400> SEQUENCE: 140

Glu Val Gln Leu Val Glu Ser Gly Gly Leu Val Gln Pro Gly Gly
1               5                   10                  15

Ser Leu Lys Leu Ser Cys Val Val Ser Gly Phe Thr Phe Ser Asp Tyr
                20                  25                  30

Tyr Met Ala Trp Val Arg Gln Thr Pro Thr Lys Gly Leu Glu Trp Val
            35                  40                  45

Ala Ser Ile Asn Tyr Asp Gly Asp Thr Tyr Tyr Arg Asp Ser Val
        50                  55                  60

Lys Gly Arg Phe Thr Val Ser Arg Asn Asn Ala Lys Ser Ser Leu Phe
65                  70                  75                  80

Leu Gln Met Asp Ser Leu Arg Ser Glu Asp Thr Ala Thr Tyr Tyr Cys
                85                  90                  95

Lys Thr Glu Glu Asp Tyr Asp Gly Ser Tyr Val Met Asp Ala Trp Gly
                   100                 105                 110

Gln Gly Ala Ser Val Ile Val Ser Ser
            115                 120

<210> SEQ ID NO 141
<211> LENGTH: 106
<212> TYPE: PRT
<213> ORGANISM: Artificial Sequence
<220> FEATURE:
<223> OTHER INFORMATION: Synthetic

<400> SEQUENCE: 141

Asp Ile Gln Met Thr Gln Ser Pro Ser Phe Leu Ser Ala Ser Val Gly
1               5                   10                  15

Asp Arg Val Thr Ile Ser Cys Lys Ala Ser Gln Asn Ile Asn Lys Glu
                20                  25                  30

Leu Thr Trp Tyr Gln Gln Lys Leu Gly Lys Ala Pro Lys Arg Leu Ile
            35                  40                  45

Tyr Asn Thr Asn Ile Leu Gln Thr Gly Ile Pro Ser Arg Phe Ser Gly
        50                  55                  60

Ser Gly Ser Asn Thr Asp Tyr Thr Leu Thr Ile Ser Ser Leu Gln Pro
65                  70                  75                  80

Glu Asp Phe Ala Thr Tyr Phe Cys Leu Gln Gln Ser Ser Leu Tyr Thr
                85                  90                  95

Phe Gly Ala Gly Thr Lys Leu Glu Leu Lys
                   100                 105

<210> SEQ ID NO 142
<211> LENGTH: 5
<212> TYPE: PRT
<213> ORGANISM: Artificial Sequence
<220> FEATURE:
<223> OTHER INFORMATION: Synthetic

<400> SEQUENCE: 142
```

```
Asp Tyr Tyr Met Ala
1               5

<210> SEQ ID NO 143
<211> LENGTH: 17
<212> TYPE: PRT
<213> ORGANISM: Artificial Sequence
<220> FEATURE:
<223> OTHER INFORMATION: Synthetic

<400> SEQUENCE: 143

Ser Ile Asn Tyr Asp Gly Gly Asp Thr Tyr Tyr Arg Asp Ser Val Lys
1               5                   10                  15

Gly

<210> SEQ ID NO 144
<211> LENGTH: 12
<212> TYPE: PRT
<213> ORGANISM: Artificial Sequence
<220> FEATURE:
<223> OTHER INFORMATION: Synthetic

<400> SEQUENCE: 144

Glu Glu Asp Tyr Asp Gly Ser Tyr Val Met Asp Ala
1               5                   10

<210> SEQ ID NO 145
<211> LENGTH: 11
<212> TYPE: PRT
<213> ORGANISM: Artificial Sequence
<220> FEATURE:
<223> OTHER INFORMATION: Synthetic

<400> SEQUENCE: 145

Lys Ala Ser Gln Asn Ile Asn Lys Glu Leu Thr
1               5                   10

<210> SEQ ID NO 146
<211> LENGTH: 7
<212> TYPE: PRT
<213> ORGANISM: Artificial Sequence
<220> FEATURE:
<223> OTHER INFORMATION: Synthetic

<400> SEQUENCE: 146

Asn Thr Asn Ile Leu Gln Thr
1               5

<210> SEQ ID NO 147
<211> LENGTH: 8
<212> TYPE: PRT
<213> ORGANISM: Artificial Sequence
<220> FEATURE:
<223> OTHER INFORMATION: Synthetic

<400> SEQUENCE: 147

Leu Gln Gln Ser Ser Leu Tyr Thr
1               5

<210> SEQ ID NO 148
<211> LENGTH: 123
<212> TYPE: PRT
<213> ORGANISM: Artificial Sequence
<220> FEATURE:
<223> OTHER INFORMATION: Synthetic
```

<400> SEQUENCE: 148

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Tyr Asp Gly Gly Asp Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Glu Asp Tyr Asp Gly Ser Tyr Val Met Asp Ala Trp Gly
            100                 105                 110

Gln Gly Thr Leu Val Thr Val Ser Ser Gly Ser
        115                 120

<210> SEQ ID NO 149
<211> LENGTH: 123
<212> TYPE: PRT
<213> ORGANISM: Artificial Sequence
<220> FEATURE:
<223> OTHER INFORMATION: Synthetic

<400> SEQUENCE: 149

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Tyr Asp Gly Gly Asp Thr Tyr Tyr Arg Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Thr Glu Glu Asp Tyr Asp Gly Ser Tyr Val Met Asp Ala Trp Gly
            100                 105                 110

Gln Gly Thr Leu Val Thr Val Ser Ser Gly Ser
        115                 120

<210> SEQ ID NO 150
<211> LENGTH: 123
<212> TYPE: PRT
<213> ORGANISM: Artificial Sequence
<220> FEATURE:
<223> OTHER INFORMATION: Synthetic

<400> SEQUENCE: 150

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Thr Phe Ser Asp Tyr
            20                  25                  30

Tyr Met Ala Trp Val Arg Gln Ala Pro Gly Lys Gly Leu Glu Trp Val
        35                  40                  45

Ala Ser Ile Asn Tyr Asp Gly Gly Asp Thr Tyr Tyr Arg Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Thr Glu Glu Asp Tyr Asp Gly Ser Tyr Val Met Asp Ala Trp Gly
             100                 105                 110

Gln Gly Thr Leu Val Thr Val Ser Ser Gly Ser
         115                 120

<210> SEQ ID NO 151
<211> LENGTH: 123
<212> TYPE: PRT
<213> ORGANISM: Artificial Sequence
<220> FEATURE:
<223> OTHER INFORMATION: Synthetic

<400> SEQUENCE: 151

Glu Val Gln Leu Val Glu Ser Gly Gly Gly Leu Val Gln Pro Gly Gly
 1               5                  10                  15

Ser Leu Arg Leu Ser Cys Ala Val Ser Gly Phe Thr Phe Ser Asp Tyr
             20                  25                  30

Tyr Met Ala Trp Val Arg Gln Ala Pro Gly Lys Gly Leu Glu Trp Val
         35                  40                  45

Ala Ser Ile Asn Tyr Asp Gly Gly Asp Thr Tyr Tyr Arg Asp Ser Val
 50                  55                  60

Lys Gly Arg Phe Thr Val Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Thr Glu Glu Asp Tyr Asp Gly Ser Tyr Val Met Asp Ala Trp Gly
             100                 105                 110

Gln Gly Ala Leu Val Thr Val Ser Ser Gly Ser
         115                 120

<210> SEQ ID NO 152
<211> LENGTH: 106
<212> TYPE: PRT
<213> ORGANISM: Artificial Sequence
<220> FEATURE:
<223> OTHER INFORMATION: Synthetic

<400> SEQUENCE: 152

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asn Ile Asn Lys Glu
             20                  25                  30

Leu Thr Trp Tyr Gln Gln Lys Pro Gly Lys Ala Pro Lys Arg Leu Ile
         35                  40                  45

Tyr Asn Thr Asn Ile Leu Gln Thr Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Gln Ser Ser Leu Tyr Thr
                 85                  90                  95

Phe Gly Gln Gly Thr Lys Leu Glu Ile Lys
             100                 105

<210> SEQ ID NO 153
<211> LENGTH: 106
<212> TYPE: PRT
<213> ORGANISM: Artificial Sequence
<220> FEATURE:
<223> OTHER INFORMATION: Synthetic

<400> SEQUENCE: 153

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Glu
            20                  25                  30

Leu Thr Trp Tyr Gln Gln Lys Pro Gly Lys Ala Pro Lys Arg Leu Ile
        35                  40                  45

Tyr Asn Thr Asn Ile Leu Gln Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Leu Gln Gln Ser Ser Leu Tyr Thr
                85                  90                  95

Phe Gly Gln Gly Thr Lys Leu Glu Ile Lys
            100                 105

<210> SEQ ID NO 154
<211> LENGTH: 106
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Glu
            20                  25                  30

Leu Thr Trp Tyr Gln Gln Lys Pro Gly Lys Ala Pro Lys Arg Leu Ile
        35                  40                  45

Tyr Asn Thr Asn Ile Leu Gln Thr Gly Ile Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Phe Cys Leu Gln Gln Ser Ser Leu Tyr Thr
                85                  90                  95

Phe Gly Gln Gly Thr Lys Leu Glu Ile Lys
            100                 105

<210> SEQ ID NO 155
<211> LENGTH: 106
<212> TYPE: PRT
<213> ORGANISM: Artificial Sequence
<220> FEATURE:
<223> OTHER INFORMATION: Synthetic

<400> SEQUENCE: 155

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Ile Asn Lys Glu
            20                  25                  30

```
Leu Thr Trp Tyr Gln Gln Lys Pro Gly Lys Ala Pro Lys Arg Leu Ile
         35                  40                  45

Tyr Asn Thr Asn Ile Leu Gln Thr Gly Ile Pro Ser Arg Phe Ser Gly
 50                  55                  60

Ser Gly Ser Gly Thr Glu Tyr Thr Leu Thr Ile Ser Ser Leu Gln Pro
 65                  70                  75                  80

Glu Asp Phe Ala Thr Tyr Phe Cys Leu Gln Gln Ser Ser Leu Tyr Thr
                 85                  90                  95

Phe Gly Gln Gly Thr Lys Leu Glu Ile Lys
                100                 105
```

<210> SEQ ID NO 156
<211> LENGTH: 120
<212> TYPE: PRT
<213> ORGANISM: Artificial Sequence
<220> FEATURE:
<223> OTHER INFORMATION: Synthetic

<400> SEQUENCE: 156

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Ile Asp Phe Ser Arg Tyr
             20                  25                  30

Trp Met Ser Trp Val Arg Gln Ala Pro Gly Lys Gly Leu Glu Trp Val
         35                  40                  45

Ala Glu Ile Asn Pro Glu Ser Ser Thr Ile Asn Tyr Ala Pro Ser Leu
 50                  55                  60

Lys Asp Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asp Asp Tyr Glu Tyr Tyr Ala Met Asp Tyr Trp Gly Gln
                100                 105                 110

Gly Thr Thr Val Thr Val Ser Ser
            115                 120
```

<210> SEQ ID NO 157
<211> LENGTH: 123
<212> TYPE: PRT
<213> ORGANISM: Artificial Sequence
<220> FEATURE:
<223> OTHER INFORMATION: Synthetic

<400> SEQUENCE: 157

```
Glu Val Gln Leu Val Glu Ser Gly Gly Gly Leu Val Gln Pro Gly Gly
 1               5                   10                  15

Ser Leu Arg Leu Ser Cys Ala Ala Ser Gly Phe Thr Phe Ser Ser Tyr
             20                  25                  30

Ala Met Ser Trp Val Arg Gln Ala Pro Gly Lys Gly Leu Glu Trp Val
         35                  40                  45

Ala Thr Ile Ser Glu Gly Gly Ser Asp Ala Tyr Tyr Pro Asp Asn Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Asp Tyr Tyr Gly Ser Gly Tyr Glu Glu Ser Pro Met Asp Tyr
                100                 105                 110
```

Trp Gly Gln Gly Thr Leu Val Thr Val Ser Ser
        115                 120

<210> SEQ ID NO 158
<211> LENGTH: 120
<212> TYPE: PRT
<213> ORGANISM: Artificial Sequence
<220> FEATURE:
<223> OTHER INFORMATION: Synthetic

<400> SEQUENCE: 158

Glu Val Gln Leu Val Glu Ser Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ala Ser Ser Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Ser His Tyr Ala Met Asp Tyr Trp Gly Gln
            100                 105                 110

Gly Thr Thr Val Thr Val Ser Ser
        115                 120

<210> SEQ ID NO 159
<211> LENGTH: 107
<212> TYPE: PRT
<213> ORGANISM: Artificial Sequence
<220> FEATURE:
<223> OTHER INFORMATION: Synthetic

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Gly
            20                  25                  30

Val Ser Trp Ser Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ser Thr Pro Leu
                85                  90                  95

Thr Phe Gly Gly Gly Thr Lys Leu Glu Ile Lys
            100                 105

<210> SEQ ID NO 160
<211> LENGTH: 120
<212> TYPE: PRT
<213> ORGANISM: Artificial Sequence
<220> FEATURE:
<223> OTHER INFORMATION: Synthetic

<400> SEQUENCE: 160

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ala Gly Lys Trp Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gln Asp Asp Tyr Thr Thr Tyr Ala Met Asp Tyr Trp Gly Gln
        100                 105                 110

Gly Thr Thr Val Thr Val Ser Ser
        115                 120

<210> SEQ ID NO 161
<211> LENGTH: 107
<212> TYPE: PRT
<213> ORGANISM: Artificial Sequence
<220> FEATURE:
<223> OTHER INFORMATION: Synthetic

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Gly
            20                  25                  30

Val Ser Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ser Thr Pro Leu
            85                  90                  95

Thr Phe Gly Gly Gly Thr Lys Leu Glu Ile Lys
        100                 105

<210> SEQ ID NO 162
<211> LENGTH: 120
<212> TYPE: PRT
<213> ORGANISM: Artificial Sequence
<220> FEATURE:
<223> OTHER INFORMATION: Synthetic

<400> SEQUENCE: 162

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

```
Leu Gln Met Asn Ser Leu Arg Ala Glu Asp Thr Ala Val Tyr Tyr Cys
                85                  90                  95

Ala Arg Gln Asp Asp Tyr Leu Thr Tyr Ala Met Asp Tyr Trp Gly Gln
            100                 105                 110

Gly Thr Thr Val Thr Val Ser Ser
        115                 120

<210> SEQ ID NO 163
<211> LENGTH: 107
<212> TYPE: PRT
<213> ORGANISM: Artificial Sequence
<220> FEATURE:
<223> OTHER INFORMATION: Synthetic

<400> SEQUENCE: 163

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
            20                  25                  30

Val Asp Trp Phe Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ser Thr Pro Leu
                85                  90                  95

Thr Phe Gly Gly Gly Thr Lys Leu Glu Ile Lys
            100                 105

<210> SEQ ID NO 164
<211> LENGTH: 120
<212> TYPE: PRT
<213> ORGANISM: Artificial Sequence
<220> FEATURE:
<223> OTHER INFORMATION: Synthetic

<400> SEQUENCE: 164

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Thr Thr Ile Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Arg His Tyr Ala Met Asp Tyr Trp Gly Gln
            100                 105                 110

Gly Thr Thr Val Thr Val Ser Ser
        115                 120

<210> SEQ ID NO 165
<211> LENGTH: 107
<212> TYPE: PRT
```

<213> ORGANISM: Artificial Sequence
<220> FEATURE:
<223> OTHER INFORMATION: Synthetic

<400> SEQUENCE: 165

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Gly
            20                  25                  30

Val Ala Trp Phe Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ser Thr Pro Leu
                85                  90                  95

Thr Phe Gly Gly Gly Thr Lys Leu Glu Ile Lys
            100                 105

<210> SEQ ID NO 166
<211> LENGTH: 120
<212> TYPE: PRT
<213> ORGANISM: Artificial Sequence
<220> FEATURE:
<223> OTHER INFORMATION: Synthetic

<400> SEQUENCE: 166

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Thr Leu Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Arg Asn Tyr Ala Met Asp Tyr Trp Gly Gln
            100                 105                 110

Gly Thr Thr Val Thr Val Ser Ser
        115                 120

<210> SEQ ID NO 167
<211> LENGTH: 107
<212> TYPE: PRT
<213> ORGANISM: Artificial Sequence
<220> FEATURE:
<223> OTHER INFORMATION: Synthetic

<400> SEQUENCE: 167

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Gly
            20                  25                  30

Val Ser Trp Phe Gln Gln Lys Pro Gly Lys Ala Pro Lys Leu Leu Ile
        35                  40                  45

```
Tyr Ser Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ser Thr Pro Leu
                85                  90                  95

Thr Phe Gly Gly Gly Thr Lys Leu Glu Ile Lys
                100                 105

<210> SEQ ID NO 168
<211> LENGTH: 120
<212> TYPE: PRT
<213> ORGANISM: Artificial Sequence
<220> FEATURE:
<223> OTHER INFORMATION: Synthetic

<400> SEQUENCE: 168

Glu Val Gln Leu Val Glu Ser Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Thr Gly Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Trp Thr Tyr Ala Met Asp Tyr Trp Gly Gln
                100                 105                 110

Gly Thr Thr Val Thr Val Ser Ser
            115                 120

<210> SEQ ID NO 169
<211> LENGTH: 107
<212> TYPE: PRT
<213> ORGANISM: Artificial Sequence
<220> FEATURE:
<223> OTHER INFORMATION: Synthetic

<400> SEQUENCE: 169

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Ala
            20                  25                  30

Val Ser Trp Thr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ser Thr Pro Leu
                85                  90                  95

Thr Phe Gly Gly Gly Thr Lys Leu Glu Ile Lys
                100                 105
```

<210> SEQ ID NO 170
<211> LENGTH: 120
<212> TYPE: PRT
<213> ORGANISM: Artificial Sequence
<220> FEATURE:
<223> OTHER INFORMATION: Synthetic

<400> SEQUENCE: 170

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Asn Phe Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Ser Val Tyr Ala Met Asp Tyr Trp Gly Gln
            100                 105                 110

Gly Thr Thr Val Thr Val Ser Ser
        115                 120
```

<210> SEQ ID NO 171
<211> LENGTH: 107
<212> TYPE: PRT
<213> ORGANISM: Artificial Sequence
<220> FEATURE:
<223> OTHER INFORMATION: Synthetic

<400> SEQUENCE: 171

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Gly
            20                  25                  30

Val Thr Trp Phe Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Ser Thr Pro Leu
                85                  90                  95

Thr Phe Gly Gly Gly Thr Lys Leu Glu Ile Lys
            100                 105
```

<210> SEQ ID NO 172
<211> LENGTH: 120
<212> TYPE: PRT
<213> ORGANISM: Artificial Sequence
<220> FEATURE:
<223> OTHER INFORMATION: Synthetic

<400> SEQUENCE: 172

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30
```

Trp Met Ser Trp Val Arg Gln Ala Pro Gly Lys Gly Leu Glu Trp Val
            35                  40                  45

Ala Glu Ile Asn Pro Glu Arg Asn Tyr Ile Asn Tyr Ala Pro Ser Leu
 50                  55                  60

Lys Asp Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asp Asp Tyr Asp Lys Tyr Ala Met Asp Tyr Trp Gly Gln
                100                 105                 110

Gly Thr Thr Val Thr Val Ser Ser
            115                 120

<210> SEQ ID NO 173
<211> LENGTH: 107
<212> TYPE: PRT
<213> ORGANISM: Artificial Sequence
<220> FEATURE:
<223> OTHER INFORMATION: Synthetic

<400> SEQUENCE: 173

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val Asn Thr Gly
                20                  25                  30

Val Thr Trp Tyr Gln Gln Lys Pro Gly Lys Ala Pro Lys Leu Leu Ile
            35                  40                  45

Tyr Ser Ala Ser Tyr Arg Tyr Thr Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Tyr Ser Thr Pro Leu
                 85                  90                  95

Thr Phe Gly Gly Gly Thr Lys Leu Glu Ile Lys
                100                 105

<210> SEQ ID NO 174
<211> LENGTH: 120
<212> TYPE: PRT
<213> ORGANISM: Artificial Sequence
<220> FEATURE:
<223> OTHER INFORMATION: Synthetic

<400> SEQUENCE: 174

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ile Asp Phe Ser Arg Tyr
                20                  25                  30

Trp Met Ser Trp Val Arg Gln Ala Pro Gly Lys Gly Leu Glu Trp Val
            35                  40                  45

Ala Glu Ile Asn Pro Glu Ser Ser Thr Ile Asn Tyr Ala Pro Ser Leu
 50                  55                  60

Lys Asp Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gln Asp Asp Tyr Glu Tyr Tyr Thr Met Asp Tyr Trp Gly Gln

Gly Thr Thr Val Thr Val Ser Ser
            115                 120

<210> SEQ ID NO 175
<211> LENGTH: 107
<212> TYPE: PRT
<213> ORGANISM: Artificial Sequence
<220> FEATURE:
<223> OTHER INFORMATION: Synthetic

<400> SEQUENCE: 175

Asp Ile Gln Met Thr Gln Ser Pro Ser Ser Leu Ser Ala Ser Val Gly
1               5                   10                  15

Asp Arg Val Thr Ile Thr Cys Lys Val Ser Gln Asp Val Asn Thr Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Trp Ser Thr Pro Leu
                85                  90                  95

Thr Phe Gly Gly Gly Thr Lys Leu Glu Ile Lys
            100                 105

<210> SEQ ID NO 176
<211> LENGTH: 120
<212> TYPE: PRT
<213> ORGANISM: Artificial Sequence
<220> FEATURE:
<223> OTHER INFORMATION: Synthetic

<400> SEQUENCE: 176

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Glu Asp Tyr Glu Tyr Tyr Ala Leu Asp Tyr Trp Gly Gln
            100                 105                 110

Gly Thr Thr Val Thr Val Ser Ser
            115                 120

<210> SEQ ID NO 177
<211> LENGTH: 107
<212> TYPE: PRT
<213> ORGANISM: Artificial Sequence
<220> FEATURE:
<223> OTHER INFORMATION: Synthetic

<400> SEQUENCE: 177

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Asn Thr Gly
            20                  25                  30

Val Tyr Trp Tyr Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Tyr Ser Thr Pro Leu
                85                  90                  95

Thr Phe Gly Gly Gly Thr Lys Leu Glu Ile Lys
            100                 105

<210> SEQ ID NO 178
<211> LENGTH: 120
<212> TYPE: PRT
<213> ORGANISM: Artificial Sequence
<220> FEATURE:
<223> OTHER INFORMATION: Synthetic

<400> SEQUENCE: 178

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Ser Thr Ile Asn Tyr Ala Pro Ser Leu
50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Thr Arg Tyr Tyr Ala Met Asp Tyr Trp Gly Gln
            100                 105                 110

Gly Thr Thr Val Thr Val Ser Ser
            115                 120

<210> SEQ ID NO 179
<211> LENGTH: 107
<212> TYPE: PRT
<213> ORGANISM: Artificial Sequence
<220> FEATURE:
<223> OTHER INFORMATION: Synthetic

<400> SEQUENCE: 179

Asp Ile Gln Met Thr Gln Ser Pro Ser Ser Leu Ser Ala Ser Val Gly
1               5                   10                  15

Asp Arg Val Thr Ile Thr Cys Lys Val Ser Gln Asp Val Asn Thr Gly
            20                  25                  30

Val Ala Trp Tyr Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
50                  55                  60

Ser Gly Ser Gly Thr Asp Phe Thr Phe Thr Ile Ser Ser Leu Gln Pro

```
                65                  70                  75                  80
Glu Asp Ile Ala Thr Tyr Tyr Cys Gln Gln Tyr Tyr Ser Thr Pro Leu
                    85                  90                  95

Thr Phe Gly Gly Gly Thr Lys Leu Glu Ile Lys
            100                 105
```

<210> SEQ ID NO 180
<211> LENGTH: 120
<212> TYPE: PRT
<213> ORGANISM: Artificial Sequence
<220> FEATURE:
<223> OTHER INFORMATION: Synthetic

<400> SEQUENCE: 180

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Leu Tyr Tyr Thr Met Asp Tyr Trp Gly Gln
            100                 105                 110

Gly Thr Thr Val Thr Val Ser Ser
        115                 120
```

<210> SEQ ID NO 181
<211> LENGTH: 120
<212> TYPE: PRT
<213> ORGANISM: Artificial Sequence
<220> FEATURE:
<223> OTHER INFORMATION: Synthetic

<400> SEQUENCE: 181

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Glu Thr Tyr Thr Met Asp Tyr Trp Gly Gln
            100                 105                 110

Gly Thr Thr Val Thr Val Ser Ser
        115                 120
```

<210> SEQ ID NO 182
<211> LENGTH: 120

<212> TYPE: PRT
<213> ORGANISM: Artificial Sequence
<220> FEATURE:
<223> OTHER INFORMATION: Synthetic

<400> SEQUENCE: 182

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Leu Thr Tyr Thr Met Asp Tyr Trp Gly Gln
            100                 105                 110

Gly Thr Thr Val Thr Val Ser Ser
        115                 120

<210> SEQ ID NO 183
<211> LENGTH: 120
<212> TYPE: PRT
<213> ORGANISM: Artificial Sequence
<220> FEATURE:
<223> OTHER INFORMATION: Synthetic

<400> SEQUENCE: 183

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ala Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Glu Tyr Tyr Thr Met Asp Tyr Trp Gly Gln
            100                 105                 110

Gly Thr Thr Val Thr Val Ser Ser
        115                 120

<210> SEQ ID NO 184
<211> LENGTH: 120
<212> TYPE: PRT
<213> ORGANISM: Artificial Sequence
<220> FEATURE:
<223> OTHER INFORMATION: Synthetic

<400> SEQUENCE: 184

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr

```
                    20                  25                  30
Trp Met Ser Trp Val Arg Gln Ala Pro Gly Lys Gly Leu Glu Trp Val
            35                  40                  45

Ala Glu Ile Asn Pro Glu Ser Ser Ile Asn Tyr Ala Pro Ser Leu
 50                  55                  60

Lys Asp Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gln Asp Asp Tyr Glu Tyr Tyr Thr Met Asp Tyr Trp Gly Gln
                100                 105                 110

Gly Thr Thr Val Thr Val Ser Ser
            115                 120

<210> SEQ ID NO 185
<211> LENGTH: 120
<212> TYPE: PRT
<213> ORGANISM: Artificial Sequence
<220> FEATURE:
<223> OTHER INFORMATION: Synthetic

<400> SEQUENCE: 185

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
            35                  40                  45

Ala Glu Ile Asn Pro Glu Ser Ser Thr Ile Asn Tyr Ala Pro Ser Leu
 50                  55                  60

Lys Asp Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Gln Asp Asp Tyr Ser Tyr Tyr Thr Met Asp Tyr Trp Gly Gln
                100                 105                 110

Gly Thr Thr Val Thr Val Ser Ser
            115                 120

<210> SEQ ID NO 186
<211> LENGTH: 120
<212> TYPE: PRT
<213> ORGANISM: Artificial Sequence
<220> FEATURE:
<223> OTHER INFORMATION: Synthetic

<400> SEQUENCE: 186

Glu Val Gln Leu Val Glu Ser Gly Gly Gly Leu Val Gln Pro Gly Gly
 1               5                  10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
            35                  40                  45

Ala Glu Ile Asn Pro Glu Ser Ser Thr Ile Asn Tyr Ala Pro Ser Leu
 50                  55                  60

Lys Asp Arg Phe Thr Ile Ser Arg Asp Asn Ala Lys Asn Ser Leu Tyr
 65                  70                  75                  80
```

Leu Gln Met Asn Ser Leu Arg Ala Glu Asp Thr Ala Val Tyr Tyr Cys
                85                  90                  95

Ala Arg Gln Asp Asp Tyr Glu His Tyr Thr Met Asp Tyr Trp Gly Gln
            100                 105                 110

Gly Thr Thr Val Thr Val Ser Ser
        115                 120

<210> SEQ ID NO 187
<211> LENGTH: 120
<212> TYPE: PRT
<213> ORGANISM: Artificial Sequence
<220> FEATURE:
<223> OTHER INFORMATION: Synthetic

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Ser Thr Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Ser His Tyr Thr Met Asp Tyr Trp Gly Gln
            100                 105                 110

Gly Thr Thr Val Thr Val Ser Ser
        115                 120

<210> SEQ ID NO 188
<211> LENGTH: 120
<212> TYPE: PRT
<213> ORGANISM: Artificial Sequence
<220> FEATURE:
<223> OTHER INFORMATION: Synthetic

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ala Ser Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Glu Tyr Tyr Thr Met Asp Tyr Trp Gly Gln
            100                 105                 110

Gly Thr Thr Val Thr Val Ser Ser
        115                 120

<210> SEQ ID NO 189

<211> LENGTH: 120
<212> TYPE: PRT
<213> ORGANISM: Artificial Sequence
<220> FEATURE:
<223> OTHER INFORMATION: Synthetic

<400> SEQUENCE: 189

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ser Ser Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Ser His Tyr Thr Met Asp Tyr Trp Gly Gln
            100                 105                 110

Gly Thr Thr Val Thr Val Ser Ser
            115                 120

<210> SEQ ID NO 190
<211> LENGTH: 120
<212> TYPE: PRT
<213> ORGANISM: Artificial Sequence
<220> FEATURE:
<223> OTHER INFORMATION: Synthetic

<400> SEQUENCE: 190

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Asn Pro Glu Ala Ser Ser Ile Asn Tyr Ala Pro Ser Leu
    50                  55                  60

Lys Asp Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gln Asp Asp Tyr Ser His Tyr Thr Met Asp Tyr Trp Gly Gln
            100                 105                 110

Gly Thr Thr Val Thr Val Ser Ser
            115                 120

<210> SEQ ID NO 191
<211> LENGTH: 11
<212> TYPE: PRT
<213> ORGANISM: Artificial Sequence
<220> FEATURE:
<223> OTHER INFORMATION: Synthetic

<400> SEQUENCE: 191

Gln Asp Asp Tyr Asp Tyr Tyr Ala Met Asp Tyr
1               5                   10

<210> SEQ ID NO 192
<211> LENGTH: 11
<212> TYPE: PRT
<213> ORGANISM: Artificial Sequence
<220> FEATURE:
<223> OTHER INFORMATION: Synthetic

<400> SEQUENCE: 192

Lys Ala Ser Gln Asp Val Ser Thr Gly Val Ala
1               5                   10

<210> SEQ ID NO 193
<211> LENGTH: 9
<212> TYPE: PRT
<213> ORGANISM: Artificial Sequence
<220> FEATURE:
<223> OTHER INFORMATION: Synthetic

<400> SEQUENCE: 193

His Gln Tyr Tyr Thr Ile Pro Leu Thr
1               5

<210> SEQ ID NO 194
<211> LENGTH: 5
<212> TYPE: PRT
<213> ORGANISM: Artificial Sequence
<220> FEATURE:
<223> OTHER INFORMATION: Synthetic

<400> SEQUENCE: 194

Glu Tyr Ile Met His
1               5

<210> SEQ ID NO 195
<211> LENGTH: 17
<212> TYPE: PRT
<213> ORGANISM: Artificial Sequence
<220> FEATURE:
<223> OTHER INFORMATION: Synthetic

<400> SEQUENCE: 195

Gly Ile Asn Pro Asp Asn Gly Asp Thr Thr Tyr Asn Gln Lys Phe Lys
1               5                   10                  15

Gly

<210> SEQ ID NO 196
<211> LENGTH: 5
<212> TYPE: PRT
<213> ORGANISM: Artificial Sequence
<220> FEATURE:
<223> OTHER INFORMATION: Synthetic

<400> SEQUENCE: 196

Gly Val Leu Asp Tyr
1               5

<210> SEQ ID NO 197
<211> LENGTH: 16
<212> TYPE: PRT
<213> ORGANISM: Artificial Sequence
<220> FEATURE:
<223> OTHER INFORMATION: Synthetic

<400> SEQUENCE: 197

Lys Ser Ser Gln Ser Leu Leu Asp Ser Asp Gly Lys Thr Tyr Leu Asn
1               5                   10                  15

<210> SEQ ID NO 198
<211> LENGTH: 7
<212> TYPE: PRT
<213> ORGANISM: Artificial Sequence
<220> FEATURE:
<223> OTHER INFORMATION: Synthetic

<400> SEQUENCE: 198

Leu Val Ser Lys Leu Asp Ser
1               5

<210> SEQ ID NO 199
<211> LENGTH: 9
<212> TYPE: PRT
<213> ORGANISM: Artificial Sequence
<220> FEATURE:
<223> OTHER INFORMATION: Synthetic

<400> SEQUENCE: 199

Trp Gln Gly Thr His Phe Pro Phe Thr
1               5

<210> SEQ ID NO 200
<211> LENGTH: 17
<212> TYPE: PRT
<213> ORGANISM: Artificial Sequence
<220> FEATURE:
<223> OTHER INFORMATION: Synthetic

<400> SEQUENCE: 200

Gly Ile His Pro Asp Asn Gly Asp Thr Thr Tyr Asn Gln Lys Phe Thr
1               5                   10                  15

Gly

<210> SEQ ID NO 201
<211> LENGTH: 16
<212> TYPE: PRT
<213> ORGANISM: Artificial Sequence
<220> FEATURE:
<223> OTHER INFORMATION: Synthetic

<400> SEQUENCE: 201

Lys Ser Ser Gln Ser Leu Leu Asp Ser Asp Gly Arg Thr Tyr Leu Asn
1               5                   10                  15

<210> SEQ ID NO 202
<211> LENGTH: 17
<212> TYPE: PRT
<213> ORGANISM: Artificial Sequence
<220> FEATURE:
<223> OTHER INFORMATION: Synthetic

<400> SEQUENCE: 202

Ser Ile Ser Tyr Asp Gly Gly Asp Ser Phe Tyr Arg Asp Ser Val Lys
1               5                   10                  15

Gly

<210> SEQ ID NO 203
<211> LENGTH: 11
<212> TYPE: PRT
<213> ORGANISM: Artificial Sequence
<220> FEATURE:
<223> OTHER INFORMATION: Synthetic

<400> SEQUENCE: 203

```
Glu Glu Asp Tyr Ser Gly Ser Phe Pro Asp Tyr
1               5                   10

<210> SEQ ID NO 204
<211> LENGTH: 11
<212> TYPE: PRT
<213> ORGANISM: Artificial Sequence
<220> FEATURE:
<223> OTHER INFORMATION: Synthetic

<400> SEQUENCE: 204

Lys Ala Ser Gln Asn Ile Asn Lys Tyr Leu Asn
1               5                   10

<210> SEQ ID NO 205
<211> LENGTH: 7
<212> TYPE: PRT
<213> ORGANISM: Artificial Sequence
<220> FEATURE:
<223> OTHER INFORMATION: Synthetic

<400> SEQUENCE: 205

Asp Thr Asn Asn Leu Gln Ala
1               5

<210> SEQ ID NO 206
<211> LENGTH: 8
<212> TYPE: PRT
<213> ORGANISM: Artificial Sequence
<220> FEATURE:
<223> OTHER INFORMATION: Synthetic

<400> SEQUENCE: 206

Leu Gln His Asn Ser Leu Tyr Thr
1               5

<210> SEQ ID NO 207
<211> LENGTH: 5
<212> TYPE: PRT
<213> ORGANISM: Artificial Sequence
<220> FEATURE:
<223> OTHER INFORMATION: Synthetic

<400> SEQUENCE: 207

Asp Tyr Ala Trp Asn
1               5

<210> SEQ ID NO 208
<211> LENGTH: 16
<212> TYPE: PRT
<213> ORGANISM: Artificial Sequence
<220> FEATURE:
<223> OTHER INFORMATION: Synthetic

<400> SEQUENCE: 208

Tyr Ile Ser Tyr Ser Gly Asp Thr Ser Tyr Asn Pro Ser Leu Arg Ser
1               5                   10                  15

<210> SEQ ID NO 209
<211> LENGTH: 5
<212> TYPE: PRT
<213> ORGANISM: Artificial Sequence
<220> FEATURE:
<223> OTHER INFORMATION: Synthetic

<400> SEQUENCE: 209
```

Gly His Phe Asp Tyr
1               5

<210> SEQ ID NO 210
<211> LENGTH: 16
<212> TYPE: PRT
<213> ORGANISM: Artificial Sequence
<220> FEATURE:
<223> OTHER INFORMATION: Synthetic

<400> SEQUENCE: 210

Lys Ser Ser Gln Ser Leu Leu Asp Ser Asp Gly Glu Thr Tyr Leu Asn
1               5                   10                  15

<210> SEQ ID NO 211
<211> LENGTH: 9
<212> TYPE: PRT
<213> ORGANISM: Artificial Sequence
<220> FEATURE:
<223> OTHER INFORMATION: Synthetic

<400> SEQUENCE: 211

Trp Gln Gly Thr His Phe Pro Tyr Thr
1               5

<210> SEQ ID NO 212
<211> LENGTH: 17
<212> TYPE: PRT
<213> ORGANISM: Artificial Sequence
<220> FEATURE:
<223> OTHER INFORMATION: Synthetic

<400> SEQUENCE: 212

Gly Ile Asn Pro Asn Asn Gly Gly Thr Thr Tyr Asn Gln Lys Phe Lys
1               5                   10                  15

Gly

<210> SEQ ID NO 213
<211> LENGTH: 5
<212> TYPE: PRT
<213> ORGANISM: Artificial Sequence
<220> FEATURE:
<223> OTHER INFORMATION: Synthetic

<400> SEQUENCE: 213

Gly Val Met Asp Tyr
1               5

<210> SEQ ID NO 214
<211> LENGTH: 16
<212> TYPE: PRT
<213> ORGANISM: Artificial Sequence
<220> FEATURE:
<223> OTHER INFORMATION: Synthetic

<400> SEQUENCE: 214

Tyr Ile Ser Tyr Thr Gly Ser Ser Ser Tyr Asn Pro Ser Leu Lys Ser
1               5                   10                  15

<210> SEQ ID NO 215
<211> LENGTH: 7
<212> TYPE: PRT
<213> ORGANISM: Artificial Sequence
<220> FEATURE:
<223> OTHER INFORMATION: Synthetic

<400> SEQUENCE: 215

```
Gln Val Ser Lys Leu Asp Ser
1               5

<210> SEQ ID NO 216
<211> LENGTH: 7
<212> TYPE: PRT
<213> ORGANISM: Artificial Sequence
<220> FEATURE:
<223> OTHER INFORMATION: Synthetic

<400> SEQUENCE: 216

Thr Ser Ala Met Val Val Ser
1               5

<210> SEQ ID NO 217
<211> LENGTH: 16
<212> TYPE: PRT
<213> ORGANISM: Artificial Sequence
<220> FEATURE:
<223> OTHER INFORMATION: Synthetic

<400> SEQUENCE: 217

Ala Ile Asp Trp Glu Gly Asp Lys Tyr Tyr Asn Pro Ser Leu Glu Ser
1               5                   10                  15

<210> SEQ ID NO 218
<211> LENGTH: 12
<212> TYPE: PRT
<213> ORGANISM: Artificial Sequence
<220> FEATURE:
<223> OTHER INFORMATION: Synthetic

<400> SEQUENCE: 218

Met Ser Ser Ala Asp Ser His Ser Val Leu Asp Ala
1               5                   10

<210> SEQ ID NO 219
<211> LENGTH: 11
<212> TYPE: PRT
<213> ORGANISM: Artificial Sequence
<220> FEATURE:
<223> OTHER INFORMATION: Synthetic

<400> SEQUENCE: 219

Lys Ala Ser Gln Asn Ile His Asn Tyr Leu Asn
1               5                   10

<210> SEQ ID NO 220
<211> LENGTH: 7
<212> TYPE: PRT
<213> ORGANISM: Artificial Sequence
<220> FEATURE:
<223> OTHER INFORMATION: Synthetic

<400> SEQUENCE: 220

Asn Thr Asn Asn Leu Gln Thr
1               5

<210> SEQ ID NO 221
<211> LENGTH: 8
<212> TYPE: PRT
<213> ORGANISM: Artificial Sequence
<220> FEATURE:
<223> OTHER INFORMATION: Synthetic

<400> SEQUENCE: 221
```

Leu Gln His Ser Ser Ser Leu Thr
1               5

<210> SEQ ID NO 222
<211> LENGTH: 5
<212> TYPE: PRT
<213> ORGANISM: Artificial Sequence
<220> FEATURE:
<223> OTHER INFORMATION: Synthetic

<400> SEQUENCE: 222

Asp Phe Tyr Ile Asn
1               5

<210> SEQ ID NO 223
<211> LENGTH: 19
<212> TYPE: PRT
<213> ORGANISM: Artificial Sequence
<220> FEATURE:
<223> OTHER INFORMATION: Synthetic

<400> SEQUENCE: 223

Phe Met Arg Asn Lys Ala Asn Gly Tyr Thr Thr Glu Tyr Asn Pro Ser
1               5                   10                  15

Val Lys Gly

<210> SEQ ID NO 224
<211> LENGTH: 15
<212> TYPE: PRT
<213> ORGANISM: Artificial Sequence
<220> FEATURE:
<223> OTHER INFORMATION: Synthetic

<400> SEQUENCE: 224

Ser Arg Tyr Asn Ala Asp Asp Tyr Tyr Val Gly Val Met Asp Val
1               5                   10                  15

<210> SEQ ID NO 225
<211> LENGTH: 11
<212> TYPE: PRT
<213> ORGANISM: Artificial Sequence
<220> FEATURE:
<223> OTHER INFORMATION: Synthetic

<400> SEQUENCE: 225

Leu Ala Ser Glu Asp Ile Tyr Asn Asn Leu Ala
1               5                   10

<210> SEQ ID NO 226
<211> LENGTH: 7
<212> TYPE: PRT
<213> ORGANISM: Artificial Sequence
<220> FEATURE:
<223> OTHER INFORMATION: Synthetic

<400> SEQUENCE: 226

Tyr Thr Asn Ser Leu Gln Asp
1               5

<210> SEQ ID NO 227
<211> LENGTH: 9
<212> TYPE: PRT
<213> ORGANISM: Artificial Sequence
<220> FEATURE:
<223> OTHER INFORMATION: Synthetic

<400> SEQUENCE: 227

```
Leu Gln Asp Ser Glu Tyr Pro Trp Thr
1               5
```

<210> SEQ ID NO 228
<211> LENGTH: 6
<212> TYPE: PRT
<213> ORGANISM: Artificial Sequence
<220> FEATURE:
<223> OTHER INFORMATION: Synthetic

<400> SEQUENCE: 228

```
Ser Asp Tyr Ala Trp Asn
1               5
```

<210> SEQ ID NO 229
<211> LENGTH: 16
<212> TYPE: PRT
<213> ORGANISM: Artificial Sequence
<220> FEATURE:
<223> OTHER INFORMATION: Synthetic

<400> SEQUENCE: 229

```
Tyr Ile Ser Tyr Ser Gly Asp Thr Ser Tyr Asn Pro Ser Leu Lys Ser
1               5                   10                  15
```

<210> SEQ ID NO 230
<211> LENGTH: 7
<212> TYPE: PRT
<213> ORGANISM: Artificial Sequence
<220> FEATURE:
<223> OTHER INFORMATION: Synthetic

<400> SEQUENCE: 230

```
Leu Val Ser Asn Leu Asp Ser
1               5
```

<210> SEQ ID NO 231
<211> LENGTH: 16
<212> TYPE: PRT
<213> ORGANISM: Artificial Sequence
<220> FEATURE:
<223> OTHER INFORMATION: Synthetic

<400> SEQUENCE: 231

```
Tyr Ile Ser Tyr Ser Gly Ser Thr Ser Tyr Asn Pro Ser Leu Lys Ser
1               5                   10                  15
```

<210> SEQ ID NO 232
<211> LENGTH: 17
<212> TYPE: PRT
<213> ORGANISM: Artificial Sequence
<220> FEATURE:
<223> OTHER INFORMATION: Synthetic

<400> SEQUENCE: 232

```
Thr Ile Ser Asp Gly Gly Ser Asp Thr Tyr Tyr Pro Asp Asn Val Lys
1               5                   10                  15

Gly
```

<210> SEQ ID NO 233
<211> LENGTH: 14
<212> TYPE: PRT
<213> ORGANISM: Artificial Sequence
<220> FEATURE:
<223> OTHER INFORMATION: Synthetic

<400> SEQUENCE: 233

Asp Tyr Tyr Gly Ser Ser Tyr Glu Asp Tyr Ala Met Asp Tyr
1               5                   10

<210> SEQ ID NO 234
<211> LENGTH: 11
<212> TYPE: PRT
<213> ORGANISM: Artificial Sequence
<220> FEATURE:
<223> OTHER INFORMATION: Synthetic

<400> SEQUENCE: 234

Lys Ala Ser Gln Asp Ile Asn Lys Tyr Ile Thr
1               5                   10

<210> SEQ ID NO 235
<211> LENGTH: 6
<212> TYPE: PRT
<213> ORGANISM: Artificial Sequence
<220> FEATURE:
<223> OTHER INFORMATION: Synthetic

<400> SEQUENCE: 235

Ser Asp Tyr Ala Trp Ser
1               5

<210> SEQ ID NO 236
<211> LENGTH: 16
<212> TYPE: PRT
<213> ORGANISM: Artificial Sequence
<220> FEATURE:
<223> OTHER INFORMATION: Synthetic

<400> SEQUENCE: 236

Tyr Ile Ser Tyr Ser Asp Ser Thr Ser Tyr Asn Pro Ser Leu Lys Ser
1               5                   10                  15

<210> SEQ ID NO 237
<211> LENGTH: 16
<212> TYPE: PRT
<213> ORGANISM: Artificial Sequence
<220> FEATURE:
<223> OTHER INFORMATION: Synthetic

<400> SEQUENCE: 237

Tyr Ile Thr Tyr Ser Asp Ser Thr Ser Tyr Asn Pro Ser Leu Lys Ser
1               5                   10                  15

<210> SEQ ID NO 238
<211> LENGTH: 17
<212> TYPE: PRT
<213> ORGANISM: Artificial Sequence
<220> FEATURE:
<223> OTHER INFORMATION: Synthetic

<400> SEQUENCE: 238

Asp Ile Asn Pro Asn Asn Asp Gly Thr Thr Tyr Asn Gln Lys Phe Lys
1               5                   10                  15

Asp

<210> SEQ ID NO 239
<211> LENGTH: 10
<212> TYPE: PRT
<213> ORGANISM: Artificial Sequence
<220> FEATURE:
<223> OTHER INFORMATION: Synthetic

```
<400> SEQUENCE: 239

Leu Ser Trp Ser Phe Phe Ala Met Asp Tyr
1               5                  10

<210> SEQ ID NO 240
<211> LENGTH: 11
<212> TYPE: PRT
<213> ORGANISM: Artificial Sequence
<220> FEATURE:
<223> OTHER INFORMATION: Synthetic

<400> SEQUENCE: 240

Lys Ala Ser Gln Asp Val Ser Ser Gly Val Ala
1               5                  10

<210> SEQ ID NO 241
<211> LENGTH: 7
<212> TYPE: PRT
<213> ORGANISM: Artificial Sequence
<220> FEATURE:
<223> OTHER INFORMATION: Synthetic

<400> SEQUENCE: 241

Ser Ala Ser His Arg His Thr
1               5

<210> SEQ ID NO 242
<211> LENGTH: 9
<212> TYPE: PRT
<213> ORGANISM: Artificial Sequence
<220> FEATURE:
<223> OTHER INFORMATION: Synthetic

<400> SEQUENCE: 242

Gln Gln Tyr Tyr Asn Thr Pro Trp Thr
1               5

<210> SEQ ID NO 243
<211> LENGTH: 5
<212> TYPE: PRT
<213> ORGANISM: Artificial Sequence
<220> FEATURE:
<223> OTHER INFORMATION: Synthetic

<400> SEQUENCE: 243

Thr Tyr Trp Ile Glu
1               5

<210> SEQ ID NO 244
<211> LENGTH: 17
<212> TYPE: PRT
<213> ORGANISM: Artificial Sequence
<220> FEATURE:
<223> OTHER INFORMATION: Synthetic

<400> SEQUENCE: 244

Glu Ile Leu Pro Gly Ser Glu Ser Thr Asp Tyr Asn Glu Lys Phe Lys
1               5                  10                  15

Asp

<210> SEQ ID NO 245
<211> LENGTH: 9
<212> TYPE: PRT
<213> ORGANISM: Artificial Sequence
<220> FEATURE:
```

<223> OTHER INFORMATION: Synthetic

<400> SEQUENCE: 245

Asp Tyr Tyr Gly Tyr Tyr Phe Asp Tyr
1               5

<210> SEQ ID NO 246
<211> LENGTH: 11
<212> TYPE: PRT
<213> ORGANISM: Artificial Sequence
<220> FEATURE:
<223> OTHER INFORMATION: Synthetic

<400> SEQUENCE: 246

Lys Ala Ser Gln Asp Val Ser Thr Ala Val Val
1               5                   10

<210> SEQ ID NO 247
<211> LENGTH: 9
<212> TYPE: PRT
<213> ORGANISM: Artificial Sequence
<220> FEATURE:
<223> OTHER INFORMATION: Synthetic

<400> SEQUENCE: 247

Gln Gln His Tyr Ser Ser Pro Arg Thr
1               5

<210> SEQ ID NO 248
<211> LENGTH: 17
<212> TYPE: PRT
<213> ORGANISM: Artificial Sequence
<220> FEATURE:
<223> OTHER INFORMATION: Synthetic

<400> SEQUENCE: 248

Glu Ile Leu Pro Gly Ser Asp Ser Thr Asn Ser Asn Glu Lys Phe Glu
1               5                   10                  15

Gly

<210> SEQ ID NO 249
<211> LENGTH: 9
<212> TYPE: PRT
<213> ORGANISM: Artificial Sequence
<220> FEATURE:
<223> OTHER INFORMATION: Synthetic

<400> SEQUENCE: 249

Asp Tyr Tyr Gly Phe Tyr Phe Asp Tyr
1               5

<210> SEQ ID NO 250
<211> LENGTH: 11
<212> TYPE: PRT
<213> ORGANISM: Artificial Sequence
<220> FEATURE:
<223> OTHER INFORMATION: Synthetic

<400> SEQUENCE: 250

Lys Ala Ser Gln Asp Val Ser Thr Ala Val Ala
1               5                   10

<210> SEQ ID NO 251
<211> LENGTH: 7
<212> TYPE: PRT
<213> ORGANISM: Artificial Sequence

```
<220> FEATURE:
<223> OTHER INFORMATION: Synthetic

<400> SEQUENCE: 251

Ser Thr Ser Tyr Arg Tyr Thr
1               5

<210> SEQ ID NO 252
<211> LENGTH: 9
<212> TYPE: PRT
<213> ORGANISM: Artificial Sequence
<220> FEATURE:
<223> OTHER INFORMATION: Synthetic

<400> SEQUENCE: 252

Gln Gln His Tyr Thr Thr Pro Arg Thr
1               5

<210> SEQ ID NO 253
<211> LENGTH: 17
<212> TYPE: PRT
<213> ORGANISM: Artificial Sequence
<220> FEATURE:
<223> OTHER INFORMATION: Synthetic

<400> SEQUENCE: 253

Asp Ile Asn Pro Asn Asn Gly Asp Thr Thr Tyr Asn Gln Lys Phe Lys
1               5                   10                  15

Gly

<210> SEQ ID NO 254
<211> LENGTH: 10
<212> TYPE: PRT
<213> ORGANISM: Artificial Sequence
<220> FEATURE:
<223> OTHER INFORMATION: Synthetic

<400> SEQUENCE: 254

Tyr Asp Glu Asp His Tyr Ala Met Asp Tyr
1               5                   10

<210> SEQ ID NO 255
<211> LENGTH: 9
<212> TYPE: PRT
<213> ORGANISM: Artificial Sequence
<220> FEATURE:
<223> OTHER INFORMATION: Synthetic

<400> SEQUENCE: 255

Gln Gln Tyr Tyr Thr Thr Pro Trp Thr
1               5

<210> SEQ ID NO 256
<211> LENGTH: 17
<212> TYPE: PRT
<213> ORGANISM: Artificial Sequence
<220> FEATURE:
<223> OTHER INFORMATION: Synthetic

<400> SEQUENCE: 256

Asp Ile Asn Pro Asn Asn Gly Asp Ile Ile Tyr Asn Gln Lys Phe Lys
1               5                   10                  15

Gly

<210> SEQ ID NO 257
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 257

Tyr Tyr Asp Pro Tyr Tyr His Ala Met Asp Tyr
1               5                   10

<210> SEQ ID NO 258
<211> LENGTH: 9
<212> TYPE: PRT
<213> ORGANISM: Artificial Sequence
<220> FEATURE:
<223> OTHER INFORMATION: Synthetic

<400> SEQUENCE: 258

Gln Gln Gln Tyr Ser Val Pro Leu Thr
1               5

<210> SEQ ID NO 259
<211> LENGTH: 5
<212> TYPE: PRT
<213> ORGANISM: Artificial Sequence
<220> FEATURE:
<223> OTHER INFORMATION: Synthetic

<400> SEQUENCE: 259

Ser Tyr Trp Met His
1               5

<210> SEQ ID NO 260
<211> LENGTH: 17
<212> TYPE: PRT
<213> ORGANISM: Artificial Sequence
<220> FEATURE:
<223> OTHER INFORMATION: Synthetic

<400> SEQUENCE: 260

Gly Ile Asp Pro Asp Ser Gly Ala Thr Lys Asp Asn Glu Lys Phe Lys
1               5                   10                  15

Thr

<210> SEQ ID NO 261
<211> LENGTH: 15
<212> TYPE: PRT
<213> ORGANISM: Artificial Sequence
<220> FEATURE:
<223> OTHER INFORMATION: Synthetic

<400> SEQUENCE: 261

Gly Ser Thr Val Val Ala Pro Gly Asp Tyr Phe Ala Met Asp Tyr
1               5                   10                  15

<210> SEQ ID NO 262
<211> LENGTH: 15
<212> TYPE: PRT
<213> ORGANISM: Artificial Sequence
<220> FEATURE:
<223> OTHER INFORMATION: Synthetic

<400> SEQUENCE: 262

Arg Ala Ser Glu Ser Val Asp Asn Tyr Gly Ile Ser Phe Met His
1               5                   10                  15
```

```
<210> SEQ ID NO 263
<211> LENGTH: 7
<212> TYPE: PRT
<213> ORGANISM: Artificial Sequence
<220> FEATURE:
<223> OTHER INFORMATION: Synthetic

<400> SEQUENCE: 263

Arg Ala Ser Asn Leu Asp Ser
1               5

<210> SEQ ID NO 264
<211> LENGTH: 9
<212> TYPE: PRT
<213> ORGANISM: Artificial Sequence
<220> FEATURE:
<223> OTHER INFORMATION: Synthetic

<400> SEQUENCE: 264

Gln Gln Ser Asn Lys Asp Pro Trp Thr
1               5

<210> SEQ ID NO 265
<211> LENGTH: 7
<212> TYPE: PRT
<213> ORGANISM: Artificial Sequence
<220> FEATURE:
<223> OTHER INFORMATION: Synthetic

<400> SEQUENCE: 265

Val Phe Gly Met Gly Val Gly
1               5

<210> SEQ ID NO 266
<211> LENGTH: 16
<212> TYPE: PRT
<213> ORGANISM: Artificial Sequence
<220> FEATURE:
<223> OTHER INFORMATION: Synthetic

<400> SEQUENCE: 266

His Ile Trp Trp Asp Asp Glu Lys Tyr Tyr Asn Pro Ala Leu Lys Ser
1               5                   10                  15

<210> SEQ ID NO 267
<211> LENGTH: 9
<212> TYPE: PRT
<213> ORGANISM: Artificial Sequence
<220> FEATURE:
<223> OTHER INFORMATION: Synthetic

<400> SEQUENCE: 267

Ile Asp Gly Tyr Tyr Asp Phe Asp Tyr
1               5

<210> SEQ ID NO 268
<211> LENGTH: 16
<212> TYPE: PRT
<213> ORGANISM: Artificial Sequence
<220> FEATURE:
<223> OTHER INFORMATION: Synthetic

<400> SEQUENCE: 268

Arg Ser Ser His Ser Ile Val Gln Asp Asn Gly Asn Thr Tyr Leu Gln
1               5                   10                  15

<210> SEQ ID NO 269
```

<211> LENGTH: 7
<212> TYPE: PRT
<213> ORGANISM: Artificial Sequence
<220> FEATURE:
<223> OTHER INFORMATION: Synthetic

<400> SEQUENCE: 269

Lys Val Ser Asn Arg Phe Ser
1               5

<210> SEQ ID NO 270
<211> LENGTH: 9
<212> TYPE: PRT
<213> ORGANISM: Artificial Sequence
<220> FEATURE:
<223> OTHER INFORMATION: Synthetic

<400> SEQUENCE: 270

Phe Gln Gly Ser Tyr Val Pro Tyr Thr
1               5

<210> SEQ ID NO 271
<211> LENGTH: 7
<212> TYPE: PRT
<213> ORGANISM: Artificial Sequence
<220> FEATURE:
<223> OTHER INFORMATION: Synthetic

<400> SEQUENCE: 271

Thr Ser Gly Met His Val Gly
1               5

<210> SEQ ID NO 272
<211> LENGTH: 16
<212> TYPE: PRT
<213> ORGANISM: Artificial Sequence
<220> FEATURE:
<223> OTHER INFORMATION: Synthetic

<400> SEQUENCE: 272

His Ile Tyr Trp Asp Asp Asp Lys Arg Tyr Asn Pro Ser Leu Lys Ser
1               5                   10                  15

<210> SEQ ID NO 273
<211> LENGTH: 13
<212> TYPE: PRT
<213> ORGANISM: Artificial Sequence
<220> FEATURE:
<223> OTHER INFORMATION: Synthetic

<400> SEQUENCE: 273

Arg Gly Gly Asp Tyr Asp Tyr Asp Glu Gly Phe Asp Tyr
1               5                   10

<210> SEQ ID NO 274
<211> LENGTH: 16
<212> TYPE: PRT
<213> ORGANISM: Artificial Sequence
<220> FEATURE:
<223> OTHER INFORMATION: Synthetic

<400> SEQUENCE: 274

Arg Ser Ser Gln Ser Leu Val His Ser Asn Gly Phe Thr Tyr Leu His
1               5                   10                  15

<210> SEQ ID NO 275
<211> LENGTH: 9

```
<212> TYPE: PRT
<213> ORGANISM: Artificial Sequence
<220> FEATURE:
<223> OTHER INFORMATION: Synthetic

<400> SEQUENCE: 275

Ser Gln Ser Thr His Val Pro Tyr Thr
1               5

<210> SEQ ID NO 276
<211> LENGTH: 6
<212> TYPE: PRT
<213> ORGANISM: Artificial Sequence
<220> FEATURE:
<223> OTHER INFORMATION: Synthetic

<400> SEQUENCE: 276

Thr Asp Tyr Tyr Met Thr
1               5

<210> SEQ ID NO 277
<211> LENGTH: 17
<212> TYPE: PRT
<213> ORGANISM: Artificial Sequence
<220> FEATURE:
<223> OTHER INFORMATION: Synthetic

<400> SEQUENCE: 277

Asn Ile Asn Tyr Asp Gly Ser Arg Thr Asn Tyr Leu Asp Ser Leu Lys
1               5                   10                  15
Ser

<210> SEQ ID NO 278
<211> LENGTH: 11
<212> TYPE: PRT
<213> ORGANISM: Artificial Sequence
<220> FEATURE:
<223> OTHER INFORMATION: Synthetic

<400> SEQUENCE: 278

Asp Gly Asn Tyr His Phe Tyr Gly Met Asp Tyr
1               5                   10

<210> SEQ ID NO 279
<211> LENGTH: 7
<212> TYPE: PRT
<213> ORGANISM: Artificial Sequence
<220> FEATURE:
<223> OTHER INFORMATION: Synthetic

<400> SEQUENCE: 279

Trp Ala Ser Thr Arg His Thr
1               5

<210> SEQ ID NO 280
<211> LENGTH: 9
<212> TYPE: PRT
<213> ORGANISM: Artificial Sequence
<220> FEATURE:
<223> OTHER INFORMATION: Synthetic

<400> SEQUENCE: 280

Gln Gln His Tyr Ser Thr Pro Trp Thr
1               5

<210> SEQ ID NO 281
```

```
<211> LENGTH: 5
<212> TYPE: PRT
<213> ORGANISM: Artificial Sequence
<220> FEATURE:
<223> OTHER INFORMATION: Synthetic

<400> SEQUENCE: 281

Asn His Leu Ile Glu
1               5

<210> SEQ ID NO 282
<211> LENGTH: 17
<212> TYPE: PRT
<213> ORGANISM: Artificial Sequence
<220> FEATURE:
<223> OTHER INFORMATION: Synthetic

<400> SEQUENCE: 282

Val Ile Asn Pro Gly Ser Gly Gly Thr Lys Tyr Asn Glu Lys Phe Lys
1               5                   10                  15

Gly

<210> SEQ ID NO 283
<211> LENGTH: 13
<212> TYPE: PRT
<213> ORGANISM: Artificial Sequence
<220> FEATURE:
<223> OTHER INFORMATION: Synthetic

<400> SEQUENCE: 283

Ser Ser Asp Gly Tyr Tyr Glu Glu Asp Tyr Phe Asp Tyr
1               5                   10

<210> SEQ ID NO 284
<211> LENGTH: 10
<212> TYPE: PRT
<213> ORGANISM: Artificial Sequence
<220> FEATURE:
<223> OTHER INFORMATION: Synthetic

<400> SEQUENCE: 284

Ser Ala Ser Ser Ser Val Asn Tyr Met Gln
1               5                   10

<210> SEQ ID NO 285
<211> LENGTH: 7
<212> TYPE: PRT
<213> ORGANISM: Artificial Sequence
<220> FEATURE:
<223> OTHER INFORMATION: Synthetic

<400> SEQUENCE: 285

Asp Thr Ser Glu Leu Ala Ser
1               5

<210> SEQ ID NO 286
<211> LENGTH: 9
<212> TYPE: PRT
<213> ORGANISM: Artificial Sequence
<220> FEATURE:
<223> OTHER INFORMATION: Synthetic

<400> SEQUENCE: 286

Gln Gln Trp Ser Ser Asp Pro Ile Thr
1               5
```

```
<210> SEQ ID NO 287
<211> LENGTH: 17
<212> TYPE: PRT
<213> ORGANISM: Artificial Sequence
<220> FEATURE:
<223> OTHER INFORMATION: Synthetic

<400> SEQUENCE: 287

Asn Ile Asn Tyr Asp Gly Ser Asp Thr Tyr Tyr Leu Asp Ser Leu Lys
1               5                   10                  15
Ser

<210> SEQ ID NO 288
<211> LENGTH: 12
<212> TYPE: PRT
<213> ORGANISM: Artificial Sequence
<220> FEATURE:
<223> OTHER INFORMATION: Synthetic

<400> SEQUENCE: 288

Asp Val Ala Tyr Asp Asp Ser Tyr Ala Met Asp Tyr
1               5                   10

<210> SEQ ID NO 289
<211> LENGTH: 8
<212> TYPE: PRT
<213> ORGANISM: Artificial Sequence
<220> FEATURE:
<223> OTHER INFORMATION: Synthetic

<400> SEQUENCE: 289

Leu Gln Tyr Asp Ser Leu Tyr Thr
1               5

<210> SEQ ID NO 290
<211> LENGTH: 7
<212> TYPE: PRT
<213> ORGANISM: Artificial Sequence
<220> FEATURE:
<223> OTHER INFORMATION: Synthetic

<400> SEQUENCE: 290

Thr Ser Asn Met Gly Val Gly
1               5

<210> SEQ ID NO 291
<211> LENGTH: 16
<212> TYPE: PRT
<213> ORGANISM: Artificial Sequence
<220> FEATURE:
<223> OTHER INFORMATION: Synthetic

<400> SEQUENCE: 291

His Ile Trp Trp Asp Asp Val Lys Arg Tyr Asn Pro Ala Leu Lys Ser
1               5                   10                  15

<210> SEQ ID NO 292
<211> LENGTH: 9
<212> TYPE: PRT
<213> ORGANISM: Artificial Sequence
<220> FEATURE:
<223> OTHER INFORMATION: Synthetic

<400> SEQUENCE: 292

Ser Thr Thr Leu Val Ala Phe Asp Tyr
1               5
```

<210> SEQ ID NO 293
<211> LENGTH: 17
<212> TYPE: PRT
<213> ORGANISM: Artificial Sequence
<220> FEATURE:
<223> OTHER INFORMATION: Synthetic

<400> SEQUENCE: 293

Lys Ser Ser Gln Ser Leu Leu Asn Ser Gly Asn Gln Lys Asn Tyr Leu
1               5                   10                  15

Thr

<210> SEQ ID NO 294
<211> LENGTH: 7
<212> TYPE: PRT
<213> ORGANISM: Artificial Sequence
<220> FEATURE:
<223> OTHER INFORMATION: Synthetic

<400> SEQUENCE: 294

Trp Ala Ser Thr Arg Glu Ser
1               5

<210> SEQ ID NO 295
<211> LENGTH: 8
<212> TYPE: PRT
<213> ORGANISM: Artificial Sequence
<220> FEATURE:
<223> OTHER INFORMATION: Synthetic

<400> SEQUENCE: 295

Gln Asn Asp Tyr Ser Tyr Pro Thr
1               5

<210> SEQ ID NO 296
<211> LENGTH: 7
<212> TYPE: PRT
<213> ORGANISM: Artificial Sequence
<220> FEATURE:
<223> OTHER INFORMATION: Synthetic

<400> SEQUENCE: 296

Thr Ser Gly Met Gly Ile Gly
1               5

<210> SEQ ID NO 297
<211> LENGTH: 16
<212> TYPE: PRT
<213> ORGANISM: Artificial Sequence
<220> FEATURE:
<223> OTHER INFORMATION: Synthetic

<400> SEQUENCE: 297

His Ile Trp Trp Asp Asp Ile Lys Arg Tyr Asn Pro Ala Leu Lys Ser
1               5                   10                  15

<210> SEQ ID NO 298
<211> LENGTH: 9
<212> TYPE: PRT
<213> ORGANISM: Artificial Sequence
<220> FEATURE:
<223> OTHER INFORMATION: Synthetic

<400> SEQUENCE: 298

Ser Thr Thr Val Val Ala Phe Asp Tyr
1               5

```
<210> SEQ ID NO 299
<211> LENGTH: 8
<212> TYPE: PRT
<213> ORGANISM: Artificial Sequence
<220> FEATURE:
<223> OTHER INFORMATION: Synthetic

<400> SEQUENCE: 299

Gln Asn Asp Tyr Asp Tyr Pro Thr
1               5

<210> SEQ ID NO 300
<211> LENGTH: 7
<212> TYPE: PRT
<213> ORGANISM: Artificial Sequence
<220> FEATURE:
<223> OTHER INFORMATION: Synthetic

<400> SEQUENCE: 300

Thr Tyr Gly Met Gly Val Gly
1               5

<210> SEQ ID NO 301
<211> LENGTH: 16
<212> TYPE: PRT
<213> ORGANISM: Artificial Sequence
<220> FEATURE:
<223> OTHER INFORMATION: Synthetic

<400> SEQUENCE: 301

Asn Ile Trp Trp Asp Asp Asp Lys Tyr Tyr Asn Pro Ser Leu Gln Asn
1               5                   10                  15

<210> SEQ ID NO 302
<211> LENGTH: 12
<212> TYPE: PRT
<213> ORGANISM: Artificial Sequence
<220> FEATURE:
<223> OTHER INFORMATION: Synthetic

<400> SEQUENCE: 302

Ser Glu Leu Ile Met Pro Tyr Val Pro Phe Asp Tyr
1               5                   10

<210> SEQ ID NO 303
<211> LENGTH: 11
<212> TYPE: PRT
<213> ORGANISM: Artificial Sequence
<220> FEATURE:
<223> OTHER INFORMATION: Synthetic

<400> SEQUENCE: 303

Gln Ala Ser Gln Asp Ile Asp Asn His Leu Ile
1               5                   10

<210> SEQ ID NO 304
<211> LENGTH: 7
<212> TYPE: PRT
<213> ORGANISM: Artificial Sequence
<220> FEATURE:
<223> OTHER INFORMATION: Synthetic

<400> SEQUENCE: 304

Tyr Ala Thr Asn Leu Ala Asn
1               5
```

<210> SEQ ID NO 305
<211> LENGTH: 9
<212> TYPE: PRT
<213> ORGANISM: Artificial Sequence
<220> FEATURE:
<223> OTHER INFORMATION: Synthetic

<400> SEQUENCE: 305

Leu Gln Phe Lys Gln Tyr Pro Phe Thr
1               5

<210> SEQ ID NO 306
<211> LENGTH: 6
<212> TYPE: PRT
<213> ORGANISM: Artificial Sequence
<220> FEATURE:
<223> OTHER INFORMATION: Synthetic

<400> SEQUENCE: 306

Ser Ser Tyr Trp Trp Thr
1               5

<210> SEQ ID NO 307
<211> LENGTH: 7
<212> TYPE: PRT
<213> ORGANISM: Artificial Sequence
<220> FEATURE:
<223> OTHER INFORMATION: Synthetic

<400> SEQUENCE: 307

Ile Tyr His Ser Gly Arg Pro
1               5

<210> SEQ ID NO 308
<211> LENGTH: 11
<212> TYPE: PRT
<213> ORGANISM: Artificial Sequence
<220> FEATURE:
<223> OTHER INFORMATION: Synthetic

<400> SEQUENCE: 308

Thr Ala Ala Val Ser Tyr Trp Tyr Phe Asp Leu
1               5                   10

<210> SEQ ID NO 309
<211> LENGTH: 11
<212> TYPE: PRT
<213> ORGANISM: Artificial Sequence
<220> FEATURE:
<223> OTHER INFORMATION: Synthetic

<400> SEQUENCE: 309

Gln Ala Ser Gln Asp Ile Gly Asn Asp Leu Ile
1               5                   10

<210> SEQ ID NO 310
<211> LENGTH: 7
<212> TYPE: PRT
<213> ORGANISM: Artificial Sequence
<220> FEATURE:
<223> OTHER INFORMATION: Synthetic

<400> SEQUENCE: 310

Tyr Ala Ser Asn Leu Ala Asn
1               5

```
<210> SEQ ID NO 311
<211> LENGTH: 6
<212> TYPE: PRT
<213> ORGANISM: Artificial Sequence
<220> FEATURE:
<223> OTHER INFORMATION: Synthetic

<400> SEQUENCE: 311

Ser Arg Asn Trp Trp Gly
1               5

<210> SEQ ID NO 312
<211> LENGTH: 7
<212> TYPE: PRT
<213> ORGANISM: Artificial Sequence
<220> FEATURE:
<223> OTHER INFORMATION: Synthetic

<400> SEQUENCE: 312

Ile Tyr His Ser Gly Gly Thr
1               5

<210> SEQ ID NO 313
<211> LENGTH: 11
<212> TYPE: PRT
<213> ORGANISM: Artificial Sequence
<220> FEATURE:
<223> OTHER INFORMATION: Synthetic

<400> SEQUENCE: 313

Glu Phe Gly Asp Ser Val Trp Tyr Phe Asp Leu
1               5                   10

<210> SEQ ID NO 314
<211> LENGTH: 11
<212> TYPE: PRT
<213> ORGANISM: Artificial Sequence
<220> FEATURE:
<223> OTHER INFORMATION: Synthetic

<400> SEQUENCE: 314

Gln Ala Ser Gln Asp Ile Gly Asn Asp Leu Val
1               5                   10

<210> SEQ ID NO 315
<211> LENGTH: 7
<212> TYPE: PRT
<213> ORGANISM: Artificial Sequence
<220> FEATURE:
<223> OTHER INFORMATION: Synthetic

<400> SEQUENCE: 315

Tyr Ala Thr Asn Leu Ala Asp
1               5

<210> SEQ ID NO 316
<211> LENGTH: 9
<212> TYPE: PRT
<213> ORGANISM: Artificial Sequence
<220> FEATURE:
<223> OTHER INFORMATION: Synthetic

<400> SEQUENCE: 316

Leu Gln Phe Lys Gln Tyr Pro Tyr Thr
1               5

<210> SEQ ID NO 317
```

```
<211> LENGTH: 6
<212> TYPE: PRT
<213> ORGANISM: Artificial Sequence
<220> FEATURE:
<223> OTHER INFORMATION: Synthetic

<400> SEQUENCE: 317

Ser Ser Tyr Trp Trp Ile
1               5

<210> SEQ ID NO 318
<211> LENGTH: 11
<212> TYPE: PRT
<213> ORGANISM: Artificial Sequence
<220> FEATURE:
<223> OTHER INFORMATION: Synthetic

<400> SEQUENCE: 318

Glu Ala Gly Asp Ser Val Trp Tyr Phe Asp Leu
1               5                   10

<210> SEQ ID NO 319
<211> LENGTH: 11
<212> TYPE: PRT
<213> ORGANISM: Artificial Sequence
<220> FEATURE:
<223> OTHER INFORMATION: Synthetic

<400> SEQUENCE: 319

Gln Ala Ser Gln Asp Ile Gly Asn Glu Leu Ile
1               5                   10

<210> SEQ ID NO 320
<211> LENGTH: 7
<212> TYPE: PRT
<213> ORGANISM: Artificial Sequence
<220> FEATURE:
<223> OTHER INFORMATION: Synthetic

<400> SEQUENCE: 320

Tyr Ala Thr Ser Leu Ala Asp
1               5

<210> SEQ ID NO 321
<211> LENGTH: 7
<212> TYPE: PRT
<213> ORGANISM: Artificial Sequence
<220> FEATURE:
<223> OTHER INFORMATION: Synthetic

<400> SEQUENCE: 321

Pro Tyr Gly Met Gly Val Gly
1               5

<210> SEQ ID NO 322
<211> LENGTH: 16
<212> TYPE: PRT
<213> ORGANISM: Artificial Sequence
<220> FEATURE:
<223> OTHER INFORMATION: Synthetic

<400> SEQUENCE: 322

Asn Ile Trp Trp Asp Asp Asp Lys Tyr Tyr Asn Pro Ser Leu Ile Asn
1               5                   10                  15

<210> SEQ ID NO 323
<211> LENGTH: 12
```

```
<212> TYPE: PRT
<213> ORGANISM: Artificial Sequence
<220> FEATURE:
<223> OTHER INFORMATION: Synthetic

<400> SEQUENCE: 323

Ser Glu Leu Val Met Pro Tyr Val Pro Phe Asp Tyr
1               5                   10

<210> SEQ ID NO 324
<211> LENGTH: 11
<212> TYPE: PRT
<213> ORGANISM: Artificial Sequence
<220> FEATURE:
<223> OTHER INFORMATION: Synthetic

<400> SEQUENCE: 324

Gln Ala Ser Gln Asp Ile Glu Asn Asp Leu Val
1               5                   10

<210> SEQ ID NO 325
<211> LENGTH: 12
<212> TYPE: PRT
<213> ORGANISM: Artificial Sequence
<220> FEATURE:
<223> OTHER INFORMATION: Synthetic

<400> SEQUENCE: 325

Ser Glu Leu Val Met Pro Tyr Val Pro Phe Asp Phe
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Synthetic

<400> SEQUENCE: 326

Gln Ala Ser Gln Asp Ile Gly Ile Glu Leu Ile
1               5                   10

<210> SEQ ID NO 327
<211> LENGTH: 7
<212> TYPE: PRT
<213> ORGANISM: Artificial Sequence
<220> FEATURE:
<223> OTHER INFORMATION: Synthetic

<400> SEQUENCE: 327

Tyr Thr Ala Asn Leu Ala Ser
1               5

<210> SEQ ID NO 328
<211> LENGTH: 9
<212> TYPE: PRT
<213> ORGANISM: Artificial Sequence
<220> FEATURE:
<223> OTHER INFORMATION: Synthetic

<400> SEQUENCE: 328

Leu Gln Tyr Lys Gln Tyr Pro Phe Thr
1               5

<210> SEQ ID NO 329
<211> LENGTH: 11
<212> TYPE: PRT
```

```
<213> ORGANISM: Artificial Sequence
<220> FEATURE:
<223> OTHER INFORMATION: Synthetic

<400> SEQUENCE: 329

Gln Ala Ser Gln Asp Ile Glu Asn Asp Leu Ile
1               5                   10

<210> SEQ ID NO 330
<211> LENGTH: 16
<212> TYPE: PRT
<213> ORGANISM: Artificial Sequence
<220> FEATURE:
<223> OTHER INFORMATION: Synthetic

<400> SEQUENCE: 330

Asn Ile Trp Trp Asp Asp Asp Lys Tyr Ser Asn Pro Ser Leu Gln Ser
1               5                   10                  15

<210> SEQ ID NO 331
<211> LENGTH: 16
<212> TYPE: PRT
<213> ORGANISM: Artificial Sequence
<220> FEATURE:
<223> OTHER INFORMATION: Synthetic

<400> SEQUENCE: 331

Asn Ile Trp Trp Asp Asp Asp Lys Tyr Tyr Asn Pro Ser Leu Lys Asn
1               5                   10                  15

<210> SEQ ID NO 332
<211> LENGTH: 12
<212> TYPE: PRT
<213> ORGANISM: Artificial Sequence
<220> FEATURE:
<223> OTHER INFORMATION: Synthetic

<400> SEQUENCE: 332

Ser Glu Ile Val Met Pro Tyr Val Pro Phe Asp Tyr
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Synthetic

<400> SEQUENCE: 333

Gln Ala Ser Gln Asp Ile Gly Ile Asp Leu Ile
1               5                   10

<210> SEQ ID NO 334
<211> LENGTH: 5
<212> TYPE: PRT
<213> ORGANISM: Artificial Sequence
<220> FEATURE:
<223> OTHER INFORMATION: Synthetic

<400> SEQUENCE: 334

Asp Tyr Ala Met Ala
1               5

<210> SEQ ID NO 335
<211> LENGTH: 17
<212> TYPE: PRT
<213> ORGANISM: Artificial Sequence
```

<220> FEATURE:
<223> OTHER INFORMATION: Synthetic

<400> SEQUENCE: 335

Thr Val Phe Tyr Asp Gly Ser Asp Thr Phe Tyr Arg Asp Ser Val Lys
1               5                   10                  15
Gly

<210> SEQ ID NO 336
<211> LENGTH: 18
<212> TYPE: PRT
<213> ORGANISM: Artificial Sequence
<220> FEATURE:
<223> OTHER INFORMATION: Synthetic

<400> SEQUENCE: 336

Glu Gly Asp Tyr Tyr Ser Arg His Val Tyr Val Gly Tyr Asn Trp Phe
1               5                   10                  15
Pro His

<210> SEQ ID NO 337
<211> LENGTH: 11
<212> TYPE: PRT
<213> ORGANISM: Artificial Sequence
<220> FEATURE:
<223> OTHER INFORMATION: Synthetic

<400> SEQUENCE: 337

Leu Thr Ser Glu Asp Ile Asn Ser Glu Leu Ala
1               5                   10

<210> SEQ ID NO 338
<211> LENGTH: 7
<212> TYPE: PRT
<213> ORGANISM: Artificial Sequence
<220> FEATURE:
<223> OTHER INFORMATION: Synthetic

<400> SEQUENCE: 338

Asn Ala Asn Ser Leu Gln Asp
1               5

<210> SEQ ID NO 339
<211> LENGTH: 9
<212> TYPE: PRT
<213> ORGANISM: Artificial Sequence
<220> FEATURE:
<223> OTHER INFORMATION: Synthetic

<400> SEQUENCE: 339

Gln Gln Tyr Asn Ser Tyr Pro Leu Thr
1               5

<210> SEQ ID NO 340
<211> LENGTH: 17
<212> TYPE: PRT
<213> ORGANISM: Artificial Sequence
<220> FEATURE:
<223> OTHER INFORMATION: Synthetic

<400> SEQUENCE: 340

Glu Ile Asn Pro Glu Ala Ser Ser Ile Asn Tyr Ala Pro Ser Leu Lys
1               5                   10                  15
Asp

```
<210> SEQ ID NO 341
<211> LENGTH: 11
<212> TYPE: PRT
<213> ORGANISM: Artificial Sequence
<220> FEATURE:
<223> OTHER INFORMATION: Synthetic

<400> SEQUENCE: 341

Gln Asp Asp Tyr Ser His Tyr Ala Met Asp Tyr
1               5                   10

<210> SEQ ID NO 342
<211> LENGTH: 11
<212> TYPE: PRT
<213> ORGANISM: Artificial Sequence
<220> FEATURE:
<223> OTHER INFORMATION: Synthetic

<400> SEQUENCE: 342

Lys Ala Ser Gln Asp Val Asn Thr Gly Val Ser
1               5                   10

<210> SEQ ID NO 343
<211> LENGTH: 17
<212> TYPE: PRT
<213> ORGANISM: Artificial Sequence
<220> FEATURE:
<223> OTHER INFORMATION: Synthetic

<400> SEQUENCE: 343

Glu Ile Asn Pro Glu Ala Gly Lys Trp Asn Tyr Ala Pro Ser Leu Lys
1               5                   10                  15

Asp

<210> SEQ ID NO 344
<211> LENGTH: 11
<212> TYPE: PRT
<213> ORGANISM: Artificial Sequence
<220> FEATURE:
<223> OTHER INFORMATION: Synthetic

<400> SEQUENCE: 344

Gln Asp Asp Tyr Thr Thr Tyr Ala Met Asp Tyr
1               5                   10

<210> SEQ ID NO 345
<211> LENGTH: 11
<212> TYPE: PRT
<213> ORGANISM: Artificial Sequence
<220> FEATURE:
<223> OTHER INFORMATION: Synthetic

<400> SEQUENCE: 345

Gln Asp Asp Tyr Leu Thr Tyr Ala Met Asp Tyr
1               5                   10

<210> SEQ ID NO 346
<211> LENGTH: 11
<212> TYPE: PRT
<213> ORGANISM: Artificial Sequence
<220> FEATURE:
<223> OTHER INFORMATION: Synthetic

<400> SEQUENCE: 346

Lys Ala Ser Gln Asp Val Asn Thr Ala Val Asp
1               5                   10
```

<210> SEQ ID NO 347
<211> LENGTH: 17
<212> TYPE: PRT
<213> ORGANISM: Artificial Sequence
<220> FEATURE:
<223> OTHER INFORMATION: Synthetic

<400> SEQUENCE: 347

Glu Ile Asn Pro Glu Thr Thr Ile Ile Asn Tyr Ala Pro Ser Leu Lys
1               5                   10                  15

Asp

<210> SEQ ID NO 348
<211> LENGTH: 11
<212> TYPE: PRT
<213> ORGANISM: Artificial Sequence
<220> FEATURE:
<223> OTHER INFORMATION: Synthetic

<400> SEQUENCE: 348

Gln Asp Asp Tyr Arg His Tyr Ala Met Asp Tyr
1               5                   10

<210> SEQ ID NO 349
<211> LENGTH: 17
<212> TYPE: PRT
<213> ORGANISM: Artificial Sequence
<220> FEATURE:
<223> OTHER INFORMATION: Synthetic

<400> SEQUENCE: 349

Glu Ile Asn Pro Glu Ser Thr Leu Ile Asn Tyr Ala Pro Ser Leu Lys
1               5                   10                  15

Asp

<210> SEQ ID NO 350
<211> LENGTH: 11
<212> TYPE: PRT
<213> ORGANISM: Artificial Sequence
<220> FEATURE:
<223> OTHER INFORMATION: Synthetic

<400> SEQUENCE: 350

Gln Asp Asp Tyr Arg Asn Tyr Ala Met Asp Tyr
1               5                   10

<210> SEQ ID NO 351
<211> LENGTH: 17
<212> TYPE: PRT
<213> ORGANISM: Artificial Sequence
<220> FEATURE:
<223> OTHER INFORMATION: Synthetic

<400> SEQUENCE: 351

Glu Ile Asn Pro Glu Ser Thr Gly Ile Asn Tyr Ala Pro Ser Leu Lys
1               5                   10                  15

Asp

<210> SEQ ID NO 352
<211> LENGTH: 11
<212> TYPE: PRT
<213> ORGANISM: Artificial Sequence
<220> FEATURE:
<223> OTHER INFORMATION: Synthetic

```
<400> SEQUENCE: 352

Gln Asp Asp Tyr Trp Thr Tyr Ala Met Asp Tyr
1               5                   10

<210> SEQ ID NO 353
<211> LENGTH: 11
<212> TYPE: PRT
<213> ORGANISM: Artificial Sequence
<220> FEATURE:
<223> OTHER INFORMATION: Synthetic

<400> SEQUENCE: 353

Lys Ala Ser Gln Asp Val Asn Thr Ala Val Ser
1               5                   10

<210> SEQ ID NO 354
<211> LENGTH: 17
<212> TYPE: PRT
<213> ORGANISM: Artificial Sequence
<220> FEATURE:
<223> OTHER INFORMATION: Synthetic

<400> SEQUENCE: 354

Glu Ile Asn Pro Glu Ser Asn Phe Ile Asn Tyr Ala Pro Ser Leu Lys
1               5                   10                  15

Asp

<210> SEQ ID NO 355
<211> LENGTH: 11
<212> TYPE: PRT
<213> ORGANISM: Artificial Sequence
<220> FEATURE:
<223> OTHER INFORMATION: Synthetic

<400> SEQUENCE: 355

Gln Asp Asp Tyr Ser Val Tyr Ala Met Asp Tyr
1               5                   10

<210> SEQ ID NO 356
<211> LENGTH: 11
<212> TYPE: PRT
<213> ORGANISM: Artificial Sequence
<220> FEATURE:
<223> OTHER INFORMATION: Synthetic

<400> SEQUENCE: 356

Lys Ala Ser Gln Asp Val Asn Thr Gly Val Thr
1               5                   10

<210> SEQ ID NO 357
<211> LENGTH: 17
<212> TYPE: PRT
<213> ORGANISM: Artificial Sequence
<220> FEATURE:
<223> OTHER INFORMATION: Synthetic

<400> SEQUENCE: 357

Glu Ile Asn Pro Glu Arg Asn Tyr Ile Asn Tyr Ala Pro Ser Leu Lys
1               5                   10                  15

Asp

<210> SEQ ID NO 358
<211> LENGTH: 11
<212> TYPE: PRT
```

<213> ORGANISM: Artificial Sequence
<220> FEATURE:
<223> OTHER INFORMATION: Synthetic

<400> SEQUENCE: 358

Gln Asp Asp Tyr Asp Lys Tyr Ala Met Asp Tyr
1               5                   10

<210> SEQ ID NO 359
<211> LENGTH: 11
<212> TYPE: PRT
<213> ORGANISM: Artificial Sequence
<220> FEATURE:
<223> OTHER INFORMATION: Synthetic

<400> SEQUENCE: 359

Gln Asp Asp Tyr Glu Tyr Tyr Thr Met Asp Tyr
1               5                   10

<210> SEQ ID NO 360
<211> LENGTH: 11
<212> TYPE: PRT
<213> ORGANISM: Artificial Sequence
<220> FEATURE:
<223> OTHER INFORMATION: Synthetic

<400> SEQUENCE: 360

Lys Val Ser Gln Asp Val Asn Thr Gly Val Ala
1               5                   10

<210> SEQ ID NO 361
<211> LENGTH: 9
<212> TYPE: PRT
<213> ORGANISM: Artificial Sequence
<220> FEATURE:
<223> OTHER INFORMATION: Synthetic

<400> SEQUENCE: 361

Gln Gln Tyr Trp Ser Thr Pro Leu Thr
1               5

<210> SEQ ID NO 362
<211> LENGTH: 11
<212> TYPE: PRT
<213> ORGANISM: Artificial Sequence
<220> FEATURE:
<223> OTHER INFORMATION: Synthetic

<400> SEQUENCE: 362

Gln Glu Asp Tyr Glu Tyr Tyr Ala Leu Asp Tyr
1               5                   10

<210> SEQ ID NO 363
<211> LENGTH: 11
<212> TYPE: PRT
<213> ORGANISM: Artificial Sequence
<220> FEATURE:
<223> OTHER INFORMATION: Synthetic

<400> SEQUENCE: 363

Lys Ala Ser Gln Asp Val Asn Thr Gly Val Tyr
1               5                   10

<210> SEQ ID NO 364
<211> LENGTH: 9
<212> TYPE: PRT
<213> ORGANISM: Artificial Sequence
<220> FEATURE:
<223> OTHER INFORMATION: Synthetic

<400> SEQUENCE: 364

Gln Gln Gly Tyr Ser Thr Pro Leu Thr
1               5

<210> SEQ ID NO 365
<211> LENGTH: 11
<212> TYPE: PRT
<213> ORGANISM: Artificial Sequence
<220> FEATURE:
<223> OTHER INFORMATION: Synthetic

<400> SEQUENCE: 365

Gln Asp Asp Thr Arg Tyr Tyr Ala Met Asp Tyr
1               5                   10

<210> SEQ ID NO 366
<211> LENGTH: 11
<212> TYPE: PRT
<213> ORGANISM: Artificial Sequence
<220> FEATURE:
<223> OTHER INFORMATION: Synthetic

<400> SEQUENCE: 366

Gln Asp Asp Tyr Leu Tyr Tyr Thr Met Asp Tyr
1               5                   10

<210> SEQ ID NO 367
<211> LENGTH: 11
<212> TYPE: PRT
<213> ORGANISM: Artificial Sequence
<220> FEATURE:
<223> OTHER INFORMATION: Synthetic

<400> SEQUENCE: 367

Gln Asp Asp Tyr Glu Thr Tyr Thr Met Asp Tyr
1               5                   10

<210> SEQ ID NO 368
<211> LENGTH: 11
<212> TYPE: PRT
<213> ORGANISM: Artificial Sequence
<220> FEATURE:
<223> OTHER INFORMATION: Synthetic

<400> SEQUENCE: 368

Gln Asp Asp Tyr Leu Thr Tyr Thr Met Asp Tyr
1               5                   10

<210> SEQ ID NO 369
<211> LENGTH: 17
<212> TYPE: PRT
<213> ORGANISM: Artificial Sequence
<220> FEATURE:
<223> OTHER INFORMATION: Synthetic

<400> SEQUENCE: 369

Glu Ile Asn Pro Glu Ala Ser Thr Ile Asn Tyr Ala Pro Ser Leu Lys
1               5                   10                  15

Asp

<210> SEQ ID NO 370
<211> LENGTH: 17
<212> TYPE: PRT

```
<213> ORGANISM: Artificial Sequence
<220> FEATURE:
<223> OTHER INFORMATION: Synthetic

<400> SEQUENCE: 370

Glu Ile Asn Pro Glu Ser Ser Ile Asn Tyr Ala Pro Ser Leu Lys
1               5                   10                  15

Asp

<210> SEQ ID NO 371
<211> LENGTH: 11
<212> TYPE: PRT
<213> ORGANISM: Artificial Sequence
<220> FEATURE:
<223> OTHER INFORMATION: Synthetic

<400> SEQUENCE: 371

Gln Asp Asp Tyr Ser Tyr Tyr Thr Met Asp Tyr
1               5                   10

<210> SEQ ID NO 372
<211> LENGTH: 11
<212> TYPE: PRT
<213> ORGANISM: Artificial Sequence
<220> FEATURE:
<223> OTHER INFORMATION: Synthetic

<400> SEQUENCE: 372

Gln Asp Asp Tyr Glu His Tyr Thr Met Asp Tyr
1               5                   10

<210> SEQ ID NO 373
<211> LENGTH: 11
<212> TYPE: PRT
<213> ORGANISM: Artificial Sequence
<220> FEATURE:
<223> OTHER INFORMATION: Synthetic

<400> SEQUENCE: 373

Gln Asp Asp Tyr Ser His Tyr Thr Met Asp Tyr
1               5                   10
```

ANTI-CXCL13 ANTIBODIES

CROSS REFERENCE TO RELATED APPLICATIONS

This application is a U.S. National Stage Application under 35 U.S.C. 371 of International Application No. PCT/CN2019/106409, filed Sep. 18, 2019, which claims priority to International Application PCT/CN2018/106158, filed Sep. 18, 2018. The contents of each of the aforementioned are hereby incorporated by reference in their entirety into the present disclosure.

SEQUENCE LISTING

The instant application contains a Sequence Listing which has been filed electronically in ASCII format and is hereby incorporated by reference in its entirety. Said ASCII copy, created on Jun. 19, 2020, is named 271416US SL.txt and is 231,643 bytes in size.

The present invention claims the priority of the PCT/CN2018/106158, filed on Sep. 18, 2018, the contents of which are incorporated herein by its entirety.

BACKGROUND

Chemokine (C-X-C motif) ligand 13 (CXCL13), also known as B lymphocyte chemoattractant (BLC) or B cell-attracting chemokine 1 (BCA-1), is a protein ligand that in humans is encoded by the CXCL13 gene. CXCL13 is a small chemokine belonging to the CXC chemokine family. As its name suggests, this chemokine is selectively chemotactic for B cells belonging to both the B-1 and B-2 subsets, and elicits its effects by interacting with chemokine receptor CXCR5.

CXCL13 and its receptor CXCR5 control the organization of B cells within follicles of lymphoid tissues, and is expressed highly in the liver, spleen, lymph nodes, and gut of humans. The gene for CXCL13 is located on human chromosome 4 in a cluster of other CXC chemokines.

In T lymphocytes, CXCL13 expression is thought to reflect a germinal center origin of the T cell, particularly a subset of T cells called follicular B helper T cells (or TFH cells). Hence, expression of CXCL13 in T-cell lymphomas, such as Angioimmunoblastic T-cell Lymphoma, is thought to reflect a germinal center origin of the neoplastic T-cells.

The need for therapies that target CXCL13-mediated signaling pathways has become increasingly apparent in the recent years. The mechanisms of action for such treatments would include, e.g., blockade of CXCL13 interaction with its receptor resulting in interference with B cell and follicular B-helper T cell migration into inflamed tissues and germinal center formation (e.g., in the case of autoimmune disease) and inhibition of cancer cell proliferation and ability to spread in oncological disorders.

SUMMARY

The present disclosure provides antibodies or fragments thereof having binding specificity to the human chemokine (C-X-C motif) ligand 13 (CXCL13) protein, as well as bispecific antibodies having specificity to CXCL13 and another antigen such as BAFF and IFNαRI. These antibodies and fragments are useful in the treatment of autoimmune diseases as well as cancer.

One embodiment of the present disclosure provides an antibody or fragment thereof having specificity to a human chemokine (C-X-C motif) ligand 13 (CXCL13) protein, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein: the HCDR1 comprises the amino acid sequence of SEQ ID NO:127 (RYWMS); the HCDR2 comprises the amino acid sequence of SEQ ID NO:128 (EINPDSSTINYAPSLKD), SEQ ID NO:129 (EINPESSTINYAPSLKD), SEQ ID NO:340 (EINPEASSINYAPSLKD), SEQ ID NO:343, (EINPEAGKWNYAPSLKD), SEQ ID NO:347 (EINPETTIINYAPSLKD), SEQ ID NO:349 (EINPESTLINYAPSLKD), SEQ ID NO:351, INPESTGINYAPSLKD), SEQ ID NO:354 (EINPESNFINYAPSLKD), SEQ ID NO:357 (EINPERNYINYAPSLKD), SEQ ID NO:369 (EINPEASTINYAPSLKD), or SEQ ID NO:370 (EINPESSSINYAPSLKD); the HCDR3 comprises the amino acid sequence of SEQ ID NO:130 (QDDYEYYAMDY), SEQ ID NO:341 (QDDYSHYAMDY), SEQ ID NO:344 (QDDYTTYAMDY), SEQ ID NO:345 (QDDYLTYAMDY), SEQ ID NO:348 (QDDYRHYAMDY), SEQ ID NO:350 (QDDYRNYAMDY), SEQ ID NO:352 (QDDYWTYAMDY), SEQ ID NO:355 (QDDYSVYAMDY), SEQ ID NO:358 (QDDYDKYAMDY), SEQ ID NO:359 (QDDYEYYTMDY), SEQ ID NO:362 (QEDYEYYALDY), SEQ ID NO:365 (QDDTRYYAMDY), SEQ ID NO:366 (QDDYLYYTMDY), SEQ ID NO:367 (QDDYETYTMDY), SEQ ID NO:368 (QDDYLTYTMDY), SEQ ID NO:371 (QDDYSYYTMDY), SEQ ID NO:372 (QDDYEHYTMDY), or SEQ ID NO:373 (QDDYSHYTMDY); the LCDR1 comprises the amino acid sequence of SEQ ID NO:131 (KASQDVNTGVA), SEQ ID NO:342 (KASQDVNTGVS), SEQ ID NO:346 (KASQDVNTAVD), SEQ ID NO:353 (KASQDVNTAVS), SEQ ID NO:356 (KASQDVNTGVT), SEQ ID NO:360 (KVSQDVNTGVA), or SEQ ID NO:363 (KASQDVNTGVY); the LCDR2 comprises the amino acid sequence of SEQ ID NO:132 (SASYRYT); and the LCDR3 comprises the amino acid sequence of SEQ ID NO:133 (QQYYSTPLT), SEQ ID NO:361 (QQYWSTPLT), or SEQ ID NO:364 (QQGYSTPLT).

In some embodiments, the HCDR1, HCDR2, HCDR3, LCDR1, LCD2 and LCDR3 comprise SEQ ID NO:127, 129, 367, 360, 132 and 133, respectively. In some embodiments, the heavy chain variable region comprises the amino acid sequence of SEQ ID NO:181 or an amino acid sequence having at least 90% sequence identity to SEQ ID NO:181, and the light chain variable region comprises the amino acid sequence of SEQ ID NO:179 or an amino acid sequence having at least 90% sequence identity to SEQ ID NO:179.

In some embodiments, the antibody or fragment thereof is humanized and wherein the heavy chain variable region comprises one or more back mutations selected from the group consisting of 5Q, 47I, 48G, and 85V, according to Kabat numbering, and combinations thereof, or wherein the light chain variable region comprises a mutation 78V according to Kabat numbering.

In some embodiments, the heavy chain variable region comprises the amino acid sequence of SEQ ID NO:181, and the light chain variable region comprises the amino acid sequence of SEQ ID NO:179.

In some embodiments, the HCDR1, HCDR2, HCDR3, LCDR1, LCD2 and LCDR3 comprise SEQ ID NO:127, 129, 359, 360, 132 and 133, respectively. In some embodiments, the heavy chain variable region comprises the amino acid sequence of SEQ ID NO:174 or an amino acid sequence having at least 90% sequence identity to SEQ ID NO:174, and the light chain variable region comprises the amino acid sequence of SEQ ID NO:179 or an amino acid sequence having at least 90% sequence identity to SEQ ID NO:179.

In some embodiments, the HCDR1, HCDR2, HCDR3, LCDR1, LCD2 and LCDR3 comprise SEQ ID NO:127, 129, 359, 360, 132 and 361, respectively. In some embodiments, the heavy chain variable region comprises the amino acid sequence of SEQ ID NO:174 or an amino acid sequence having at least 90% sequence identity to SEQ ID NO:174, and the light chain variable region comprises the amino acid sequence of SEQ ID NO:175 or an amino acid sequence having at least 90% sequence identity to SEQ ID NO:175.

In some embodiments, the HCDR1, HCDR2, HCDR3, LCDR1, LCD2 and LCDR3 comprise SEQ ID NO:127, 129, 130, 131, 132 and 133, respectively. In some embodiments, the heavy chain variable region comprises the amino acid sequence of SEQ ID NO:156 or an amino acid sequence having at least 90% sequence identity to SEQ ID NO:156, and the light chain variable region comprises the amino acid sequence of SEQ ID NO:138 or an amino acid sequence having at least 90% sequence identity to SEQ ID NO:138.

In some embodiments, the HCDR1, HCDR2, HCDR3, LCDR1, LCD2 and LCDR3 comprise SEQ ID NO:127, 128, 130, 131, 132 and 133, respectively. In some embodiments, the heavy chain variable region comprises the amino acid sequence of SEQ ID NO:134 or an amino acid sequence having at least 90% sequence identity to SEQ ID NO:134, and the light chain variable region comprises the amino acid sequence of SEQ ID NO:138 or an amino acid sequence having at least 90% sequence identity to SEQ ID NO:138.

In some embodiments, the antibody or fragment thereof is humanized and the heavy chain variable region comprises one or more back mutations selected from the group consisting of 5Q, 47I, 48G, and 85V, according to Kabat numbering, and combinations thereof, or wherein the light chain variable region comprises a mutation 78V according to Kabat numbering.

Also provided, in one embodiment, is an antibody or fragment thereof having specificity to a human chemokine (C-X-C motif) ligand 13 (CXCL13) protein, wherein the antibody or fragment thereof can bind to one or more amino acid residues selected from the group consisting of F20, P22, R24 and F25 of the CXCL13 protein.

In some embodiments, the antibody or fragment thereof can bind to F20 and P22, F20 and R24, F20 an F25, P22 and R24, P22 and F25, or R24 and F25 of the CXCL13 protein. In some embodiments, the antibody or fragment thereof can bind to of F20, P22, and R24; F20, P22, and F25; F20, R24 and F25; or P22, R24 and F25 of the CXCL13 protein. In some embodiments, the antibody or fragment thereof can bind to F20, P22, R24 and F25 of the CXCL13 protein. In some embodiments, the antibody or fragment thereof can further bind to the cynomolgus CXCL13 protein.

In one embodiment, provided is a bispecific antibody, comprising a first antigen-binding portion having specificity to a human chemokine (C-X-C motif) ligand 13 (CXCL13) protein and a second antigen-binding portion having specificity to a human B-cell-activating factor (BAFF) protein, wherein the first antigen-binding portion comprises an antibody fragment of the present disclosure. In some embodiments, the bispecific antibody has a format comprising a full antibody fused to two single chain fragments (scFv) or to two Fab fragments. In some embodiments, the second portion comprises an antigen-binding fragment of Belimumab.

Methods and uses are also provided. In one embodiment, a method of suppressing an immune response or treating an autoimmune disease or disorder in a patient in need thereof is provided, comprising administering to the patient the antibody or fragment thereof of a bispecific antibody of the present disclosure.

In one embodiment, provided is a method of treating cancer in a patient in need thereof, comprising administering to the patient the antibody or fragment thereof.

BRIEF DESCRIPTION OF THE DRAWINGS

FIG. 2 shows that the anti-CXCL13 antibodies, 64C10G1, 21H12D9, 329F2E1, 411A11E9, 71F4A3 and 1H3A11 could effectively dose-dependent block the IP1 signal and the inhibition efficiency was similar.

DETAILED DESCRIPTION

Definitions

Figure 1:
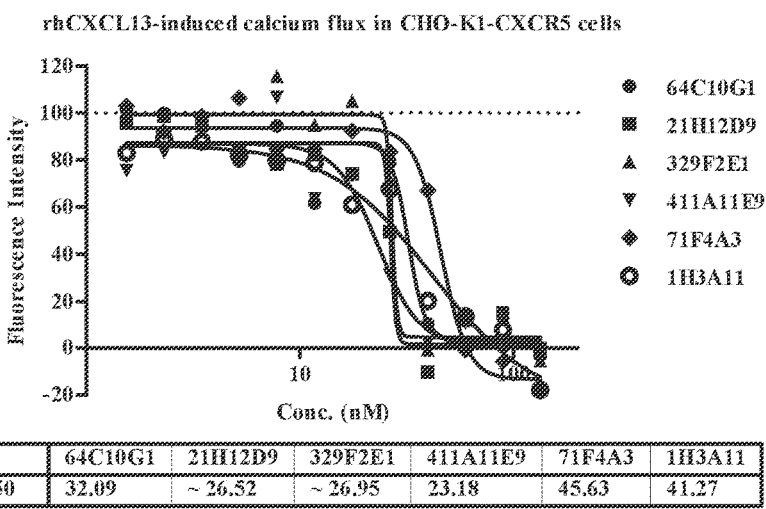
FIG. 1 shows chimeric antibodies of anti-CXCL13 had potent activity in blocking of CXCL13 induced calcium flux in CHO-K1-CXCR5 cells, except 415A3D1.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, an "antibody" or "antigen-binding polypeptide" refers to a polypeptide or a polypeptide complex that specifically recognizes and binds to an antigen. An antibody can be a whole antibody and any antigen binding fragment or a single chain thereof. Thus the term "antibody" includes any protein or peptide containing molecule that comprises at least a portion of an immunoglobulin molecule having biological activity of binding to the antigen. Examples of such include, but are not limited to a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein.

The terms "antibody fragment" or "antigen-binding fragment", as used herein, is a portion of an antibody such as F(ab')$_2$, F(ab)$_2$, Fab', Fab, Fv, scFv and the like. Regardless of structure, an antibody fragment binds with the same antigen that is recognized by the intact antibody. The term "antibody fragment" includes aptamers, spiegelmers, and diabodies. The term "antibody fragment" also includes any synthetic or genetically engineered protein that acts like an antibody by binding to a specific antigen to form a complex.

A "single-chain variable fragment" or "scFv" refers to a fusion protein of the variable regions of the heavy ($V_H$) and light chains ($V_L$) of immunoglobulins. In some aspects, the regions are connected with a short linker peptide of ten to about 25 amino acids. The linker can be rich in glycine for flexibility, as well as serine or threonine for solubility, and can either connect the N-terminus of the $V_H$ with the C-terminus of the $V_L$, or vice versa. This protein retains the specificity of the original immunoglobulin, despite removal of the constant regions and the introduction of the linker. ScFv molecules are known in the art and are described, e.g., in U.S. Pat. No. 5,892,019.

The term antibody encompasses various broad classes of polypeptides that can be distinguished biochemically. Those skilled in the art will appreciate that heavy chains are classified as gamma, mu, alpha, delta, or epsilon ($\gamma$, $\mu$, $\alpha$, $\delta$, $\epsilon$) with some subclasses among them (e.g., $\gamma 1$-$\gamma 4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgG_5$, etc. are well characterized and are known to confer functional specialization. Modified versions of each of these classes and isotypes are readily discernable to the skilled artisan in view of the instant disclosure and, accordingly, are within the scope of the instant disclosure. All immunoglobulin classes are clearly within the scope of the present disclosure, the following discussion will generally be directed to the IgG class of immunoglobulin molecules. With regard to IgG, a standard immunoglobulin molecule comprises two identical light chain polypeptides of molecular weight approximately 23,000 Daltons, and two identical heavy chain polypeptides of molecular weight 53,000-70,000. The four chains are typically joined by disulfide bonds in a "Y" configuration wherein the light chains bracket the heavy chains starting at the mouth of the "Y" and continuing through the variable region.

Antibodies, antigen-binding polypeptides, variants, or derivatives thereof of the disclosure include, but are not limited to, polyclonal, monoclonal, multispecific, human, humanized, primatized, or chimeric antibodies, single chain antibodies, epitope-binding fragments, e.g., Fab, Fab' and F(ab')$_2$, Fd, Fvs, single-chain Fvs (scFv), single-chain antibodies, disulfide-linked Fvs (sdFv), fragments comprising either a VK or VH domain, fragments produced by a Fab expression library, and anti-idiotypic (anti-Id) antibodies (including, e.g., anti-Id antibodies to LIGHT antibodies disclosed herein). Immunoglobulin or antibody molecules of the disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Light chains are classified as either kappa or lambda (K, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VK) and heavy (VH) chain portions determine antigen recognition and specificity. Conversely, the constant domains of the light chain (CK) and the heavy chain (CH1, CH2 or CH3) confer important biological properties such as secretion, transplacental mobility, Fc receptor binding, complement binding, and the like. By convention the numbering of the constant region domains increases as they become more distal from the antigen-binding site or amino-terminus of the antibody. The N-terminal portion is a variable region and at the C-terminal portion is a constant region; the CH3 and CK domains actually comprise the carboxy-terminus of the heavy and light chain, respectively.

As indicated above, the variable region allows the antibody to selectively recognize and specifically bind epitopes on antigens. That is, the VK domain and VH domain, or subset of the complementarity determining regions (CDRs), of an antibody combine to form the variable region that defines a three dimensional antigen-binding site. This quaternary antibody structure forms the antigen-binding site present at the end of each arm of the Y.

More specifically, the antigen-binding site is defined by three CDRs on each of the VH and VK chains (i.e. CDR-H1, CDR-H2, CDR-H3, CDR-L1, CDR-L2 and CDR-L3). In some instances, e.g., certain immunoglobulin molecules derived from camelid species or engineered based on camelid immunoglobulins, a complete immunoglobulin molecule may consist of heavy chains only, with no light chains. See, e.g., Hamers-Casterman et al., *Nature* 363:446-448 (1993).

In naturally occurring antibodies, the six "complementarity determining regions" or "CDRs" present in each antigen-binding domain are short, non-contiguous sequences of amino acids that are specifically positioned to form the antigen-binding domain as the antibody assumes its three dimensional configuration in an aqueous environment. The remainder of the amino acids in the antigen-binding domains, referred to as "framework" regions, show less inter-molecular variability. The framework regions largely adopt a β-sheet conformation and the CDRs form loops which connect, and in some cases form part of, the β-sheet structure. Thus, framework regions act to form a scaffold that provides for positioning the CDRs in correct orientation by inter-chain, non-covalent interactions. The antigen-binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see "Sequences of Proteins of Immunological Interest," Kabat, E., et al., U.S. Department of Health and Human Services, (1983); and Chothia and Lesk, *J. Mol. Biol.,* 196:901-917 (1987)).

In the case where there are two or more definitions of a term which is used and/or accepted within the art, the definition of the term as used herein is intended to include all such meanings unless explicitly stated to the contrary. A specific example is the use of the term "complementarity determining region" ("CDR") to describe the non-contiguous antigen combining sites found within the variable region of both heavy and light chain polypeptides. This particular region has been described by Kabat et al., U.S. Dept. of Health and Human Services, "Sequences of Proteins of Immunological Interest" (1983) and by Chothia et al., *J. Mol. Biol.* 196:901-917 (1987), which are incorporated herein by reference in their entireties. The CDR definitions according to Kabat and Chothia include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth in the table below as a comparison. The exact residue numbers which encompass a particular CDR will vary depending on the sequence and size of the CDR. Those skilled in the art can routinely determine which residues comprise a particular CDR given the variable region amino acid sequence of the antibody.

Antibodies disclosed herein may be from any animal origin including birds and mammals. Preferably, the antibodies are human, murine, donkey, rabbit, goat, guinea pig, camel, llama, horse, or chicken antibodies. In another embodiment, the variable region may be condricthoid in origin (e.g., from sharks).

As used herein, the term "heavy chain constant region" includes amino acid sequences derived from an immunoglobulin heavy chain. A polypeptide comprising a heavy chain constant region comprises at least one of: a CH1 domain, a hinge (e.g., upper, middle, and/or lower hinge region) domain, a CH2 domain, a CH3 domain, or a variant or fragment thereof. For example, an antigen-binding polypeptide for use in the disclosure may comprise a polypeptide chain comprising a CH1 domain; a polypeptide chain comprising a CH1 domain, at least a portion of a hinge domain, and a CH2 domain; a polypeptide chain comprising a CH1 domain and a CH3 domain; a polypeptide chain comprising a CH1 domain, at least a portion of a hinge domain, and a CH3 domain, or a polypeptide chain comprising a CH1 domain, at least a portion of a hinge domain, a CH2 domain, and a CH3 domain. In another embodiment, a polypeptide of the disclosure comprises a polypeptide chain comprising a CH3 domain. Further, an antibody for use in the disclosure may lack at least a portion of a CH2 domain (e.g., all or part of a CH2 domain). As set forth above, it will be understood by one of ordinary skill in the art that the heavy chain constant region may be modified such that they vary in amino acid sequence from the naturally occurring immunoglobulin molecule.

The heavy chain constant region of an antibody disclosed herein may be derived from different immunoglobulin molecules. For example, a heavy chain constant region of a polypeptide may comprise a CH1 domain derived from an $IgG_1$ molecule and a hinge region derived from an $IgG_3$ molecule. In another example, a heavy chain constant region can comprise a hinge region derived, in part, from an $IgG_1$ molecule and, in part, from an $IgG_3$ molecule. In another example, a heavy chain portion can comprise a chimeric hinge derived, in part, from an $IgG_1$ molecule and, in part, from an $IgG_4$ molecule.

As used herein, the term "light chain constant region" includes amino acid sequences derived from antibody light chain. Preferably, the light chain constant region comprises at least one of a constant kappa domain or constant lambda domain.

A "light chain-heavy chain pair" refers to the collection of a light chain and heavy chain that can form a dimer through a disulfide bond between the CL domain of the light chain and the CH1 domain of the heavy chain.

As previously indicated, the subunit structures and three dimensional configuration of the constant regions of the various immunoglobulin classes are well known. As used herein, the term "VH domain" includes the amino terminal variable domain of an immunoglobulin heavy chain and the term "CH1 domain" includes the first (most amino terminal) constant region domain of an immunoglobulin heavy chain. The CH1 domain is adjacent to the VH domain and is amino terminal to the hinge region of an immunoglobulin heavy chain molecule.

As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system; see Kabat et al., U.S. Dept. of Health and Human Services, "Sequences of Proteins of Immunological Interest" (1983). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

As used herein, the term "hinge region" includes the portion of a heavy chain molecule that joins the CH1 domain to the CH2 domain. This hinge region comprises approximately 25 residues and is flexible, thus allowing the two N-terminal antigen-binding regions to move independently. Hinge regions can be subdivided into three distinct domains: upper, middle, and lower hinge domains (Roux et al., *J. Immunol* 161:4083 (1998)).

As used herein the term "disulfide bond" includes the covalent bond formed between two sulfur atoms. The amino acid cysteine comprises a thiol group that can form a disulfide bond or bridge with a second thiol group. In most naturally occurring IgG molecules, the CH1 and CK regions are linked by a disulfide bond and the two heavy chains are linked by two disulfide bonds at positions corresponding to 239 and 242 using the Kabat numbering system (position 226 or 229, EU numbering system).

As used herein, the term "chimeric antibody" will be held to mean any antibody wherein the immunoreactive region or site is obtained or derived from a first species and the constant region (which may be intact, partial or modified in accordance with the instant disclosure) is obtained from a second species. In certain embodiments the target binding region or site will be from a non-human source (e.g. mouse or primate) and the constant region is human.

By "specifically binds" or "has specificity to," it is generally meant that an antibody binds to an epitope via its antigen-binding domain, and that the binding entails some complementarity between the antigen-binding domain and the epitope. According to this definition, an antibody is said to "specifically bind" to an epitope when it binds to that epitope, via its antigen-binding domain more readily than it would bind to a random, unrelated epitope. The term "specificity" is used herein to qualify the relative affinity by which a certain antibody binds to a certain epitope. For example, antibody "A" may be deemed to have a higher specificity for a given epitope than antibody "B," or antibody "A" may be said to bind to epitope "C" with a higher specificity than it has for related epitope "D."

As used herein, the terms "treat" or "treatment" refer to both therapeutic treatment and prophylactic or preventative measures, wherein the object is to prevent or slow down (lessen) an undesired physiological change or disorder, such as the progression of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

By "subject" or "individual" or "animal" or "patient" or "mammal," is meant any subject, particularly a mammalian subject, for whom diagnosis, prognosis, or therapy is desired.

Mammalian subjects include humans, domestic animals, farm animals, and zoo, sport, or pet animals such as dogs, cats, guinea pigs, rabbits, rats, mice, horses, cattle, cows, and so on.

As used herein, phrases such as "to a patient in need of treatment" or "a subject in need of treatment" includes subjects, such as mammalian subjects, that would benefit from administration of an antibody or composition of the present disclosure used, e.g., for detection, for a diagnostic procedure and/or for treatment.

Anti-CXCL13 Antibodies

The present disclosure provides antibodies, including bispecific antibodies and fragments, that have binding specificity to the human chemokine (C-X-C motif) ligand 13 (CXCL13) protein. As demonstrated in the experimental examples, numerous murine anti-human CXCL13 antibodies were obtained, having high binding affinity to the human CXCL13 protein. Some of them can also cross react with cynomolgus, and mouse CXCL13 proteins.

Four of the murine antibody clones, 21H12D9, 64C10G1, 71F4A3, and 411A11E9, were selected for further humanization and characterization. The humanized antibodies retained high binding activity to the CXCL13 protein, inhibited CXCL13 induced calcium flux, blocked CXCL13 mediated IP1 signaling, blocked CXCL13 derived cell migration, inhibited production of anti-KLH specific IgG, neutralized CXCL13 in peripheral blood, and blocked germinal center (GC) B cell production, class switch, and GC formation. In in vivo tests, the antibodies were able to inhibit primary splenocytes migration toward CXCL13, and decrease GC B cell population.

Interestingly, the antibodies that cross bind human and cynomolgus CXCL13 bound to the same epitope of CXCL13. The epitope included amino acid residues F20, P22, R24 and F25 on the human protein.

In accordance with one embodiment of the present disclosure, provided are antibodies and fragments thereof that include the heavy chain and light chain variable domains with the CDR regions of the antibodies prepared in the experimental examples. The CDRs are summarized in Table A below.

TABLE A

CDR Sequences of the mouse antibodies

| Antibody chain | CDR Sequences (CDR1, CDR2, CDR3 in order, for VH or VL) | SEQ ID NO: |
|---|---|---|
| 329F2E1-VH | RYWMS | 127 |
|  | EINPDSSTINYAPSLKD | 128 |
|  | QDDYDYYAMDY | 191 |
| 329F2E1-VL | KASQDVSTGVA | 192 |
|  | SASYRYT | 132 |
|  | HQYYTIPLT | 193 |
| 348B10B1-VH | EYIMH | 194 |
|  | GINPDNGDTTYNQKFKG | 195 |
|  | GVLDY | 196 |
| 348B10B1-VL | KSSQSLLDSDGKTYLN | 197 |
|  | LVSKLDS | 198 |
|  | WQGTHFPFT | 199 |
| 360A3D4E3-VH | EYIMH | 194 |
|  | GIHPDNGDTTYNQKFTG | 200 |
|  | GVLDY | 196 |
| 360A3D4E3-VL | KSSQSLLDSDGRTYLN | 201 |
|  | LVSKLDS | 198 |
|  | WQGTHFPFT | 199 |
| 414D10F5-VH | DYYMA | 142 |
|  | SISYDGGDSFYRDSVKG | 202 |
|  | EEDYSGSFPDY | 203 |
| 414D10F5-VL | KASQNINKYLN | 204 |
|  | DTNNLQA | 205 |
|  | LQHNSLYT | 206 |
| 339A9E7-VH | DYAWN | 207 |
|  | YISYSGDTSYNPSLRS | 208 |
|  | GHFDY | 209 |
| 339A9E7-VL | KSSQSLLDSDGETYLN | 210 |
|  | LVSKLDS | 198 |
|  | WQGTHFPYT | 211 |
| 339H3E2-VH | EYIMH | 194 |
|  | GINPNNGGTTYNQKFKG | 212 |
|  | GVMDY | 213 |
| 339H3E2-VL | KSSQSLLDSDGKTYLN | 197 |
|  | LVSKLDS | 198 |
|  | WQGTHFPFT | 199 |
| 367F1C2-VH | DYAWN | 207 |
|  | YISYTGSSSYNPSLKS | 214 |
|  | GHFDY | 209 |
| 367F1C2-VL | KSSQSLLDSDGKTYLN | 197 |
|  | QVSKLDS | 215 |
|  | WQGTHFPYT | 211 |
| 21H12D9-VH | DYYMN | 97 |
|  | VINPNNGGTTYKEKFKG | 98 |
|  | DDYDAGY | 99 |
| 21H12D9-VL | KASQNVDTAVA | 100 |
|  | SASHRYT | 101 |
|  | QQYTDFPLT | 102 |

TABLE A-continued

CDR Sequences of the mouse antibodies

| Antibody chain | CDR Sequences (CDR1, CDR2, CDR3 in order, for VH or VL) | SEQ ID NO: |
|---|---|---|
| 408E3F3 -VH | TSAMVS<br>AIDWEGDKYYNPSLES<br>MSSADSHSVLDA | 216<br>217<br>218 |
| 408E3F3 -VL | KASQNIHNYLN<br>NTNNLQT<br>LQHSSSLT | 219<br>220<br>221 |
| 415A3D1F4 -VH | DFYIN<br>FMRNKANGYTTEYNPSVKG<br>SRYNADDYYVGVMDV | 222<br>223<br>224 |
| 415A3D1F4 -VL | LASEDIYNNLA<br>YTNSLQD<br>LQDSEYPWT | 225<br>226<br>227 |
| 348E12F12 -VH | SDYAWN<br>YISYSGDTSYNPSLKS<br>GHFDY | 228<br>229<br>209 |
| 348E12F12 -VL | KSSQSLLDSDGKTYLN<br>LVSNLDS<br>WQGTHFPYT | 197<br>230<br>211 |
| 368D6D10 -VH | SDYAWN<br>YISYSGSTSYNPSLKS<br>GHFDY | 228<br>231<br>209 |
| 368D6D10 -VL | KSSQSLLDSDGKTYLN<br>LVSKLDS<br>WQGTHFPYT | 197<br>198<br>211 |
| 1H3A11 -VH | SYAMS<br>TISDGGSDTYYPDNVKG<br>DYYGSSYEDYAMDY | 112<br>232<br>233 |
| 1H3A11 -VL | KASQDINKYIT<br>YTSTLQP<br>LQYDNLYT | 234<br>118<br>119 |
| 355A1F6 -VH | SDYAWS<br>YISYSDSTSYNPSLKS<br>GHFDY | 235<br>236<br>209 |
| 355A1F6 -VL | KSSQSLLDSDGKTYLN<br>LVSKLDS<br>WQGTHFPYT | 197<br>198<br>211 |
| 353F9C4 -VH | SDYAWS<br>YITYSDSTSYNPSLKS<br>GHFDY | 235<br>237<br>209 |
| 353F9C4 -VL | KSSQSLLDSDGKTYLN<br>LVSKLDS<br>WQGTHFPYT | 197<br>198<br>211 |
| 19H7E10 -VH | DYYMN<br>DINPNNDGTTYNQKFKG<br>LSWSFFAMDY | 97<br>238<br>239 |
| 19H7E10 -VL | KASQDVSSGVA<br>SASHRHT<br>QQYYNTPWT | 240<br>241<br>242 |
| 411A11E9 -VH | DYYMA<br>SINYDGGDTYYRDSVKG<br>EEDYDGSYVMDA | 142<br>143<br>144 |
| 411A11E9 -VL | KASQNINKELT<br>NTNILQT<br>LQQSSLYT | 145<br>146<br>147 |
| 64C10G1 -VH | SYAMS<br>TISDGGSDAYYPDNVKG<br>DYYGSGYEDSPMDY | 112<br>113<br>115 |
| 64C10G1-VL | KASQDINKYIA<br>YTSTLQP<br>LQYDNLYT | 117<br>118<br>119 |
| 397C3B3-VH | SDYAWN<br>YISYSGSTSYNPSLKS<br>GHFDY | 228<br>231<br>209 |
| 397C3B3-VL | KSSQSLLDSDGKTYLN<br>LVSKLDS<br>WQGTHFPYT | 197<br>198<br>211 |
| 71F4A3-VH | RYWMS<br>EINPDSSTINYAPSLKD<br>QDDYEYYAMDY | 127<br>128<br>130 |
| 71F4A3-VL | KASQDVNTGVA<br>SASYRYT<br>QQYYSTPLT | 131<br>132<br>133 |
| 119H10D6-VH | TYWIE<br>EILPGSESTDYNEKFKD<br>DYYGYYFDY | 243<br>244<br>245 |
| 119H10D6-VL | KASQDVSTAVV<br>SASYRYT<br>QQHYSSPRT | 246<br>132<br>247 |
| 130D6G1-VH | TYWIE<br>EILPGSDSTNSNEKFEG<br>DYYGFYFDY | 243<br>248<br>249 |
| 130D6G1-VL | KASQDVSTAVA<br>STSYRYT<br>QQHYTTPRT | 250<br>251<br>252 |
| 156H3H7 -VH | DYYMN<br>DINPNNGDTTYNQKFKG<br>YDEDHYAMDY | 97<br>253<br>254 |
| 156H3H7 -VL | KASQDVSTGVA<br>SASHRYT<br>QQYYTTPWT | 192<br>101<br>255 |
| 168A2D4-VH | DYYMN<br>DINPNNGDIIYNQKFKG<br>YYDPYYHAMDY | 97<br>256<br>257 |
| 168A2D4-VL | KASQDVSTGVA<br>SASYRYT<br>QQQYSVPLT | 192<br>132<br>258 |
| 168D6F2-VH | SYWMH<br>GIDPDSGATKDNEKFKT<br>GSTVVAPGDYFAMDY | 259<br>260<br>261 |
| 168D6F2-VL | RASESVDNYGISFMH<br>RASNLDS<br>QQSNKDPWT | 262<br>263<br>264 |
| 175E3B 10-VH | VFGMGVG<br>HIWWDDEKYYNPALKS<br>IDGYYDFDY | 265<br>266<br>267 |
| 175E3B 10-VL | RSSHSIVQDNGNTYLQ<br>KVSNRFS<br>FQGSYVPYT | 268<br>269<br>270 |
| 177D2G10-VH | TSGMHVG<br>HIYWDDDKRYNPSLKS<br>RGGDYDYDEGFDY | 271<br>272<br>273 |

TABLE A-continued

CDR Sequences of the mouse antibodies

| Antibody chain | CDR Sequences (CDR1, CDR2, CDR3 in order, for VH or VL) | SEQ ID NO: |
| --- | --- | --- |
| 177D2G10-VL | RSSQSLVHSNGFTYLH | 274 |
|  | KVSNRFS | 269 |
|  | SQSTHVPYT | 275 |
| 178B2E8-VH | TDYYMT | 276 |
|  | NINYDGSRTNYLDSLKS | 277 |
|  | DGNYHFYGMDY | 278 |
| 178B2E8-VL | KASQDVSTAVA | 250 |
|  | WASTRHT | 279 |
|  | QQHYSTPWT | 280 |
| 178E2B3-VH | NHLIE | 281 |
|  | VINPGSGGTKYNEKFKG | 282 |
|  | SSDGYYEEDYFDY | 283 |
| 178E2B3-VL | SASSSVNYMQ | 284 |
|  | DTSELAS | 285 |
|  | QQWSSDPIT | 286 |
| 181B11G12-VH | DYYMA | 142 |
|  | NINYDGSDTYYLDSLKS | 287 |
|  | DVAYDDSYAMDY | 288 |
| 181B11G12-VL | KASQDINKYIA | 117 |
|  | YTSTLQP | 118 |
|  | LQYDSLYT | 289 |
| 184H10B5-VH | VFGMGVG | 265 |
|  | HIWWDDEKYYNPALKS | 266 |
|  | IDGYYDFDY | 267 |
| 184H10B5-VL | RSSHSIVQDNGNTYLQ | 268 |
|  | KVSNRFS | 269 |
|  | FQGSYVPYT | 270 |
| 345G1B4-VH | TSNMGVG | 290 |
|  | HIWWDDVKRYNPALKS | 291 |
|  | STTLVAFDY | 292 |
| 345G1B4-VL | KSSQSLLNSGNQKNYLT | 293 |
|  | WASTRES | 294 |
|  | QNDYSYPT | 295 |
| 396A5A1-VH | TSGMGIG | 296 |
|  | HIWWDDIKRYNPALKS | 297 |
|  | STTVVAFDY | 298 |
| 396A5A1-VL | KSSQSLLNSGNQKNYLT | 293 |
|  | WASTRES | 294 |
|  | QNDYDYPT | 299 |
| 402H2G12-VH | TYGMGVG | 300 |
|  | NIWWDDDKYYNPSLQN | 301 |
|  | SELIMPYVPFDY | 302 |
| 402H2G12-VL | QASQDIDNHLI | 303 |
|  | YATNLAN | 304 |
|  | LQFKQYPFT | 305 |
| 409G9C2-VH | SSYWWT | 306 |
|  | IYHSGRP | 307 |
|  | TAAVSYWYFDL | 308 |
| 409G9C2-VL | QASQDIGNDLI | 309 |
|  | YASNLAN | 310 |
|  | LQFKQYPFT | 305 |
| 410A4D10-VH | SRNWWG | 311 |
|  | IYHSGGT | 312 |
|  | EFGDSVWYFDL | 313 |

TABLE A-continued

CDR Sequences of the mouse antibodies

| Antibody chain | CDR Sequences (CDR1, CDR2, CDR3 in order, for VH or VL) | SEQ ID NO: |
| --- | --- | --- |
| 410A4D10-VL | QASQDIGNDLV | 314 |
|  | YATNLAD | 315 |
|  | LQFKQYPYT | 316 |
| 414G3F4-VH | SSYWWI | 317 |
|  | IYHSGRP | 307 |
|  | EAGDSVWYFDL | 318 |
| 414G3F4-VL | QASQDIGNELI | 319 |
|  | YATSLAD | 320 |
|  | LQFKQYPFT | 305 |
| 416C9H8-VH | PYGMGVG | 321 |
|  | NIWWDDDKYYNPSLIN | 322 |
|  | SELVMPYVPFDY | 323 |
| 416C9H8-VL | QASQDIENDLV | 324 |
|  | YATNLAN | 304 |
|  | LQFKQYPYT | 316 |
| 418D3H6-VH | TYGMGVG | 300 |
|  | NIWWDDDKYYNPSLIN | 322 |
|  | SELVMPYVPFDF | 325 |
| 418D3H6-VL | QASQDIGIELI | 326 |
|  | YTANLAS | 327 |
|  | LQYKQYPFT | 328 |
| 423A6H6-VH | TYGMGVG | 300 |
|  | NIWWDDDKYYNPSLQN | 301 |
|  | SELIMPYVPFDY | 302 |
| 423A6H6-VL | QASQDIDNHLI | 303 |
|  | YATNLAN | 304 |
|  | LQFKQYPFT | 305 |
| 424H7F2-VH | PYGMGVG | 321 |
|  | NIWWDDDKYYNPSLIN | 322 |
|  | SELVMPYVPFDY | 323 |
| 424H7F2-VL | QASQDIENDLI | 329 |
|  | YATNLAN | 304 |
|  | LQFKQYPYT | 316 |
| 427C4F11-VH | TYGMGVG | 300 |
|  | NIWWDDDKYSNPSLQS | 330 |
|  | SELVMPYVPFDY | 323 |
| 427C4F11-VL | QASQDIDNHLI | 303 |
|  | YATNLAN | 304 |
|  | LQFKQYPFT | 305 |
| 430D9B3-VH | PYGMGVG | 321 |
|  | NIWWDDDKYYNPSLIN | 322 |
|  | SELVMPYVPFDY | 323 |
| 430D9B3-VL | QASQDIENDLI | 329 |
|  | YATNLAN | 304 |
|  | LQFKQYPYT | 316 |
| 432C12E1-VH | TYGMGVG | 300 |
|  | NIWWDDDKYYNPSLKN | 331 |
|  | SEIVMPYVPFDY | 332 |
| 432C12E1-VL | QASQDIGNDLI | 309 |
|  | YATNLAN | 304 |
|  | LQFKQYPFT | 305 |
| 442C9H4-VH | TYGMGVG | 300 |
|  | NIWWDDDKYYNPSLIN | 322 |
|  | SELVMPYVPFDF | 325 |

TABLE A-continued

CDR Sequences of the mouse antibodies

| Antibody chain | CDR Sequences (CDR1, CDR2, CDR3 in order, for VH or VL) | SEQ ID NO: |
|---|---|---|
| 442C9H4-VL | QASQDIGIDLI | 333 |
| | YTANLAS | 327 |
| | LQYKQYPFT | 328 |
| 445A6G7-VH | PYGMGVG | 321 |
| | NIWWDDDKYYNPSLIN | 322 |
| | SELVMPYVPFDY | 323 |
| 445A6G7-VL | QASQDIGNDLI | 309 |
| | YATNLAN | 304 |
| | LQFKQYPYT | 316 |
| 537C8D7-VH | DYAMA | 334 |
| | TVFYDGSDTFYRDSVKG | 335 |
| | EGDYYSRHVYVGYNWFPH | 336 |
| 537C8D7-VL | LTSEDINSELA | 337 |
| | NANSLQD | 338 |
| | QQYNSYPLT | 339 |

In some embodiments, the VH CDR1, CDR2, and CDR3 are selected from any set of VH CDR1, CDR2, and CDR3 shown in Table A, and the VL CDR1, CDR2, and CDR3 are selected from any set of VL CDR1, CDR2, and CDR3 shown in Table A. In some embodiments, the VH CDR1, CDR2, and CDR3 and the VL CDR1, CDR2, and CDR3 are selected from those derived from the same antibody in the examples.

In some embodiments, at least one, or two, or three, or four, or five, or six of the VH CDR1, CDR2, and CDR3 and the VL CDR1, CDR2, and CDR3 of the above are modified by one, two or three amino acid additions, deletions, substitutions, or the combinations thereof.

In one embodiment, the anti-CXCL13 antibody or fragment thereof includes the following CDRs: HCDR1: DYYMN (SEQ ID NO: 97), HCDR2: VINPNNGGT-TYKEKFKG (SEQ ID NO: 98), HCDR3: DDYDAGY (SEQ ID NO: 99), LCDR1: KASQNVDTAVA (SEQ ID NO: 100), LCDR2: SASHRYT (SEQ ID NO: 101), and LCDR3: QQYTDFPLT (SEQ ID NO: 102).

In some embodiments, the antibody is humanized but with one or more of the following back mutations on the heavy chain: 12V, 20M, 48I, 68A, 70L, 72V, 77G and 112L, according to Kabat numbering, and combinations thereof. In some embodiments, the antibody is humanized but with one or more of the following back mutations on the light chain: 13T and 78V according to Kabat numbering, and combinations thereof.

Non-limiting examples of heavy chain variable regions include SEQ ID NO: 95, and 103-106. Non-limiting example of light chain variable regions include SEQ ID NO: 96, and 107-109.

In one embodiment, the anti-CXCL13 antibody or fragment thereof includes the following CDRs: HCDR1: SYAMS (SEQ ID NO: 112), HCDR2: TISDGGS-DAYYPDNVKG (SEQ ID NO: C2), HCDR3: DYYGSGYEDSPMDY (SEQ ID NO: 115), LCDR1: KASQDINKYIA (SEQ ID NO: 117), LCDR2: YTSTLQP (SEQ ID NO: 118), and LCDR3: LQYDNLYT (SEQ ID NO: 119).

In some embodiments, the antibody is humanized but with one or more of the following back mutations on the light chain: 49H, 58I, 71Y, and 83F according to Kabat numbering, and combinations thereof.

Non-limiting examples of heavy chain variable regions include SEQ ID NO: 110, and 120. Non-limiting example of light chain variable regions include SEQ ID NO: 111, and 121-124.

In one embodiment, one or more of the amino acid residues in the CDRs are substituted with a different amino acid to avoid post-translational modification. An example anti-CXCL13 antibody or fragment thereof includes the following CDRs: HCDR1: SYAMS (SEQ ID NO: 112), HCDR2: TISEGGSDAYYPDNVKG (SEQ ID NO:114), HCDR3: DYYGSGYEESPMDY (SEQ ID NO:116), LCDR1: KASQDINKYIA (SEQ ID NO: 117), LCDR2: YTSTLQP (SEQ ID NO: 118), and LCDR3: LQYDNLYT (SEQ ID NO: 119).

In some embodiments, the antibody is humanized but with one or more of the following back mutations on the light chain: 49H, 58I, 71Y, and 83F according to Kabat numbering, and combinations thereof.

Non-limiting examples of heavy chain variable regions include SEQ ID NO: 157. Non-limiting example of light chain variable regions include SEQ ID NO: 111, and 121-124, in particular SEQ ID NO:121.

In one embodiment, the anti-CXCL13 antibody or fragment thereof includes the following CDRs: HCDR1: RYWMS (SEQ ID NO: 127), HCDR2: EINPDSSTINY-APSLKD (SEQ ID NO: 128), HCDR3: QDDYEYYAMDY (SEQ ID NO: 130), LCDR1: KASQDVNTGVA (SEQ ID NO: 131), LCDR2: SASYRYT (SEQ ID NO: 132), and LCDR3: QQYYSTPLT (SEQ ID NO: 133).

In one embodiment, one or more of the amino acid residues in the CDRs are substituted with a different amino acid to avoid post-translational modification. An example anti-CXCL13 antibody or fragment thereof includes the following CDRs: HCDR1: RYWMS (SEQ ID NO: 127), HCDR2: EINPESSTINYAPSLKD (SEQ ID NO:129), HCDR3: QDDYEYYAMDY (SEQ ID NO: 130), LCDR1: KASQDVNTGVA (SEQ ID NO: 131), LCDR2: SASYRYT (SEQ ID NO: 132), and LCDR3: QQYYSTPLT (SEQ ID NO: 133).

In some embodiments, the antibody is humanized but with one or more of the following back mutations on the heavy chain: 5Q, 47I, 48G, and 85V according to Kabat numbering, and combinations thereof. In some embodiments, the antibody is humanized but with one or more of the following back mutation on the light chain: 78V according to Kabat numbering.

Non-limiting examples of heavy chain variable regions include SEQ ID NO: 125, and 134-137. Non-limiting example of light chain variable regions include SEQ ID NO: 126, and 138-139.

Following humanization, the 71F4A3 antibody further went through rounds of affinity maturation. The CDR sequences from various variants of 71F4A3 are provided in Table B and summarized in Table C below.

TABLE B

Antibodies derived from 71F4A3 and their CDRs

| Antibody chain (SEQ ID NO:) | CDR Sequences (CDR1, CDR2, CDR3) | SEQ ID NO: |
|---|---|---|
| 71F4A3-VH (125) | RYWMS | 127 |
| | EINPDSSTINYAPSLKD | 128 |
| | QDDYEYYAMDY | 130 |

TABLE B-continued

Antibodies derived from 71F4A3 and their CDRs

| Antibody chain (SEQ ID NO:) | CDR Sequences (CDR1, CDR2, CDR3) | SEQ ID NO: |
|---|---|---|
| 71F4A3-VL (126) | KASQDVNTGVA | 131 |
| | SASYRYT | 132 |
| | QQYYSTPLT | 133 |
| 71F4A3-VH1 (134) | RYWMS | 127 |
| | EINPDSSTINYAPSLKD | 128 |
| | QDDYEYYAMDY | 130 |
| 71F4A3-VH2 (135) | RYWMS | 127 |
| | EINPDSSTINYAPSLKD | 128 |
| | QDDYEYYAMDY | 130 |
| 71F4A3-VH3 (136) | RYWMS | 127 |
| | EINPDSSTINYAPSLKD | 128 |
| | QDDYEYYAMDY | 130 |
| 71F4A3-VH4 (137) | RYWMS | 127 |
| | EINPDSSTINYAPSLKD | 128 |
| | QDDYEYYAMDY | 130 |
| 71F4A3-VL1 (138) | KASQDVNTGVA | 131 |
| | SASYRYT | 132 |
| | QQYYSTPLT | 133 |
| 71F4A3-VL2 (139) | KASQDVNTGVA | 131 |
| | SASYRYT | 132 |
| | QQYYSTPLT | 133 |
| 71F4A3-VH (D54E) (156) | RYWMS | 127 |
| | EINPESSTINYAPSLKD | 129 |
| | QDDYEYYAMDY | 130 |
| 71F4A3-VL (138) | KASQDVNTGVA | 131 |
| | SASYRYT | 132 |
| | QQYYSTPLT | 133 |
| 71F4A3-BC1-VH (158) | RYWMS | 127 |
| | EINPEASSINYAPSLKD | 340 |
| | QDDYSHYAMDY | 341 |
| 71F4A3-BC1-VL (159) | KASQDVNTGVS | 342 |
| | SASYRYT | 132 |
| | QQYYSTPLT | 133 |
| 71F4A3-BC4-VH (160) | RYWMS | 127 |
| | EINPEAGKWNYAPSLKD | 343 |
| | QDDYTTYAMDY | 344 |
| 71F4A3-BC4-VL (161) | KASQDVNTGVS | 342 |
| | SASYRYT | 132 |
| | QQYYSTPLT | 133 |
| 71F4A3-BE3-VH (162) | RYWMS | 127 |
| | EINPESSTINYAPSLKD | 129 |
| | QDDYLTYAMDY | 345 |
| 71F4A3-BE3-VL (163) | KASQDVNTAVD | 346 |
| | SASYRYT | 132 |
| | QQYYSTPLT | 133 |
| 71F4A3-BD12-VH (164) | RYWMS | 127 |
| | EINPETTIINYAPSLKD | 347 |
| | QDDYRHYAMDY | 348 |
| 71F4A3-BD12-VL (165) | KASQDVNTGVA | 131 |
| | SASYRYT | 132 |
| | QQYYSTPLT | 133 |
| 71F4A3-4H1-VH (166) | RYWMS | 127 |
| | EINPESTLINYAPSLKD | 349 |
| | QDDYRNYAMDY | 350 |
| 71F4A3-4H1-VL (167) | KASQDVNTGVS | 342 |
| | SASYRYT | 132 |
| | QQYYSTPLT | 133 |
| 71F4A3-5A4-VH (168) | RYWMS | 127 |
| | EINPESTGINYAPSLKD | 351 |
| | QDDYWTYAMDY | 352 |
| 71F4A3-5A4-VL (169) | KASQDVNTAVS | 353 |
| | SASYRYT | 132 |
| | QQYYSTPLT | 133 |
| 71F4A3-3F12-VH (170) | RYWMS | 127 |
| | EINPESNFINYAPSLKD | 354 |
| | QDDYSVYAMDY | 355 |
| 71F4A3-3F12-VL (171) | KASQDVNTGVT | 356 |
| | SASYRYT | 132 |
| | QQYYSTPLT | 133 |
| 71F4A3-B12-VH (172) | RYWMS | 127 |
| | EINPERNYINYAPSLKD | 357 |
| | QDDYDKYAMDY | 358 |
| 71F4A3-B12-VL (173) | KASQDVNTGVT | 356 |
| | SASYRYT | 132 |
| | QQYYSTPLT | 133 |
| 71F4A3-VH (D54E) (156) | RYWMS | 127 |
| | EINPESSTINYAPSLKD | 129 |
| | QDDYEYYAMDY | 130 |
| 71F4A3-VL (138) | KASQDVNTGVA | 131 |
| | SASYRYT | 132 |
| | QQYYSTPLT | 133 |
| 005-3-18-VH (174) | RYWMS | 127 |
| | EINPESSTINYAPSLKD | 129 |
| | QDDYEYYTMDY | 359 |
| 005-3-18-VL (175) | KVSQDVNTGVA | 360 |
| | SASYRYT | 132 |
| | QQYWSTPLT | 361 |
| 005-3-23-VH (176) | RYWMS | 127 |
| | EINPESSTINYAPSLKD | 129 |
| | QEDYEYYALDY | 362 |
| 005-3-23-VL (177) | KASQDVNTGVY | 363 |
| | SASYRYT | 132 |
| | QQGYSTPLT | 364 |
| 005-2-45-VH (178) | RYWMS | 127 |
| | EINPESSTINYAPSLKD | 129 |
| | QDDTRYYAMDY | 365 |
| 005-2-45-VL (138) | KASQDVNTGVA | 131 |
| | SASYRYT | 132 |
| | QQYYSTPLT | 133 |
| 71F4-B-VH (174) | RYWMS | 127 |
| | EINPESSTINYAPSLKD | 129 |
| | QDDYEYYTMDY | 359 |
| 71F4-B-VL (179) | KVSQDVNTGVA | 360 |
| | SASYRYT | 132 |
| | QQYYSTPLT | 133 |
| 71F4-B-L-VH (180) | RYWMS | 127 |
| | EINPESSTINYAPSLKD | 129 |
| | QDDYLYYTMDY | 366 |
| 71F4-B-L-VL (179) | KVSQDVNTGVA | 360 |
| | SASYRYT | 132 |
| | QQYYSTPLT | 133 |

TABLE B-continued

Antibodies derived from 71F4A3 and their CDRs

| Antibody chain (SEQ ID NO:) | CDR Sequences (CDR1, CDR2, CDR3) | SEQ ID NO: |
|---|---|---|
| 71F4-B-T-VH (181) | RYWMS<br>EINPESSTINYAPSLKD<br>QDDYETYTMDY | 127<br>129<br>367 |
| 71F4-B-T-VL (179) | KVSQDVNTGVA<br>SASYRYT<br>QQYYSTPLT | 360<br>132<br>133 |
| 71F4-B-LT-VH (182) | RYWMS<br>EINPESSTINYAPSLKD<br>QDDYLTYTMDY | 127<br>129<br>368 |
| 71F4-B-LT-VL (179) | KVSQDVNTGVA<br>SASYRYT<br>QQYYSTPLT | 360<br>132<br>133 |
| 71F4-B-A-VH (183) | RYWMS<br>EINPEASTINYAPSLKD<br>QDDYEYYTMDY | 127<br>369<br>359 |
| 71F4-B-VL (179) | KVSQDVNTGVA<br>SASYRYT<br>QQYYSTPLT | 360<br>132<br>133 |
| 71F4-B-S1-VH (184) | RYWMS<br>EINPESSSINYAPSLKD<br>QDDYEYYTMDY | 127<br>370<br>359 |
| 71F4-B-S1-VL (179) | KVSQDVNTGVA<br>SASYRYT<br>QQYYSTPLT | 360<br>132<br>133 |
| 71F4-B-S2-VH (185) | RYWMS<br>EINPESSTINYAPSLKD<br>QDDYSYYTMDY | 127<br>129<br>371 |
| 71F4-B-S2-VL (179) | KVSQDVNTGVA<br>SASYRYT<br>QQYYSTPLT | 360<br>132<br>133 |
| 71F4-B-H-VH (186) | RYWMS<br>EINPESSTINYAPSLKD<br>QDDYEHYTMDY | 127<br>129<br>372 |
| 71F4-B-H-VL (179) | KVSQDVNTGVA<br>SASYRYT<br>QQYYSTPLT | 360<br>132<br>133 |
| 71F4-B-SH-VH (187) | RYWMS<br>EINPESSTINYAPSLKD<br>QDDYSHYTMDY | 127<br>129<br>373 |
| 71F4-B-SH-VL (179) | KVSQDVNTGVA<br>SASYRYT<br>QQYYSTPLT | 360<br>132<br>133 |
| 71F4-B-AS-VH (188) | RYWMS<br>EINPEASSINYAPSLKD<br>QDDYEYYTMDY | 127<br>340<br>359 |
| 71F4-B-AS-VL (179) | KVSQDVNTGVA<br>SASYRYT<br>QQYYSTPLT | 360<br>132<br>133 |
| 71F4-B-SSH-VH (189) | RYWMS<br>EINPESSSINYAPSLKD<br>QDDYSHYTMDY | 127<br>370<br>373 |
| 71F4-B-SSH-VL (179) | KVSQDVNTGVA<br>SASYRYT<br>QQYYSTPLT | 360<br>132<br>133 |
| 71F4-B-ASH-VH (190) | RYWMS<br>EINPEASSINYAPSLKD<br>QDDYSHYTMDY | 127<br>340<br>373 |
| 71F4-B-ASH-VL (179) | KVSQDVNTGVA<br>SASYRYT<br>QQYYSTPLT | 360<br>132<br>133 |

TABLE C

Summary of CDRs of antibodies derived from 71F4A3

| CDR | Sequence (SEQ ID NO:) |
|---|---|
| CDRH1 | RYWMS (127) |
| CDRH2 | EINPDSSTINYAPSLKD (128)<br>EINPESSTINYAPSLKD (129)<br>EINPEASSINYAPSLKD (340)<br>EINPEAGKWNYAPSLKD (343)<br>EINPETTIINYAPSLKD (347)<br>EINPESTLINYAPSLKD (349)<br>EINPESTGINYAPSLKD (351)<br>EINPESNFINYAPSLKD (354)<br>EINPERNYINYAPSLKD (357)<br>EINPEASTINYAPSLKD (369)<br>EINPESSSINYAPSLKD (370) |
| CDRH3 | QDDYEYYAMDY (130)<br>QDDYSHYAMDY (341)<br>QDDYTTYAMDY (344)<br>QDDYLTYAMDY (345)<br>QDDYRHYAMDY (348)<br>QDDYRNYAMDY (350)<br>QDDYWTYAMDY (352)<br>QDDYSVYAMDY (355)<br>QDDYDKYAMDY (358)<br>QDDYEYYTMDY (359)<br>QEDYEYYALDY (362)<br>QDDTRYYAMDY (365)<br>QDDYLYYTMDY (366)<br>QDDYETYTMDY (367)<br>QDDYLTYTMDY (368)<br>QDDYSYYTMDY (371)<br>QDDYEHYTMDY (372)<br>QDDYSHYTMDY (373) |
| CDRL1 | KASQDVNTGVA (131)<br>KASQDVNTGVS (342)<br>KASQDVNTAVD (346)<br>KASQDVNTAVS (353)<br>KASQDVNTGVT (356)<br>KVSQDVNTGVA (360)<br>KASQDVNTGVY (363) |
| CDRL2 | SASYRYT (132) |
| CDRL3 | QQYYSTPLT (133)<br>QQYWSTPLT (361)<br>QQGYSTPLT (364) |

In one embodiment, provided is an antibody or fragment thereof having specificity to a human chemokine (C-X-C motif) ligand 13 (CXCL13) protein, wherein the antibody or fragment thereof comprises CDR sequences as listed in Table B or Table C.

In one embodiment, provided is an antibody or fragment thereof having specificity to a human chemokine (C-X-C motif) ligand 13 (CXCL13) protein, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein: the HCDR1 comprises the amino acid sequence of SEQ ID NO:127 (RYWMS); the HCDR2 comprises the amino acid sequence of SEQ ID NO:128 (EINPDSSTINYAPSLKD), SEQ ID NO:129 (EINPESSTINYAPSLKD), SEQ ID NO:340 (EINPEASSINYAPSLKD), SEQ ID NO:343, (EINPEAGKWNYAPSLKD), SEQ ID NO:347 (EINPETTIINYAPSLKD), SEQ ID NO:349 (EINPESTLINYAPSLKD), SEQ ID NO:351, INPESTGINYAPSLKD), SEQ ID NO:354 (EINPESNFINYAPSLKD), SEQ ID NO:357 (EINPERNYINYAPSLKD), SEQ ID NO:369 (EINPEASTINYAPSLKD), or SEQ ID NO:370 (EINPESSSINYAPSLKD); the HCDR3 comprises the amino acid sequence of SEQ ID NO:130 (QDDYEYYAMDY), SEQ ID NO:341 (QDDYSHYAMDY), SEQ ID NO:344 (QDDYTTYAMDY), SEQ ID NO:345 (QDDYLTYAMDY), SEQ ID NO:348 (QDDYRHYAMDY), SEQ ID NO:350 (QDDYRNYAMDY), SEQ ID NO:352 (QDDYWTYAMDY), SEQ ID NO:355 (QDDYSVYAMDY), SEQ ID NO:358 (QDDYDKYAMDY), SEQ ID NO:359 (QDDYEYYTMDY), SEQ ID NO:362 (QEDYEYYALDY), SEQ ID NO:365 (QDDTRYYAMDY), SEQ ID NO:366 (QDDYLYYTMDY), SEQ ID NO:367 (QDDYETYTMDY), SEQ ID NO:368 (QDDYLTYTMDY), SEQ ID NO:371 (QDDYSYYTMDY), SEQ ID NO:372 (QDDYEHYTMDY), or SEQ ID NO:373 (QDDYSHYTMDY); the LCDR1 comprises the amino acid sequence of SEQ ID NO:131 (KASQDVNTGVA), SEQ ID NO:342 (KASQDVNTGVS), SEQ ID NO:346 (KASQDVNTAVD), SEQ ID NO:353 (KASQDVNTAVS), SEQ ID NO:356 (KASQDVNTGVT), SEQ ID NO:360 (KVSQDVNTGVA), or SEQ ID NO:363 (KASQDVNTGVY); the LCDR2 comprises the amino acid sequence of SEQ ID NO:132 (SASYRYT); and the LCDR3 comprises the amino acid sequence of SEQ ID NO:133 (QQYYSTPLT), SEQ ID NO:361 (QQYWSTPLT), or SEQ ID NO:364 (QQGYSTPLT).

In some embodiments, the HCDR1, HCDR2, HCDR3, LCDR1, LCD2 and LCDR3 comprise SEQ ID NO:127, 129, 367, 360, 132 and 133, respectively. In some embodiments, the heavy chain variable region comprises the amino acid sequence of SEQ ID NO:181 or an amino acid sequence having at least 90% sequence identity to SEQ ID NO:181, and the light chain variable region comprises the amino acid sequence of SEQ ID NO:179 or an amino acid sequence having at least 90% sequence identity to SEQ ID NO:179.

In some embodiments, the antibody or fragment is humanized and wherein the heavy chain variable region comprises one or more back mutations selected from the group consisting of 5Q, 47I, 48G, and 85V, according to Kabat numbering, and combinations thereof, or wherein the light chain variable region comprises a mutation 78V according to Kabat numbering.

In some embodiments, the heavy chain variable region comprises the amino acid sequence of SEQ ID NO:181, and the light chain variable region comprises the amino acid sequence of SEQ ID NO:179.

6 In some embodiments, the HCDR1, HCDR2, HCDR3, LCDR1, LCD2 and LCDR3 comprise SEQ ID NO:127, 129, 359, 360, 132 and 133, respectively. In some embodiments, the heavy chain variable region comprises the amino acid sequence of SEQ ID NO:174 or an amino acid sequence having at least 90% sequence identity to SEQ ID NO:174, and the light chain variable region comprises the amino acid sequence of SEQ ID NO:179 or an amino acid sequence having at least 90% sequence identity to SEQ ID NO:179.

In some embodiments, the HCDR1, HCDR2, HCDR3, LCDR1, LCD2 and LCDR3 comprise SEQ ID NO:127, 129, 359, 360, 132 and 361, respectively. In some embodiments, the heavy chain variable region comprises the amino acid sequence of SEQ ID NO:174 or an amino acid sequence having at least 90% sequence identity to SEQ ID NO:174, and the light chain variable region comprises the amino acid sequence of SEQ ID NO:175 or an amino acid sequence having at least 90% sequence identity to SEQ ID NO:175.

In some embodiments, the HCDR1, HCDR2, HCDR3, LCDR1, LCD2 and LCDR3 comprise SEQ ID NO:127, 129, 130, 131, 132 and 133, respectively. In some embodiments, the heavy chain variable region comprises the amino acid sequence of SEQ ID NO:156 or an amino acid sequence having at least 90% sequence identity to SEQ ID NO:156, and the light chain variable region comprises the amino acid sequence of SEQ ID NO:138 or an amino acid sequence having at least 90% sequence identity to SEQ ID NO:138.

In some embodiments, the HCDR1, HCDR2, HCDR3, LCDR1, LCD2 and LCDR3 comprise SEQ ID NO:127, 128, 130, 131, 132 and 133, respectively. In some embodiments, the heavy chain variable region comprises the amino acid sequence of SEQ ID NO:134 or an amino acid sequence having at least 90% sequence identity to SEQ ID NO:134, and the light chain variable region comprises the amino acid sequence of SEQ ID NO:138 or an amino acid sequence having at least 90% sequence identity to SEQ ID NO:138.

In one embodiment, the anti-CXCL13 antibody or fragment thereof includes the following CDRs: HCDR1: DYYMA (SEQ ID NO: 142), HCDR2: SINYDGGDTYYRDSVKG (SEQ ID NO: 143), HCDR3: EEDYDGSYVMDA (SEQ ID NO: 144), LCDR1: KASQNINKELT (SEQ ID NO: 145), LCDR2: NTNILQT (SEQ ID NO: 146), and LCDR3: LQQSSLYT (SEQ ID NO: 147).

In some embodiments, the antibody is humanized but with one or more of the following back mutations on the heavy chain: 24V, 70V, 98T and 105A according to Kabat numbering, and combinations thereof. In some embodiments, the antibody is humanized but with one or more of the following back mutations on the light chain: 58I, 71Y, and 87F according to Kabat numbering, and combinations thereof.

Non-limiting examples of heavy chain variable regions include SEQ ID NO: 140, and 148-151. Non-limiting example of light chain variable regions include SEQ ID NO: 141, and 152-155.

It was an interesting discovery that those antibodies that cross-bound to both human and cynomolgus CXCL13 proteins target an epitope that is different from known anti-CXCL13 antibodies. Accordingly, in one embodiment, provided is an antibody or fragment thereof having specificity to a human chemokine (C-X-C motif) ligand 13 (CXCL13) protein, wherein the antibody or fragment thereof can bind to one or more amino acid residues selected from the group consisting of F20, P22, R24 and F25 of the CXCL13 protein.

In some embodiments, the antibody or fragment thereof can bind to F20 and P22, F20 and R24, F20 an F25, P22 and R24, P22 and F25, or R24 and F25 of the CXCL13 protein. In some embodiments, the antibody or fragment thereof can bind to of F20, P22, and R24; F20, P22, and F25; F20, R24 and F25; or P22, R24 and F25 of the CXCL13 protein.

In some embodiments, the antibody or fragment thereof can bind to F20, P22, R24 and F25 of the CXCL13 protein.

In some embodiments, the antibody or fragment thereof can further bind to the cynomolgus CXCL13 protein.

The CDRs, heavy chain variable regions and light chain variable regions of the present disclosure can be further modified. In some embodiments, the modified heavy chain variable region or light chain variable region retains at least about 70%, 75%, 80%, 85%, 90%, 95%, 98% or 99% sequence identity and is still capable of binding to CXCL13.

In some embodiments, the modification is substitution at no more than one hot spot position from each of the CDRs. In some embodiments, the modification is substitution at one, two or three such hot spot positions. In one embodiment, the modification is substitution at one of the hot spot positions. Such substitutions, in some embodiments, are conservative substitutions.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

Amino Acid Similarity Matrix

|   | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −3 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | 1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

Conservative Amino Acid Substitutions

| For Amino Acid | Substitution With |
|---|---|
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-ME-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-ME-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

It will also be understood by one of ordinary skill in the art that antibodies as disclosed herein may be modified such that they vary in amino acid sequence from the naturally occurring binding polypeptide from which they were derived. For example, a polypeptide or amino acid sequence derived from a designated protein may be similar, e.g., have a certain percent identity to the starting sequence, e.g., it may be 60%, 70%, 75%, 80%, 85%, 90%, 95%, 98%, or 99% identical to the starting sequence.

In certain embodiments, the antibody comprises an amino acid sequence or one or more moieties not normally associated with an antibody. Exemplary modifications are described in more detail below. For example, an antibody of the disclosure may comprise a flexible linker sequence, or may be modified to add a functional moiety (e.g., PEG, a drug, a toxin, or a label).

Antibodies, variants, or derivatives thereof of the disclosure include derivatives that are modified, i.e., by the covalent attachment of any type of molecule to the antibody such that covalent attachment does not prevent the antibody from binding to the epitope. For example, but not by way of limitation, the antibodies can be modified, e.g., by glycosylation, acetylation, pegylation, phosphorylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the antibodies may contain one or more non-classical amino acids.

In some embodiments, the antibodies may be conjugated to therapeutic agents, prodrugs, peptides, proteins, enzymes, viruses, lipids, biological response modifiers, pharmaceutical agents, or PEG.

The antibodies may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art.

Bi-Functional Molecules

Bi-functional molecules such as bispecific antibodies are also provided. In one embodiment, the bi-functional molecule has a first specificity to CXCL13 as well as a second specificity. The second specificity, in one embodiment is to another cytokine or to an immune cell.

For instance, B-cell activating factor (BAFF), also known as tumor necrosis factor ligand superfamily member 13B, is a cytokine that belongs to the tumor necrosis factor (TNF) ligand family. This cytokine is a ligand for receptors TNFRSF13B/TACI, TNFRSF17/BCMA, and TNFRSF13C/BAFF-R. This cytokine is expressed in B cell lineage cells, and acts as a potent B cell activator. It has been also shown to play an important role in the proliferation and differentiation of B cells. The anti-BAFF specificity can be derived from an anti-BAFF antibody such as Belimumab.

In another example, the second specificity can be at IFNαRI (interferon-alpha/beta receptor alpha chain, or IFNAR1). Type I IFNs, particularly the IFN-αs and IFN-β, have received attention for their roles in the pathogenesis autoimmune and inflammatory syndromes. By signaling through a common receptor (IFNAR), these pleiotropic cytokines affect almost every aspect of innate and adaptive immune responses, including upregulation of MHC and costimulatory molecules, and production of B cell survival factors (BAFF, April) by antigen-presenting cells, culminating in the engagement and expansion of autoreactive T and B cells.

In some embodiments, the immune cell is selected from the group consisting of a T cell, a B cell, a monocyte, a macrophage, a neutrophil, a dendritic cell, a phagocyte, a natural killer cell, an eosinophil, a basophil, and a mast cell. Molecules on the immune cell which can be targeted include, for example, CD3, CD16, CD19, CD28, and CD64. Other examples include PD-1, CTLA-4, LAG-3 (also known as CD223), CD28, CD122, 4-1BB (also known as CD137), TIM3, OX-40 or OX40L, CD40 or CD40L, LIGHT, ICOS/ICOSL, GITR/GITRL, TIGIT, CD27, VISTA, B7H3, B7H4, HEVM or BTLA (also known as CD272), killer-cell immunoglobulin-like receptors (KIRs), and CD47.

The anti-CXCL13 specificity can also be combined with specificity to a tumor antigen. A "tumor antigen" is an antigenic substance produced in tumor cells, i.e., it triggers an immune response in the host. Tumor antigens are useful in identifying tumor cells and are potential candidates for use in cancer therapy. Normal proteins in the body are not antigenic. Certain proteins, however, are produced or over-expressed during tumorigenesis and thus appear "foreign" to the body. This may include normal proteins that are well sequestered from the immune system, proteins that are normally produced in extremely small quantities, proteins that are normally produced only in certain stages of development, or proteins whose structure is modified due to mutation.

An abundance of tumor antigens are known in the art and new tumor antigens can be readily identified by screening. Non-limiting examples of tumor antigens include EGFR, Her2, EpCAM, CD20, CD30, CD33, CD47, CD52, CD133, CD73, CEA, gpA33, Mucins, TAG-72, CIX, PSMA, folate-binding protein, GD2, GD3, GM2, VEGF, VEGFR, Integrin, αVβ3, α5β1, ERBB2, ERBB3, MET, IGF1R, EPHA3, TRAILR1, TRAILR2, RANKL, FAP and Tenascin.

Different format of bispecific antibodies are also provided. In some embodiments, each of the anti-CXCL13 fragment and the second fragment each is independently selected from a Fab fragment, a single-chain variable fragment (scFv), or a single-domain antibody. In some embodiments, the bispecific antibody further includes a Fc fragment.

Polynucleotides Encoding the Antibodies and Methods of Preparing the Antibodies

The present disclosure also provides isolated polynucleotides or nucleic acid molecules encoding the antibodies, variants or derivatives thereof of the disclosure. The polynucleotides of the present disclosure may encode the entire heavy and light chain variable regions of the antigen-binding polypeptides, variants or derivatives thereof on the same polynucleotide molecule or on separate polynucleotide molecules. Additionally, the polynucleotides of the present disclosure may encode portions of the heavy and light chain variable regions of the antigen-binding polypeptides, variants or derivatives thereof on the same polynucleotide molecule or on separate polynucleotide molecules.

Methods of making antibodies are well known in the art and described herein. In certain embodiments, both the variable and constant regions of the antigen-binding polypeptides of the present disclosure are fully human. Fully human antibodies can be made using techniques described in the art and as described herein. For example, fully human antibodies against a specific antigen can be prepared by administering the antigen to a transgenic animal which has been modified to produce such antibodies in response to antigenic challenge, but whose endogenous loci have been disabled. Exemplary techniques that can be used to make such antibodies are described in U.S. Pat. Nos. 6,150,584; 6,458,592; 6,420,140 which are incorporated by reference in their entireties.

Treatment and Diagnostic Methods

As described herein, the antibodies, variants or derivatives of the present disclosure may be used in certain treatment and diagnostic methods.

The present disclosure is further directed to antibody-based therapies which involve administering the antibodies of the disclosure to a patient such as an animal, a mammal, and a human for treating one or more of the disorders or conditions described herein. Therapeutic compounds of the disclosure include, but are not limited to, antibodies of the disclosure (including variants and derivatives thereof as described herein) and nucleic acids or polynucleotides encoding antibodies of the disclosure (including variants and derivatives thereof as described herein).

One embodiment provides a method of suppressing an immune response in a patient in need thereof. The method entails administering to the patient an antibody, fragment, or bi-functional molecule of the present disclosure. In some embodiments, the patient is a tissue or organ transplant recipient.

In some embodiments, a method of treating an autoimmune disease or disorder is provided. Non-limiting examples of autoimmune disease or disorder include type 1 diabetes, rheumatoid arthritis (RA), psoriasis/psoriatic arthritis, multiple sclerosis, systemic lupus erythematosus (lupus), inflammatory bowel disease, Addison's disease, Graves' disease, Sjögren's syndrome, Hashimoto's thyroiditis, myasthenia gravis, vasculitis, pernicious anemia, and celiac disease.

The antibodies of the disclosure can also be used to treat or inhibit cancer. Accordingly, in some embodiments, provided are methods for treating a cancer in a patient in need thereof. The method, in one embodiment, entails administering to the patient an effective amount of an antibody of the present disclosure. Non-limiting examples of cancers include bladder cancer, liver cancer, colon cancer, rectal cancer, endometrial cancer, leukemia, lymphoma, pancreatic cancer, small cell lung cancer, non-small cell lung cancer, breast cancer, urethral cancer, head and neck cancer, gastrointestinal cancer, stomach cancer, oesophageal cancer, ovarian cancer, renal cancer, melanoma, prostate cancer and thyroid cancer.

Additional diseases or conditions associated with increased cell survival, that may be treated, prevented, diagnosed and/or prognosed with the antibodies or variants, or derivatives thereof of the disclosure include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyo sarcoma, colon carcinoma, pancreatic cancer, breast cancer, thyroid cancer, endometrial cancer, melanoma, prostate cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma and retinoblastoma.

A specific dosage and treatment regimen for any particular patient will depend upon a variety of factors, including the particular antibodies, variant or derivative thereof used, the patient's age, body weight, general health, sex, and diet, and the time of administration, rate of excretion, drug combination, and the severity of the particular disease being treated. Judgment of such factors by medical caregivers is within the ordinary skill in the art. The amount will also depend on the individual patient to be treated, the route of administration, the type of formulation, the characteristics of the compound used, the severity of the disease, and the desired effect. The amount used can be determined by pharmacological and pharmacokinetic principles well known in the art.

Methods of administration of the antibodies, variants or include but are not limited to intradermal, intramuscular, intraperitoneal, intravenous, subcutaneous, intranasal, epidural, and oral routes. The antigen-binding polypeptides or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Thus, pharmaceutical compositions containing the antigen-binding polypeptides of the disclosure may be administered orally, rectally, parenterally, intracisternally, intravaginally, intraperitoneally, topically (as by powders, ointments, drops or transdermal patch), bucally, or as an oral or nasal spray.

The term "parenteral" as used herein refers to modes of administration which include intravenous, intramuscular, intraperitoneal, intrasternal, subcutaneous and intra-articular injection and infusion.

Administration can be systemic or local. In addition, it may be desirable to introduce the antibodies of the disclosure into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

It may be desirable to administer the antigen-binding polypeptides or compositions of the disclosure locally to the area in need of treatment; this may be achieved by, for example, and not by way of limitation, local infusion during surgery, topical application, e.g., in conjunction, with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the disclosure, care must be taken to use materials to which the protein does not absorb.

Methods of detecting expression of a human chemokine (C-X-C motif) ligand 13 (CXCL13) protein in a sample are also provided, in some embodiments, comprising contacting the sample with the antibody or fragment thereof, and detecting the binding which indicates expression of CXCL13 in the sample.

Compositions

The present disclosure also provides pharmaceutical compositions. Such compositions comprise an effective amount of an antibody, and an acceptable carrier. In some embodiments, the composition further includes a second anticancer agent (e.g., an immune checkpoint inhibitor).

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. Further, a "pharmaceutically acceptable carrier" will generally be a non-toxic solid, semisolid or liquid filler, diluent, encapsulating material or formulation auxiliary of any type.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfate; chelating agents such as ethylenediaminetetraacetic acid; and agents for the adjustment of tonicity such as sodium chloride or dextrose are also envisioned. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences by E. W. Martin, incorporated herein by reference. Such compositions will contain a therapeutically effective amount of the antigen-binding polypeptide, preferably in purified form, together with a suitable amount of carrier so as to provide the form for proper administration to the patient. The formulation should suit the mode of administration. The parental preparation can be enclosed in ampoules, disposable syringes or multiple dose vials made of glass or plastic.

In an embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

EXAMPLES

Example 1. Generation of Mouse Monoclonal Antibodies Against Human CXCL13

This example shows generation of anti-human-CXCL13 mouse monoclonal antibodies using the hybridoma technology.

Immunizations

Recombinant human CXCL13 proteins were used as the immunogen to raise anti-human CXCL13 antibodies. C57BL/6, Balb/c, SJL mice or wistar rats were first immunized subcutaneously (s.c.). with 50 µg immunogen and then immunized intraperitoneally (i.p.). or s.c. biweekly with 25 µg immunogen. Immune response was monitored by retroorbital bleeds. Plasma was screened by ELISA binding assay. In short, human CXCL13 or mouse CXCL13 or cynomolgus CXCL13 was coated at 0.5 µg/ml overnight and then blocked by 5% BSA in PBS. Serial diluted sera were incubated with the coated antigen for 1 h at room temperature (RT). The resulting plates were washed with PBS/T and incubated with goat anti-mouse IgG-HRP for 1 hour at RT. The plates were developed with TMB substrate and stopped with 1N HCl and analyzed by spectrophotometer at OD 450-630 nm. The mice with high titers of anti-CXCL13 immunoglobulin were selected for fusion and further screening. Four days prior to sacrifice and removal of the spleens, the mice were boosted i.p. with 25 antigen. The spleens were used for fusion.

Fusion and Hybridoma Screening

Splenocytes were electro-fused with mouse myeloma cell line SP2/0 cells and plated into 96-well culture plate. The hybridoma supernatants were tested by ELISA binding assay for anti-human CXCL13 binders. Supernatants of positive binding clones were screened for function in blocking of human CXCL13 binding to its ligand CXCR5 by Cell-based receptor blocking ELISA assay. Briefly, $5 \times 10^4$ CHO-K1-CXCR5 cells were plated in 96-well plate with 100 µl of culture medium and incubated at 37° C. overnight. Cells were fixed with 100 µl of 2% PFA at RT for 1 hr after washing with PBS for 1 time. Blocking was done with 1% BSA in PBST for 1 hr at RT. Supernatants were diluted with PBS and pre-incubated with equal volume of 0.3 µg/ml human CXCL13 for 30 min at RT. 100 µl of antibody-antigen complex was then transferred into each cell wells for 30 min at RT. The samples were washed with 1×PBST for 3 times and 100 µl of 3 µg/ml of human Mab5261 antibody was add into each well to capture human CXCL13 and anti-human Fc-HRP was used to indirectly detect human CXCL13 when it bound to CHO-K1-CXCR5 cells. The secondary antibody was revealed by 100 µl of TMB and stopped with 100 µl 1N HCl. Reading was done at 450 nM.

Clones showing strong blocking ability in this assay were selected for subcloning. Supernatants of one-round sub-clones were used to confirm ELISA-based human CXCL13 or mouse CXCL13 or cynomolgus CXCL13 binding and receptor blocking ability, followed by sequencing and further analysis. After these screenings, 20 clones (329F2E1, 348B10B1, 360A3D4E3, 414D10F5, 339A9E7, 339H3E2, 367F1C2, 21H12D9, 408E3F3, 415A3D1F4, 348E12F12, 368D6D10, 1H3A11, 355A1F6, 353F9C4, 19H7E10, 411A11E9, 64C10G1, 397C3B3) that cross bound to human CXCL13 and cynomolgus CXCL13 were identified and 14 clones (402H2G12, 409G9C2, 410A4D10, 414G3F4, 416C9H8, 418D3H6, 423A6H6, 424H7F2, 427C4F11, 430D9B3, 432C12E1, 442C9H4, 445A6G7, 537C8D7) that cross bound to human CXCL13 and mouse CXCL13 were identified, and 13 clones (119H10D6, 30D6G1, 156H3H7, 168A2D4, 168D6F2, 175E3B10, 177D2G10, 178B2E8, 178E2B3, 181B11G12, 184H10B5, 345G1B4, 396A5A1) that only bound to human CXCL13 were identified.

Those antibodies were purified from hybridoma supernatants by binding with Protein G column and characterized by ELISA binding assays and cell-based blocking ELISA assays. The binding and blocking properties are listed in Tablet and sequences of all the clones are listed in Table 2. 27 clones binding to only huCXCL13 or binding to both huCXCL13 and mouse CXCL13 showed completely or partially blocking activity. 11/20 clones bound to both human CXCL13 and cynomolgus CXCL13 appeared to completely block human CXCL13 to human CXCR5. 11 blockers bound to both huCXCL13 and cynoCXCL13 were produced as chimeric human IgG1 antibodies for further Characterization.

TABLE 1

Binding and blocking properties

| Antibodies | EC50(ng/ml) | | | IC50(ug/ml) |
| | bind to huCXCL13 | bind to Cyno CXCL13 | bind to mouse CXCL13 | blocking assays |
| --- | --- | --- | --- | --- |
| 329F2E1 | 16.58 | 12.46 | N.B | 0.615 |
| 348B10B1 | 12.36 | 16.57 | N.B | NA |
| 360A3D4E3 | 6.641 | 17.77 | N.B | NA |
| 414D10F5 | 10.45 | 18.98 | N.B | 1.142 |
| 339A9E7 | 21.56 | 24.54 | N.B | 13.33 |
| 339H3E2 | 38.76 | 31.9 | N.B | NA |
| 367F1C2 | 66.79 | 55.71 | N.B | NA |
| 21H12D9 | 15.64 | 61.85 | N.B | 1.273 |
| 408E3F3 | 23.68 | 70.59 | N.B | 1.493 |
| 415A3D1F4 | 13.23 | 71.14 | N.B | 0.6983 |
| 348E12F12 | 63.6 | 76.53 | N.B | NA |
| 368D6D10 | 86.44 | 139.9 | N.B | NA |
| 1H3A11 | 63.28 | 144.6 | N.B | 10.14 |
| 355A1F6 | 94.25 | 153.9 | N.B | NA |
| 353F9C4 | 134.5 | 171.6 | N.B | NA |

TABLE 1-continued

Binding and blocking properties

| Antibodies | EC50(ng/ml) | | | IC50(ug/ml) |
| | bind to huCXCL13 | bind to Cyno CXCL13 | bind to mouse CXCL13 | blocking assays |
| --- | --- | --- | --- | --- |
| 19H7E10 | 38.52 | 195.9 | N.B | 2.218 |
| 411A11E9 | 20.14 | 252.4 | N.B | 0.793 |
| 64C10G1 | 31.39 | 347 | N.B | 0.3303 |
| 397C3B3 | 344.1 | 400.6 | N.B | NA |
| 71F4A3 | 26.63 | 1013 | N.B | 3.017 |
| 119H10D6 | 39.29 | N.B | N.B | 0.5334 |
| 130D6G1 | 19.18 | N.B | N.B | 1.232 |
| 156H3H7 | 13.44 | N.B | N.B | 4.592 |
| 168A2D4 | 134.3 | N.B | N.B | 0.2898 |
| 168D6F2 | 21.77 | N.B | N.B | 2.093 |
| 175E3B10 | 32.63 | N.B | N.B | 1.418 |
| 177D2G10 | 54.42 | N.B | N.B | ~911.9 |
| 178B2E8 | 420.3 | N.B | N.B | ~3.372e+009 |
| 178E2B3 | 15.33 | N.B | N.B | 0.9739 |
| 181B11G12 | 22.34 | N.B | N.B | 0.7025 |
| 184H10B5 | 27.24 | N.B | N.B | 4.85 |
| 345G1B4 | 13.8 | N.B | N.B | 3.24 |
| 396A5A1 | 13.51 | N.B | N.B | 1.005 |
| 402H2G12 | 5.777 | N.B | 35.71 | 8.719 |
| 409G9C2 | 2266 | N.B | 538.2 | 11.74 |
| 410A4D10 | 2139 | N.B | 760.8 | 8.38 |
| 414G3F4 | 3662 | N.B | 3008 | 26.45 |
| 416C9H8 | 5840 | N.B | 1966 | 8.456 |
| 418D3H6 | 48660 | N.B | 7492 | 23.33 |
| 423A6H6 | 1558 | N.B | 248.2 | 8.959 |
| 424H7F2 | 10.95 | N.B | 12.09 | 1.1 |
| 427C4F11 | 1329 | N.B | 201.8 | 7.918 |
| 430D9B3 | 26.45 | N.B | 54.71 | 3.849 |
| 432C12E1 | 5099 | N.B | 744.3 | 12.65 |
| 433E4H11 | 2872 | N.B | 700.8 | 14.25 |
| 442C9H4 | 9852 | N.B | 2960 | 18.2 |
| 445A6G7 | 2908 | N.B | 1228 | 14.88 |
| 537C8D7 | 12.78 | N.B | 37.47 | 2.455 |

N.B. = No binding,
NA = Not available

TABLE 2

Sequences of Antibodies Selected from Screening

| Antibody chain | Sequences (with signal peptide) | SEQ ID NO: |
| --- | --- | --- |
| 329F2E1-VH | MDFGLIFFIVALLKGVQCEVKLLQSGGGLVQPGGSLKLSCAASGIDFSRY WMSWVRRAPGKGLEWIGEINPDSSTINYAPSLKDKFIISRDNAKNTLYLQ MSKVRSEDTALYYCARQDDYDYYAMDYWGQGTSVTVSS | 1 |
| 329F2E1-VL | MGIKMESQIQVFVFVFLWLSGVDGDIVMTQSHKFMSTSVGDRVSITCKAS QDVSTGVAWYQQKPGQSPKLLIYSASYRYTGVPDRFTGSGSRTDFTFTIS SVQTEDPAVYYCHQYYTIPLTFGAGTELELK | 2 |
| 348B10B1 -VH | MGWSWIFLFLLSGTAGVLSEVQLQQSGPELVKPGASVKISCKTSGYTFTE YIMHWVKQSHGRSLEWIGGINPDNGDTTYNQKFKGKATLTVDKSSTTAYM ELRSLTSEDSAVYYCAGGVLDYWGQGTSVTVSS | 3 |
| 348B10B1 -VL | MMSPAQFLFLLVLWIRETNGDVVMTQTPLTLSVTIGQPASISCKSSQSLL DSDGKTYLNWLLQRPGQSPKRLIYLVSKLDSGVPDRFTGSGSGTDFTLKI SRVEAEDLGVFYCWQGTHFPPFTFGSGTKLEIK | 4 |
| 360A3D4E3 -VH | MGWSWIFLFLLSGTAGVLSEVQLQQSGPELVKPGASVKISCKTSGYTFTE YIMHWVKQSHERSLEWIGGIHPDNGDTTYNQKFTGKATLTVDKSSTTAYM ELRSLTSEDSAVYYCAGGVLDYWGQGTSVTVSS | 5 |
| 360A3D4E3 -VL | MMSPAQFLFLLVLWIRETNGDVVMTQTPLTLSVTFGQPASISCKSSQSLL DSDGRTYLNWLLQRPGQSPQRLIYLVSKLDSGVPDRFTGSGSGTDFTLKI SRVEAEDLGVFYCWQGTHFPPFTFGSGTKLEIK | 6 |

TABLE 2-continued

Sequences of Antibodies Selected from Screening

| Antibody chain | Sequences (with signal peptide) | SEQ ID NO: |
|---|---|---|
| 414D10F5 -VH | MDIRLSLVFLVLFIKGVQCEVQLAESGGGLVQPGRSLKLSCSASGFTFSD YYMAWFRQAPPKGLEWVASISYDGGDSFYRDSVKGRFTISRDNAKSSLYL QMDSLRSEDTATYYCTTEEDYSGSFPDYWGQGVMVTVSS | 7 |
| 414D10F5 -VL | MMAPVQLLGLLLIWLPAMRCDIQMTQSPSFLSASVGDRVTINCKASQNIN KYLNWYQQKLGEAPKRLIYDTNNLQAGIPSRFSGSGSGTDYTLTINSLQP EDFATYFCLQHNSLYTFGGGTKLELK | 8 |
| 339A9E7 -VH | MRVLILLWLFTAFPGILSDVQLQESGPGLVKPSQSLSLTCTVTGYSITSD YAWNWNRQFPGNKLEWMGYISYSGDTSYNPSLRSRISITRDTSKNQFFLQ LNSVTAEDTAKYYCVAGHFDYWGQGTTLTVSS | 9 |
| 339A9E7 -VL | MMSPAQFLFLLVLWIRETNGDVVMTQTPLTLSITLGQPASISCKSSQSLL DSDGETYLNWLLQRPGQSPKRLIYLVSKLDSGVPDRFTGSGSGTDFTLKI SRVEAEDLGVYYCWQGTHFPYTFGGGTKLEIK | 10 |
| 339H3E2 -VH | MGWSWIFLFLLSGTAGVLSEVQLQQSGPELVKPGASVKISCKTSGYTFTE YIMHWVKQSHGRSLEWIGGINPNNGGTTYNQKFKGKATLTVDKSSSTAYM ELRSLTSEDSAVYYCAGGVMDYWGQGTSVTVSS | 11 |
| 339H3E2 -VL | MMSPAQFLFLLVLWIRETNGDVVMTQTPLTLSVTIGQPASISCKSSQSLL DSDGKTYLNWLLQRPGQSPKRLIYLVSKLDSGVPDRFTGSGSGTDFTLKI SRVEAEDLGVFYCWQGTHFPFTFGSGTKLEIK | 12 |
| 367F1C2 -VH | MRVLILLWLLTALPGILSDVQLQESGPGLVKPSQSLSLTCTVTGYSITSD YAWNWIRHFPGNKLEWMGYISYTGSSSYNPSLKSRISITRDTSKNQFFLQ LNSVTSEDTATYYCVAGHFDYWGPGTTLTVSS | 13 |
| 367F1C2 -VL | MMSPAQFLFLLVLWIREANGDVVMTQTPLTLSVTIGQPASISCKSSQSLL DSDGKTYLNWLLQRPGQSPKRLIYQVSKLDSGVPDRFTGSGSGTDFTLKI SRVEAEDLGVYYCWQGTHFPYTFGGGTKLEIK | 14 |
| 21H12D9 -VH | MGWSWIFLFLLSGTAGVHSEVQLQQSGPVLVRPGASVKMSCKASGYTFTD YYMNWVKQSHGKSLEWIGVINPNNGGTTYKEKFKGKATLTVDKSSGTAYM ELNSLTSEDSAVYYCARDDYDAGYWGQGTTLTVSS | 15 |
| 21H12D9 -VL | MGFKMEFHTQVFVFVFLWLSGVDGDIVMTQFQKFMSTTVGDRVSITCKAS QNVDTAVAWYQHKPGQSPKLLIYSASHRYTGVPDRFTGSGSGTDFTLTIS NVQSEDLADYFCQQYTDFPLTFGAGTKLELK | 16 |
| 408E3F3 -VH | MDRLTSSILLLLVPAYVLSHVTLRESGPGVLQPSKTLSLTCSFSGFSLST SAMVVSWIRQSSGMSLEWLAAIDWEGDKYYNPSLESRLTVSRDISDTQVF LRITSVDVADTATYYCAVMSSADSHSVLDAWGQGVSVTVSS | 17 |
| 408E3F3 -VL | MMAALQLLGVLLLWLPAMRCDIKMTQSPSFLSASVGDRVTINCKASQNIH NYLNWYQQKFGEAPRLLIYNTNNLQTGIPSRFSGSGSGTDFTLTISSLQP EDVATYFCLQHSSSLTFGSGTKLEIN | 18 |
| 415A3D1F4 -VH | MKLWLNWIFLLTLLNGIQCEVKLLESGGGLVQAGGSMRLSCGAFGFTVTD FYINWIRQPAGKAPEWLGFMRNKANGYTTEYNPSVKGRFTISRNNTQNMP YLQMNTLRTEDTAIYYCARSRYNADDYYVGVMDVWGQGASVTVSS | 19 |
| 415A3D1F4 -VL | MGVPTQLLVLLLLWITDAICDIQMTQFPASLSASLGETVSIECLASEDTY NNLAWYQQKPGKSPQLLIYYTNSLQDGVPSRFSGTGSGTQYSLKINSLES EDAATYFCLQDSEYPWTFGGGTKLKLK | 20 |
| 348E12F12 -VH | MRVLILLWLFTAFPGILSDVQLQESGPGLVKPSQSLSLTCTVTGYSITSD YAWNWIRQFPGNKLEWMGYISYSGDTSYNPSLKSRISITRDTSKNQFFLQ LNSVTTEDTATYYCVAGHFDYWGQGTTLTVSS | 21 |
| 348E12F12 -VL | MMSPAQFLFLLVLWIRETNGDVVMAQTPLTLSVTIGQPASISCKSSQSLL DSDGKTYLNWLLQRPGQSPKRLIYLVSNLDSGVPDRFTGSGSGTDFTLKI IRVEAEDLGLYYCWQGTHFPYTFGGGTKLEIK | 22 |
| 368D6D10 -VH | MRVLILLWLFTAFPGILSDVQLQESGPGLVKPSQSLSLTCTVTGYSITSD YAWNWIRQFPGNKLEWMGYISYSGSTSYNPSLKSRISITRDTSKNQFFLQ LNSVTTEDTATYYCVAGHFDYWGQGTTLTVSS | 23 |
| 368D6D10 -VL | MMSPAQFLFLLVLWIRETNGDVVMTQTPLTLSITIGQPASISCKSSQSLL DSDGKTYLNWLLQRPGQSPKRLIYLVSKLDSGVPDRFTGSGSGTDFTLKI SRVEAEDLGVYYCWQGTHFPYTFGGGTKLEIK | 24 |

TABLE 2-continued

Sequences of Antibodies Selected from Screening

| Antibody chain | Sequences (with signal peptide) | SEQ ID NO: |
|---|---|---|
| 1H3A11-VH | MNFGLSLIFLVLVLKGVQCEVQLVESGGGLVKPGGSLKLSCAASGFTFSS YAMSWVRQTPEKRLEWVATISDGGSDTYYPDNVKGRFTISRDNAKNNLYL QMSHLKSEDTAMYYCARDYYGSSYEDYAMDYWGQGTSVTVSS | 25 |
| 1H3A11-VL | MRPSIQFLGLLLFWLHGAQCDIQMTQSPSSLSASLGGKVTITCKASQDIN KYITWYQHKPGKGPRLLIHYTSTLQPGIPSRFSGSGSGRDYSFSISNLEP EDIATYYCLQYDNLYTFGGGTKLEIK | 26 |
| 355A1F6-VH | MRVLILLWLFTAFPGILSDVQLQESGPGLVKPSQSLSLTCTVTGYSITSD YAWSWIRQFPGNKLEWMGYISYSDSTSYNPSLKSRISITRDTSKNQFFLQ LNSVTAEDTATYYCAAGHFDYWGQGTILTVSS | 27 |
| 355A1F6-VL | MMSPAQFLFLLVLWIREINGDVVMTQTPLTLSVTIGQPASISCKSSQSLL DSDGKTYLNWLLQRPGQSPKRLIYLVSKLDSGVPDRFTGSGSGTDFTLKI SRVEAEDLGVYYCWQGTHFPYTFGGGTKLEIK | 28 |
| 353F9C4-VH | MRVLILLWLFTAFPGILSDVQLQESGPGLVKPSQSLSLTCTVTGYSITSD YAWSWIRQFPGNKLEWMGYITYSDSTSYNPSLKSRISITRDTSKNQFFLQ LNSVTAEDTATYYCAAGHFDYWGQGTILTVSS | 29 |
| 353F9C4-VL | MMSPAQFLFLLVLWIREINGDVVMTQTPLTLSVTIGQPASISCKSSQSLL DSDGKTYLNWLLQRPGQSPKRLIYLVSKLDSGVPDRFTGSGSGTDFTLKI SRVEAEDLGVYYCWQGTHFPYTFGGGTKLEIK | 30 |
| 19H7E10-VH | MGWSWIFLFLLSGTAGVLSEVQLQQSGPELVKPGASVKISCQASGYAFSD YYMNWVKQSHGKRLEWIGDINPNNDGTTYNQKFKDKATLTVDKSSSTAYM DLRSLTSEDSAVYYCARLSWSFFAMDYWGQGTSVTVSS | 31 |
| 19H7E10-VL | MGIKMESQIQVFVFVFLWVSGVDGDIVMTQSHKFMSTSVGDRVSITCKAS QDVSSGVAWYQQKPGQSPKVLIYSASHRHTGVPDRFTASGSGTDFTFTIS SVQAEDLAVYYCQQYYNTPWTFGGGTKLEIK | 32 |
| 411A11E9-VH | MDIRLSLGFLVLFIKGVQCEVQLVESGGGLVQPGGSLKLSCVVSGFTFSD YYMAWVRQTPTKGLEWVASINYDGGDTYYRDSVKGRFTVSRNNAKSSLFL QMDSLRSEDTATYYCKTEEDYDGSYVMDAWGQGASVIVSS | 33 |
| 411A11E9-VL | MMAPVQLLGLLLIWLPAMRCDIQMTQSPSFLSASVGDRVTISCKASQNIN KELTWYQQKLGKAPKRLIYNTNILQTGIPSRFSGSGSNTDYTLTISSLQP EDFATYFCLQQSSLYTFGAGTKLELK | 34 |
| 64C10G1-VH | MNFGLSLIFLVLVLKGIQCEVQLVESGGGLVKPGGSLKLSCAASGFTFSS YAMSWVRQTPEKRLEWVATISDGGSDAYYPDNVKGRFTISRDNAKNNLYL QMSHLKSEDTAMYYCARDYYGSYEDSPMDYWGQGTSVTVSS | 35 |
| 64C10G1-VL | MRPSIQFLGLLLFWLHGAQCDIQMTQSPSSLSASLGGKVTITCKASQDIN KYIAWYQHKPGKGPRLLIHYTSTLQPGIPSRFSGSGSGRDYSFSISNLEP EDFATYYCLQYDNLYTFGGGTKLEIK | 36 |
| 397C3B3-VH | MRVLILLWLFTAFPGILSDVQLQESGPGLVKPSQSLSLTCTVTGYSITSD YAWNWIRQFPGNKLEWMGYISYSGSTSYNPSLKSRISINRDTSKNQFFLQ LNSVTTEDTATYYCVAGHFDYWGQGTTLTVSS | 37 |
| 397C3B3-VL | MMSPAQFLFLLVLWIRETNGDVVMTQTPLTLSITIGQSASISCKSSQSLL DSDGKTYLNWLLQRPGQSPKRLISLVSKLDSGVPDRFTGSGSGTDFTLKI SRVEAEDLGVYYCWQGTHFPYTFGGGTKLEIK | 38 |
| 71F4A3-VH | MDFGLIFFIVALLKGVQCEVKLLQSGGGLVQPGGSLKLSCAASGIDFSRY WMSWVRRAPGKGLEWIGEINPDSSTINYAPSLKDKFIISRDNAKNTLYLQ MSKVRSEDTALYYCARQDDYEYYAMDYWGQGTSVTVSS | 39 |
| 71F4A3-VL | MGIKMESQIQVSVFVILWLSGVDGDIVMTQSHKSMSTSVGDRVSITCKAS QDVNTGVAWYRQKPGQSPKLLIYSASYRYTGVPDRFTGSGSGTDFTFTIS SVQAEDLAVYYCQQYYSTPLTFGAGTKLELK | 40 |
| 119H10D6-VH | MEWTWVFLFLLSVTAGVHSQVQLQQSGAELMKPGASVKISCKATGYTFNT YWIEWVKQRPGHGLEWIGEILPGSESTDYNEKFKDKATFTADISSNTAYM QLSSLTSEDSAVYYCARDYYGYYFDYWGQGTTLTVSS | 41 |
| 119H10D6-VL | MGIKMESQIQVFVFVFLWLSGVDGDIVMTQSHKFMSTSVGDRVSITCKAS QDVSTAVVWYQQKPGQSPKLLIYSASYRYTGVPDRFSGSGSGTDFTFTIS SVQAEDLAVYYCQQHYSSPRTFGGGTKLEIK | 42 |

TABLE 2-continued

Sequences of Antibodies Selected from Screening

| Antibody chain | Sequences (with signal peptide) | SEQ ID NO: |
|---|---|---|
| 130D6G1-VH | MEWTWVFLFLLSVTAGVHSQVQLQQSGAELMKPGASVKISCKSTGYTFST YWIEWVKQRPGHGLEWIGEILPGSDSTNSNEKFEGKATFTADTSSNTAYM QLSSLTSEDSAVYYCARDYYGFYFDYWGQGTTLTVSS | 43 |
| 130D6G1-VL | MGIKMESQIQVFVFVFLWLSGVDGDIVMTQSHKFMSTSVGDRVNITCKAS QDVSTAVAWYQQKPGQSPKLLIYSTSYRYTGVPDRFTGSGSGTDFTFTIS NVQAEDLAVYYCQQHYTTPRTFGGGTKLEIK | 44 |
| 156H3H7-VH | MGWSWIFLFLLSGTAGVLSEVQLQQSGPELVKPGASVKISCKASGYTFTD YYMNWVRQSHGKSLEWIGDINPNNGDTTYNQKFKGKATLTVDTSSSTVYM ELRSLTSEDSAVYYCAGYDEDHYAMDYWGQGTSVTVSS | 45 |
| 156H3H7-VL | MGIKMESQMQVFVFVFLWLSGVDGDYVMTQSHKFMSTSVGDRVSITCKAS QDVSTGVAWYQQNPGQSPKLLIYSASHRYTGVPDRFTGSGSGTDFTFTIS SVQAEDLAVYYCQQYYTTPWTFGGGTKLEIK | 46 |
| 168A2D4-VH | MGWSWIILFLVSGTAGVLSEVQLQQSGPELVKPGASVKISCKASGNTLTD YYMNWVKQSHGKSLEWIGDINPNNGDIIYNQKFKGKATLTVAKSSSTAYM ELRSLTSEDSAVYYCAIYYDPYYHAMDYWGQGTSVTVSS | 47 |
| 168A2D4-VL | MGIKMESQIQVFVFVFLWLSGVDGDIVMTQSHKFMSTSVRDRVSITCKAS QDVSTGVAWYQQKPGQSPKLLIYSASYRYTGVPDRFTGSGSGTDFTFTIS SVQAEDLAVYYCQQQYSVPLTFGAGTKLELK | 48 |
| 168D6F2-VH | MGWSCIMLFLAATATGVHSQVQLQQPGAELVKPGASVKLSCQASGYTFTS YWMHWVKQRPGRGLEWIGGIDPDSGATKDNEKFKTKATLTVDKPSRTAYI QLSSLTSEDSAVFYCARGSTVVAPGDYFAMDYWGQGTSVTVSS | 49 |
| 168D6F2-VL | METDTLLLWVLLLWVPGSTGDIVLTPSPTSLAVSLGQRATMSCRASESVD NYGISFMHWYQQKPGQPPKLLIYRASNLDSGIPARFSASGSRTDFTLTIN PVETDDVATYYCQQSNKDPWTFGGGTKLEIK | 50 |
| 175E3B10-VH | MGRLTSSFLLLIVPAYVLSQVTLKESGPGILQPSQTLSLTCSFSEFSLSV FGMGVGWIRQPSGKGLEWLAHIWWDDEKYYNPALKSRLTISKDTSKNQVF LKIANVDTADTATYFCARIDGYYDFDYWGQGTTLTVSS | 51 |
| 175E3B10-VL | MKLPVRLLVLMFWIPASSSDVLMTQTPLSLPVSLGTQASIFCRSSHSIVQ DNGNTYLQWYLQKPGQSPKLLIYKVSNRFSGVPDRFSGSGSGTDFTLKIS RVEAEDLGVYYCFQGSYVPYTFGGGTKLEIK | 52 |
| 177D2G10-VH | MDRLTSSFLLLIVPAYVLSQIALKESGPGILQSSQTLSLTCSFSGFSLST SGMHVGWFRQPSGKTLEWLAHIYWDDDKRYNPSLKSRLTISKDTSRNQVF LNLTNVDTADTATYYCARRGGDYDYDEGFDYWGQGTTLTVSS | 53 |
| 177D2G10-VL | MKLPVRLLVLMFWIPASSSDVVMTQTPLSLPVSLGDQASISCRSSQSLVH SNGFTYLHWYLQKPGQSPKLLIYKVSNRFSGVPDRFSGSGSGTEFTLRIS RVEAEDLGVYFCSQSTHVPYTFGGGTKLEIK | 54 |
| 178B2E8-VH | MYFRLSSVFLVLILKGVQCEVKLVESEGGLVQPGSSMKLSCTASGFTFTD YYMTWVRQVPEKGLEWVANINYDGSRTNYLDSLKSRFIISRDNAKNILYL QMSSLKSEDTATYYCARDGNYHFYGMDYWGQGTSVTVSS | 55 |
| 178B2E8-VL | MGIKMESQIQAFVFVFLWLSGVDGDFVLTQSHKFMSTSVGDRVSITCKAS QDVSTAVAWYQQKPGQSPQLLIYWASTRHTGVPDRFTGSGSGTDYTLTIS SVQAEDLALYYCQQHYSTPWTFGGGTKLEIK | 56 |
| 178E2B3-VH | MEWSRVFIFLLSVTAGIHSQVQLQQSGAELVRPGTSVKVSCKASGYAFTN HLIEWVKQRPGQGLEWIGVINPGSGGTKYNEKFKGKATVTADKSSSTVYM QLNSLTSEDSAVYFCARSSDGYYEEDYFDYWGQGTTLTVSS | 57 |
| 178E2B3-VL | MDFQVQIFSFLLISASVIISRGQIVLTQSPAIMSASPGEKVTMTCSASSS VNYMQWYQQKSGTSPKRWIYDTSELASGVPDRFSGSGSGTSYSLTISSME AEDVATYYCQQWSSDPITFGAGTKLELK | 58 |
| 181B11G12-VH | MYFRLSSVFLVLILKGVQCEVKLVESEGGLVQPGSSMKLSCTASGFTFSD YYMAWVRQVPEKGLEWVANINYDGSDTYYLDSLKSRFIISRDNAKNILYL QMSSLKSEDTATYYCVRDVAYDDSYAMDYWGQGTSVTVSS | 59 |
| 181B11G12-VL | MRPSIQFLGLLLFWLHGAQCDIQMTQSPSSLSASLGGKVTITCKASQDIN KYIAWYQHKPGKGPRLLIHYTSTLQPIPSRFSGSGSGRDYSFSISNLEP EDIATYYCLQYDSLYTFGGGTKLEIK | 60 |

TABLE 2-continued

Sequences of Antibodies Selected from Screening

| Antibody chain | Sequences (with signal peptide) | SEQ ID NO: |
|---|---|---|
| 184H10B5-VH | MGRLTSSFLLLIVPAYVLSQVTLKESGPGILQPSQTLSLTCSFSEFSLSV FGMGVGWIRQPSGKGLEWLAHIWWDDEKYYNPALKSRLTISKDTSKNQVF LKIANVDTADTATYYCARIDGYYDFDYWGQGTTLTVSS | 61 |
| 184H10B5-VL | MKLPVRLLVLMFWIPASSSDVLMTQTPLSLPVSLGTQASISCRSSHSIVQ DNGNTYLQWYLQKPGQSPQLLIYKVSNRFSGVPDRFSGSGSGTDFTLKIS RVEAEDLGVYYCFQGSYVPYTFGGGTKLEIK | 62 |
| 345G1B4-VH | MGRLTSSFLLLIVPAYVLSQVTLKESGPGILQPSQTLSLTCSFSGFSLST SNMGVGWIRQPSGKGLEWLAHIWWDDVKRYNPALKSRLTISKDTSSSQVF LKIASVDTADTATYYCARSTTLVAFDYWGQGTTLTVSS | 63 |
| 345G1B4-VL | MESQTQVLMSLLFWVSGTCGDIVMTQSPSSLTVTAGEKVTMSCKSSQSLL NSGNQKNYLTWYQQKPGQPPKLLIYWASTRESGVPDRFTGSGSGTDFTLT ISSVQAEDLAVYYCQNDYSYPTFGGGTKLEIK | 64 |
| 396A5A1-VH | MGRLTSSFLLLIVPAYVLSQVTLKESGPGILQPSQTLSLTCSFSGFSLST SGMGIGWIRQPSGKGLEWLAHIWWDDIKRYNPALKSRLTVSKDTSTSQVF LNIASVDTADIATYFCARSTTVVAFDYWGQGTTLTVSS | 65 |
| 396A5A1-VL | MESQTQVLMSLLFWVSGTCGDILMTQSPSSLTVTAGEKVTMSCKSSQSLL NSGNQKNYLTWYQQKPGQPPKLLIYWASTRESGVPDRFTGTGSGTDFTLT ISSVQAEDLAIYYCQNDYDYPTFGGGTKLEIK | 66 |
| 402H2G12-VH | MDRLTSSFLLLIVPAYVLSQVTLKESGPGILQPSQTLSLTCTFSGFSLST YGMGVGWIRQPSGKGLEWLANIWWDDDKYYNPSLQNRLTISKDTSNNQAF LKINNVDTADTATYYCARSELIMPYVPFDYWGQGVRVTVSS | 67 |
| 402H2G12-VL | MDMRAHTQFLGFLLLWFPGARCDIQMTQSPSSMSASLGDRVTITCQASQD IDNHLIWFQQKPGKSPRPMIYYATNLANGVPSRFSGSRSGSDYSLTISSL ESEDMADYHCLQFKQYPFTFGSGTKLEIK | 68 |
| 409G9C2-VH | EVQLQQSGPGLVKPSGTLSLTCAVSGGSITSSYWWTWVRQPPGKGLEWIG EIYHSGRPNYNPSLKSRATISVDKSRNQFSLNLTSVTAADTAVYYCAKTA AVSYWYFDLWGRGTLVTVSS | 69 |
| 409G9C2-VL | DIKMNQSPSSMSASLGDRVTITCQASQDIGNDLIWFQQKPGKSPRPLIYY ASNLANGVPSRFSGRRSESNYSLTISSLESEDMADYHCLQFKQYPFTFGA GTKLELK | 70 |
| 410A4D10-VH | EVQLQQSGPGLVRPSGTLSLTCAVSGGSISSRNWWGWVRQPPGKGLEWIG EIYHSGGTNYNPSLKSRVTISVDKSKNQFSLKLSSVTAADTAVYYCAREF GDSVWYFDLWGRGTLVTVSS | 71 |
| 410A4D10-VL | DIVITQSPSSMSASLGDRVTITCQASQDIGNDLVWFQQKPGKSPRPLIYY ATNLADGVPSRFSGRRSESKYSLTISNLESEDMADYHCLQFKQYPYTFGA GTKLELK | 72 |
| 414G3F4-VH | EVQLQQSGPGLVKPSGTLSLTCAVSGGSITSSYWWIWVRQPPGKGLEWIG EIYHSGRPNYNPSLESRVTISVDKSKNQFSLTLSSVTAADTAVYYCAREA GDSVWYFDLWGRGTLVTVSS | 73 |
| 414G3F4-VL | DILLTQSPSSISASLGDRVTITCQASQDIGNELIWFQQKPGKSPRPMIYY ATSLADGVPSRFSGSTSGSDYSLTIGSLESEDMADYHRLQFKQYPFTFGS GTRLEIK | 74 |
| 416C9H8-VH | QVTLKESGPEILQPSQTLSLTCTFSGFSLSPYGMGVGWIRQPSGKGLEWL ANIWWDDDKYYNPSLINRLTISKDTSNNQAFLKITNVDTTDSATYYCVRS ELVMPYVPFDYWGQGVMVTVSS | 75 |
| 416C9H8-VL | DIQMTQSPSSMSASLGDRVTITCQASQDIENDLVWFQQKPGRSPRPLIYY ATNLANGVPSRFSGRRSESDYSLTISSLESEDMADYHCLQFKQYPYTFGA GTKLELK | 76 |
| 418D3H6-VH | QVTLKESGPGILQPSQTLSLTCTFSGFSLSTYGMGVGWIRQPSGKGLEWL ANIWWDDDKYYNPSLINRLTISKNTSNNQAFLKITNVDAPDTATYYCARS ELVMPYVPFDFWGQGIMVTVSS | 77 |
| 418D3H6-VL | DIQMTQSPSSLSASLGDRITMTCQASQDIGIELIWFQQKPGKSPWPVIYY TANLASGVPSRFSGSRSGSHYSLTISSLESEDMADYHCLQYKQYPFTFGS GTKLEIK | 78 |

TABLE 2-continued

Sequences of Antibodies Selected from Screening

| Antibody chain | Sequences (with signal peptide) | SEQ ID NO: |
|---|---|---|
| 423A6H6-VH | QVTLKESGPGILQPSQTLSLTCTFSGFSLSTYGMGVGWIRQPSGKGLEWL ANIWWDDDKYYNPSLQNRLTISKDTSNNQAFLKITNVDTADTATYYCARS ELIMPYVPFDYWGQGVRVTVSS | 79 |
| 423A6H6-VL | DIQMTQSPSSMSASLGDRVTITCQASQDIDNHLIWFQQKPGKSPRPMIYY ATNLANGVPSRFSGSRSGSDYSLTISSLESEDMADYHCLQFKQYPFTFGS GTKLEIK | 80 |
| 424H7F2-VH | MDRLTSSFLLLIVPAYVLSQVTLKESGPEILQPSQTLTLTCTFSGFSLSP YGMGVGWIRQPSGKGLEWLANIWWDDDKYYNPSLINRLTISKDTSNNQAF LKITNVDTTDSATYYCVRSELVMPYVPFDYWGQGVMVTVSS | 81 |
| 424H7F2-VL | MDMRAHTQFLGFLLLWFPGARCDIQMTQSPSSMSASLGDRVTITCQASQD IENDLIWFQQKPGKSPRPLIYYATNLANGVPSRFSGRRSESNYALTISSL ESEDMADYHCLQFKQYPYTFGAGTKLELK | 82 |
| 427C4F11-VH | QVTLKESGPGILQPSQTLSLTCTFSGFSLTTYGMGVGWIRQPSGKGLEWL ANIWWDDDKYSNPSLQSRLTISKDTSNNQAFLTITNVDTADTATYYCARS ELVMPYVPFDYWGQGVRVTVSS | 83 |
| 427C4F11-VL | DIQMTQSPSSMSASLGDRVTITCQASQDIDNHLIWFQQKPGRSPRPMIYY ATNLANGVPSRFSGSRSGSDYSLTISSLESEDMADYHCLQFKQYPFTFGS GTKLEIK | 84 |
| 430D9B3-VH | MDRLTSSFLLLIVPAYVLSQVTLKESGPEILQPSQTLSLTCTFSGFSLSP YGMGVGWIRQPSGKGLEWLANIWWDDDKYYNPSLINRLTISKDTSNNQAF LKITNVDTTDSATYYCVRSELVMPYVPFDYWGQGVMVTVSS | 85 |
| 430D9B3-VL | MDMRAHTQFLGFLLLWFPGARCDIQMTQSPSSMSASLGDRVTITCQASQD IENDLIWFQQKPGKSPRPLIYYATNLANGVPSRFSGRRSESNYSLTISSL ESEDMADYHCLQFKQYPYTFGAGTKLELK | 86 |
| 432C12E1-VH | QVTLKESGPGILQPSQTLSLTCTFSGFSLSTYGMGVGWIRQPSGKGLEWL ANIWWDDDKYYNPSLKNRLTISKDTSNNQAFLKITNVDTADTATYYCARS EIVMPYVPFDYWGQGVMVTVSS | 87 |
| 432C12E1-VL | DIQMTQSPSSMSASLGDRVTITCQASQDIGNDLIWFQQKPGKSPRPMIYY ATNLANGVPSRFSGSGSGSVYSLTISSLESEDMADYHCLQFKQYPFTFGS GTKLEIK | 88 |
| 442C9H4 -VH | QVTLKESGPGILQPSQTLSLTCSFSGFSLSTYGMGVGWIRQPSGKGLEWL ANIWWDDDKYYNPSLINRLTISKNTSNNQAFLKITNVDAPDTATYYCARS ELVMPYVPFDFWGQGIMVTVSS | 89 |
| 442C9H4 -VL | DIQMTQSPSSLSASLGDRITITCQASQDIGIDLIWFQQKPGKSPWPVIYY TANLASGVPSRFSGSRSGSHYSLTISSLESEDMADYHCLQYKQYPFTFGS GTKLEIK | 90 |
| 445A6G7-VH | QVTLKESGPEILQPSQTLSLTCTFSGFSLSPYGMGVGWIRQPSGKGLEWL ANIWWDDDKYYNPSLINRLTISKDTSNNQAFLKITNVDTTDSATYYCVRS ELVMPYVPFDYWGQGVMVTVSS | 91 |
| 445A6G7-VL | DIQMTQSPSSMSASLGDRVTITCQASQDIGNDLIWFQQKPGKSPRPLIYY ATNLANGVPSRFSGRRSESNYSLTISSLESEDMADYHCLQFKQYPYTFGA GTKLELK | 92 |
| 537C8D7-VH | MDIRLSLVFLVLFIKGVQCEVQLVESGGGLVLPGRSLKLSCAASGFTFSD YAMAWVRQAPKKGLEWVATVFYDGSDTFYRDSVKGRFTISRDNAKSTLYL QMDSLRSEDTATYYCAREGDYYSRHVYVGYNWFPHWGQGTLVTVSS | 93 |
| 537C8D7-VL | MGVPTHLLGLLLLWITHAMCDIRMTQSPASLSASLGETVNIECLTSEDIN SELAWYQQKPGKFPQFLIYNANSLQDGVPSRFSGSGSGTQYSLKINSLQS EDVATYFCQQYNSYPLTFGSGTELEIK | 94 |

Example 2. Blocking Properties of Anti-CXCL13 Chimeric Antibodies in Cell-Based Blocking Assay This example tested the blocking of the anti-CXCL13 chimeric antibodies to CHO-K1-CXCR5 cells. Briefly, $5\times10^4$ CHO-K1-CXCR5 cells were plated in 96-well plate with 100 μl of culture medium and incubated at 37° C. overnight. Cells were fixed with 100 μl of 2% PFA at RT for 1 hr after washing with PBS for 1 time. Samples were blocked with 1% BSA in PBST for 1 hr at RT. Antibodies were serial diluted from 50 μg/ml by 3-fold with 1% BSA/PBST and pre-incubated with equal volume of 0.3 μg/ml human CXCL13 for 30 min at RT. 100 μl of antibody-antigen complex was transferred into each cell wells for 30 min at RT. Samples were washed with 1×PBST for 3 times and 100 μl of 3 μg/ml of human Mab5261 antibody was added into each well to capture human CXCL13 and anti-human Fc-HRP was used to indirectly detect human CXCL13 when it bound to CHO-K1-CXCR5 cells.

The secondary antibody was revealed by 100 μl of TMB and stopped with 100 μl N HCl. Then read at 450 nM. $IC_{50}$ values were summarized in Table 3, which showed $IC_{50}$ of blocking properties. Among all clones, 415A3D1, 64C10G1, 1H3A11, 414D10F5, 411A11E9, 21H12D9, 71F4A3, 329F2E1 show completely blocking activity and 408E3F3, 19H7E10, 339A6E7 appeared to be partial blockers.

TABLE 3

Blocking properties of chimeric antibodies

| Antibodies | IC50 (μg/ml) |
| --- | --- |
| 415A3D1 | 0.985 |
| 64C10G1 | 1.099 |
| 1H3A11 | 1.19 |
| 414D10F5 | 1.262 |
| 411A11E9 | 1.713 |
| 21H12D9 | 1.892 |
| 71F4A3 | 3.017 |
| 408E3F3 | 7.636 |
| 19H7E10 | 15.1 |
| 329F2E1 | 3.546 |
| 339A6E7 | ~1.425e+011 |

Example 3. Binding Properties of Anti-CXCL13 Chimeric Antibodies

Elisa based binding assay. Antibodies that functionally blocked human CXCL13 were more fully characterized for binding to huCXCL13 and cynoCXCL13. Briefly, 100 μl of human CXCL13 or cynomolgus CXCL13 was coated at 0.5 μg/ml overnight and then blocked by 200 μl of 5% BSA in PBS. Serial diluted antibodies were incubated with the coated antigen for 30 min at RT. The resulting plates were washed with PBS/T and incubated with goat anti-human IgG Fc-HRP for 30 min RT. The plates were developed with TMB substrate after washing with 1×PBST for 5 times and reaction stopped with 1N HCl and analyzed by spectrophotometer at OD 450-630 nm. $EC_{50}$ values are showed in table 4.

TABLE 4

Binding properties of chimeric antibodies

| Antibodies | $EC_{50}$ (ng/ml) | |
| --- | --- | --- |
| | hu CXCL13 | cyno CXCL13 |
| 415A3D1 | 72.89 | 46.94 |
| 64C10G1 | 40.06 | 56.26 |
| 1H3A11 | 55.34 | 143.9 |
| 411A11E9 | 48.46 | 100.4 |
| 414D10F5 | 62.84 | 1190 |
| 21H12D9 | 53.62 | 48.8 |
| 71F4A3 | 38.06 | 81.44 |
| 329F2E1 | 51.13 | 41.62 |

HuCXCL13 binding affinity by Surface Plasmon Resonance. 411A11E9, 415A3D1, 64C10G1, 21H12D9, 329F2E1, 71F4A3 were selected to produce Fab and tested binding affinity. The binding of the antibodies to huCXCL13 was examined by Biacore 8K. 10 mM HEPES, 150 mM NaCl, 3 mM EDTA, 0.05% Tween-20, pH 7.4 served as running buffer and 10 mM glycine-HCl, pH2.0 served as regeneration buffer. CXCL13 protein was immobilized on Sensor Chip CM5 using amine coupling method (immobilization level~30 RU). The serial concentrations of Fab (0-16 nM) were injected over immobilized CXCL13 at the flow rate of 30 μl/min. The dissociation phases were 600 s. The results are shown in Table 5 below.

TABLE 5

Affinity tested by biacore

| Antibodies | ka (1/Ms) | kd (1/s) | KD (M) |
| --- | --- | --- | --- |
| 21H12D9 | 2.14E+06 | 7.31E−04 | 3.41E−10 |
| 329F2E1 | 9.66E+05 | 5.81E−04 | 6.02E−10 |
| 411A11E9 | 2.06E+06 | 3.26E−04 | 1.58E−10 |
| 415A3D1 | 2.56E+06 | 3.06E−03 | 1.20E−09 |
| 64C10G1 | 2.81E+06 | 5.00E−04 | 1.78E−10 |
| 71F4A3 | 1.85E+06 | 2.85E−04 | 1.54E−10 |

Example 4. Blocking Properties of Anti-CXCL13 Chimeric Antibodies in Signaling Assay Inhibition of CXCL13 induced calcium flux by anti-CXCL13 chimeric antibodies. Treatment with then human CXCL13 simulated the intracellular calcium mobilization in CHO-K1-CXCR5 cells. When serially diluted anti-CXCL13 antibodies were added into the assay, the antibodies dose-dependently inhibited calcium flux production in CHO-K1-CXCR5 cells. Based on the result of binding affinity and cell-based blocking, 64C10G1, 1H3A11, 411A11E9, 21H12D9, 71F4A3, 329F2E1, and 415A3D1 were chosen to test in this calcium flux assay.

CHO-K1-CXCR5 cells ($1.5 \times 10^4$ cells/well) in medium were coated to a 384-well assay plate. The next day, they were incubated with 0.75 μg/ml rhCXCL13 with or without serially diluted anti-CXCL13 antibodies in assay buffer (HEPES, 20 nM HBSS) at 37° C. for 30 min. The calcium dye working buffer was prepared and added into cells. Then, transfer mix to cells and obtain the fluorescence intensity (FI) by FLIPRTERA. Statistical analyses were performed by the Graphpad Prism (v5.0) software.

As shown in FIG. 1, compared to positive calcium flux FI (dashed line) which was induced by CXCL13, all the chimeric antibodies of anti-CXCL13 had similarly potent activity in blocking of CXCL13 induced calcium flux in CHO-K1-CXCR5 cells, except 415A3D1.

Blocking of CXCL13 mediated IP1 signaling by anti-CXCL13 chimeric antibodies. CXCL13 bound to ligand CXCR5, which is a G protein-coupled receptor, on CHO-K1-CXCR5 cells can induce the accumulation of inositol monophosphate (IP1), a stable downstream metabolite of IP3 induced by activation of a phospholipase C (PLC) cascade. An IP1 kit (Cisbio) was used to test the blocking efficacy of anti-CXCL13 antibodies. The kit is a competitive immunoassay intended to measure IP1 accumulation in cells by HTRF technology. Native IP1 produced by cells competed with d2-labeled IP1 for binding to anti-IP1-Cryptate. When the CHO-K1-CXCR5 cells are stimulated with CXCL13, the IP1 will be produced by cells and compete with d2-labeled IP1 leading to the detection signal down-regulated compared to without being treated with CXCL13.

0.25 μg/ml CXCL13 was incubated with or without serially diluted anti-CXCL13 antibodies in stimulation medium (F12 culture medium containing 5 mM LiCl, which function is to accumulate IP1) for 20 minutes at RT in a 384-well assay plate. $5\times10^4$ cells were transferred into each well. Incubate the plate for 1 hour in a cell incubator (37° C., humidified, 5% CO2). After incubation, IP1-d2 and anti-IP1-Cryptate working solution mix were added into each well. The plate was sealed and incubated for 1 hour at RT. Finally, the seal was removed and the plate was read on the HTRF compatible reader to obtain the value at 665 nm/615 nm.

Figure 2:
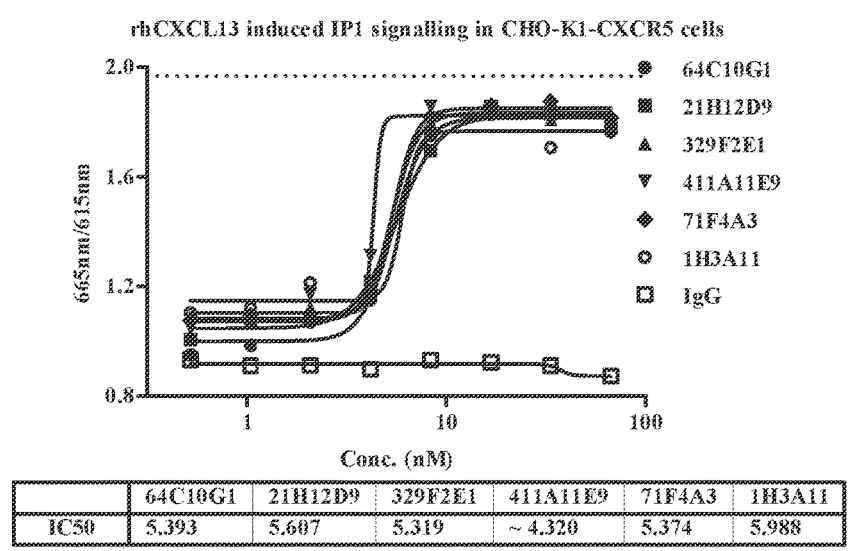

As shown in FIG. 2, IgG curve means the production of IP1 induced by CXCL13. The dashed line indicates the basal level of IP1 in CHO-K1-CXCR5 cells without CXCL13 treatment. All the anti-CXCL13 antibodies, 64C10G1, 21H12D9, 329F2E1, 411A11E9, 71F4A3 and 1H3A11, could effectively dose-dependently blocked the IP1 signal and the inhibition efficiency was similar.

Example 5. In Vitro Blocking of CXCL13 Derived Cells Migration by Anti-CXCL13 Chimeric Antibody Blocking of BaF3-CXCR5 (human) cells migration toward CXCL13. It is known that CXCL13 binds to its receptor CXCR5 and can derive cells migration. To evaluate the inhibition potency of the anti-CXCL13 antibodies in migration assay, human CXCR5 overexpression cell line, BaF3-CXCR5 cells, were used.

The mix of 50 ng/ml CXCL13 was incubated with or without serially diluted anti-CXCL13 antibodies in dilution media (Gey's Balanced Salt Solution+0.1% BSA) in a 96-well culture plate for 30 minutes at RT. Then, transfer 68.5 µl/well mix to the bottom of the 5 µm pore size transwell plate (Corning, 3387). 100 µl/well ($6.5\times10^5$ cells) BaF3-CXCR5 cells were added into the top chamber. In addition, wells that only had chemotaxis medium added to the bottom plate and cells to top chamber to remove the background signal. After 3 hours incubation in an incubator, the chamber was disassembled and all the volume was transferred from the bottom plate to a 96-well culture plate. 10 µl/well of Resazurin (R&D) was added to the assay plate and the plate was incubated for additional 16-24 hours in an incubator. Fluorescence was measured at wavelengths 544 nm and 590 nm.

Figure 3:
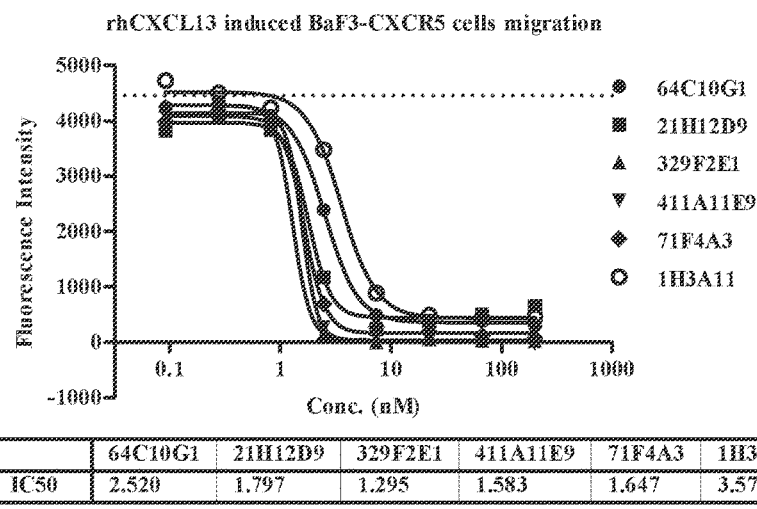
FIG. 3 shows that the BaF3-CXCR5 cells migration was dose-dependent inhibited by anti-CXCL13 antibodies.

The background signal was removed and the GraphPad (v5.0) software was used to obtain the titration fitting curve. In FIG. 3, the dashed lines indicate the CXCL13 induced the migration FI. When the anti-CXCL13 antibodies, 64C10G1, 21H12D9, 329F2E1, 411A11E9, 71F4A3 and 1H3A11, were added into the assay, the FI was dose-dependently down-regulated, which means the BaF3-CXCR5 cells migration was dose-dependently inhibited by anti-CXCL13 antibodies. The inhibition potency of tested antibodies in this BaF3-CXCR5 cells migration were comparable.

Inhibition of primary human tonsil cells migration to CXCL13. To further investigate the blocking function of anti-CXCL13 antibodies, the primary human Tonsil cells migration assay was used. The effect of anti-CXCL13 antibodies mentioned above on primary human tonsil cells migration was tested.

Human tonsil tissues were crashed with 1 mL syringe plunger and passed through 70 µm cell strainer. Collect and wash the cells with PBS. Then, obtain lymphocytes by Ficoll. Wash and re-suspend the lymphocytes with chemotaxis medium (RPMI 1640 containing 0.5% BSA). Then, incubate 0.5 µg/ml CXCL13 with serial concentrations antibodies or control IgG in chemotaxis medium at RT for 30 minutes. Transfer 150 µl/well mix to the bottom of the 5 µm pore size 96-well transwell plate (Corning, 3387), and add 50 µl/well human tonsil cells ($5\times10^5$ cells) to the top chamber. Besides, design wells that only add chemotaxis medium to bottom plate and cells to top chamber to remove the background signal. After incubation 3 hours in an incubator, disassemble the chamber and discard the filter. Add 1.67 µg/ml calcein-AM (ThermoFisher) into the each well and incubate for additional 20 minutes in the incubator. Measure the fluorescence at wavelength 485 nm and 520 nm.

Figure 4:
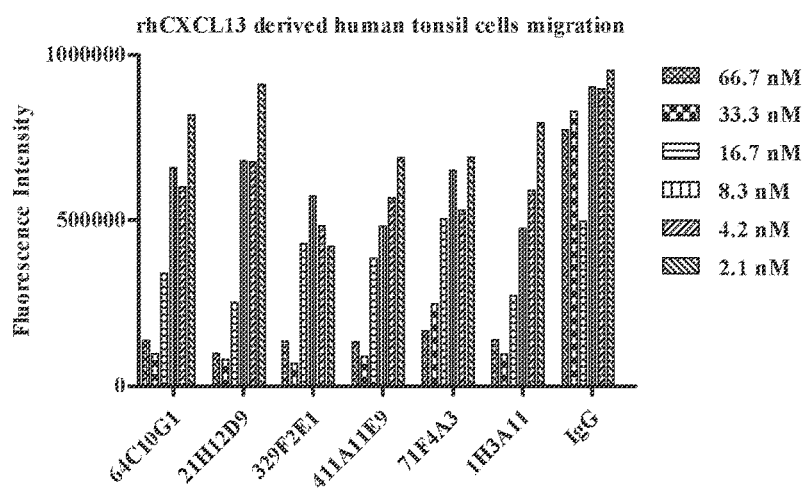
FIG. 4 shows that all chimeric anti-CXCL13 antibodies inhibited primary human tonsil cells chemotaxis in a titratable manner.

Delete the background fluorescence intensity (FI) from raw data and obtain the histogram by the GraphPad (v5.0) software. As shown in the FIG. 4, compare to IgG treated, all anti-CXCL13 antibodies inhibited primary human tonsil cells chemotaxis in a titratable manner.

Example 6. In Vivo Efficacy of Anti-CXCL13 Antibody Therapy in Cynomolgus Monkey In the normal immune response, CXCL13 and its receptor CXCR5 are involved in the homing of B cells and germinal center formation. Ccynomolgus monkeys Immunized with T-cell-dependent antibody response (TDAR) of keyhole limpet hemocyanin (KLH) is a comprehensive immune response model. In this immune response model, we can evaluate the B and T lymphocyte interactions, class switch and germinal center formation through antigen specific antibody production (i.e., IgM to IgG specific antibody response).

Cynomolgus monkey were randomized into 2 groups (3 monkeys/group) and immunized with 1 ml 10 mg/ml KLH by intramuscular injection on Day 0. 30 mg/kg anti-CXCL13 chimeric antibody 64C10G1 was administered via intravenous injection to alternating peripheral vessels on day −1, 4, 9. Equal volume Saline was administered at the same time of control group monkeys. The serum was collected from the Cephalic or femoral vein on day −4, −1, 4, 9 and 14 for anti-KLH-specific IgG/IgM detection. Elisa for the serum level of monkey anti-KLH IgG and IgM was performed according to the manufacturer's instruction (Life Diagnostics, KLHM-3-INT and KLHG-3-INT). On the day 14, collect the whole blood and obtain the peripheral blood mononuclear cells (PBMC) by Ficoll. Analyze the B cell population (CD20$^+$, Biolegend) and CXCR5 (Thermofisher) expression on B cell surface by flow cytometer (Becton-Dickinson). Data acquisition and analysis were conducted using flowjo software.

Figure 5:
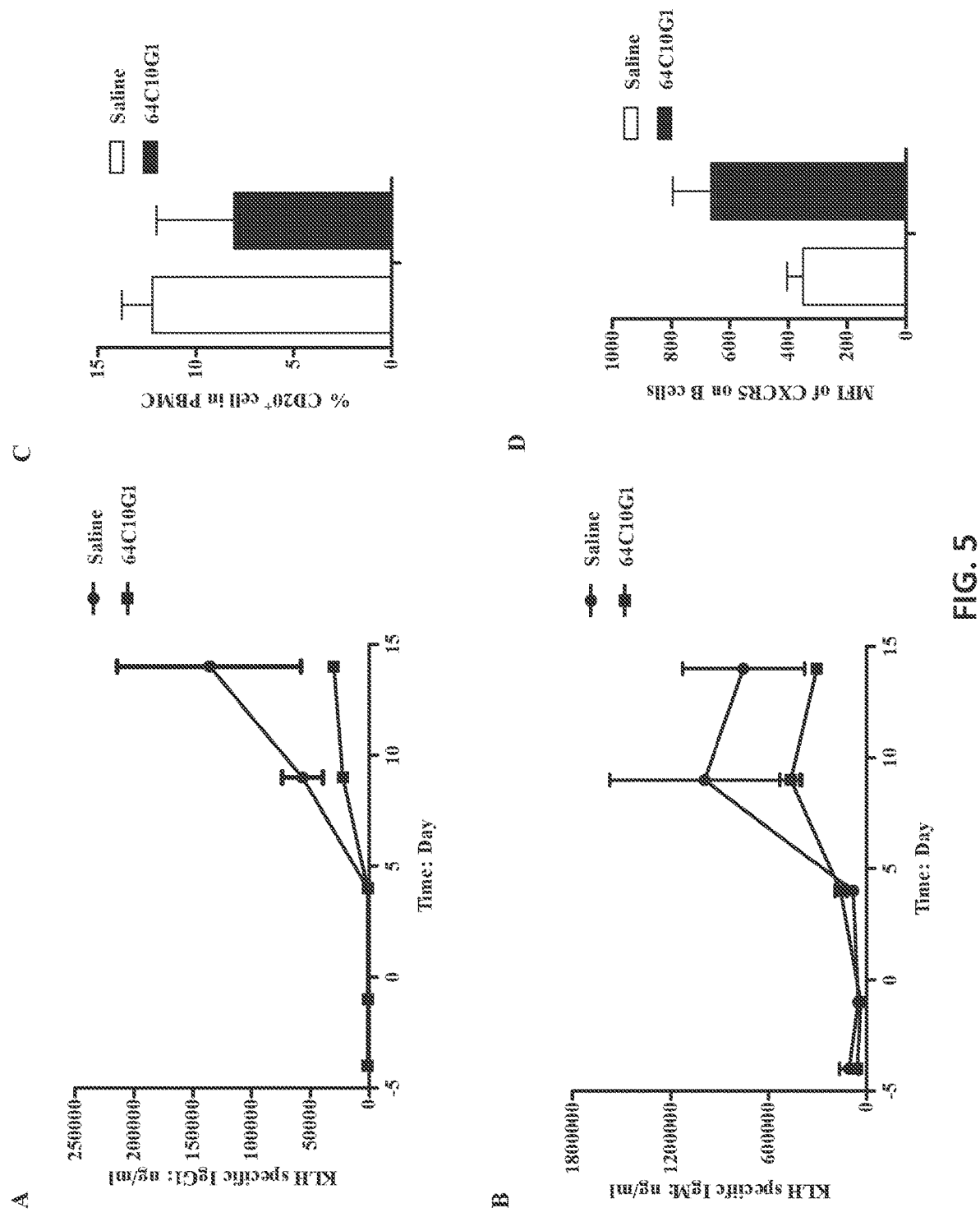
FIG. 5 shows with an in vivo model that the anti-CXCL13 antibody 64C10G1 had potent efficacy in blocking—antigen specific high affinity antibody production, class switch, that meant inhibition of germinal center formation.
Figure 6:
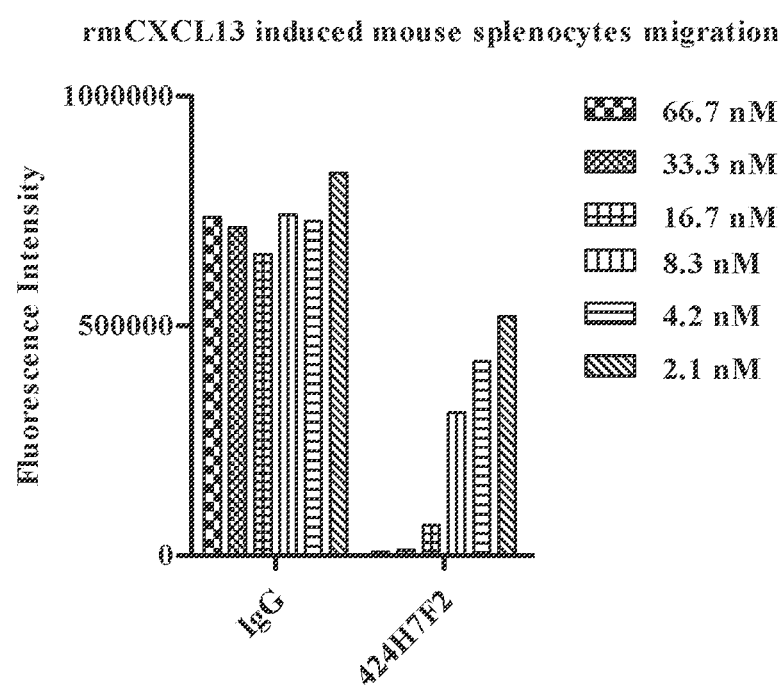
FIG. 6 shows that 424H7F2 mouse monoclonal antibody could dose-dependent inhibit primary mouse splenocytes migration toward mouse CXCL13.

As shown in FIG. 5A, though there was the individual difference in Saline group, we could see the anti-CXCL13 antibody 64C10G1 treatment could inhibit the production of anti-KLH specific IgG. The IgM level of KLH specific was also slightly inhibited in the FIG. 5B. As shown in FIG. 5C, we speculated that the antibody 64C10G1 neutralized the antigen CXCL13 in peripheral blood, resulting in the reduction of B cells population in periphery. CXCL13 reduction in peripheral blood resulted in the decreased in the binding and internalization of its receptor CXCR5, which in turn increased the expression of CXCR5 on B cell surface in FIG. 5D. The results of this in vivo model showed the anti-CXCL13 antibody 64C10G1 had potent efficacy in blocking GC B cells production, class switch, antigen specific high affinity antibody production, that meant inhibition of germinal center formation.

Example 7. Blocking of CXCL13-Dependent Migration of Mouse Splenocytes by Surrogate Anti-CXCL13 Mouse Monoclonal Antibody We obtained a surrogate anti-CXCL13 antibody 424H7F2 which could cross bind to mouse CXCL13 from hybridoma screening mentioned in Example 1. To investigate the blocking activity, we tested the effect of 424H7F2 on rmCXCL13 induced primary mouse splenocytes migration.

Sacrificed the C57BL/6 mice on day 10 which were immunized with MOG$_{35-55}$ peptide with adjuvant and obtained their spleens. Spleens were crashed 1-ml syringe plunger and passed through 40 µm cell strainer. Red blood cells were lysed with lysis buffer. The cells were filtered and washed with chemotaxis medium. 1 µg/ml rmCXCL13 (R&D) were incubated with different concentrations anti-CXCL13 antibody 424H7F2 or control IgG at room temperature for 30 minutes. Then, transfer 150 µl/well Mix to the bottom of a 0.5 µm transwell plate and 50 µl/well splenocytes (1×10$^7$/ml) to the top chamber. Incubate the transwell plate in a cell incubator for 3 hours. Finally, discard the filter and add 1.67 µg/ml calcium-am to each well, and incubate additional 20 minutes. Fluorescence is measured at wavelengths of 485 nm and 520 nm.

As the result in FIG. 6, 424H7F2 mouse monoclonal antibody could dose-dependent inhibit primary mouse splenocytes migration toward mouse CXCL13.

Example 8. In Vivo Efficacy of Anti-CXCL13 Mouse Monoclonal Antibody Therapy in Mouse NP-CGG Model To determine if the anti-CXCL13 antibody can mediated inhibition of CXCL13 function in germinal center (GC) formation in secondary lymphoid organs and isotype class switching by naïve B cells, C57BL/6 mice were immunized with NP-CGG (100 µg/mouse) via intraperitoneal injection on day 0 and injected 30 mg/kg anti-CXCL13 antibody 424H7F2 or PBS via intraperitoneal on day −1, 2, 5, 8, 11. On day 14, sacrifice the mice and analyze the population of germinal center B cells (B220$^+$IgD$^-$GL7$^+$Fas$^+$), class switch (B220$^+$IgD$^-$GL7$^+$IgM$^-$IgG1$^+$) by flow cytometry in spleen, the high affinity NP-specific (NP5) IgG1 level by Elisa in serum, and GC formation by IHC staining (IgD$^-$PNA$^+$) in spleen.

Figure 7:
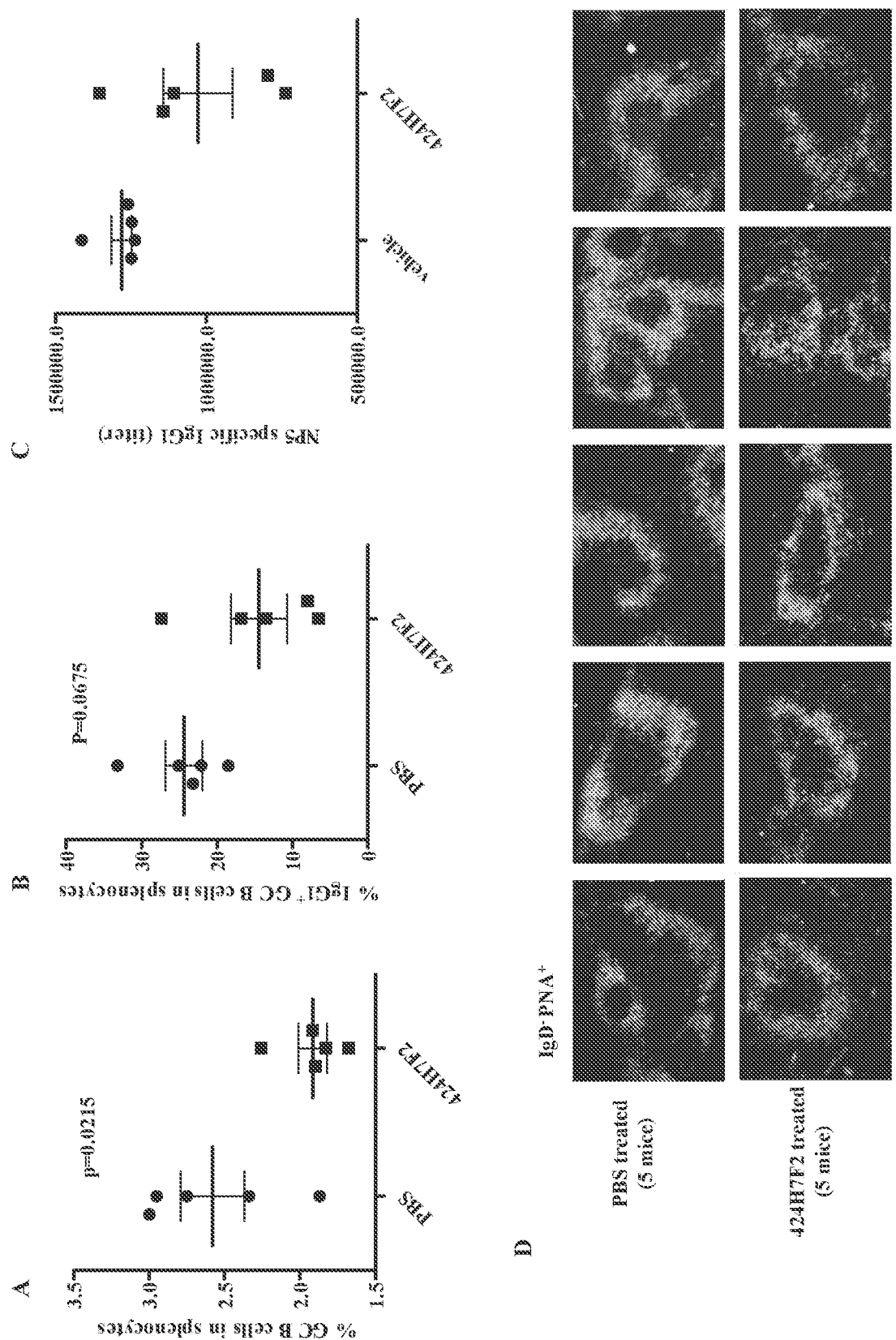
FIG. 7 shows that the mouse anti-CXCL13 antibody 424H7F2 mediated inhibition of CXCL13 function in germinal center (GC) formation in secondary lymphoid organs and isotype class switching by naïve B cells and antigen specific high affinity antibody production.

The GC B cells population was significantly decreased by anti-CXCL13 antibody 424H7F2 treated in the mouse spleen compare to control group (FIG. 7A). In the FIG. 7B, the IgG1$^+$ B cells population was reduced in the 424H7F2 treated mice which indicated the class switch was impaired by anti-CXCL13 antibody. And the reduction of NP5-specific IgG1 antibody in serum in 424H7F2 treated mice showed the affinity maturation of antigen specific IgG1 was blocked by anti-CXCL13 antibody (FIG. 7C). The IHC result directly showed GCs formation were seriously impaired in the mice with anti-CXCL13 antibody 424H7F2 treatment compare to control group (FIG. 7D). Combining all the results revealed that the in vivo CXCL13 function was effectively blocked by anti-CXCL13 antibody 424H7F2.

Example 9. Epitope Mapping of Anti-CXCL13 Antibody to Find Out the Critical Binding Residues The epitope binning results showed all the anti-CXCL13 antibodies cross binding to cynomolgus had a same epitope, including 64C10G1, 21H12D9, 329F2E1, 411A11E9, 71F4A3 and 1H3A11. We used the 64C10G1 to do epitope mapping to identify the critical binding residues to antigen CXCL13. Besides, for the screening, a control antibody was synthesized according to the sequence in a published patent (WO2012/031099 A2).

Cells were transfected with different WT construct or 64C10G1 Fab mutant construct which each amino acid was mutant to alanine, totally 87 amino acids. Then, binding of the test Fab to each mutant clone in the alanine scanning library was determined, in duplicate, by high-throughput flow cytometry. For each point, background fluorescence was subtracted from the raw data, which were then normalized to Fab reactivity with WT target protein. For each mutant clone, the mean binding value was plotted as a function of expression (represented by control reactivity). To identify preliminary primary critical clones (red circles), a threshold (dashed lines) of >70% WT binding to control Ab and <20% WT binding to test Fab was applied.

Figure 8:
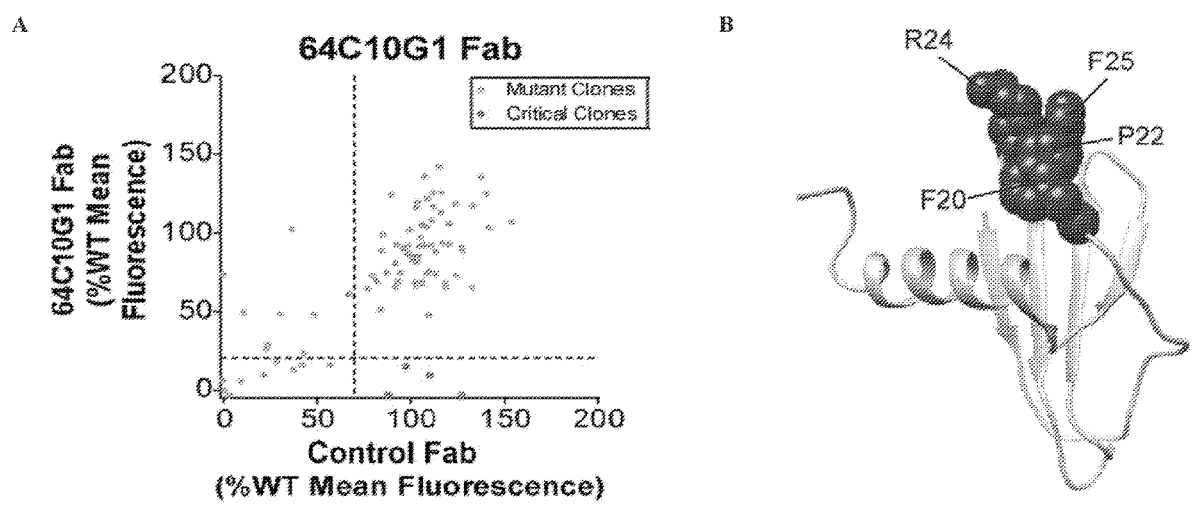
FIG. 8 shows identification of the epitope residues on the human CXCL13 protein.

As shown in FIG. 8A, the mutant clones in the bottom right corner (red circles) meet the set thresholds, whose mutation were negative for binding to 64C10G1 Fab, but positive for binding to control Fabs, including F20, P22, R24 and F25 (Table 6), which indicated these residues were critical for 64C10G1 Fab binding. We draw the crystal structure diagram in the FIG. 8B, and the critical residues for 64C10G1 Fab binding were visualized and shown on this crystal structure.

TABLE 6

Identification of critical residues for 64C10G1 Fab binding
Binding reactivity (% WT)

| Mutation | 64C10G1 Fab | Control Fab |
| --- | --- | --- |
| F20A | 9.4 (2) | 109.9 (1) |
| P22A | 14.8 (1) | 97.4 (12) |
| R24A | −3.3 (1) | 88.0 (10) |
| F25A | −3.2 (0) | 127.3 (1) |

Example 10. Mouse mAb Humanization and Affinity Determination

A. 21H12D9

The mouse antibody 21H12D9 variable region genes were employed to create a humanized MAb. In the first step of this process, the amino acid sequences of the VH and VK of 21H12D9 were compared against the available database of human Ig gene sequences to identify the overall best-matching human germline Ig gene sequences. For the heavy chain, the closest human match was the IGHV1-2*02 gene. For the light chain, the best human match was the IGKV1-12*01 gene.

Humanized variable domain sequences were then designed where the CDR1-3 sequences of the 21H12D9 VH were grafted onto framework sequences of the IGHV1-2*02 gene and the CDR1-3 of the 21H12D9 light chain were grafted onto framework sequences of the IGKV1-12*01 gene. And then a human acceptor pir||S49530 anti-Sm antibody VH chain (VH1/DK1 or DM1/JH4b)—human was selected for CDR grafting to obtain humanized VH1. AIT38653.1 immunoglobulin G heavy chain variable region, partial [*Homo sapiens*] was selected for CDR grafting to obtain humanized VL1. A 3D model was then generated to determine if there were any framework positions where replacing the mouse amino acid to the human amino acid could affect binding and/or CDR conformation. In the case of the heavy chain, K12, V20, M48, V68, M70, R72, S77 and V112 (Kabat numbering) in human framework was identified and subjected to back-mutations to their moue counterpart amino acid i.e.: K12V, V20M, M48I, V68A, M70L, R72V, S77G and V112L. In the case of the light chain, A13, L78 (Kabat numbering) in human framework was identified and subjected to back-mutation to their moue counterpart amino acid i.e.: A13T, L78V.

human Ig gene sequences to find the overall best-matching human germline Ig gene sequences. For the heavy chain, the closest human match was the IGHV3-7*01 gene. For the

TABLE 7

21H12D9 mouse antibody sequences and CDRs

| Antibody chain or domain | Sequences (CDR underlined and bold) | SEQ ID NO: |
|---|---|---|
| 21H12D9 -VH | EVQLQQSGPVLVRPGASVKMSCKASGYTFTDYYMNWVKQSHGKSLEWIGV INPNNGGTTYKEKFKGKATLTVDKSSGTAYMELNSLTSEDSAVYYCARDD YDAGYWGQGTTLTVSS | 95 |
| 21H12D9 -VL | DIVMTQFQKFMSTTVGDRVSITCKASQNVDTAVAWYQHKPGQSPKLLIYS ASHRYTGVPDRFTGSGSGTDFTLTISNVQSEDLADYFCQQYTDFPLTFGA GTKLELK | 96 |
| CDRH1 | DYYMN | 97 |
| CDRH2 | VINPNNGGTTYKEKFKG | 98 |
| CDRH3 | DDYDAGY | 99 |
| CDRL1 | KASQNVDTAVA | 100 |
| CDRL2 | SASHRYT | 101 |
| CDRL3 | QQYTDFPLT | 102 |

The humanized sequences are listed in Table 8: 21H12D9-VH1 and 21H12D9-VL1 are fully humanized sequences and 21H12D9-VH2, 21H12D9-VH3, 21H12D9-VH4, 21H12D9-VL2, 21H12D9-VL3 are sequences with different back mutation.

light chain the closest human match was the IGKV1-33*01 gene. Humanized variable domain sequences were then designed where the CDR1-3 sequences of the 64C10G1 VH were grafted onto framework sequences of the IGHV3-7*01 gene and the CDR1-3 of the 64C10G1 light chain were

TABLE 8

Humanized sequences

| Antibody chain | Sequences (back mutations bold and underlined) | SEQ ID NO: |
|---|---|---|
| 21H12D9-VH1 | QVQLVQSGAEVKKPGASVKVSCKASGYTFTDYYMNWVRQAPGQGLEWMGV INPNNGGTTYKEKFKGRVTMTRDTSISTAYMELSRLRSDDTAVYYCARDD YDAGYWGQGTLVTVSS | 103 |
| 21H12D9-VH2 | QVQLVQSGAEVVKPGASVKVSCKASGYTFTDYYMNWVRQAPGQGLEWMGV INPNNGGTTYKEKFKGRVTMTVDTSISTAYMELSRLRSDDTAVYYCARDD YDAGYWGQGTLVTVSS | 104 |
| 21H12D9-VH3 | QVQLVQSGAEVVKPGASVKVSCKASGYTFTDYYMNWVRQAPGQGLEWIGV INPNNGGTTYKEKFKGRATLTVDTSISTAYMELSRLRSDDTAVYYCARDD YDAGYWGQGTLVTVSS | 105 |
| 21H12D9-VH4 | QVQLVQSGAEVVKPGASVKMSCKASGYTFTDYYMNWVRQAPGQGLEWIGV INPNNGGTTYKEKFKGRATLTVDTSIGTAYMELSRLRSDDTAVYYCARDD YDAGYWGQGTLLTVSS | 106 |
| 21H12D9-VL1 | DIQMTQSPSSVSASVGDRVTITCKASQNVDTAVAWYQQKPGKAPKLLIYS ASHRYTGVPSRFSGSGSGTDFTLTISSLQPEDFATYYCQQYTDFPLTFGQ GTRLEIK | 107 |
| 21H12D9-VL2 | DIQMTQSPSSVSTSVGDRVTITCKASQNVDTAVAWYQQKPGKAPKLLIYS ASHRYTGVPSRFSGSGSGTDFTLTISSLQPEDFATYYCQQYTDFPLTFGQ GTRLEIK | 108 |
| 21H12D9-VL3 | DIQMTQSPSSVSTSVGDRVTITCKASQNVDTAVAWYQQKPGKAPKLLIYS ASHRYTGVPSRFSGSGSGTDFTLTISSVQPEDFATYYCQQYTDFPLTFGQ GTRLEIK | 109 |

B. 64C10G1

The mouse antibody 64C10G1 variable region genes were employed to create a humanized MAb. In the first step of this process, the amino acid sequences of the VH and VK of 64C10G1 were compared against the available database of grafted onto framework sequences of the IGKV1-33*01 gene. And then a human acceptor AAV48954.1: anti-pneumococcal antibody 8B3 immunoglobulin heavy chain variable region, partial [Homo sapiens] was selected for CDR grafting to obtain humanized VH1. ACY78416.1: immunoglobulin kappa light chain variable region, partial [*Homo sapiens*] was selected for CDR grafting to obtain humanized VL1. A 3D model was then generated to determine if there were any framework positions where replacing the mouse amino acid to the human amino acid could affect binding and/or CDR conformation. In the case of the light chain, Y49, V58, F71, I83 (Kabat numbering) in human framework was identified and subjected to back-mutation to their moue counterpart amino acid i.e.: Y49H, V58I, F71Y, I83F.

process, the amino acid sequences of the VH and VK of 71F4A3 were compared against the available database of human Ig gene sequences to find the overall best-matching human germline Ig gene sequences. For the heavy chain, the closest human match was the IGHV3-7*01 gene. For the light chain the closest human match was the IGKV1-33*01 gene. Humanized variable domain sequences were then designed where the CDR1-3 sequences of the 71F4A3 VH were grafted onto framework sequences of the IGHV3-7*01

TABLE 9

64C10G1 mouse antibody sequences and CDRs

| Antibody chain or domain | Sequences (CDR underlined and bold) | SEQ ID NO: |
|---|---|---|
| 64C10G1-VH | EVQLVESGGGLVKPGGSLKLSCAASGFTFSSYAMSWVRQTPEKRLEWVAT ISDGGSDAYYPDNVKGRFTISRDNAKNNLYLQMSHLKSEDTAMYYCARDY YGSGYEDSPMDYWGQGTSVTVSS | 110 |
| 64C10G1-VL | DIQMTQSPSSLSASLGGKVTITCKASQDINKYIAWYQHKPGKGPRLLIHY TSTLQPGIPSRFSGSGSGRDYSFSISNLEPEDFATYYCLQYDNLYTFGGG TKLEIK | 111 |
| CDRH1 | SYAMS | 112 |
| CDRH2 | TISDGGSDAYYPDNVKG | 113 |
| CDRH2 (PTM) | TISEGGSDAYYPDNVKG | 114 |
| CDRH3 | DYYGSGYEDSPMDY | 115 |
| CDRH3 (PTM) | DYYGSGYEESPMDY | 116 |
| CDRL1 | KASQDINKYIA | 117 |
| CDRL2 | YTSTLQP | 118 |
| CDRL3 | LQYDNLYT | 119 |

The humanized sequences are listed in Table 10: 64C10G1-VH1 and 64C10G1-VL1 are fully humanized sequences, 64C10G1-VL2, 64C10G1-VL3 are sequences with different back mutations.

gene and the CDR1-3 of the 71F4A3 light chain were grafted onto framework sequences of the IGKV1-33*01 gene. And then a human acceptor AAA18280.1: immunoglobulin heavy chain variable region, partial [*Homo sapiens*]

TABLE 10

Humanized sequences

| Antibody chain | Sequences (back mutations bold and underlined) | SEQ ID NO: |
|---|---|---|
| 64C10G1-VH1 | EVQLVESGGGLVQPGGSLRLSCAASGFTFSSYAMSWVRQAPGKGLEWVAT ISDGGSDAYYPDNVKGRFTISRDNAKNSLYLQMNSLRAEDTAVYYCARDY YGSGYEDSPMDYWGQGTLVTVSS | 120 |
| 64C10G1-VL1 | DIQMTQSPSSLSASVGDRVTITCKASQDINKYIAWYQQKPGKAPKLLIYY TSTLQPGVPSRFSGSGSGTDFTFTISSLQPEDIATYYCLQYDNLYTFGGG TKLEIK | 121 |
| 64C10G1-VL2 | DIQMTQSPSSLSASVGDRVTITCKASQDINKYIAWYQQKPGKAPKLLIHY TSTLQPGVPSRFSGSGSGTDFTFTISSLQPEDFATYYCLQYDNLYTFGGG TKLEIK | 122 |
| 64C10G1-VL3 | DIQMTQSPSSLSASVGDRVTITCKASQDINKYIAWYQQKPGKAPKLLIHY TSTLQPGIPSRFSGSGSGTDFTFTISSLQPEDFATYYCLQYDNLYTFGGG TKLEIK | 123 |
| 64C10G1-VL4 | DIQMTQSPSSLSASVGDRVTITCKASQDINKYIAWYQQKPGKAPKLLIHY TSTLQPGIPSRFSGSGSGTDYTFTISSLQPEDFATYYCLQYDNLYTFGGG TKLEIK | 124 |

C. 71F4A3

The mouse antibody 71F4A3 variable region genes were employed to create a humanized MAb. In the first step of this was selected for CDR grafting to obtain humanized VH1. ACY78416.1: immunoglobulin kappa light chain variable region, partial [*Homo sapiens*] was selected for CDR grafting to obtain humanized VL1. A 3D model was then generated to determine if there were any framework positions where replacing the mouse amino acid to the human amino acid could affect binding and/or CDR conformation. In the case of the heavy chain, E5, V47, A48, L85 (Kabat numbering) in human framework was identified and subjected to back-mutation to their moue counterpart amino acid i.e.: E5Q, V47I, A48G, L85V. In the case of the light chain, L78 (Kabat numbering) in human framework was identified and subjected to back-mutation to their moue counterpart amino acid i.e.: L78V.

TABLE 11

71F4A3 mouse antibody sequences and CDRs

| Antibody chain or domain | Sequences (CDR underlined and bold) | SEQ ID NO: |
|---|---|---|
| 71F4A3-VH | EVKLLQSGGGLVQPGGSLKLSCAASGIDFSRYWMSWVRRAPGKGLEWIGE INPDSSTINYAPSLKDKFIISRDNAKNTLYLQMSKVRSEDTALYYCARQD DYEYYAMDYWGQGTSVTVSS | 125 |
| 71F4A3-VL | DIVMTQSHKSMSTSVGDRVSITCKASQDVNTGVAWYRQKPGQSPKLLIYS ASYRYTGVPDRFTGSGSGTDFTFTISSVQAEDLAVYYCQQYYSTPLTFGA GTKLELK | 126 |
| CDRH1 | RYWMS | 127 |
| CDRH2 | EINPDSSTINYAPSLKD | 128 |
| CDRH2 (PTM) | EINPESSTINYAPSLKD | 129 |
| CDRH3 | QDDYEYYAMDY | 130 |
| CDRL1 | KASQDVNTGVA | 131 |
| CDRL2 | SASYRYT | 132 |
| CDRL3 | QQYYSTPLT | 133 |

The humanized sequences are listed in Table 12: 71F4A3-VH1 and 71F4A3-VL1 are fully humanized sequences, 71F4A3-VH2, 71F4A3-VH3, 71F4A3-VH4, 71F4A3-VL2 are sequences with different back mutations.

TABLE 12

Humanized sequences

| Antibody chain | Sequences (back mutations bold and underlined) | SEQ ID NO: |
|---|---|---|
| 71F4A3-VH1 | EVQLVESGGGLVQPGGSLRLSCAASGIDFSRYWMSWVRQAPGKGLEWVAEI NPDSSTINYAPSLKDRFTISRDNAKNSLYLQMNSLRAEDTAVYYCARQDD YEYYAMDYWGQGTTVTVSS | 134 |
| 71F4A3-VH2 | EVQLVQSGGGLVQPGGSLRLSCAASGIDFSRYWMSWVRQAPGKGLEWVAEI NPDSSTINYAPSLKDRFTISRDNAKNSLYLQMNSLRAEDTAVYYCARQDD YEYYAMDYWGQGTTVTVSS | 135 |
| 71F4A3-VH3 | EVQLVQSGGGLVQPGGSLRLSCAASGIDFSRYWMSWVRQAPGKGLEWVGEI NPDSSTINYAPSLKDRFTISRDNAKNSLYLQMNSVRAEDTAVYYCARQDD YEYYAMDYWGQGTTVTVSS | 136 |
| 71F4A3-VH4 | EVQLVQSGGGLVQPGGSLRLSCAASGIDFSRYWMSWVRQAPGKGLEWIGEI NPDSSTINYAPSLKDRFTISRDNAKNSLYLQMNSVRAEDTAVYYCARQDD YEYYAMDYWGQGTTVTVSS | 137 |
| 71F4A3-VL1 | DIQMTQSPSSLSASVGDRVTITCKASQDVNTGVAWYQQKPGKAPKLLIYS ASYRYTGVPSRFSGSGSGTDFTFTISSLQPEDIATYYCQQYYSTPLTFGG GTKLEIK | 138 |
| 71F4A3-VL2 | DIQMTQSPSSLSASVGDRVTITCKASQDVNTGVAWYQQKPGKAPKLLIYS ASYRYTGVPSRFSGSGSGTDFTFTISSVQPEDIATYYCQQYYSTPLTFGG GTKLEIK | 139 |

D. 411A11E9

The mouse antibody 411A11E9 variable region genes were employed to create a humanized MAb. In the first step of this process, the amino acid sequences of the VH and VK of 411A11E9 were compared against the available database of human Ig gene sequences to identify the overall best-matching human germline Ig gene sequences. For the heavy chain, the closest human match was the IGHV3-7*01 gene. For the light chain, the best human match was the IGKV1-17*01 gene.

Humanized variable domain sequences were then designed where the CDR1-3 sequences of the 411A11E9 VH were grafted onto framework sequences of the IGHV3-7*01 gene and the CDR1-3 of the 411A11E9 light chain were grafted onto framework sequences of the IGKV1-17*01 gene. And then a human acceptor ACS96177.1 immunoglobulin heavy chain variable region, partial [*Homo sapiens*] was selected for CDR grafting to obtain humanized VH1. AAZ09050.1 immunoglobulin kappa light chain variable region, partial [*Homo sapiens*] was selected for CDR grafting to obtain humanized VL1. A 3D model was then generated to determine if there were any framework positions where replacing the mouse amino acid to the human amino acid could affect binding and/or CDR conformation. In the case of the heavy chain, A24, I70, R98, T105 (Kabat numbering) in human framework was identified and subjected to back-mutations to their moue counterpart amino acid i.e.: A24V, I70V, R98T, T105A. In the case of the light chain, V58, F71, Y87 (Kabat numbering) in human framework was identified and subjected to back-mutation to their moue counterpart amino acid i.e.: V58I, F71Y, Y87F.

TABLE 13

411A11E9 mouse antibody sequences and CDRs

| Antibody chain or domain | Sequences (CDR underlined and bold) | SEQ ID NO: |
|---|---|---|
| 411A11E9-VH | EVQLVESGGGLVQPGGSLKLSCVVSGFTFSDYYMAWVRQTPTKGLEWVAS INYDGGDTYYRDSVKGRFTVSRNNAKSSLFLQMDSLRSEDTATYYCKTEE DYDGSYVMDAWGQGASVIVSS | 140 |
| 411A11E9-VL | DIQMTQSPSFLSASVGDRVTISCKASQNINKELTWYQQKLGKAPKRLIYN TNILQTGIPSRFSGSGSNTDYTLTISSLQPEDFATYFCLQQSSLYTFGAG TKLELK | 141 |
| CDRH1 | DYYMA | 142 |
| CDRH2 | SINYDGGDTYYRDSVKG | 143 |
| CDRH3 | EEDYDGSYVMDA | 144 |
| CDRL1 | KASQNINKELT | 145 |
| CDRL2 | NTNILQT | 146 |
| CDRL3 | LQQSSLYT | 147 |

The humanized sequences are listed in Table 14: 411A11E9-VH1 and 411A11E9-VL1 are fully humanized sequences and 411A11E9-VH2, 411A11E9-VH3, 411A11E9-VH4, 411A11E9-VL2, 411A11E9-VL3, 411A11E9-VL4 are sequences with different back mutation.

TABLE 14

Humanized sequences

| Antibody chain | Sequences (back mutations bold and underlined) | SEQ ID NO: |
|---|---|---|
| 411A11E9-VH1 | EVQLVESGGGLVQPGGSLRLSCAASGFTFSDYYMAWVRQAPGKGLEWVAS INYDGGDTYYRDSVKGRFTISRDNAKNSLYLQMNSLRAEDTAVYYCAREE DYDGSYVMDAWGQGTLVTSSGS | 148 |
| 411A11E9-VH2 | EVQLVESGGGLVQPGGSLRLSCAASGFTFSDYYMAWVRQAPGKGLEWVAS INYDGGDTYYRDSVKGRFTISRDNAKNSLYLQMNSLRAEDTAVYYCATEE DYDGSYVMDAWGQGTLVTSSGS | 149 |
| 411A11E9-VH3 | EVQLVESGGGLVQPGGSLRLSCAVSGFTFSDYYMAWVRQAPGKGLEWVAS INYDGGDTYYRDSVKGRFTISRDNAKNSLYLQMNSLRAEDTAVYYCATEE DYDGSYVMDAWGQGTLVTSSGS | 150 |
| 411A11E9-VH4 | EVQLVESGGGLVQPGGSLRLSCAVSGFTFSDYYMAWVRQAPGKGLEWVAS INYDGGDTYYRDSVKGRFTVSRDNAKNSLYLQMNSLRAEDTAVYYCATEE DYDGSYVMDAWGQGALVTSSGS | 151 |
| 411A11E9-VL1 | DIQMTQSPSSLSASVGDRVTITCKASQNINKELTWYQQKPGKAPKRLIYN TNILQTGVPSRFSGSGSGTEFTLTISSLQPEDFATYYCLQQSSLYTFGQG TKLEIK | 152 |

TABLE 14-continued

Humanized sequences

| Antibody chain | Sequences (back mutations bold and underlined) | SEQ ID NO: |
|---|---|---|
| 411A11E9-VL2 | DIQMTQSPSSLSASVGDRVTITCKASQNINKELTWYQQKPGKAPKRLIYN TNILQTGVPSRFSGSGSGTEFTLTISSLQPEDFATYFCLQQSSLYTFGQG TKLEIK | 153 |
| 411A11E9-VL3 | DIQMTQSPSSLSASVGDRVTITCKASQNINKELTWYQQKPGKAPKRLIYN TNILQTGIPSRFSGSGSGTEFTLTISSLQPEDFATYFCLQQSSLYTFGQG TKLEIK | 154 |
| 411A11E9-VL4 | DIQMTQSPSSLSASVGDRVTITCKASQNINKELTWYQQKPGKAPKRLIYN TNILQTGIPSRFSGSGSGTEYTLTISSLQPEDFATYFCLQQSSLYTFGQG TKLEIK | 155 |

The humanized VH and VL genes were produced synthetically as humanized Fab and then respectively cloned into vectors containing the human gamma 1 and human kappa constant domains. Humanized VH and VK were paired to produce Fabs and then purified for further off-rate ranking (Table 15) and affinity testing.

TABLE 15

Off-rate ranking by Biacore

| Fabs | ka (1/Ms) | kd (1/s) | KD (M) |
|---|---|---|---|
| 411A11E9-Chimeric | 4050000 | 0.00287 | 7.08E−10 |
| 411A11E9-VH1VL1 | 12500000 | 0.013 | 1.04E−09 |
| 411A11E9-VH1VL2 | 78200 | 0.00114 | 1.45E−08 |
| 411A11E9-VH1VL3 | 523000 | 0.00176 | 3.37E−09 |
| 411A11E9-VH1VL4 | 346000 | 0.00063 | 1.82E−09 |
| 411A11E9-VH2VL1 | 2370000 | 0.00283 | 1.19E−09 |
| 411A11E9-VH2VL2 | 2580000 | 0.00271 | 1.05E−09 |
| 411A11E9-VH2VL3 | 2360000 | 0.00335 | 1.42E−09 |
| 411A11E9-VH2VL4 | 1660000 | 0.00105 | 6.34E−10 |
| 411A11E9-VH3VL1 | 2290000 | 0.00242 | 1.06E−09 |
| 411A11E9-VH3VL2 | 1780000 | 0.00163 | 9.19E−10 |
| 411A11E9-VH3VL3 | 2050000 | 0.00207 | 1.01E−09 |
| 411A11E9-VH3VL4 | 2190000 | 0.00109 | 4.98E−10 |
| 411A11E9-VH4VL1 | 2730000 | 0.00281 | 1.03E−09 |
| 411A11E9-VH4VL2 | 2080000 | 0.00196 | 9.44E−10 |
| 411A11E9-VH4VL3 | 2140000 | 0.00266 | 1.24E−09 |
| 411A11E9-VH4VL4 | 1740000 | 0.00107 | 6.11E−10 |
| 71F4A3-Chimeric | 3300000 | 0.00184 | 5.56E−10 |
| 71F4A3-VH3VL1 | 2140000 | 0.000987 | 4.62E−10 |
| 71F4A3-VH1VL1 (Hz71F4) | 3200000 | 0.00136 | 4.26E−10 |
| 71F4A3-VH1VL2 | 2850000 | 0.00147 | 5.16E−10 |
| 71F4A3-VH2VL1 | 1950000 | 0.00108 | 5.54E−10 |
| 71F4A3-VH2VL2 | 2250000 | 0.00137 | 6.07E−10 |
| 71F4A3-VH3VL2 | 2500000 | 0.00139 | 5.57E−10 |
| 71F4A3-VH4VL1 | 1700000 | 0.001 | 5.9E−10 |
| 71F4A3-VH4VL2 | 2570000 | 0.00136 | 5.3E−10 |
| 21VH12D9-Chimeric | 1170000 | 0.00139 | 1.18E−09 |
| 21VH12D9-VH1VL2 | 380000 | 0.000757 | 1.99E−09 |
| 21VH12D9-VH2VL2 | 414000 | 0.000802 | 1.94E−09 |
| 21VH12D9-VH1VL3 | 584000 | 0.000975 | 1.67E−09 |
| 21VH12D9-VH2VL1 | 570000 | 0.000991 | 1.74E−09 |
| 21VH12D9-VH2VL3 | 501000 | 0.000992 | 1.98E−09 |
| 21VH12D9-VH4VL1 | 618000 | 0.00107 | 1.73E−09 |
| 21VH12D9-VH4VL2 | 742000 | 0.00114 | 1.54E−09 |
| 21VH12D9-VH4VL3 | 729000 | 0.00116 | 1.59E−09 |
| 21VH12D9-VH3VL1 | 744000 | 0.00131 | 1.76E−09 |
| 21VH12D9-VH3VL2 | 940000 | 0.00138 | 1.47E−09 |
| 21VH12D9-VH3VL3 | 1410000 | 0.00207 | 1.47E−09 |
| 21VH12D9-VH1VL1 | 2420000 | 0.00323 | 1.33E−09 |
| 64C10G1-Chimeric | 2680000 | 0.00218 | 8.14E−10 |
| 64C10G1-VH1VL3 | 1820000 | 0.00543 | 2.98E−09 |
| 64C10G1-VH1VL4 | 1940000 | 0.00713 | 3.68E−09 |
| 64C10G1-VH1VL1 | 4330000 | 0.0255 | 5.89E−09 |
| 64C10G1-VH1VL2 | 2690000 | 0.00515 | 1.92E−09 |

Among all humanized Fab samples, 71F4A3-VH2VL1, 71F4A3-VH1VL1 (Hz71F4), 71F4A3-VH1VL2, 71F4A3-VH3VL1, 411A11E9-VH1VL4, 411A11E9-VH3VL4, 411A11E9-VH2VL4, 411A11E9-VH3VL2, 411A11E9-VH1VL2, 21H12D9-VH1VL1, 21H12D9-VH2VL2, 21H12D9-VH3VL3, 21H12D9-VH1VL2, 64C10G1-VH1VL3, 64C10G1-VH1VL4, 64C10G1-VH1VL1, 64C10G1-VH1VL2 were selected to test affinity by Biacore 8K. 10 mM HEPES, 150 mM NaCl, 3 mM EDTA, 0.05% Tween-20, pH 7.4 served as running buffer and 10 mM glycine-HCl, pH2.0 served as regeneration buffer. CXCL13 protein were immobilized on Sensor Chip CM5 using amine coupling method (immobilization level~250 RU). The serial concentrations of Fab (0-20 nM) were injected over immobilized CXCL13 at the flow rate of 30 μl/min. The dissociation phases were 600 s. The results are shown in Table 16 below.

TABLE 16

Affinity determination results

| clones | Fabs | $k_a$ (1/Ms) | $k_d$ (1/s) | $K_D$ (M) | Rmax (RU) | Chi$^2$ (RU$^2$) |
|---|---|---|---|---|---|---|
| 71F4A3 | 71F4A3-VH2VL1 | 1.70E+06 | 1.45E−03 | 8.53E−10 | 9 | 7.87E−03 |
| | 71F4A3-VH1VL1 (Hz71F4) | 2.02E+06 | 1.25E−03 | 6.19E−10 | 12 | 2.09E−02 |
| | 71F4A3-VH1VL2 | 1.84E+06 | 1.16E−03 | 6.28E−10 | 11.1 | 1.80E−02 |
| | 71F4A3-Chimeric | 1.80E+06 | 1.41E−03 | 7.82E−10 | 18.5 | 9.61E−02 |
| | 71F4A3-VH3VL1 | 1.64E+06 | 1.53E−03 | 9.34E−10 | 11.3 | 1.80E−02 |

TABLE 16-continued

Affinity determination results

| clones | Fabs | $k_a$ (1/Ms) | $k_d$ (1/s) | $K_D$ (M) | Rmax (RU) | Chi$^2$ (RU$^2$) |
|---|---|---|---|---|---|---|
| 411A11E9 | 411A11E9-Chimeric | 2.11E+06 | 1.56E−03 | 7.40E−10 | 29.9 | 3.82E−01 |
| | 411A11E9-VH1VL4 | 1.86E+06 | 1.57E−03 | 8.44E−10 | 7.3 | 8.06E−03 |
| | 411A11E9-VH3VL4 | 9.06E+05 | 8.23E−04 | 9.08E−10 | 12.4 | 2.29E−02 |
| | 411A11E9-VH2VL4 | 9.53E+05 | 8.87E−04 | 9.31E−10 | 9.5 | 8.33E−03 |
| | 411A11E9-VH3VL2 | 1.05E+06 | 1.26E−03 | 1.20E−09 | 10 | 4.91E−03 |
| | 411A11E9-VH1VL2 | 5.70E+05 | 1.61E−03 | 2.83E−09 | 5.4 | 1.76E−03 |
| 21H12D9 | 21H12D9-VH1VL1 | 1.66E+06 | 2.03E−03 | 1.23E−09 | 103.7 | 2.14E+00 |
| | 21H12D9-VH2VL2 | 1.48E+06 | 1.95E−03 | 1.32E−09 | 91.8 | 1.29E+00 |
| | 21H12D9-VH3VL3 | 1.49E+06 | 1.82E−03 | 1.22E−09 | 98.1 | 1.82E+00 |
| | 21H12D9-VH1VL2 | 1.44E+06 | 1.71E−03 | 1.19E−09 | 107.6 | 1.88E+00 |
| | 21H12D9-Chimeric | 1.82E+06 | 2.58E−03 | 1.42E−09 | 65.1 | 7.01E−01 |
| 64C10G1 | 64C10G1-Chimeric | 2.68E+06 | 2.18E−03 | 8.14E−10 | 16.2 | 1.17E−01 |
| | 64C10G1-VH1VL3 | 1.82E+06 | 5.43E−03 | 2.98E−09 | 7.2 | 8.56E−03 |
| | 64C10G1-VH1VL4 | 1.94E+06 | 7.13E−03 | 3.68E−09 | 6.5 | 1.06E−02 |
| | 64C10G1-VH1VL1 | 4.33E+06 | 2.55E−02 | 5.89E−09 | 4.9 | 9.55E−03 |
| | 64C10G1-VH1VL2 | 2.69E+06 | 5.15E−03 | 1.92E−09 | 6.2 | 1.22E−02 |

Example 11. Binding and Blocking Properties of Anti-CXCL13 Humanized Fabs

This example tested the binding and blocking properties in cell-based blocking assay of the humanized anti-CXCL13 antibodies to CXCL13 proteins.

To evaluate the humanized Fabs binding and blocking activities, the 71F4A3H, and 64C10G1H were subjected to ELISA binding test and cell-based blocking assays. The EC50 and IC50 are summarized in Table 17, which demonstrating that the potency of binding activity for humanized 71F4A3, 64C10G1 are better than that of chimeric antibodies. The potency of blocking activity, while comparing with its chimeric counterpart, the humanized 71F4A3 decreased about 2-fold, and the humanized 64C10G1 keep the blocking potency while compared with its chimeric counterpart.

TABLE 17 binding and blocking properties for humanized Fabs

| | Humanized Fabs | EC50(nM) | IC50(nM) |
|---|---|---|---|
| 71F4A3 | 71F4A3-chimeric (Fab) | 1.488 | 5.073 |
| | 71F4A3-VH2VL1(Fab) | 0.8186 | 10.46 |
| | 71F4A3-VH1VL1 (Hz71F4) (Fab) | 0.974 | 11.19 |
| | 71F4A3-VH1VL2(Fab) | 1.178 | 10.73 |
| | 71F4A3-VH3VL1(Fab) | 0.5745 | 11.27 |
| 64C10G1 | 64C10G1-chimeric (Fab) | 1.707 | 7.224 |
| | 64C10G1-VH1VL1(Fab) | 1.291 | 7.793 |
| | 64C10G1-VH1VL2(Fab) | 1.23 | 7.022 |
| | 64C10G1-VH1VL3(Fab) | 1.072 | 7.693 |
| | 64C10G1-VH1VL4(Fab) | 0.7842 | 6.878 |

Example 12. Functional Properties of Anti-CXCL13 Humanized PTM Removal Fabs

Blocking of CXCL13 induced IP1 signaling. To avoid involving too many mutation sites and based on the results of Elisa binding and cell-based blocking, we chose the 64C10G1-VH1VL2, 64C10G1-VH1VL3, 71F4A3-VH1VL1 (Hz71F4), 71F4A3-VH1VL2 sequence to remove PTM (Post-translational modification) site, the mutant positions of 64C10G1 were D53E and D107E in the VH, for 71F4A3, the mutant position was D54E in the VH, and further verify in IP1 assay which was mentioned previously.

Figure 9:
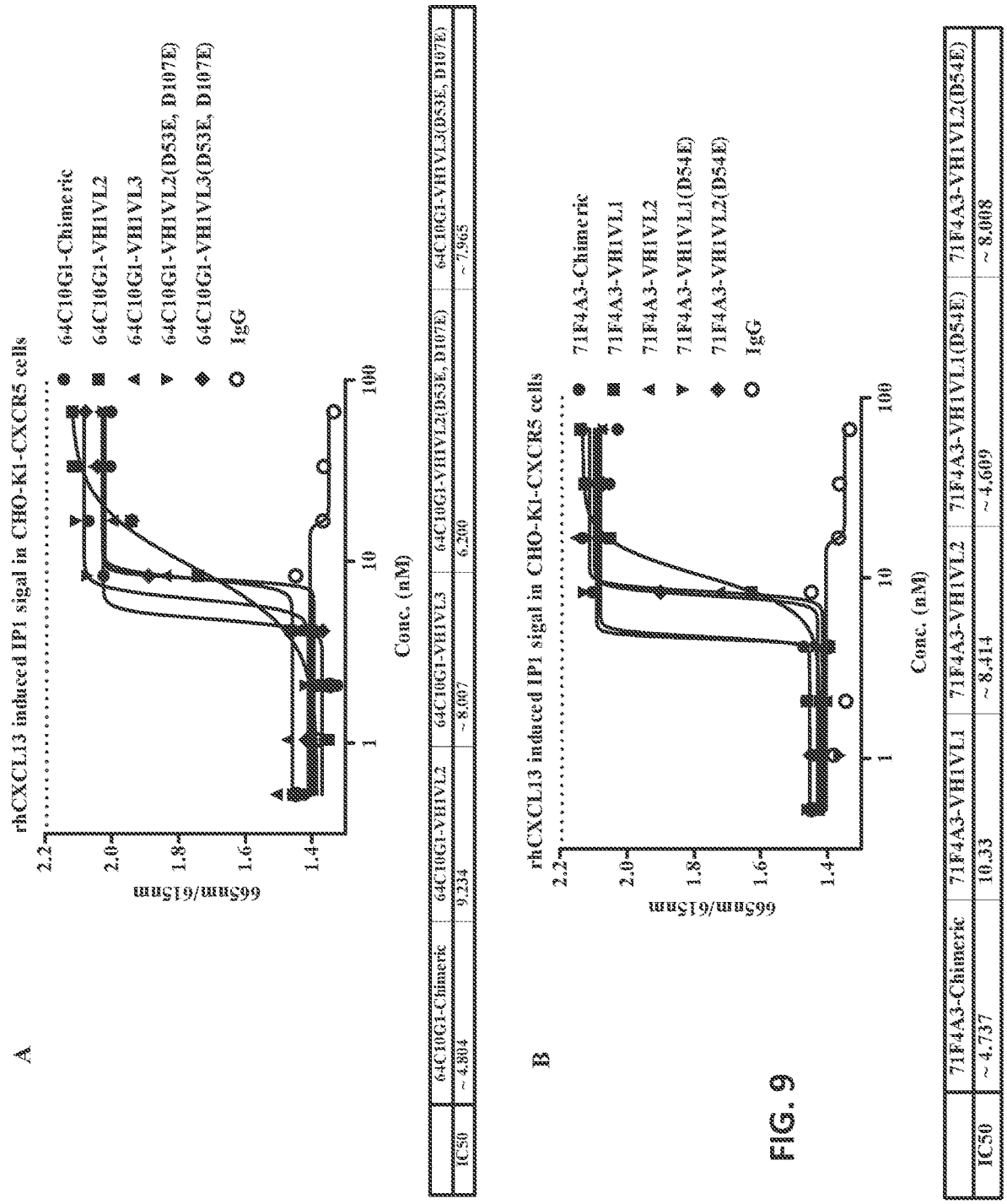
FIG. 9 shows testing results in downstream signal assays of -humanized Fabs with mutations that remove post-translatoin modifications.

As shown in FIG. 9A, though the blocking activity of humanized 64C10G1 variants were lower than chimeric antibody, 64C10G1-VH1VL2 (D53E, D107E) PTM removal antibody was slightly better than other humanized variants. In the FIG. 9B, 71F4A3-VH1VL1 (Hz71F4) (D54E) inhibition activity is better than other humanized variants and comparable with chimeric antibody.

Blocking of primary human tonsil cells migration toward human CXCL13. Based on the results of IP1 assay, we evaluated the effect of 64C10G1-VH1VL2, 64C10G1-VH1VL2 (D53E, D107E), 71F4A3-VH1VL1 (Hz71F4) and 71F4A3-VH1VL1 (Hz71F4) (D54E) on primary human tonsil cells migration assay.

Figure 10:
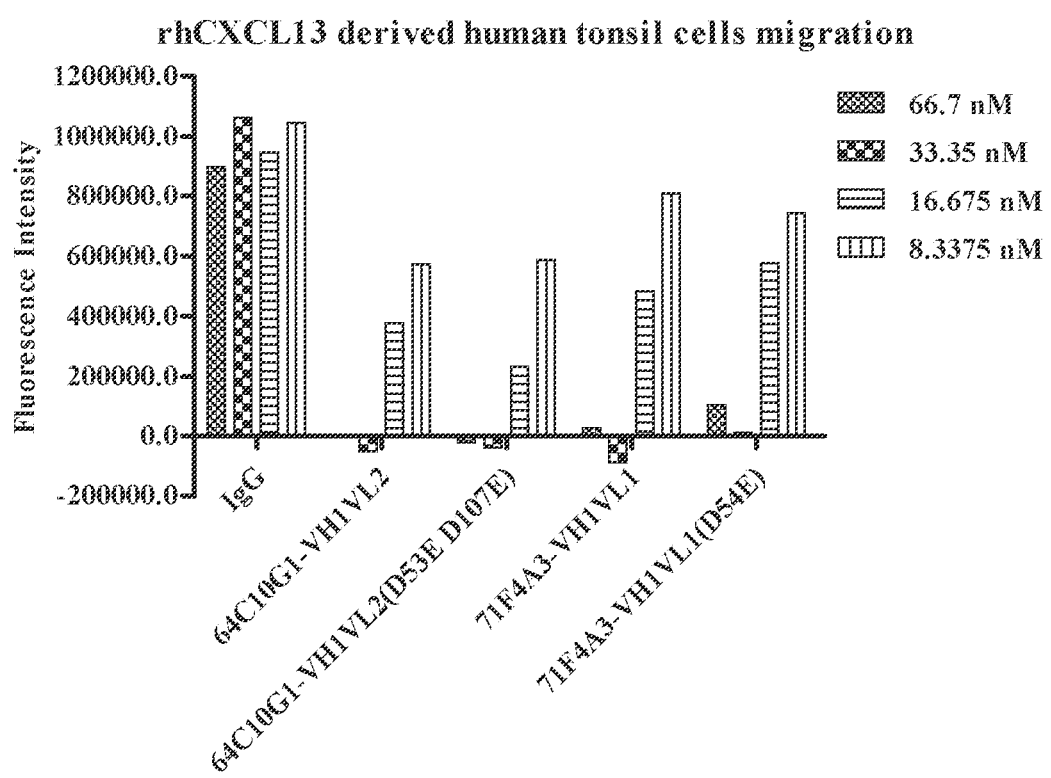
FIG. 10 shows that both 64C10G1-VH1VL2 (D53E, D107E) and 71F4A3-VH1VL1 (Hz71F4) (D54E) Fabs could dose-dependent block human CXCL13 induced the primary human tonsil cells migration.

We could see in the FIG. 10, both 64C10G1-VH1VL2 (D53E, D107E) and 71F4A3-VH1VL1 (Hz71F4) (D54E) could dose-dependent block human CXCL13 induced the primary human tonsil cells migration. And the ability of inhibition was comparable.

Example 13. Binding Properties of Anti-CXCL13 Full Length Humanized IgGs with PTM Removal This example tested the binding properties of the humanized anti-CXCL13 antibodies to huCXCL13 and cynoCXCL13 proteins.

Figure 11:
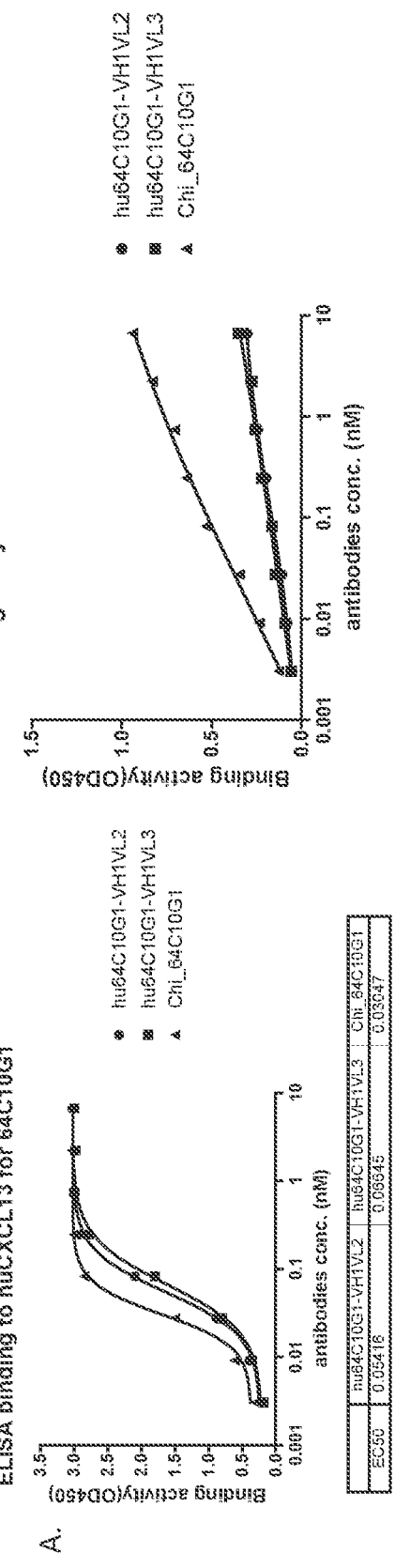
FIG. 11 shows the binding properties of humanized full length IgG1 antibodies with mutations that remove post-translatoin modifications.
Figure 11:
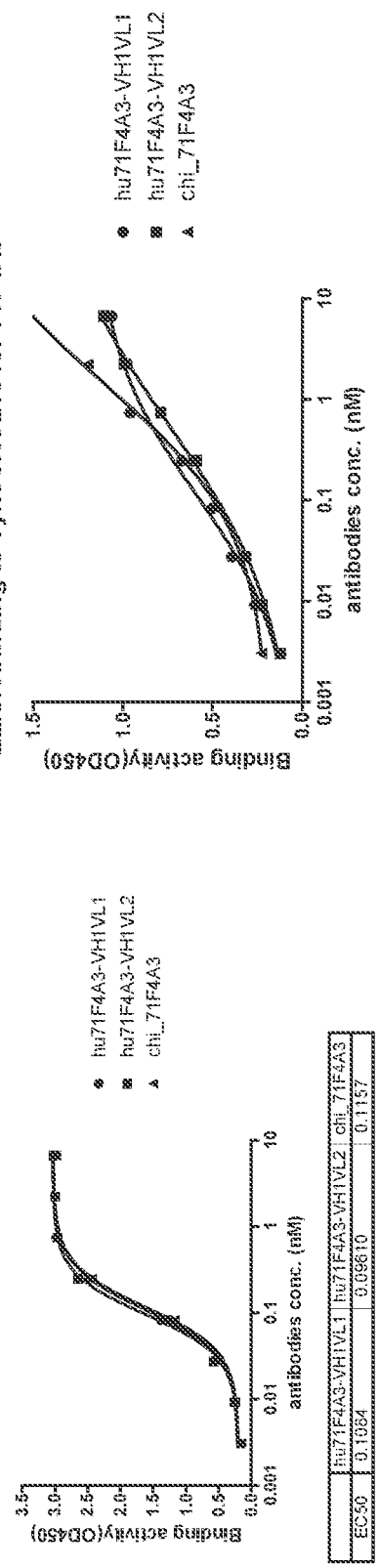

To evaluate the humanized antibodies binding activities, the 71F4A3-VH1VL1 (Hz71F4), 71F4A3-VH1VL2, 64C10G1-VH1VL2, 64C10G1-VH1VL3 were produced synthetically as humanized full length IgG1 containing the human gamma 1 and human kappa constant domains with PTM removal in the VH to increase stability of the antibody. For 71F4A3, the mutant position was D54E, and for 64C10G1, the mutant positions were D53E, D107E. The cross binding to huCXCL13 and cynoCXCL13 was tested by ELISA binding assays. The results are summarized in FIG. 11, which demonstrates that the potency of binding to huCXCL13 and cynoCXCL13 for humanized 71F4A3-VH1VL1 (Hz71F4)(D54E) and 71F4A3-VH1VL2 (D54E) are comparable with chimeric 71F4A3, but the binding potency for humanized 64C10G1-VH1VL2 (D53E, D107E) and 64C10G1-VH1VL3 (D53E, D107E) are dropped significantly while comparing with its chimeric counterpart.

Example 14. Blocking Potency of Anti-CXCL13 Full Length Humanized IgGs with PTM Removal Blocking of CXCL13 induced IP1 signaling. To evaluate the blocking potency of these humanized antibodies, the 71F4A3-VH1VL1 (Hz71F4), 64C10G1-VH1VL2 antibodies were produced synthetically as humanized full length IgG1 with the mutant position of D54E (Table 18) and D53E, D107E (Table 18a), respectively. The blocking activity was evaluated in the IP1 assay which induced by human CXCL13.

Figure 12:
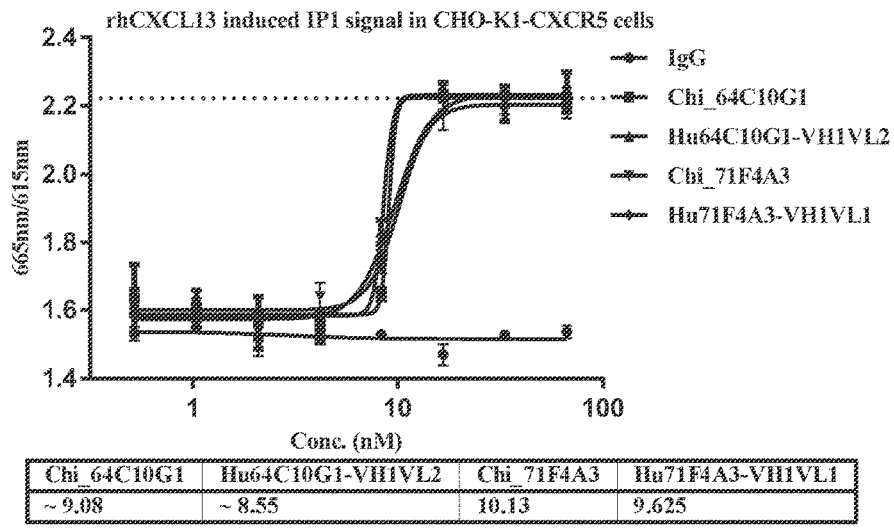
FIG. 12 shows that the tested antibodies inhibited CXCL13 induced IP1 signaling.

The results are summarized in FIG. 12, which demonstrates that humanized 71F4A3-VH1VL1 (Hz71F4) and 64C10G1-VH1VL2 could effectively block the IP signaling. And the blocking potency of both were comparable with chimeric 71F4A3, 64C10G1.

Example 15. Affinity Optimization of the Humanized Antibodies

It was contemplated that certain amino acid residues within the CDR regions or the framework regions could be changed to further improve or retain the activity and/or stability of the antibodies. With a computational tool (VectorNTI, available at www.ebi.ac.uk/tools/msa/clustalo/), with respect to their structural, conformational and functional properties, variants were designed with two different approaches.

In the first approach, mutations were chosen to target the hotspots in LCDR1, HCDR2 and HCDR3. Hotspots in CDRs were identified, as shown in Table 18. Usually, CDR3 contributes most to antigen binding and heavy chain is more important than light chain for antigen binding. Moreover, LCDR1 is important for antigen binding. For the first trial, random mutations were targeted to hotspots in LCDR1, HCDR2 and HCDR3. Eliminate hotspots that code for conserved and buried amino acids in CDRs. Remaining CDRs with hotspots are randomly mutated: HCDR2 (3 amino acids: 55S, 56S, 57T), HCDR3 (2 amino acids: 103E, 104Y), LCDR1 (3 amino acids: 32G, 34A, 36Y). After finishing construction of phage library, antigen CXCL13 screening was followed. Mutated Amino acids that could improve Kon are listed in Table 19. Sequences of lead clones that have greater Kon to human CXCL13 are listed in Table 20. Antibodies of these sequences were generated, and affinity testing was performed by Biacore T200. The results are listed in Table 21.

TABLE 18

Targeting mutations in hotspots of 71F4A3 (with D54E)

| Antibody chain | Sequences (CDRs underlined and targeted mutations bold and double underlined) | SEQ ID NO: |
|---|---|---|
| 71F4A3-VH (D54E) | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYEYYAMDYW GQGTTVTVSS | 156 |
| 71F4A3-VL | DIQMTQSPSS LSASVGDRVT ITCKASQDVN TGVAWYQQKP GKAPKLLIYS ASYRYTGVPS RFSGSGSGTD FTFTISSLQP EDIATYYCQQ YYSTPLTFGG GTKLEIK | 138 |

TABLE 18a

64C10G1-VH1VL2 with mutations D53E and D107E

| Antibody chain | Sequences (mutations bold and underlined) | SEQ ID NO: |
|---|---|---|
| 64C10G1-VH1 (D53E, D107E) | EVQLVESGGGLVQPGGSLRLSCAASGFTFSSYAMSWVRQAPGKGLEWVAT ISEGGSDAYYPDNVKGRFTISRDNAKNSLYLQMNSLRAEDTAVYYCARDY YGSGYEESPMDYWGQGTLVTVSS | 157 |
| 64C10G1-VL1 | DIQMTQSPSSLSASVGDRVTITCKASQDINKYIAWYQQKPGKAPKLLIYY TSTLQPGVPSRFSGSGSGTDFTFTISSLQPEDIATYYCLQYDNLYTFGGG TKLEIK | 121 |

TABLE 19

Mutations in 71F4A3 useful for improving binding

| Residue | Substituted with |
|---|---|
| VH-55S | A, G, R, or T |
| VH-56S | K, T, or N |
| VH-57T | S, W, F, L, G, Y or I |
| VH-103E | S, T, L, R, W or D |
| VH-104Y | H, T, N, V or K |

TABLE 19-continued

Mutations in 71F4A3 useful for improving binding

| Residue | Substituted with |
|---|---|
| VL-32G | A, |
| VL-34A | S, T, D, |
| VL-36Y | S, F |

TABLE 20

Lead clones of 71F4A3

| Antibody chain | Sequences | SEQ ID NO: |
|---|---|---|
| 71F4A3-BC1-VH | EVQLVESGGG LVQPGGSLRL SCAASGIDFS RYWMSWVRQA PGKGLEWVAE INPEASSINY APSLKDRFTI SRDNAKNSLY LQMNSLRAED TAVYYCARQD DYSHYAMDYW GQGTTVTVSS | 158 |
| 71F4A3-BC1-VL | DIQMTQSPSS LSASVGDRVT ITCKASQDVN TGVSWSQQKP GKAPKLLIYS ASYRYTGVPS RFSGSGSGTD FTFTISSLQP EDIATYYCQQ YYSTPLTFGG GTKLEIK | 159 |
| 71F4A3-BC4-VH | EVQLVESGGG LVQPGGSLRL SCAASGIDFS RYWMSWVRQA PGKGLEWVAE INPEAGKWNY APSLKDRFTI SRDNAKNSLY LQMNSLRAED TAVYYCARQD DYTTYAMDYW GQGTTVTVSS | 160 |
| 71F4A3-BC4-VL | DIQMTQSPSS LSASVGDRVT ITCKASQDVN TGVSWYQQKP GKAPKLLIYS ASYRYTGVPS RFSGSGSGTD FTFTISSLQP EDIATYYCQQ YYSTPLTFGG GTKLEIK | 161 |
| 71F4A3-BE3-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYLTYAMDYW GQGTTVTVSS | 162 |
| 71F4A3-BE3-VL | DIQMTQSPSS LSASVGDRVT ITCKASQDVN TAVDWFQQKP GKAPKLLIYS ASYRYTGVPS RFSGSGSGTD FTFTISSLQP EDIATYYCQQ YYSTPLTFGG GTKLEIK | 163 |
| 71F4A3-BD12-VH | EVQLVESGGG LVQPGGSLRL SCAASGIDFS RYWMSWVRQA PGKGLEWVAE INPETTIINY APSLKDRFTI SRDNAKNSLY LQMNSLRAED TAVYYCARQD DYRHYAMDYW GQGTTVTVSS | 164 |
| 71F4A3-BD12-VL | DIQMTQSPSS LSASVGDRVT ITCKASQDVN TGVAWFQQKP GKAPKLLIYS ASYRYTGVPS RFSGSGSGTD FTFTISSLQP EDIATYYCQQ YYSTPLTFGG GTKLEIK | 165 |
| 71F4A3-4H1-VH | EVQLVESGGG LVQPGGSLRL SCAASGIDFS RYWMSWVRQA PGKGLEWVAE INPESTLINY APSLKDRFTI SRDNAKNSLY LQMNSLRAED TAVYYCARQD DYRNYAMDYW GQGTTVTVSS | 166 |
| 71F4A3-4H1-VL | DIQMTQSPSS LSASVGDRVT ITCKASQDVN TGVSWFQQKP GKAPKLLIYS ASYRYTGVPS RFSGSGSGTD FTFTISSLQP EDIATYYCQQ YYSTPLTFGG GTKLEIK | 167 |
| 71F4A3-5A4-VH | EVQLVESGGG LVQPGGSLRL SCAASGIDFS RYWMSWVRQA PGKGLEWVAE INPESTGINY APSLKDRFTI SRDNAKNSLY LQMNSLRAED TAVYYCARQD DYWTYAMDYW GQGTTVTVSS | 168 |
| 71F4A3-5A4-VL | DIQMTQSPSS LSASVGDRVT ITCKASQDVN TAVSWTQQKP GKAPKLLIYS ASYRYTGVPS RFSGSGSGTD FTFTISSLQP EDIATYYCQQ YYSTPLTFGG GTKLEIK | 169 |

TABLE 20-continued

Lead clones of 71F4A3

| Antibody chain | Sequences | SEQ ID NO: |
|---|---|---|
| 71F4A3-3F12-VH | EVQLVESGGG LVQPGGSLRL SCAASGIDFS RYWMSWVRQA PGKGLEWVAE INPESNFINY APSLKDRFTI SRDNAKNSLY LQMNSLRAED TAVYYCARQD DYSVYAMDYW GQGTTVTVSS | 170 |
| 71F4A3-3F12-VL | DIQMTQSPSS LSASVGDRVT ITCKASQDVN TGVTWFQQKP GKAPKLLIYS ASYRYTGVPS RFSGSGSGTD FTFTISSLQP EDIATYYCQQ YYSTPLTFGG GTKLEIK | 171 |
| 71F4A3-B12-VH | EVQLVESGGG LVQPGGSLRL SCAASGIDFS RYWMSWVRQA PGKGLEWVAE INPERNYINY APSLKDRFTI SRDNAKNSLY LQMNSLRAED TAVYYCARQD DYDKYAMDYW GQGTTVTVSS | 172 |
| 71F4A3-B12-VL | DIQMTQSPSS LSASVGDRVT ITCKASQDVN TGVTWYQQKP GKAPKLLIYS ASYRYTGVPS RFSGSGSGTD FTFTISSLQP EDIATYYCQQ YYSTPLTFGG GTKLEIK | 173 |

TABLE 21

Kon results for lead clones

| Samples | ka (1/Ms) |
|---|---|
| 71F4-BC1 | 2.09E+06 |
| 71F4-BC4 | 3.62E+05 |
| 71F4-BE3 | 1.03E+06 |
| 71F4-BH2 | 1.44E+06 |
| 71F4-4H1 | 1.64E+07 |
| 71F4-5A4 | 6.58E+06 |
| 71F4-3F12 | 6.30E+06 |
| 71F4-4B12 | 5.36E+06 |
| 71F4-BD12 | 1.90E+06 |
| hz71F4 | 3.77E+05 |

In the second approach, mutations were carried out by multiple libraries including 4 different sub libraries, such as saturated mutation libraries by CDR walking for CDR L1, CDR L3, CDR H3 or CDR L2, CDR H1, CDR H2 and saturated mutation libraries by three aa mutated continuously for CDR H3 or CDR L3. CDRs were identified according AbM method by abYsis 3 (http://abysis.org/), as shown in Table 22. After finishing construction of phage sub libraries, antigen CXCL13 screening followed. Mutated Amino acids that could improve Koff are listed in Table 23. Sequences of lead clones that have lower Koff to human CXCL13 are listed in Table 24. Antibodies of these sequences were generated, and affinity testing was performed by Biacore T200. The results are listed in Table 25. To further optimize the antibodies, the lead clones were then back mutated to its humanized counterpart one aa by one aa. Sequences were generated and synthesized for antibodies. Affinity was tested by Biacore T200. Results show that one of the back mutation of 005-3-18, sequence was showed in Table 26, which is 92W back mutant to Y in the light chain and named 71F4-B, significantly promote Koff, KD (<1 nM) and blocking activity compared with Hz71F4 and 005-3-18, data were listed in Table 27.

TABLE 22

CDRs of 71F4A3

| Antibody chain | Sequences (CDRs underlined and targeted mutations bold and double underlined) | SEQ ID NO: |
|---|---|---|
| 71F4A3-VH (D54E) | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYEYYAMDYW GQGTTVTVSS | 156 |
| 71F4A3-VL | DIQMTQSPSS LSASVGDRVT ITCKASQDVN TGVAWYQQKP GKAPKLLIYS ASYRYTGVPS RFSGSGSGTD FTFTISSLQP EDIATYYCQQ YYSTPLTFGG GTKLEIK | 138 |

TABLE 23

Mutations in 71F4A3 useful for improving Koff

| Residue | Substituted with |
|---|---|
| VL-25A | V |
| VL-34A | Y |
| VL-91Y | G |
| VL-92Y | W |
| VH-100D | E |
| VH-102Y | T |
| VH-103E | R |
| VH-106A | T |
| VH-107M | L |

TABLE 24

Sequences of lead clones

| Antibody chain | Sequences | SEQ ID NO: |
|---|---|---|
| 005-3-18-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYEYYTMDYW GQGTTVTVSS | 174 |
| 005-3-18-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YWSTPLTFGG GTKLEIK | 175 |
| 005-3-23-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQE DYEYYALDYW GQGTTVTVSS | 176 |
| 005-3-23-VL | DIQMTQSPSS LSASVGDRVT ITCKASQDVN TGVYWYQQKP GKAPKLLIYS ASYRYTGVPS RFSGSGSGTD FTFTISSLQP EDIATYYCQQ GYSTPLTFGG GTKLEIK | 177 |
| 005-2-45-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DTRYYAMDYW GQGTTVTVSS | 178 |
| 005-2-45-VL | DIQMTQSPSS LSASVGDRVT ITCKASQDVN TGVAWYQQKP GKAPKLLIYS ASYRYTGVPS RFSGSGSGTD FTFTISSLQP EDIATYYCQQ YYSTPLTFGG GTKLEIK | 138 |

TABLE 25

Koff results for lead clones

| Sample | kd (1/s) |
|---|---|
| 005-3-18 | 1.58E−04 |
| 005-3-23 | 4.03E−04 |
| 005-2-45 | 7.76E−04 |
| hz71F4 | 1.26E−03 |

TABLE 26

Sequences of lead clones

| Antibody chain | Sequences (W92Y back mutation underlined and bold) | SEQ ID NO: |
|---|---|---|
| 71F4-B-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYEYYTMDYW GQGTTVTVSS | 174 |
| 71F4-B-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YYSTPLTFGG GTKLEIK | 179 |

TABLE 27

Affinity determination and blocking results for 71F4-B

| Samples | ka (1/Ms) | kd (1/s) | KD (M) | Cell blocking (IC$_{50}$ rate) |
|---|---|---|---|---|
| Hz71F4A3 | 2.50E+05 | 6.45E−04 | 2.58E−09 | 1.0 |
| 005-3-18 | 1.24E+05 | 1.53E−04 | 1.24E−09 | / |
| 71F4-B | 1.83E+05 | 3.57E−05 | 1.95E−10 | 0.7 |

To further optimization of 71F4-B, each Mutations in 71F4A3 useful for improving binding (Kon) were added into 71F4-B, the sequences were listed in Table 28. Antibodies according to these sequences were generated and affinity testing was performed by Biacore T200. The results showed that the affinity of 71F4-B-T, 71F4-B-LT, 71F4-B-H were increased almost 1 log compared to 71F4-B, the affinity of lead clones was listed in Table 29.

TABLE 28

Sequences of lead clones

| Antibody chain | Sequences | SEQ ID NO: |
|---|---|---|
| 71F4-B-L-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYLYYTMDYW GQGTTVTVSS | 180 |
| 71F4-B-L-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YSTPLTFGG GTKLEIK | 179 |
| 71F4-B-T-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYETYTMDYW GQGTTVTVSS | 181 |
| 71F4-B-T-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YSTPLTFGG GTKLEIK | 179 |
| 71F4-B-LT-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYLTYTMDYW GQGTTVTVSS | 182 |
| 71F4-B-LT-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YSTPLTFGG GTKLEIK | 179 |
| 71F4-B-A-VH | EVQLVESGGG LVQPGGSLRL SCAASGIDFS RYWMSWVRQA PGKGLEWVAE INPEASTINY APSLKDRFTI SRDNAKNSLY LQMNSLRAED TAVYYCARQD DYEYYTMDYW GQGTTVTVSS | 183 |
| 71F4-B-H-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YSTPLTFGG GTKLEIK | 179 |
| 71F4-B-S1-VH | EVQLVESGGG LVQPGGSLRL SCAASGIDFS RYWMSWVRQA PGKGLEWVAE INPESSSINY APSLKDRFTI SRDNAKNSLY LQMNSLRAED TAVYYCARQD DYEYYTMDYW GQGTTVTVSS | 184 |
| 71F4-B-S1-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YSTPLTFGG GTKLEIK | 179 |
| 71F4-B-S2-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYSYYTMDYW GQGTTVTVSS | 185 |
| 71F4-B-S2-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YSTPLTFGG GTKLEIK | 179 |
| 71F4-B-H-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYEHYTMDYW GQGTTVTVSS | 186 |
| 71F4-B-H-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YSTPLTFGG GTKLEIK | 179 |
| 71F4-B-SH-VH | EVQLVESGGG LVQPGGSLRL SCAASGIDFS RYWMSWVRQA PGKGLEWVAE INPESSTINY APSLKDRFTI SRDNAKNSLY LQMNSLRAED TAVYYCARQD DYSHYTMDYW GQGTTVTVSS | 187 |
| 71F4-B-SH-VL | DIQMTQSPSS LSASVGDRVT ITCKVSQDVN TGVAWYQQKP GKAPKLLIYS ASYRYTGVPS RFSGSGSGTD FTFTISSLQP EDIATYYCQQ YSTPLTFGG GTKLEIK | 179 |
| 71F4-B-AS-VH | EVQLVESGGG LVQPGGSLRL SCAASGIDFS RYWMSWVRQA PGKGLEWVAE INPEASSINY APSLKDRFTI SRDNAKNSLY LQMNSLRAED TAVYYCARQD DYEYYTMDYW GQGTTVTVSS | 188 |

TABLE 28-continued

Sequences of lead clones

| Antibody chain | Sequences | | | | SEQ ID NO: |
|---|---|---|---|---|---|
| 71F4-B-AS-VL | DIQMTQSPSS | LSASVGDRVT | ITCKVSQDVN | TGVAWYQQKP | 179 |
| | GKAPKLLIYS | ASYRYTGVPS | RFSGSGSGTD | FTFTISSLQP | |
| | EDIATYYCQQ | YYSTPLTFGG | GTKLEIK | | |
| 71F4-B-SSH-VH | EVQLVESGGG | LVQPGGSLRL | SCAASGIDFS | RYWMSWVRQA | 189 |
| | PGKGLEWVAE | INPESSSINY | APSLKDRFTI | SRDNAKNSLY | |
| | LQMNSLRAED | TAVYYCARQD | DYSHYTMDYW | GQGTTVTVSS | |
| 71F4-B-SSH-VL | DIQMTQSPSS | LSASVGDRVT | ITCKVSQDVN | TGVAWYQQKP | 179 |
| | GKAPKLLIYS | ASYRYTGVPS | RFSGSGSGTD | FTFTISSLQP | |
| | EDIATYYCQQ | YYSTPLTFGG | GTKLEIK | | |
| 71F4-B-ASH-H | EVQLVESGGG | LVQPGGSLRL | SCAASGIDFS | RYWMSWVRQA | 190 |
| | PGKGLEWVAE | INPEASSINY | APSLKDRFTI | SRDNAKNSLY | |
| | LQMNSLRAED | TAVYYCARQD | DYSHYTMDYW | GQGTTVTVSS | |
| 71F4-B-ASH-VL | DIQMTQSPSS | LSASVGDRVT | ITCKVSQDVN | TGVAWYQQKP | 179 |
| | GKAPKLLIYS | ASYRYTGVPS | RFSGSGSGTD | FTFTISSLQP | |
| | EDIATYYCQQ | YYSTPLTFGG | GTKLEIK | | |

TABLE 29

Affinity determination results

| Samples | ka (1/Ms) | kd (1/s) | KD (M) |
|---|---|---|---|
| 71F4-B | 1.83E+05 | 6.59E−05 | 3.60E−10 |
| 71F4-B-L | 1.94E+05 | 8.58E−05 | 4.43E−10 |
| 71F4-B-T | 2.56E+05 | 1.17E−05 | 4.56E−11 |
| 71F4-B-LT | 2.35E+05 | 1.02E−05 | 4.35E−11 |
| 71F4-B-A | 1.76E+05 | 6.82E−05 | 3.88E−10 |
| 71F4-B-S1 | 2.29E+05 | 9.26E−05 | 4.04E−10 |
| 71F4-B-S2 | 5.15E+05 | 2.68E−04 | 5.20E−10 |
| 71F4-B-H | 1.97E+05 | 1.27E−05 | 6.47E−11 |
| 71F4-B-SH | 1.92E+05 | 5.55E−05 | 2.90E−10 |
| 71F4-B-AS | 2.26E+05 | 7.25E−05 | 3.21E−10 |
| 71F4-B-SSH | 2.51E+05 | 9.46E−05 | 3.77E−10 |
| 71F4-B-ASH | 1.76E+05 | 9.17E−05 | 5.21E−10 |

Example 16. Blocking Potency of Anti-CXCL13 Affinity Matured Antibodies in Signaling Assay Inhibition of CXCL13 mediated IP1 signaling. Based on the results of binding affinity, we selected the 71F4A3-B, 71F4A3-B-T, 71F4A3-B-H, 71F4A3-B-LT to investigate in the functional IP1 signaling assay. Besides, we compared the blocking potency of in house anti-CXCL13 with the reference anti-CXCL13 antibody, Mab5261, which was mention in example 9.

Figure 13:
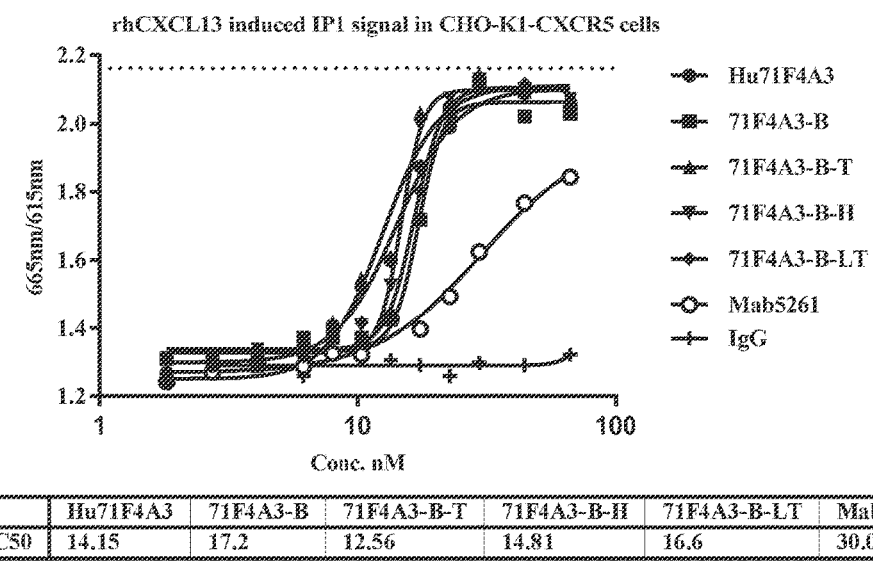
FIG. 13 shows that the tested affinity matured antibodies inhibited CXCL13 induced IP1 signaling.

As shown in the FIG. 13, all 71F4A3 affinity matured variants and Hz71F4A3 could dose-dependently inhibit the IP1 signal which was induced by CXCL13. The blocking potency of different affinity matured variants of 71F4A3 were comparable with Hz71F4A3, and the potency of 71F4A3 affinity matured variants was significantly better than the reference antibody.

Example 17. Functional Properties of Anti-CXCL13 Affinity Matured Antibodies in Cells Migration Assay Blocking of BaF3-CXCR5 (human) cells migration toward CXCL13. Furthery, we validated the activity of these affinity matured antibodies and reference antibody in BaF3-CXCR5 cell line migration assay which was mentioned on example 5.

Figure 14:
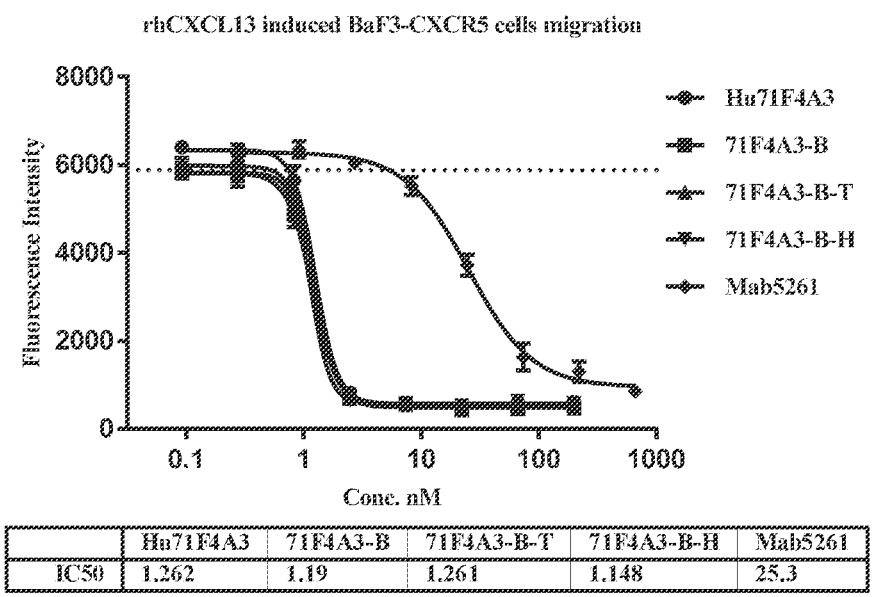
FIG. 14 shows that the antibodies tested inhibited BaF3-CXCR5 (human) cells migration toward CXCL13.

As shown in the FIG. 14, the dashed lines indicated the CXCL13 induced the migration level. When the anti-CXCL13 antibodies, Hz71F4A3, 71F4A3-B, 71F4A3-B-T, 71F4A3-B-H and Mab6261 were added into this assay system, the BaF3-CXCR5 cells migration were dose-dependently inhibited. The inhibition activity of 71F4A3 affinity matured variants were similarity with Hz71F4A3 in this cell line migration assay. And the inhibition activity of all affinity matured 71F4A3 variants were dramatically better than the reference antibody Mab5261.

Inhibition of primary human tonsil cells migration to CXCL13. Besides, we also investigated the blocking function of anti-CXCL13 affinity matured antibodies in primary human tonsil cells migration assay.

Figure 15:
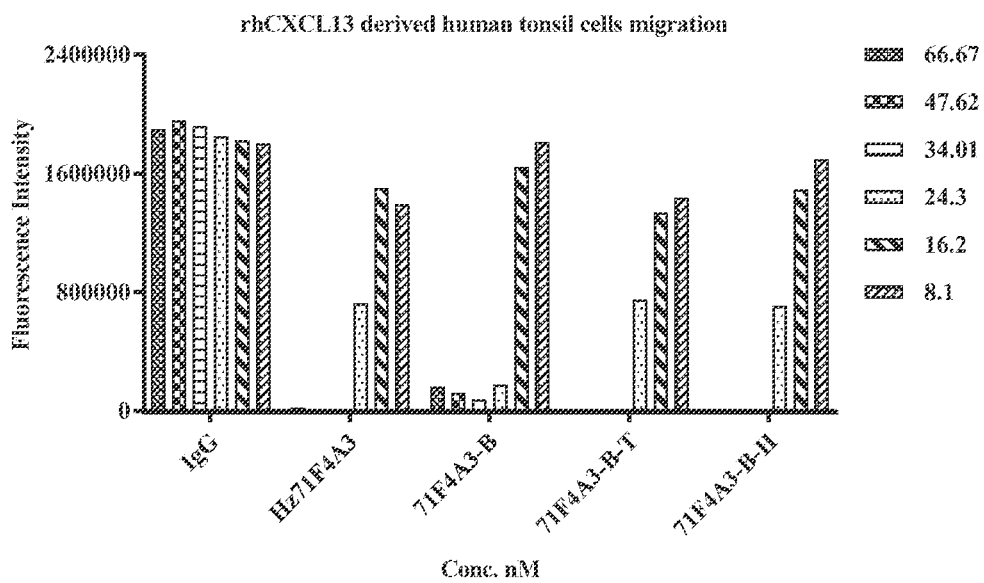
FIG. 15 shows that the affinity matured antibodies inhibited primary human tonsil cells chemotaxis induced by CXCL13 in a dose-dependently manner.

As shown in the FIG. 15, compare to IgG treated condition, all the 71F4A3 affinity matured antibodies, 71F4A3-B, 71F4A3-B-T, 71F4A3-B-H, could inhibited the primary human tonsil cells chemotaxis induced by CXCL13 in a dose-dependently manner. And the inhibition activity of 71F4A3 affinity matured antibodies were comparable with Hz71F4A3 in this primary human assay.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

What is claimed is:

1. An antibody or fragment thereof having specificity to a human chemokine (C-X-C motif) ligand 13 (CXCL13) protein, wherein the antibody or fragment thereof comprises a heavy chain variable region comprising heavy chain complementarity determining regions HCDR1, HCDR2, and HCDR3, and a light chain variable region comprising light chain complementarity determining regions LCDR1, LCDR2, and LCDR3, wherein:
   the HCDR1 comprises the amino acid sequence of SEQ ID NO: 127 (RYWMS);
   the HCDR2 comprises the amino acid sequence of SEQ ID NO: 128 (EINPDSSTINY APSLKD);
   the HCDR3 comprises the amino acid sequence of SEQ ID NO: 130 (QDDYEYYAMDY);
   the LCDR1 comprises the amino acid sequence of SEQ ID NO: 131 (KASQDVNTGVA);
   the LCDR2 comprises the amino acid sequence of SEQ ID NO: 132 (SASYRYT);
   and the LCDR3 comprises the amino acid sequence of SEQ ID NO: 133 (QQYYSTPLT), or
   the HCDR1 comprises the amino acid sequence of SEQ ID NO: 127 (RYWMS);
   the HCDR2 comprises the amino acid sequence of SEQ ID NO: 129 (EINPESSTINYAPSLKD);
   the HCDR3 comprises the amino acid sequence of SEQ ID NO: 130 (QDDYEYYAMDY);
   the LCDR1 comprises the amino acid sequence of SEQ ID NO: 131 (KASQDVNTGVA);
   the LCDR2 comprises the amino acid sequence of SEQ ID NO: 132 (SASYRYT);
   and the LCDR3 comprises the amino acid sequence of SEQ ID NO: 133 (QQYYSTPLT), or
   the HCDR1 comprises the amino acid sequence of SEQ ID NO: 127 (RYWMS);
   the HCDR2 comprises the amino acid sequence of SEQ ID NO: 129 (EINPESSTINYAPSLKD);
   the HCDR3 comprises the amino acid sequence of SEQ ID NO: 359 (QDDYEYYTMDY);
   the LCDR1 comprises the amino acid sequence of SEQ ID NO: 360 (KVSQDVNTGVA),
   The LCDR2 comprises the amino acid sequence of SEQ ID NO: 132 (SASYRYT);
   the LCDR3 comprises the amino acid sequence of SEQ ID NO: 361 (QQYWSTPLT), or
   the HCDR1 comprises the amino acid sequence of SEQ ID NO: 127 (RYWMS);

the HCDR2 comprises the amino acid sequence of SEQ ID NO: 129 (EINPESSTINYAPSLKD);
the HCDR3 comprises the amino acid sequence of SEQ ID NO: 359 (QDDYEYYTMDY);
the LCDR1 comprises the amino acid sequence of SEQ ID NO: 360 (KVSQDVNTGVA),
the LCDR2 comprises the amino acid sequence of SEQ ID NO: 132 (SASYRYT);
and the LCDR3 comprises the amino acid sequence of SEQ ID NO: 133 (QQYYSTPLT), or
the HCDR1 comprises the amino acid sequence of SEQ ID NO: 127 (RYWMS);
the HCDR2 comprises the amino acid sequence of SEQ ID NO: 129 (EINPESSTINYAPSLKD);
the HCDR3 comprises the amino acid sequence of SEQ ID NO: 367 (QDDYETYTMDY),
the LCDR1 comprises the amino acid sequence of SEQ ID NO: 360 (KVSQDVNTGVA),
the LCDR2 comprises the amino acid sequence of SEQ ID NO: 132 (SASYRYT); and the LCDR3 comprises the amino acid sequence of SEQ ID NO: 133 (QQYYSTPLT).

2. The antibody or fragment thereof of claim 1, wherein the HCDR1, HCDR2, HCDR3, LCDR1, LCD2 and LCDR3 comprise SEQ ID NO:127, 129, 367, 360, 132 and 133, respectively.

3. The antibody or fragment thereof of claim 2, wherein the heavy chain variable region comprises the amino acid sequence of SEQ ID NO:181 or an amino acid sequence having at least 90% sequence identity to SEQ ID NO:181, and the light chain variable region comprises the amino acid sequence of SEQ ID NO:179 or an amino acid sequence having at least 90% sequence identity to SEQ ID NO:179.

4. The antibody or fragment thereof of claim 3, which is humanized and wherein the heavy chain variable region comprises one or more back mutations selected from the group consisting of 5Q, 47I, 48G, and 85V, according to Kabat numbering, and combinations thereof, or wherein the light chain variable region comprises a mutation 78V according to Kabat numbering.

5. The antibody or fragment thereof of claim 2, wherein the heavy chain variable region comprises the amino acid sequence of SEQ ID NO:181, and the light chain variable region comprises the amino acid sequence of SEQ ID NO:179.

6. The antibody or fragment thereof of claim 1, wherein the HCDR1, HCDR2, HCDR3, LCDR1, LCD2 and LCDR3 comprise SEQ ID NO:127, 129, 359, 360, 132 and 133, respectively.

7. The antibody or fragment thereof of claim 6, wherein the heavy chain variable region comprises the amino acid sequence of SEQ ID NO:174 or an amino acid sequence having at least 90% sequence identity to SEQ ID NO:174, and the light chain variable region comprises the amino acid sequence of SEQ ID NO:179 or an amino acid sequence having at least 90% sequence identity to SEQ ID NO:179.

8. The antibody or fragment thereof of claim 1, wherein the HCDR1, HCDR2, HCDR3, LCDR1, LCD2 and LCDR3 comprise SEQ ID NO:127, 129, 359, 360, 132 and 361, respectively.

9. The antibody or fragment thereof of claim 8, wherein the heavy chain variable region comprises the amino acid sequence of SEQ ID NO:174 or an amino acid sequence having at least 90% sequence identity to SEQ ID NO:174, and the light chain variable region comprises the amino acid sequence of SEQ ID NO:175 or an amino acid sequence having at least 90% sequence identity to SEQ ID NO:175.

10. The antibody or fragment thereof of claim 1, wherein the HCDR1, HCDR2, HCDR3, LCDR1, LCD2 and LCDR3 comprise SEQ ID NO:127, 129, 130, 131, 132 and 133, respectively.

11. The antibody or fragment thereof of claim 10, wherein the heavy chain variable region comprises the amino acid sequence of SEQ ID NO:156 or an amino acid sequence having at least 90% sequence identity to SEQ ID NO:156, and the light chain variable region comprises the amino acid sequence of SEQ ID NO:138 or an amino acid sequence having at least 90% sequence identity to SEQ ID NO:138.

12. The antibody or fragment thereof of claim 1, wherein the HCDR1, HCDR2, HCDR3, LCDR1, LCD2 and LCDR3 comprise SEQ ID NO:127, 128, 130, 131, 132 and 133, respectively.

13. The antibody or fragment thereof of claim 12, wherein the heavy chain variable region comprises the amino acid sequence of SEQ ID NO:134 or an amino acid sequence having at least 90% sequence identity to SEQ ID NO:134, and the light chain variable region comprises the amino acid sequence of SEQ ID NO:138 or an amino acid sequence having at least 90% sequence identity to SEQ ID NO:138.

14. The antibody or fragment thereof of claim 6, which is humanized and wherein the heavy chain variable region comprises one or more back mutations selected from the group consisting of 5Q, 47I, 48G, and 85V, according to Kabat numbering, and combinations thereof, or wherein the light chain variable region comprises a mutation 78V according to Kabat numbering.

\* \* \* \* \*